US012667270B2

(12) United States Patent (10) Patent No.: US 12,667,270 B2

McKinney et al. (45) **Date of Patent: *Jun. 30, 2026**

(54) CABLE FOR USE WITH PRESSURE MONITORING CATHETERS

(71) Applicant: Sentinel Medical Technologies, LLC, Boca Raton, FL (US)

(72) Inventors: Timothy McKinney, Boca Raton, FL (US); Marc-Alan Levine, Pottstown, PA (US); Michael Leedle, Audobon, PA (US)

(73) Assignee: Sentinel Medical Technologies, LLC, Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/216,645

(22) Filed: Jun. 30, 2023

(65) Prior Publication Data

US 2024/0000332 A1 Jan. 4, 2024

Related U.S. Application Data

(63) Continuation of application No. 16/945,233, filed on Jul. 31, 2020, now Pat. No. 11,730,385.

(60) Provisional application No. 62/884,192, filed on Aug. 8, 2019.

(51) Int. Cl.
| | |
|---|---|
| *A61B 5/03* | (2006.01) |
| *A61B 5/00* | (2006.01) |
| *A61B 5/11* | (2006.01) |
| *A61M 25/10* | (2013.01) |

(52) U.S. Cl.
CPC ............ *A61B 5/036* (2013.01); *A61B 5/0004* (2013.01); *A61B 5/1116* (2013.01); *A61B*

*5/6853* (2013.01); *A61B 5/742* (2013.01); *A61M 25/1011* (2013.01); *A61B 2560/0223* (2013.01);

(Continued)

(58) Field of Classification Search
None
See application file for complete search history.

(56) References Cited

U.S. PATENT DOCUMENTS

| | | | |
|---|---|---|---|
| 3,721,229 | A | 3/1973 | Panzer |
| 4,192,319 | A | 3/1980 | Hargens et al. |
| 4,335,723 | A | 6/1982 | Patel |

(Continued)

FOREIGN PATENT DOCUMENTS

| | | |
|---|---|---|
| CA | 2961757 | 3/2016 |
| CN | 201267504 | 7/2009 |

(Continued)

OTHER PUBLICATIONS

Sawchuck, Diane, et al. "Pre-eclampsia renamed and reframed: Intra-abdominal hypertension in pregnancy" Nov. 2014, Medical Hypothese, 83, 619-632 (Year: 2014).

(Continued)

*Primary Examiner* — Benjamin S Melhus
(74) *Attorney, Agent, or Firm* — Neil D. Gershon

(57) ABSTRACT

A cable for use with a pressure monitoring catheter, the catheter including an inflatable balloon forming a fluid chamber for pressure measurement. The cable has a first end operably connectable to the catheter, a second end operably connectable to a monitor providing pressure displays, and a printed circuit. The cable includes one or both of the filter system to enable collection and analysis of data and an adjustment feature to adjust pressure values in response to patient movement.

14 Claims, 100 Drawing Sheets

(52) U.S. Cl.
CPC ................. *A61B 2560/0252* (2013.01); *A61B 2560/0257* (2013.01)

(56) References Cited

U.S. PATENT DOCUMENTS

| | | | |
|---|---|---|---|
| 4,739,769 A | 4/1988 | Mathews et al. |
| 4,873,986 A | 10/1989 | Wallace |
| 4,901,731 A | 2/1990 | Millar |
| 4,976,692 A | 12/1990 | Atad |
| 5,135,002 A | 8/1992 | Kirchner et al. |
| 5,167,237 A | 12/1992 | Rabin et al. |
| 5,398,692 A | 3/1995 | Hickey |
| 5,431,629 A | 7/1995 | Lampropoulos et al. |
| 5,433,216 A | 7/1995 | Sugrue et al. |
| 5,447,497 A | 9/1995 | Sogard et al. |
| 5,551,439 A | 9/1996 | Hickey |
| 5,566,680 A | 10/1996 | Urion |
| 5,570,671 A | 11/1996 | Hickey |
| 5,573,007 A | 11/1996 | Bobo, Sr. |
| 5,697,375 A | 12/1997 | Hickey |
| 5,707,358 A | 1/1998 | Wright |
| 5,951,497 A | 9/1999 | Wallace et al. |
| 5,980,485 A | 11/1999 | Grantz et al. |
| 5,984,879 A | 11/1999 | Wallace et al. |
| 6,021,781 A | 2/2000 | Thompson et al. |
| 6,167,886 B1 | 1/2001 | Engel |
| 6,183,421 B1 | 2/2001 | Bobo |
| 6,231,524 B1 | 5/2001 | Wallace et al. |
| 6,434,418 B1 | 8/2002 | Neal et al. |
| 6,447,462 B1 | 9/2002 | Wallace et al. |
| 6,450,971 B1 | 9/2002 | Andrus et al. |
| 6,461,332 B1 | 10/2002 | Mosel et al. |
| 6,648,879 B2 | 11/2003 | Joye et al. |
| 6,673,022 B1 | 1/2004 | Bobo et al. |
| 6,723,053 B2 | 4/2004 | Ackerman et al. |
| 6,827,710 B1 | 12/2004 | Mooney et al. |
| 6,890,307 B2 | 5/2005 | Kokate et al. |
| 7,081,096 B2 | 7/2006 | Brister et al. |
| 7,347,822 B2 | 3/2008 | Brockway et al. |
| 7,381,190 B2 | 6/2008 | Sugrue et al. |
| 7,654,967 B2 | 2/2010 | Bobo, Sr. |
| 7,722,544 B2 | 5/2010 | Williams et al. |
| 7,828,753 B2 | 11/2010 | Euliano, II et al. |
| 7,959,579 B2 | 6/2011 | Dijkman |
| 7,976,475 B2 | 7/2011 | Dijkman |
| 8,007,444 B2 | 8/2011 | Kokate et al. |
| 8,192,368 B2 | 6/2012 | Woodruff et al. |
| 8,235,426 B2 | 8/2012 | Pisula, Jr. et al. |
| 8,337,411 B2 | 12/2012 | Nishtala et al. |
| 8,360,988 B2 | 1/2013 | Bobo, Sr. et al. |
| 8,403,884 B2 | 3/2013 | Nishtala |
| 8,491,503 B2 | 7/2013 | Zaiken et al. |
| 8,535,237 B2 | 9/2013 | Nishtala |
| 8,596,688 B2 | 12/2013 | Pisula, Jr. et al. |
| 8,626,316 B2 | 1/2014 | Mohl |
| 8,636,724 B2 | 1/2014 | Wiita et al. |
| 8,636,728 B2 | 1/2014 | Watson |
| 8,646,325 B2 | 2/2014 | Hoem et al. |
| 8,708,927 B2 | 4/2014 | Dijkman |
| 8,876,729 B2 | 11/2014 | Bobo, Sr. et al. |
| 9,046,205 B2 | 6/2015 | Whitaker et al. |
| 9,055,949 B2 | 6/2015 | Belfort |
| 9,101,314 B2 | 8/2015 | Shi |
| 9,107,695 B2 | 8/2015 | Horton et al. |
| 9,108,000 B2 | 8/2015 | Kassab |
| 9,126,008 B2 | 9/2015 | Kim |
| 9,167,973 B2 | 10/2015 | Steiner et al. |
| 9,393,353 B2 | 7/2016 | Alam et al. |
| 9,439,600 B2 | 9/2016 | Mohl |
| 9,440,043 B2 | 9/2016 | Arora et al. |
| 9,510,766 B2 | 12/2016 | Weed et al. |
| 9,511,209 B2 | 12/2016 | Drasler et al. |
| 9,534,721 B2 | 1/2017 | Lombardi, III |
| 9,597,140 B2 | 3/2017 | Mihalik |
| 9,622,670 B2 | 4/2017 | Burnett et al. |
| 9,623,201 B2 | 4/2017 | Gregory et al. |
| 9,655,555 B2 | 5/2017 | Burnett et al. |
| 9,662,058 B2 | 5/2017 | Burnett et al. |
| 9,695,966 B2 | 7/2017 | Lombardi, III et al. |
| 9,713,494 B2 | 7/2017 | Nabutovsky et al. |
| 9,717,472 B2 | 8/2017 | Ahmed et al. |
| 9,724,232 B2 | 8/2017 | Kassab et al. |
| 9,734,706 B2 | 8/2017 | Moon et al. |
| 9,757,545 B2 | 9/2017 | Kassab |
| 9,782,115 B2 | 10/2017 | Shi |
| 9,782,145 B2 | 10/2017 | Hart et al. |
| 9,848,790 B2 | 12/2017 | Pintel |
| 9,877,660 B2 | 1/2018 | O'Connell et al. |
| 9,895,103 B2 | 2/2018 | Hyde et al. |
| 9,913,585 B2 | 3/2018 | McCaffrey et al. |
| 9,931,044 B2 | 4/2018 | Burnett et al. |
| 9,931,122 B2 | 4/2018 | Burnett et al. |
| 9,943,352 B2 | 4/2018 | Mihalik |
| 10,004,551 B2 | 6/2018 | Burnett |
| 10,194,813 B2 | 2/2019 | Bharucha et al. |
| 10,206,575 B2 | 2/2019 | Al-Mayah |
| 10,238,307 B2 | 3/2019 | Schlumpf et al. |
| 10,314,488 B2 | 6/2019 | Samuelsson et al. |
| 10,368,872 B2 | 8/2019 | Franklin et al. |
| 10,376,679 B2 | 8/2019 | Cox et al. |
| 10,391,275 B2 | 8/2019 | Burnett et al. |
| 10,433,741 B2 | 10/2019 | Stimpson |
| 10,478,113 B2 | 11/2019 | Damaser et al. |
| 10,485,483 B1 | 11/2019 | Brody |
| 10,517,538 B2 | 12/2019 | Burnett et al. |
| 10,531,834 B1 | 1/2020 | Smith et al. |
| 10,532,193 B2 | 1/2020 | Fischer, Jr. et al. |
| 10,537,274 B2 | 1/2020 | Damaser et al. |
| 10,537,308 B2 | 1/2020 | Zhadkevich |
| 10,542,924 B2 | 1/2020 | Imran et al. |
| 10,568,686 B2 | 2/2020 | Lee |
| 10,617,313 B2 | 4/2020 | Smith |
| 10,631,788 B2 | 4/2020 | Brody |
| 10,743,780 B2 | 8/2020 | Hoem et al. |
| 10,750,999 B2 | 8/2020 | Parks et al. |
| 10,758,135 B2 | 9/2020 | Burnett et al. |
| 10,772,998 B2 | 9/2020 | Luxon |
| 10,773,059 B1 | 9/2020 | Sardesai |
| 10,786,651 B2 | 9/2020 | Edminster et al. |
| 11,065,418 B1 | 7/2021 | Brody |
| 11,077,301 B2 | 8/2021 | Creasey |
| 11,648,380 B2 | 5/2023 | McCloskey |
| 2002/0143294 A1 | 10/2002 | Duchon et al. |
| 2002/0183628 A1 | 12/2002 | Reich et al. |
| 2003/0060800 A1 | 3/2003 | Ryan |
| 2003/0114835 A1 | 6/2003 | Noda |
| 2003/0163052 A1 | 8/2003 | Mott |
| 2003/0181856 A1 | 9/2003 | Goldman |
| 2004/0077976 A1 | 4/2004 | Wilson |
| 2004/0127813 A1 | 7/2004 | Schwamm |
| 2004/0171942 A1 | 9/2004 | Ackerman et al. |
| 2005/0015047 A1 | 1/2005 | Shah |
| 2005/0055043 A1 | 3/2005 | Foltz |
| 2005/0065408 A1 | 3/2005 | Benderev |
| 2005/0187430 A1 | 8/2005 | Aundal et al. |
| 2005/0197585 A1 | 9/2005 | Brockway et al. |
| 2005/0215989 A1 | 9/2005 | Abboud |
| 2005/0240211 A1 | 10/2005 | Sporri |
| 2005/0283092 A1 | 12/2005 | Gedebov |
| 2006/0011820 A1 | 1/2006 | Chow-Shing et al. |
| 2006/0073728 A1 | 4/2006 | Zaiken |
| 2006/0085022 A1 | 4/2006 | Hayes |
| 2006/0085024 A1 | 4/2006 | Pepper |
| 2007/0083126 A1 | 4/2007 | Marko et al. |
| 2007/0191904 A1 | 8/2007 | Libbus et al. |
| 2007/0197963 A1 | 8/2007 | Griffiths et al. |
| 2007/0282219 A1 | 12/2007 | Holte |
| 2008/0027358 A1 | 1/2008 | Gregersen et al. |
| 2008/0077043 A1 | 3/2008 | Malbrain et al. |
| 2008/0103408 A1 | 5/2008 | Denton et al. |
| 2008/0139967 A1 | 6/2008 | Euliano |
| 2008/0146990 A1 | 6/2008 | Jenson et al. |
| 2009/0221993 A1 | 9/2009 | Sohi et al. |
| 2009/0240199 A1 | 9/2009 | Rahimsobhani |

(56)                References Cited

U.S. PATENT DOCUMENTS

| | | |
|---|---|---|
| 2009/0306539 A1 | 12/2009 | Woodruff |
| 2010/0056952 A1 | 3/2010 | Liu |
| 2010/0069900 A1 | 3/2010 | Shirley |
| 2010/0094204 A1 | 4/2010 | Nishtala |
| 2010/0094328 A1 | 4/2010 | O'dea et al. |
| 2010/0113939 A1 | 5/2010 | Mashimo et al. |
| 2010/0168836 A1 | 7/2010 | Kassab |
| 2010/0249663 A1 | 9/2010 | Nishtala |
| 2011/0087109 A1 | 4/2011 | Swann |
| 2012/0010525 A1 | 1/2012 | Jacofsky et al. |
| 2012/0035595 A1 | 2/2012 | Goedje |
| 2012/0041334 A1 | 2/2012 | Goedje et al. |
| 2012/0053441 A1 | 3/2012 | Kassab |
| 2012/0179063 A1 | 7/2012 | Bharucha et al. |
| 2012/0316460 A1 | 12/2012 | Stout |
| 2012/0316461 A1 | 12/2012 | Liu |
| 2013/0030262 A1 | 1/2013 | Burnett et al. |
| 2013/0046217 A1 | 2/2013 | Mooney |
| 2013/0066166 A1 | 3/2013 | Burnett et al. |
| 2013/0079662 A1 | 3/2013 | Damaser et al. |
| 2013/0085519 A1 | 4/2013 | Kiminami |
| 2013/0211221 A1 | 8/2013 | Sunnarborg |
| 2013/0231584 A1 | 9/2013 | Burnett |
| 2013/0317367 A1 | 11/2013 | Shuler |
| 2014/0012305 A1 | 1/2014 | Horton et al. |
| 2014/0094716 A1 | 4/2014 | Zaiken et al. |
| 2014/0107550 A1 | 4/2014 | Paulson |
| 2014/0107573 A1 | 4/2014 | Wiita et al. |
| 2014/0128766 A1 | 5/2014 | Beran |
| 2014/0155745 A1 | 6/2014 | Duncan |
| 2014/0163415 A1 | 6/2014 | Zaiken |
| 2014/0200482 A1 | 7/2014 | Shi |
| 2014/0364835 A1 | 12/2014 | Allen |
| 2015/0042406 A1 | 2/2015 | Kovac et al. |
| 2015/0065807 A1 | 3/2015 | Greenberg et al. |
| 2015/0133799 A1 | 5/2015 | O'Connell et al. |
| 2015/0327836 A1 | 11/2015 | Stone et al. |
| 2015/0342512 A1 | 12/2015 | Shi |
| 2015/0351649 A1 | 12/2015 | Bobo, Sr. et al. |
| 2015/0366485 A1 | 12/2015 | Kassab |
| 2015/0366498 A1 | 12/2015 | Choi et al. |
| 2016/0029912 A1 | 2/2016 | Stimpson |
| 2016/0066831 A1 | 3/2016 | Hyde et al. |
| 2016/0074581 A1 | 3/2016 | Gerrans |
| 2016/0106323 A1 | 4/2016 | Ou et al. |
| 2016/0183819 A1 | 6/2016 | Burnett et al. |
| 2016/0220136 A1 | 8/2016 | Schultz |
| 2016/0249969 A1 | 9/2016 | Santoinanni |
| 2016/0256076 A1 | 9/2016 | Kassab |
| 2016/0310148 A1 | 10/2016 | Allen |
| 2016/0331294 A1 | 11/2016 | Imran et al. |
| 2016/0331451 A1 | 11/2016 | Nabutovsky et al. |
| 2016/0354028 A1 | 12/2016 | Damaser et al. |
| 2016/0354140 A1 | 12/2016 | Sharma |
| 2016/0374576 A1 | 12/2016 | Ziaie et al. |
| 2017/0055874 A1 | 3/2017 | Papirov et al. |
| 2017/0071566 A1 | 3/2017 | Hart et al. |
| 2017/0079868 A1 | 3/2017 | Reid, Jr. et al. |
| 2017/0100561 A1 | 4/2017 | Burnett |
| 2017/0128012 A1 | 5/2017 | Parks et al. |
| 2017/0136209 A1 | 5/2017 | Burnett et al. |
| 2017/0156610 A1 | 6/2017 | Quackenbush et al. |
| 2017/0156611 A1 | 6/2017 | Burnett et al. |
| 2017/0160175 A1 | 6/2017 | Al-Mayah |
| 2017/0209048 A1 | 7/2017 | Wiita |
| 2017/0258345 A1 | 9/2017 | Smith |
| 2017/0259035 A1 | 9/2017 | Smith et al. |
| 2017/0273623 A1 | 9/2017 | Chen et al. |
| 2017/0273853 A1 | 9/2017 | Nagata et al. |
| 2017/0332955 A1 | 11/2017 | Burnett et al. |
| 2018/0049658 A1 | 2/2018 | Smith |
| 2018/0177458 A1 | 6/2018 | Burnett et al. |
| 2018/0184929 A1 | 7/2018 | Burnett et al. |
| 2018/0311469 A1 | 11/2018 | Wiita |
| 2018/0326190 A1 | 11/2018 | Nash |
| 2018/0344183 A1 | 12/2018 | McKinney et al. |
| 2018/0344184 A1 | 12/2018 | McKinney et al. |
| 2018/0344234 A1 | 12/2018 | McKinney et al. |
| 2018/0344249 A1 | 12/2018 | McKinney |
| 2018/0344250 A1 | 12/2018 | McKinney et al. |
| 2019/0133460 A1 | 5/2019 | Wine |
| 2019/0133532 A1 | 5/2019 | Zaiken |
| 2019/0282109 A1 | 9/2019 | Schlumpf et al. |
| 2019/0321588 A1 | 10/2019 | Burnett et al. |
| 2019/0343445 A1 | 11/2019 | Burnett et al. |
| 2019/0350634 A1 | 11/2019 | Jung |
| 2020/0029906 A1 | 1/2020 | Smith et al. |
| 2020/0046237 A1 | 2/2020 | Stimpson |
| 2020/0069332 A1 | 3/2020 | Callery |
| 2020/0085378 A1 | 3/2020 | Burnett et al. |
| 2020/0164184 A1 | 5/2020 | McKinney et al. |
| 2020/0197019 A1 | 6/2020 | Harper |
| 2020/0237242 A1 | 7/2020 | Kaluzny et al. |
| 2020/0253536 A1 | 8/2020 | McKinney |
| 2020/0305742 A1 | 10/2020 | Ghodsain |
| 2020/0324037 A1 | 10/2020 | Bloomberg et al. |
| 2020/0383703 A1 | 12/2020 | Atad |
| 2020/0384241 A1 | 12/2020 | Herrera |
| 2021/0000422 A1 | 1/2021 | McKinney |
| 2021/0046277 A1 | 2/2021 | Samoocha |
| 2021/0052873 A1 | 2/2021 | Geva |
| 2021/0128413 A1 | 5/2021 | Elia |
| 2021/0177355 A1 | 6/2021 | Govari |
| 2021/0187240 A1 | 6/2021 | Waitkus |
| 2021/0244912 A1 | 8/2021 | Paz |
| 2021/0290243 A1 | 9/2021 | Franklin |
| 2021/0369185 A1 | 12/2021 | Janssen |
| 2022/0039751 A1 | 2/2022 | Chey |

FOREIGN PATENT DOCUMENTS

| | | |
|---|---|---|
| CN | 204582261 | 8/2015 |
| CN | 105073040 | 11/2015 |
| CN | 205649494 | 10/2016 |
| EP | 0097454 | 1/1984 |
| EP | 2 405 847 | 5/2013 |
| EP | 3656297 | 5/2020 |
| WO | WO 94/02195 | 2/1994 |
| WO | WO 1995/012351 | 5/1995 |
| WO | WO 2005/013834 | 2/2005 |
| WO | WO 2006/060248 | 6/2006 |
| WO | WO 2011/053500 | 5/2011 |
| WO | WO 2012/006624 | 1/2012 |
| WO | WO 2012/006625 | 1/2012 |
| WO | WO 2012/122267 | 9/2012 |
| WO | WO 2014/043650 | 3/2014 |
| WO | WO 2014/160300 | 10/2014 |
| WO | WO 2014/210453 | 12/2014 |
| WO | WO 2015/191125 | 12/2015 |
| WO | WO 2016/049654 | 3/2016 |
| WO | WO 2016/204631 | 12/2016 |
| WO | WO 2017/156451 | 9/2017 |
| WO | WO 2018/136306 | 7/2018 |
| WO | WO 2018/182913 | 10/2018 |

OTHER PUBLICATIONS

European Search Report issued on Jul. 17, 2023 for Application No. EP 20 850 354.

Exam Report EP18733733.2 Dated—Nov. 6, 2024.

Betty Shamaev & May Shoshan, Bones: Custom cushioning helps heal a bad break, May 14, 2015, Science New Explores, health & Medicine, https://www.snexplores.org/article/bones-custom-cushioning-helps-heal-bad-break#:~:text=Two%20teens%20designed%20this,an%2associated%20cast%20(left), 2015 (Year: 2015).

Millar Micro-Tip® Pressure Transducer, Apr. 15, 2005, Millar Micro-Tip® Pressure Transducer, https://www.harvardapparatus.com/media/Harvard/pdf/BS4_J_5.pdf, 2005 (Year: 2005).

Extended European Search Report mailed Mar. 2, 2020 for European Application No. EP 19210264.8.

A randomized comparison of microtip and air-charged catheter for the measurement of maximum urethral closure pressure, Ginekol Pol. 2012, 83: 586-589.

(56)            References Cited

OTHER PUBLICATIONS

Abdominal pressure in the critically ill: measurement and clinical relevance, Intensive Care Med, 1999, 25: 1453-1458.

(Abstract only) "Caring for critically injured children: An analysis of 56 pediatric damage control laparotomies". J Trauma Acute Care Surg. May 2017; 82: 901-909.

(Abstract only) "Estimation of Intra-abdominal Pressure by Bladder Pressure Measurement: Validity and Methodology", The Journal of Trauma Injury, Infection, and Critical Care, Feb. 2001, 50: 297-302.

(Abstract only) "Intra-Abdominal Pressure Monitoring in Neonates", Pediatric Critical Car Med. Feb. 2016; 17: 172-173.

(Abstract only) "Saline volume in transvesical intra-abdominal pressure measurement: Enough is enough", Intensive Care Med., Mar. 2006; 32: 455-459.

De Waele J., et al., "Saline volume in transvesical intra-abdominal pressure measurement: Enough is enough", Intensive Care Med., Mar. 2006; 32: 455-459.

Determination of Intra-abdominal Pressure Using a Transurethral Bladder Catheter: Clinical Validation of the Technique, Anesthesiology, Jan. 1989, 70( 1 ), 47-50.

European Search Report EP 20850354.0 Dated Jul. 15, 2022.

European Search Report EP 20850354, Dated Oct. 6, 2022.

International search report and written opinion for international application PCT/US2018/028687 mailed Sep. 28, 2018.

International search report and written opinion for international application PCT/US2018/028693 mailed Sep. 28, 2018.

International search report for international application PCT/US2018/032467 mailed Sep. 5, 2018.

International search report for international application PCT/US2018/034781 mailed Sep. 5, 2018.

Is clinical examination an accurate indicator or raised intra-abdominal pressure in critically injured patents? CJS, Jun. 2000, 43, No. 3: 207-211.

Mark A. Fusco, et al.,"Estimation of Intra-abdominal Pressure by Bladder Pressure Measurement: Validity and Methodology", The Journal of Trauma Injury, Infection, and Critical Care, Feb. 2001, 50: 297-302.

Measurement on intra-abdominal pressure in large incisional hernia repair to prevent abdominal compartmental syndrome, G Chir, Jan.-Feb. 2016; 37: 31-36.

Miguel A. Villalobos, et al., "Caring for critically injured children: An analysis of 56 pediatric damage control laparotomies". J Trauma Acute Care Surg. May 2017, 82: 901-909.

Mudit Mathur, MD, "Intra-Abdominal Pressure Monitoring in Neonates", Pediatric Critical Car Med. Feb. 2016; I 7: 172-173.

Pressure Measurement Techniques for Abdominal Hypertension: Conclusions from an Experimental Model, Crit Care Res Pract., May 2015: 278139.

Product information for Intra Compartment Pressure Wick's / Slit Catheter Set up (Stryker).

Product information for Intra-Compartmental Pressure Monitor System (Stryker).

Product information for Your Continuous Pressure Monitoring System (Mammendorfer Institut für Physik und Medizin GMbH).

Prospective Study of Intra-Abdominal Hypertension and Renal Function after Laparotomy, British Journal of Surgery, 1999, 82, 235-238.

Rudra, Pallab, et al. "Recent Advances In Management of Pre-Eclampsia" Sep. 2011, British Journal of Medical Practitioners, vol. 4, No. 3 (Year: 2011).

Study of the occurrence of intra-abdominal hypertension and abdominal compartment syndrome in patients of blunt abdominal trauma and its correlation with the clinical outcome in the above patents, World J Emerg Surg. Feb. 11, 2016; 11: 9.

The Measurement of Intra-Abdominal Pressure as a Criterion of Abdominal Re-exploration, 1984 Ann Surg., 199: 28-30.

"The neglected role of abdominal compliance in organ-organ interactions", Critical Care. Mar. 2016; 1-10.

User's Manual for Compartmental Pressure Monitoring System. For continuous measurement of intra compartment pressure (Synthes).

Search Report 18725349, Dated Dec. 10, 2023.

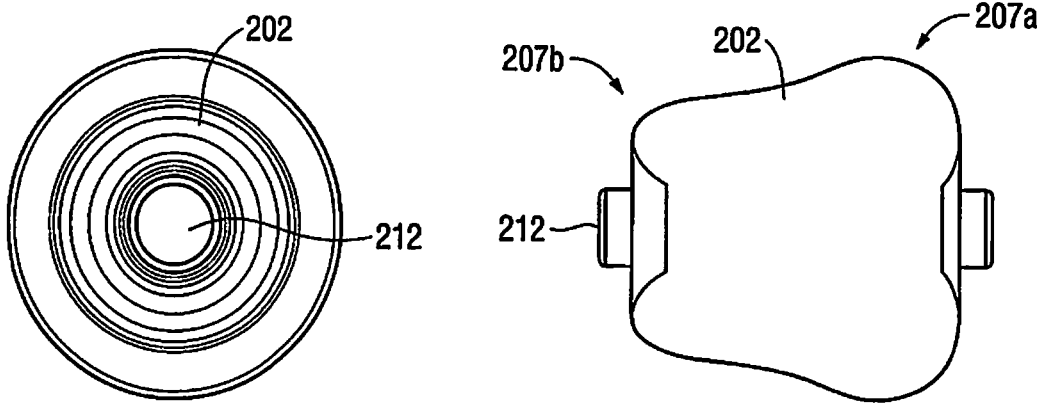
FIG. 20A                    FIG. 20B
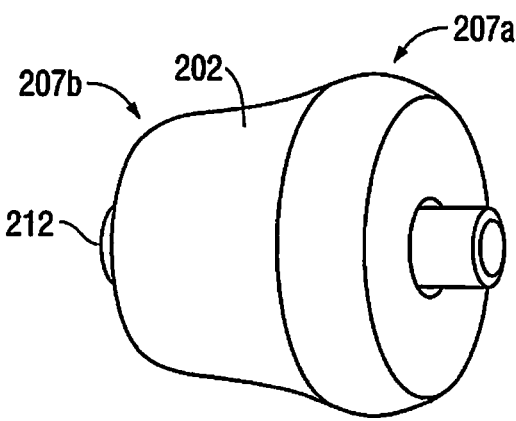
FIG. 20C

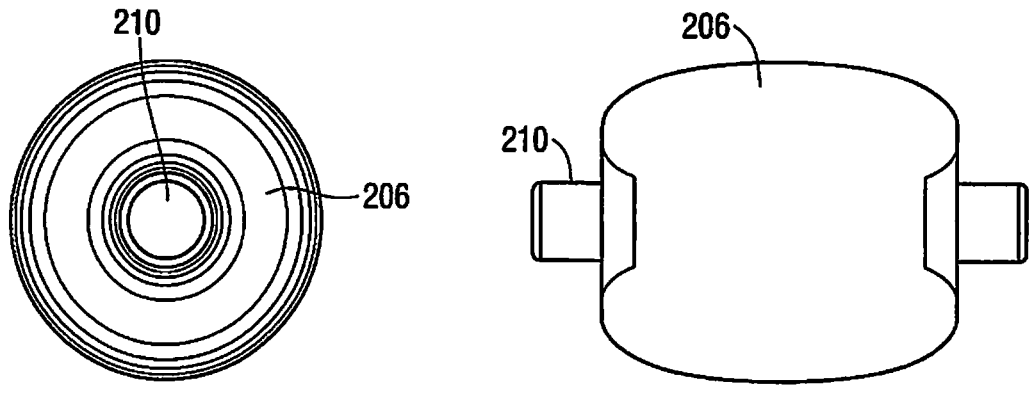
FIG. 21A          FIG. 21B
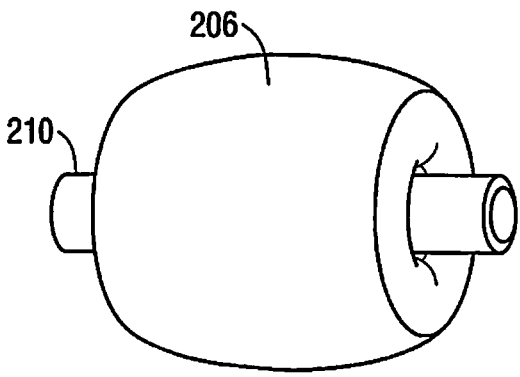
FIG. 21C

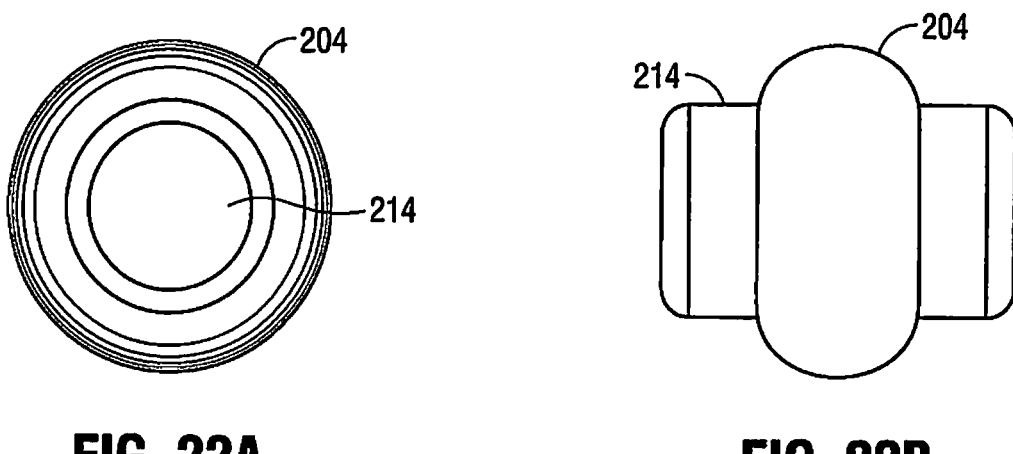
FIG. 22A          FIG. 22B
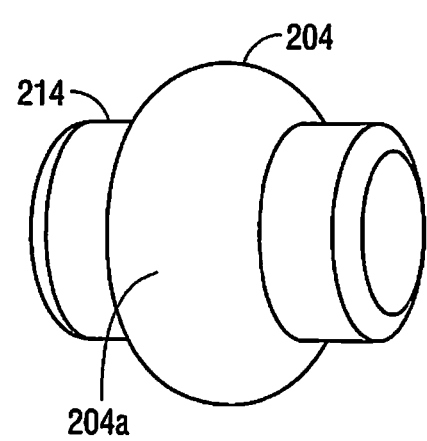
FIG. 22C
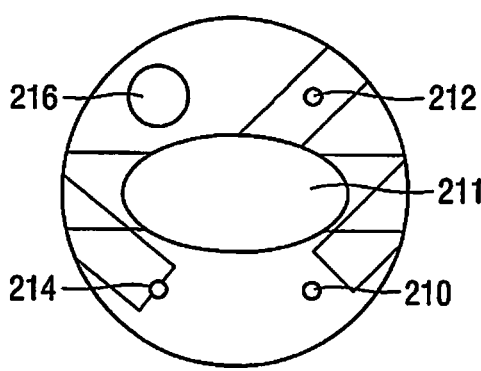
FIG. 23

546

531

540

538

536

543

542

534

544

530

542

544

532

545

547

531

531a

604

604a

604

639

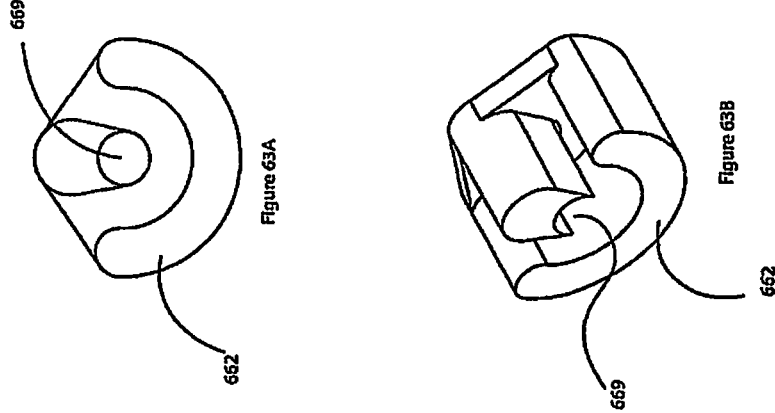
Figure 63A
Figure 63B
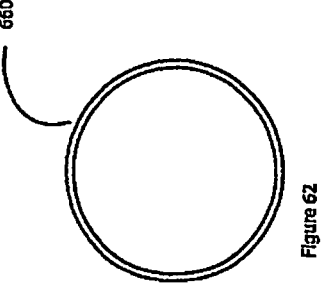
Figure 62

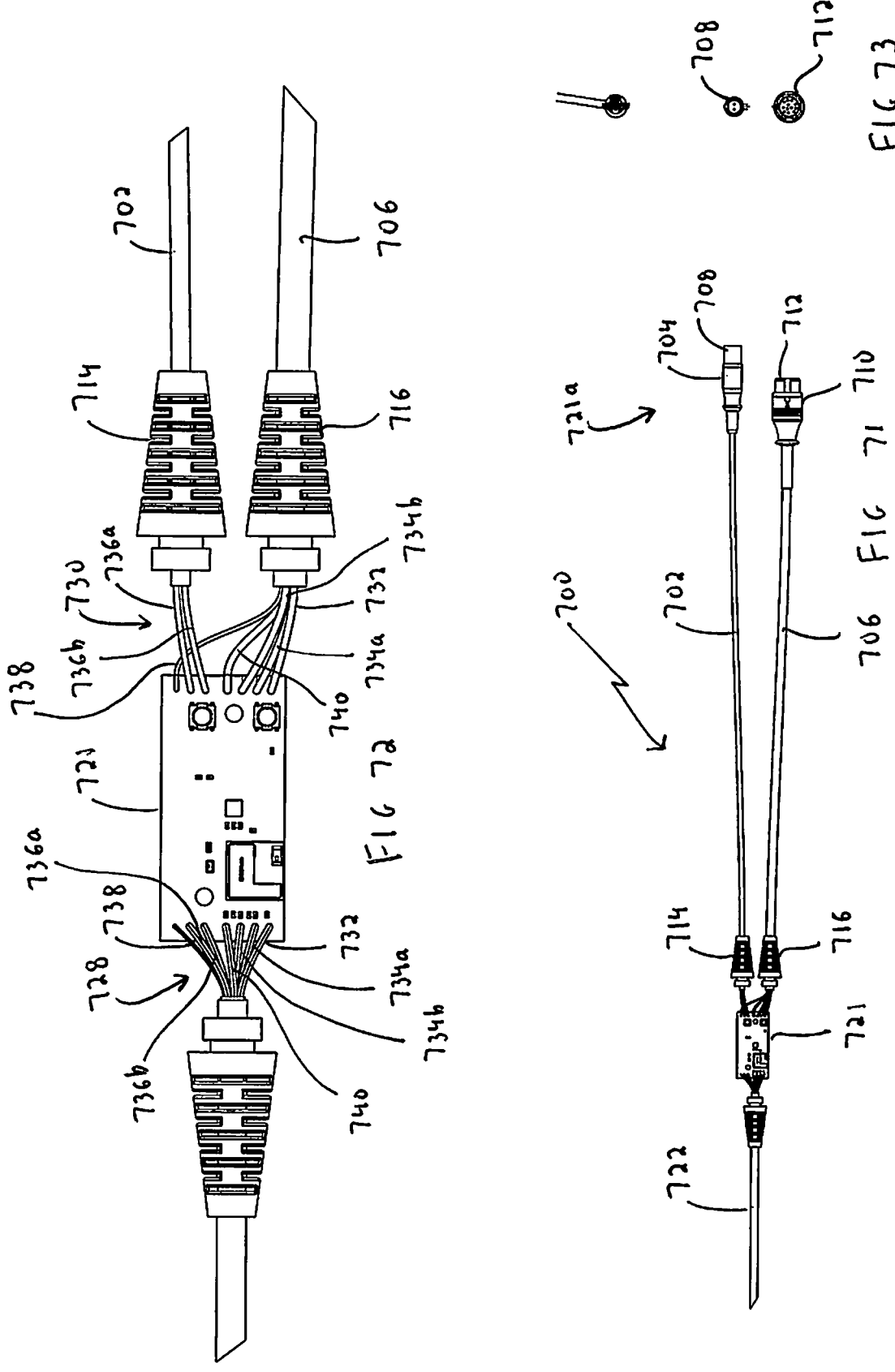

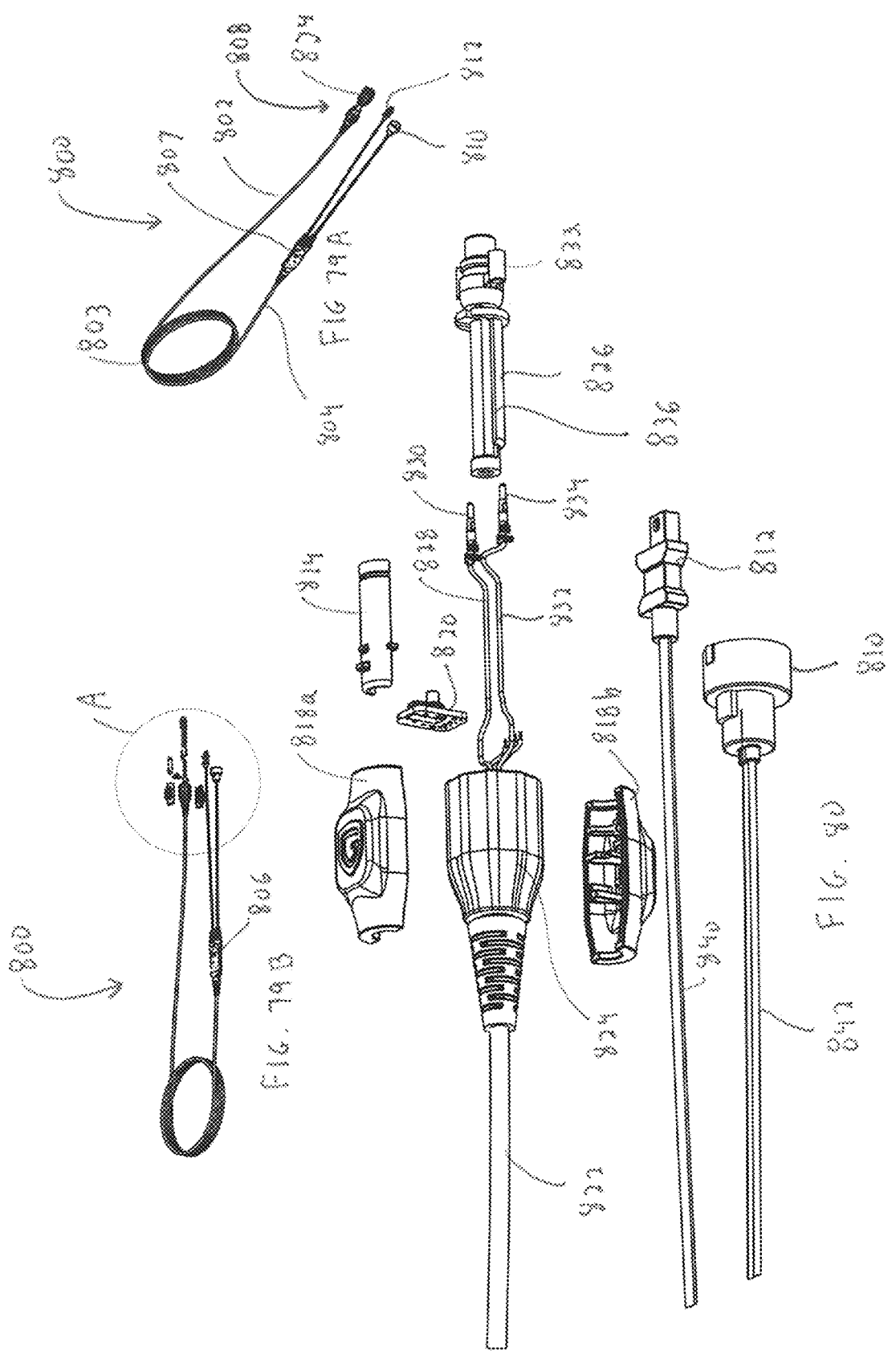

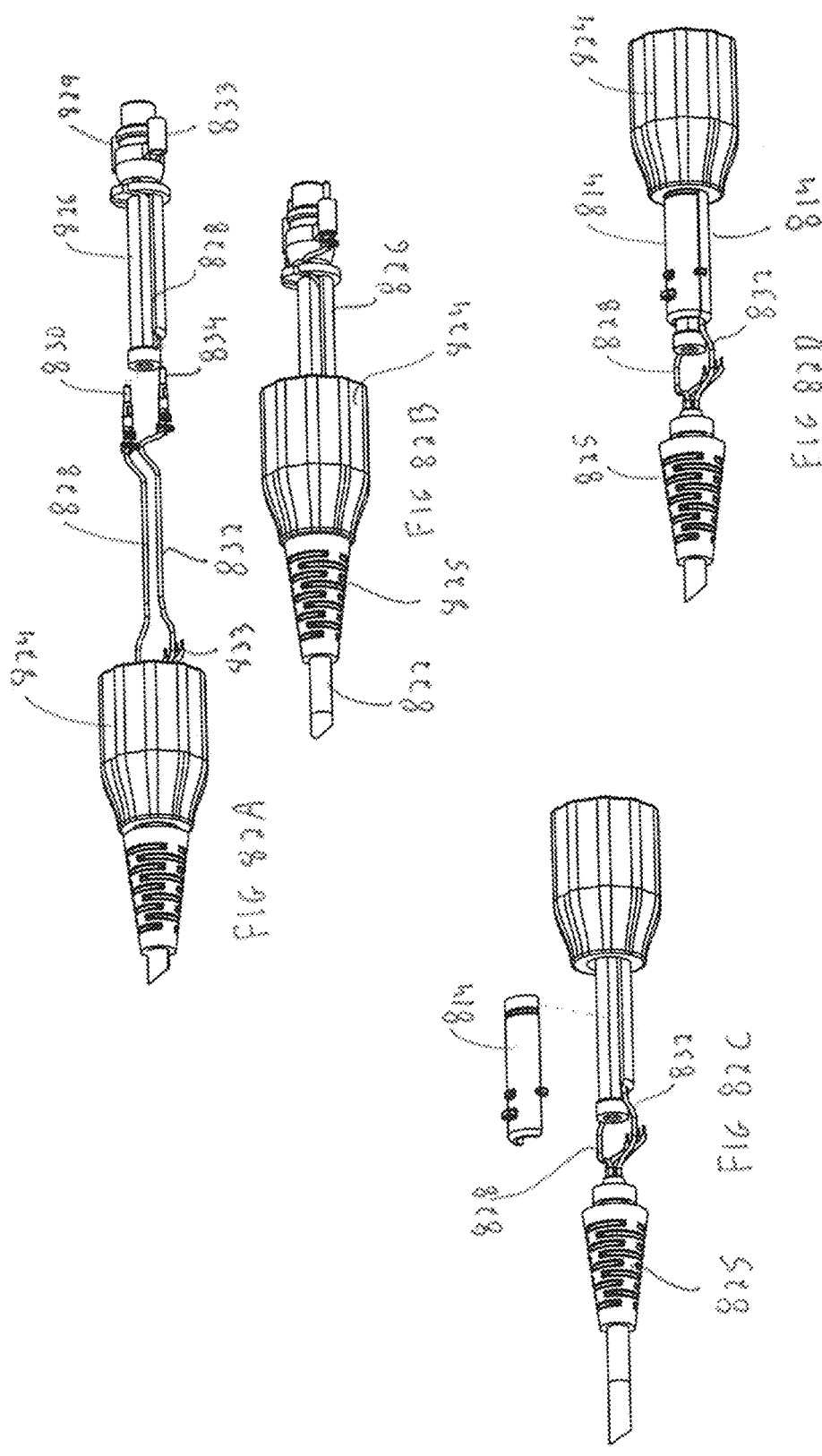

824

820

818a

818b

818a

818b

819

825

825

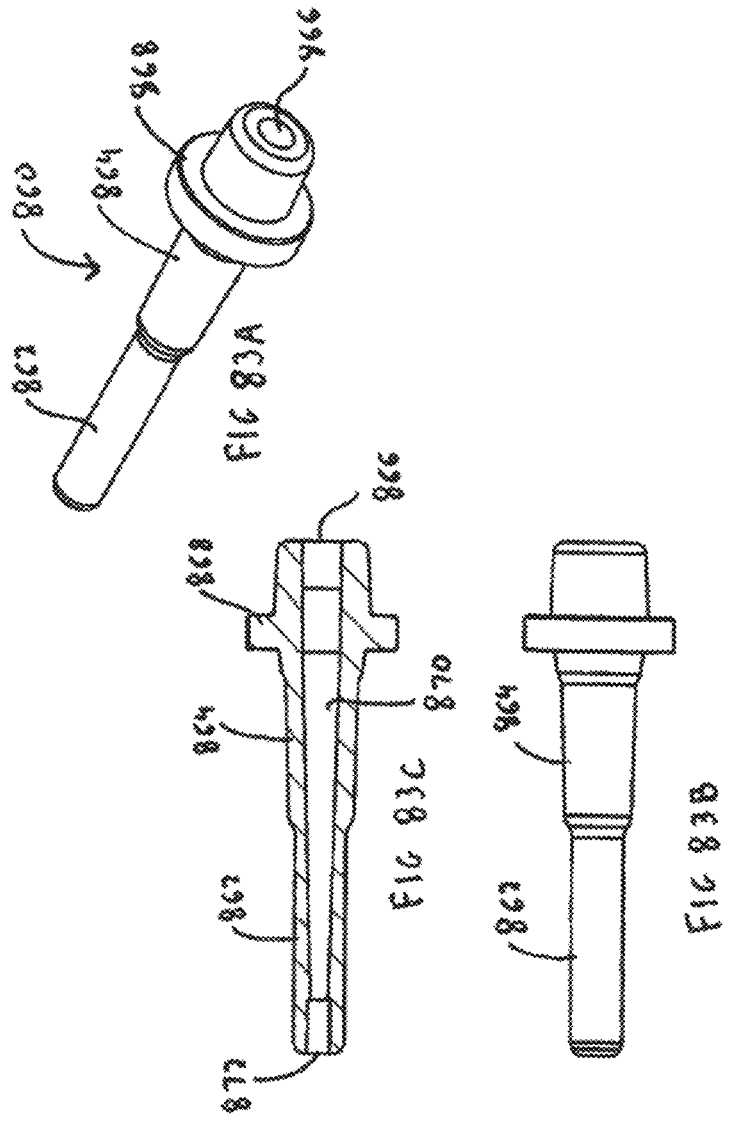

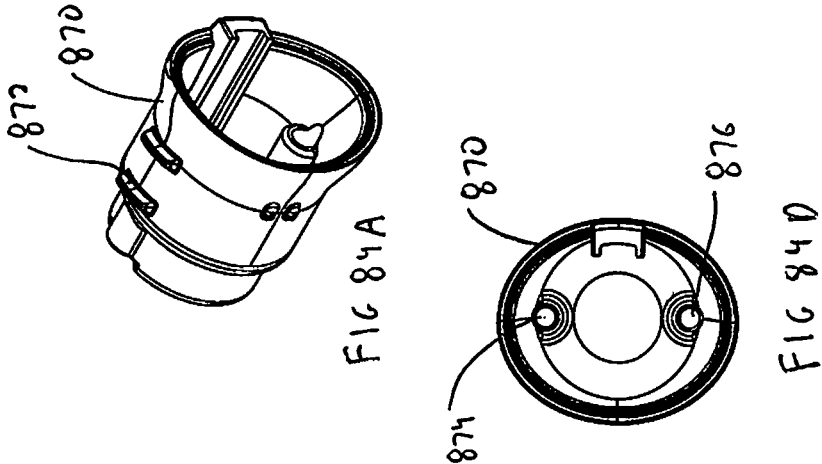
FIG 84A
FIG 84D
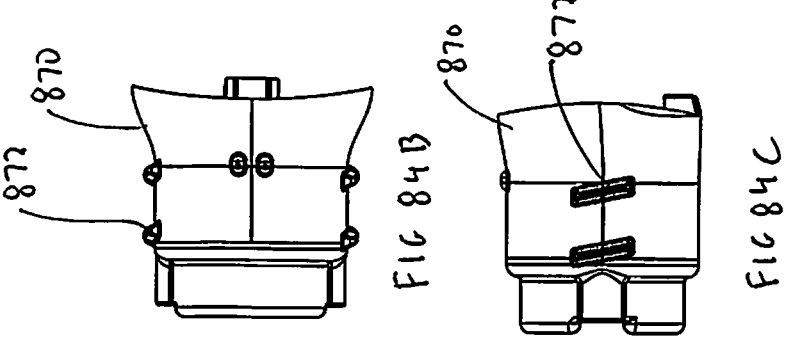
FIG 84B
FIG 84C
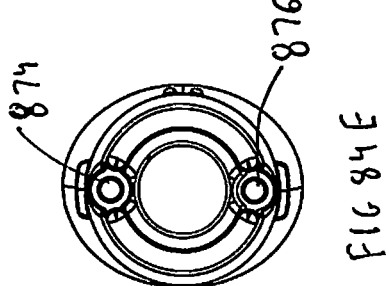
FIG 84E

880

882

CABLE FOR USE WITH PRESSURE MONITORING CATHETERS

This application is a continuation of application Ser. No. 16/945,233, filed on Jul. 31, 2020, which claims the benefit of provisional application Ser. No. 62/884,192, filed Aug. 8, 2019. The entire contents of each of these applications are incorporated herein by reference.

BACKGROUND OF THE INVENTION

1. Field of the Invention

This application relates to a cable for use with pressure monitoring catheters, and more particularly, to a smart cable for connecting a pressure monitoring catheter to a pressure monitor displaying pressure readings.

2. Background

The need for measuring intra-abdominal pressure (IAP) has become more important as physicians increasingly realized that organ failure and death were directly related to increase in IAP in certain high-risk patients. High abdominal pressure has been found to cause a decrease in function of the intestines, liver and blood vessels resulting in adverse consequences for the patients. Consequently, accurate measurement of IAP can help decrease patient morbidity and mortality. It has also been more recently discovered that pediatric and neonate population may also have need for IAP measurement to determine specific conditions.

Currently, there are few products available on the market to measure the IAP through the bladder. One device, the Bard IAP device, has a "valve clamp" which diverts urine from the main catheter drainage channel to measure IAP via converting hydrostatic pressure to a readable pressure gauge. This mechanism of IAP measurements is archaic and does not provide continuous pressure measurement when used with the standard 2-channel bladder drainage catheter. Two other manufacturers, Holtech and ConvaTec, also use a column of urine by connecting their kit to an existing bladder catheter. Their systems are cumbersome and the IAP readings are also not continuous. Biometrix has developed an IAP monitoring device which like other manufacturers relies on tapping into the main bladder drainage catheter, using a valve to measure the hydrostatic pressure. In 2008 Sugrue and colleagues, in an article "Prospective Study of Intra-Abdominal Hypertension and Renal Function after Laparotomy, British Journal of Surgery, 1999, 82, 235-238, suggested the use of 3-channel bladder drainage catheter so that the smaller channel, which was used for bladder irrigation, could be used to attach a pressure-monitoring device. The use of an extra channel made it possible to have continuous bladder drainage while measuring the bladder pressure. However, this bladder catheter did not provide a continuous pressure read because intermittently the operator needed to add 50 ml of water or saline to the bladder to record the IAP pressure. Thus, the pressure reading at best was intermittent since pressure readings were not performed when fluid was being added to the bladder. Consequently, although this was a step toward increasing the amount of pressure readings/recordings, it still was unable to conduct continuous pressure monitoring. Furthermore, it was still the same cumbersome IAP device set up which required a skilled person to add water before each IAP reading. Control of the amount of water added is critical since adding too much water to the bladder can falsely increase the pressure readings and also increase infection risk, thus further complicating the use.

It has also been recognized that most patients that have a need for measurement of IAP also need to have continuous drainage of the urinary bladder and thus devices need to account for this process.

Consequently, current devices placed in the bladder for measuring pressure require a continuous water column to maintain pressure readings. Thus, they fail to measure IAP continuously but only measure pressure intermittently. They also all rely on tapping into an existing bladder drainage catheter, which adds complications. Furthermore, they do not reduce the complexity of the procedure since they require constant retrograde insertion of a relatively large amount of fluid into the bladder, e.g., 50 cc, which increases the ICU workload. Still further, these devices increase the risk of complications and infections associated with fluid injection into the bladder. Fluid injection is also complicated since it needs to be closely monitored since too much fluid in the bladder can give false elevation of IAP readings, causing clinicians to take unnecessary steps in response to what is mistakenly believed is excess IAP.

The catheters disclosed in commonly assigned pending U.S. Publication 2018/0344234 (hereinafter the '234 publication) advantageously provide devices insertable into the bladder that accurately measures abdominal pressure without requiring adding water to the bladder to obtain such pressure readings. The devices disclosed in the '234 publication therefore advantageously avoid the complications and risks associated with such fluid insertion. These devices can also continuously measure bladder pressure without interruption, enabling a constant monitoring of IAP if desired so critical time periods are not missed. The devices also improve the accuracy of the pressure readings in the bladder to more accurately determine IAP so necessary steps can be taken to address IAP only when warranted. Still further, these devices provide these enumerated advantages while being simple to use so that so that any of clinical staff with basic knowledge of bladder catheter insertion will be able to insert the device without relying on specially trained staff members.

Although the catheters of the '234 publication are effective in pressure measurement, it would be advantageous to improve the accuracy of pressure readings, including accommodation for changes in pressure not associated with the patient's condition. Both patients and medical care facilities would greatly benefit from improved accuracy of pressure readings and improved data collection. Such improvements would improve patient outcomes and maximize use of hospital resources.

SUMMARY

The present invention provides a smart cable that is connectable to a pressure monitoring catheter at one end and a pressure monitor at the opposite end. The cable improves pressure readouts on the monitor. The cable also accommodates for changes in pressure not associated with the patient's conditions such as due to changes in the external environment. Another advantage of the cable is its data storage capability. In some embodiments, the cable enables the catheter to remain in the body during shift changes which reduces complications and reduces staff time.

The cable of the present invention is designed to be used with a single or multi-lumen catheter insertable into the bladder to determine intra-abdominal pressure via measurement of bladder pressure. The cable can be used for example with the various catheters disclosed in publication 2018/0344234 (hereinafter the '234 publication) and in publication 2020/0164184 (hereinafter the '184 publication), the entire contents of these applications are incorporated herein by reference. For example, the cable can be used with the catheter having an expandable outer balloon and an expandable inner balloon positioned within the outer balloon, wherein the inner balloon forms a gas filled chamber to monitor pressure within the bladder. The outer balloon has a circumferential area greater than a circumferential area of the inner balloon, wherein in response to pressure within the bladder exerted on the first outer wall of the expanded outer balloon, the outer balloon deforms and pressure is exerted on the second outer wall of the expanded inner balloon to deform the inner balloon and compress the gas within the inner balloon to provide a finer measurement. The catheters disclosed in the '234 publication and the '184 publication utilize a gas-charged chamber, e.g., an air-containing chamber, to measure bladder pressure across a large surface area, and thus, accurately determine intra-abdominal pressure, and enable pressure to be measured continuously without interrupting urine flow and without interruptions to add water to the bladder.

The cable of the present invention could also be used with catheters other than those disclosed in the '234 and '184 publications. The cable of the present invention is designed preferably to be used with standard monitors utilized for measuring pressure.

In accordance with one aspect of the present invention, a system is provided comprising a catheter insertable into a patient for monitoring pressure and a cable connectable to the catheter. The catheter comprises a first balloon at a distal portion of the catheter having a first outer wall expandable from a first condition to a more expanded condition and a second balloon having a second outer wall, the first balloon being external of the second balloon. The second balloon has a fluid chamber to monitor pressure within the patient, wherein in response to pressure exerted on an outer wall of the expanded first balloon a pressure is exerted on an outer wall of the expanded second balloon to deform the second balloon and compress the fluid within the second balloon to provide a pressure measurement. The cable stores a pressure value of the second balloon. The pressure value can be an initial value.

The system can in some embodiments further include a pressure sensor connectable to the catheter and communicating with the fluid chamber for measuring pressure based on compression of fluids caused by deformation of the expanded second balloon resulting from deformation of the expanded first balloon.

In some embodiments, the fluid chamber is an air chamber.

In some embodiments, the catheter has an elongated rod extending proximally therefrom, and the cable has a housing having a channel to receive the elongated rod, the channel including an O-ring seal through which the elongated rod passes. In some embodiments, the channel includes a spacer on each side of the O-ring, and the position of the O-ring effects the amount of air displaced by the elongated rod when inserted into the channel to charge the inner balloon.

The cable, in some embodiments, can include one or more of a) a temperature adjustment feature to adjust pressure values in response to temperature changes; b) a barometric pressure adjustment feature to adjust pressure values in response to barometric pressure changes or c) a movement adjustment feature to adjust pressure values in response to the patient moving from a supine position.

In some embodiments, the cable includes a filtering system to collect and analyze the data input and filter out upper values and take the lower values over specific periods of time. In some embodiments, the filter takes a predetermined number of samples representative of the lowest value and calculates an average value. In some embodiments, the average value is calculated multiple times and displayed in a line readout.

In accordance with another aspect of the present invention, a cable for use with a pressure monitoring catheter is provided. The cable comprises a first end operably connectable to the pressure monitoring catheter, a second end operably connectable to a monitor providing pressure displays, and a printed circuit. The cable includes a filtering system to collect and analyze the data input from a pressure sensor of the catheter, the filtering system filtering out upper values and taking the lower values over predetermined periods of periods of time, and further calculating an average value, the average value transmitted by the cable to the monitor for display. In some embodiments, the average value is calculated multiple times and displayed in a line readout.

In accordance with another aspect of the present invention, a cable is provided for use with a pressure monitoring catheter having a pressure sensing balloon. The cable has a first end operably connectable to the pressure monitoring catheter, a second end operably connectable to a monitor providing pressure displays, and a printed circuit. The cable stores a tare value of the pressure sensing balloon, wherein the tare value is set as zero point when the cable is connected to the catheter outside a patient and storage of the tare value enables the tare value to be maintained after disconnecting and re-connecting the cable to the catheter while the catheter remains within the patient.

In some embodiments, the cable includes a housing containing the printed circuit, and a button on a housing activates the tare function.

In accordance with another aspect of the present invention, a cable for use with a pressure monitoring catheter is provided. The cable has a first end operably connectable to the pressure monitoring catheter, a second end operably connectable to a monitor providing pressure displays, and a printed circuit. The cable includes a temperature adjustment feature to adjust pressure values in response to temperature changes to accommodate for pressure changes unrelated to a condition of a patient.

In some embodiments, the cable also includes one or both of a) a barometric pressure adjustment feature to adjust pressure values in response to barometric pressure changes to accommodate for pressure changes unrelated to a condition of a patient; and b) a movement adjustment feature to adjust pressure values in response to the patient moving from a supine position.

In accordance with another aspect of the present invention, a cable for use with a pressure monitoring catheter is provided. The cable has a first end operably connectable to the pressure monitoring catheter, a second end operably connectable to a monitor providing pressure displays, and a printed circuit. The cable includes a barometric pressure adjustment feature to adjust pressure values in response to barometric pressure changes to accommodate for pressure changes unrelated to a condition of a patient.

In accordance with another aspect of the present invention a cable for use with a pressure monitoring catheter is provided. The cable has a first end operably connectable to the pressure monitoring catheter, a second end operably connectable to a monitor providing pressure displays, and a printed circuit. The cable includes a movement adjustment feature to adjust pressure values in response to the patient moving from a supine position to an elevated position.

In some embodiments, the data output is filtered data. In some embodiments, the cable includes an indicator for indicating if the data output is for the supine or the elevated position. In some embodiments, the cable stores the pressure values in the supine position and in the elevated position. In some embodiments, the cable stores filtered data in the supine and elevated positions.

In some embodiments, the cable includes a pressure sensor and a locking mechanism for locking to a connector of a catheter, wherein attachment of the cable displaces air within the catheter to inflate a pressure measuring balloon.

In some embodiments, the displacement of air within the catheter by connection of the cable is independent of inflation of an outer balloon of the catheter which is external to the pressure measuring balloon.

In accordance with another aspect of the present invention, a method of connecting a pressure measuring catheter to a monitor displaying pressure readings from the catheter is provided. The method comprises: a) connecting a pressure sensor of a cable to a monitor configured to display pressure readings; b) zeroing the pressure sensor to atmosphere; c) inflating a first balloon of the catheter while the catheter is outside a patient, the balloon used for pressure monitoring; d) connecting a cable containing a printed circuit to a connector of the catheter; and e) activating a tare function for the pressure monitoring of the balloon, wherein a tare value of the tare function is stored in the cable.

In some embodiments, the catheter includes an inner balloon positioned inside the first balloon and the step of activating the tare function zeroes a pressure output from inside the inner balloon.

In some embodiments, the method further comprises the steps of disconnecting the cable from the catheter and reconnecting the cable to the catheter while the inner balloon remains inflated within the patient, the tare value remaining unchanged.

BRIEF DESCRIPTION OF THE DRAWINGS

So that those having ordinary skill in the art to which the subject invention appertains will more readily understand how to make and use the surgical apparatus disclosed herein, preferred embodiments thereof will be described in detail hereinbelow with reference to the drawings, wherein:

FIGS. 20A, 20B and 20C are enlarged front, side and perspective views of the outer balloon of FIG. 18A in the expanded condition;

FIGS. 21A, 21B and 21C are enlarged front, side and perspective views of the stabilizing balloon of FIG. 18A in the expanded condition;

FIGS. 22A, 22B and 22C are enlarged front, side and perspective views of the inner balloon of FIG. 18A in the expanded condition;

FIG. 23 is a transverse cross-sectional view of the catheter of FIG. 18 illustrating the five lumens of the catheter;

FIGS. 32A, 32B, 32C and 32D illustrate the manufacturing steps of assembly of the catheter of FIG. 30A wherein FIG. 32A shows the connecting pin inserted into the catheter shaft; FIG. 32B shows the inner balloon attached to the connecting pin; FIG. 32C shows the distal tip connected to the pin; and FIG. 32D shows the outer balloon attached to the shaft and distal tip;

FIG. 62 is a front view of the distal inner sleeve of the catheter of FIG. 50A;

FIG. 63A is a front view of the proximal plug of the catheter of FIG. 50A;

FIG. 63B is a perspective view of the proximal plug of FIG. 63A;

FIG. 71 is a side view of the smart cable of FIG. 70;

FIG. 72 is an enlarged view showing the printed circuit board and wire connections contained within the hub of FIG. 70;

FIG. 73 is an end view showing the temperature and pressure connectors for the monitor;

FIG. 79A is a perspective view of a cable in accordance with an alternate embodiment of the present invention;

FIG. 79B is an exploded perspective view of the cable of FIG. 79A;

FIG. 80 is an exploded view of the area of detail A of FIG. 79B;

FIGS. 82A-82G show the assembly steps of the connector wherein;

FIG. 82A shows the wires prior to positioning within the channels in the sensor housing;

FIG. 82B shows the wires within the channels prior to covering by the locking ring;

FIG. 82C shows the locking ring advanced and the cover over the wires;

FIG. 82D shows the casings covering the wires;

FIGS. 82E and 82F show the sensor being attached to the housing; and

FIGS. 82G and 82H show the clamshell halves being attached over the sensor;

FIG. 83A is a perspective view of the male rod of a catheter of the present invention;

FIG. 83B is a side view of the rod of FIG. 83A;

FIG. 83C is a cross-sectional view of the rod of FIG. 83A;

FIG. 84A is a perspective view of threaded outer cap of the catheter;

FIG. 84B is a side view of the threaded outer cap of FIG. 84A;

FIG. 84C is a side view of the cap of FIG. 84B rotated to show the threads;

FIG. 84D is a front view of the cap of FIG. 84A;

FIG. 84E is a rear view of the cap of FIG. 84A;

Figure 84G:
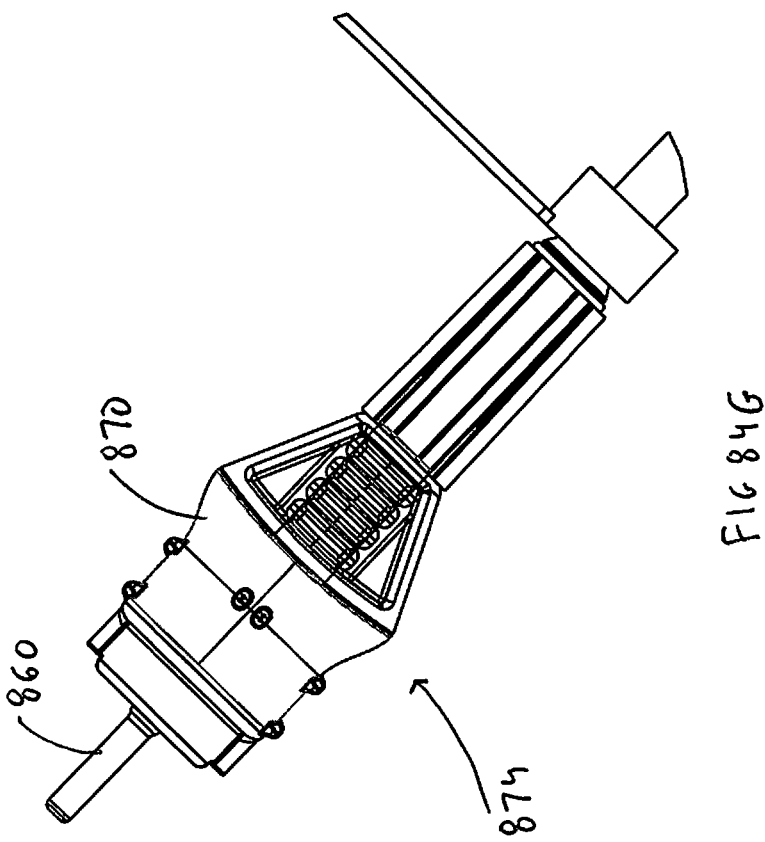
Figure 85:
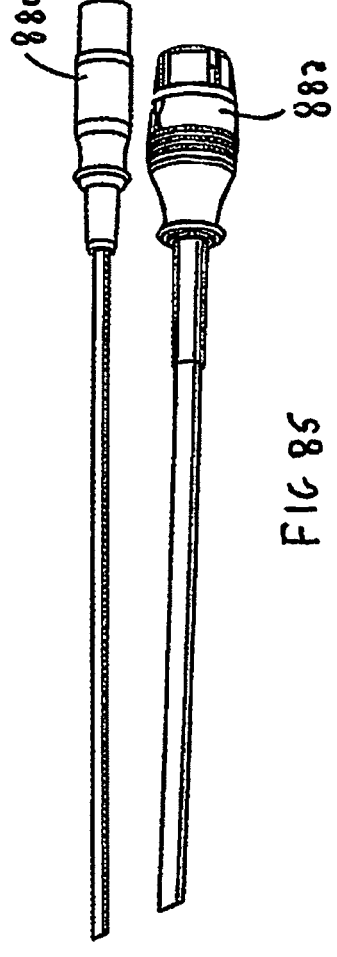
Figure 86:
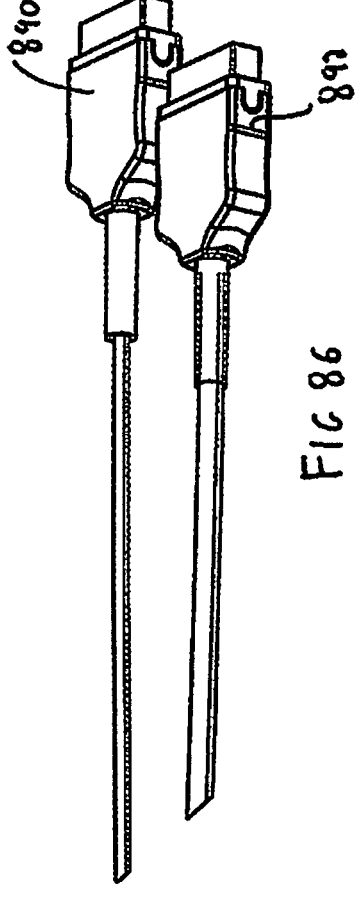
Figure 87:
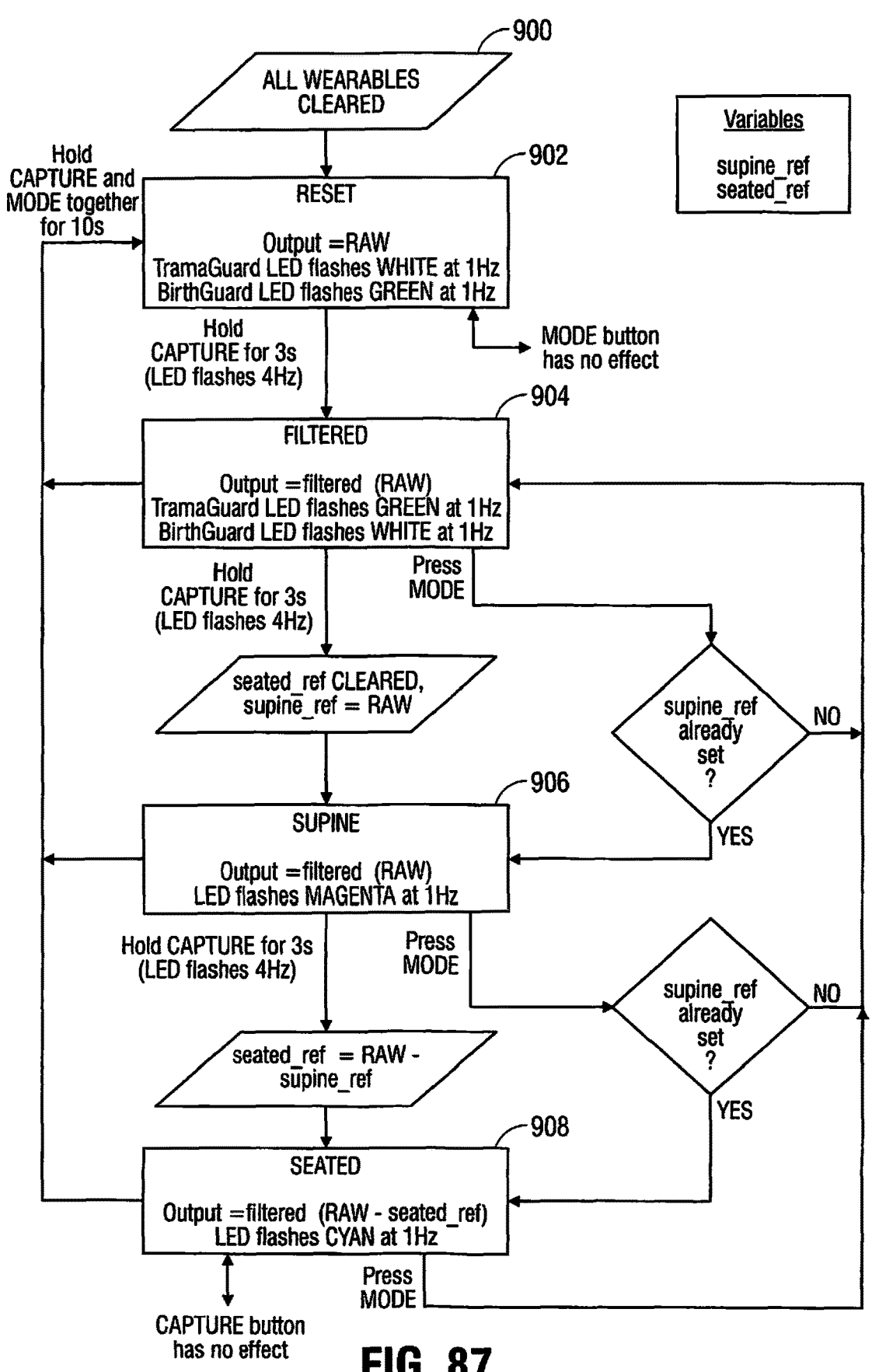

FIG. 84F is a side view of the proximal portion of the catheter showing the cap and rod of FIGS. 83A and 84A;

FIG. 84G is a close up view of the cap and plunger of FIGS. 83A and 84A of the catheter;

FIG. 85 is a perspective view of an alternate embodiment of the cable of the present invention having an adapter for connecting to a Phillips monitor;

FIG. 86 is a perspective view of an alternate embodiment of the cable of the present invention having an adapter for connecting to a GE monitor; and FIG. 87 is a flow chart illustrating use of the catheter and cable in accordance with one embodiment of the present invention.

DETAILED DESCRIPTION OF PREFERRED EMBODIMENTS

Increased abdominal pressure can cause many adverse conditions including diminishing the function of the intestines, liver, and blood vessels. Simply viewing or feeling the abdomen does not provide sufficient information or reading of health conditions.

It is recognized that urinary bladder pressure directly correlates to the intra-abdominal pressure. Although pressure readings can be determined by access to the esophagus or rectum, the bladder has been found to be the most accurate and the least invasive. In trauma or burn patients for example, time is critical and the less complicated the method for determining bladder pressure the better the clinical results.

The catheters described herein measure abdominal pressure via measurement of bladder pressure without filling the bladder with water. This avoids the risks associated with retrograde filling of the bladder with water as such retrograde filling not only increases the complications and workload for the intensive care (IC) staff and can create inaccuracies by providing false elevation of IAP readings, but can adversely affect the patient by increasing the risk of infection. Furthermore, by avoiding refilling of the bladder, bladder pressure can be measured continuously. This is because in devices requiring filling the bladder with water, water needs to be periodically added to the bladder to replace the water drained from the bladder and measurement readings are interrupted during water insertion. Due to these repeated interruptions, pressure cannot be read continuously.

Note in some cases, as much as 50 cc of fluid needs to be repeatedly added to the bladder.

The catheters described herein efficiently and effectively measure bladder pressure without requiring filling the bladder with water and enable continuous monitoring of the bladder pressure.

It should be noted that the catheters described herein can be utilized for measuring other pressure in a patient and are not limited to intra-abdominal pressure.

Figures 1A, 1B:
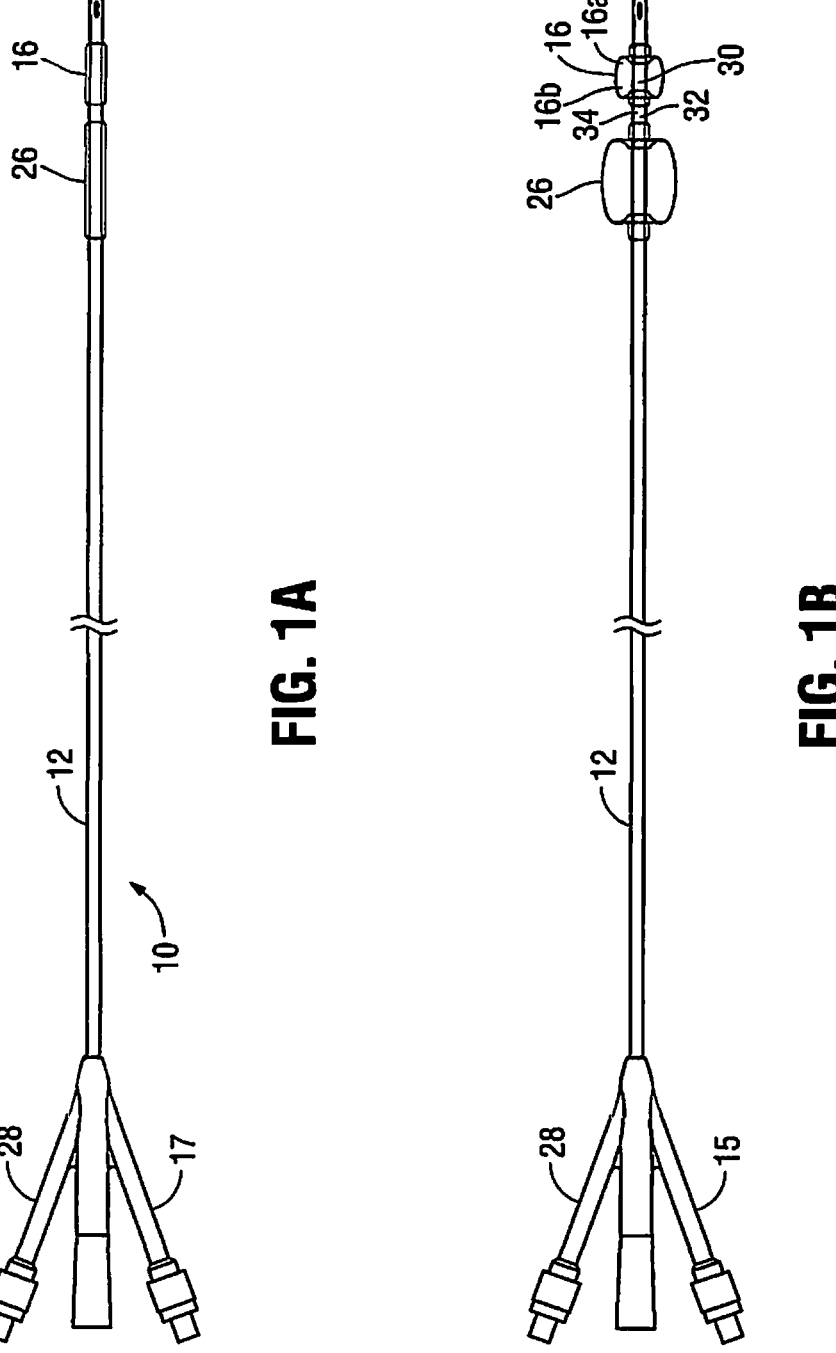
FIG. 1A is a side view of a first embodiment of the catheter of the present invention having a pressure balloon, a stabilizing balloon and a sensor positioned in the air lumen, both balloons shown in the deflated (collapsed) condition.
FIG. 1B is a side view similar to FIG. 1A showing the two balloons in the inflated (expanded) condition.
Figure 69:
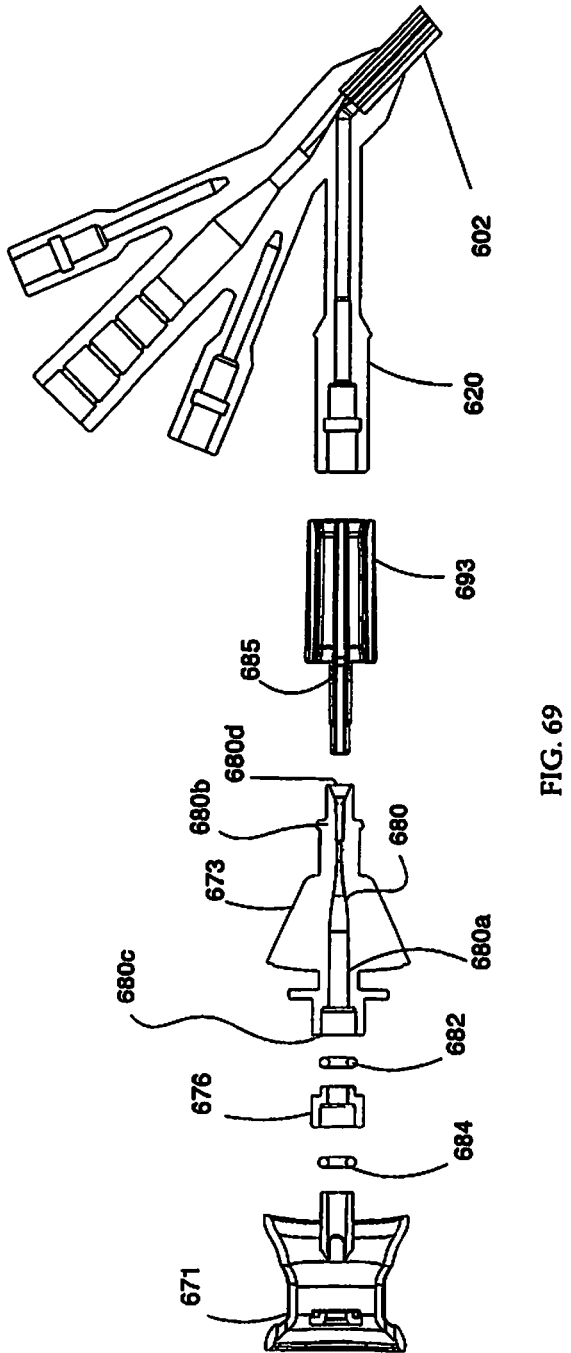
FIG. 69 is an exploded side view of the hub and connector of FIG. 64.

FIGS. 70-78 disclose the smart cable of the present invention connectable to a pressure monitor; FIGS. 1-69 disclose examples of catheters which can be used with the cable. The catheters will be discussed first to describe monitoring of intra-abdominal pressure, followed by a detailed description of the cable of the present invention.
Pressure Monitoring Catheters Referring now to the drawings and particular embodiments of the present invention wherein like reference numerals identify similar structural features of the devices disclosed herein, there is illustrated in FIGS. 1A-5 a catheter of a first embodiment of the present invention. The catheter (device) is designated generally by reference numeral 10 and is configured for insertion into and positioning within the bladder of the patient for measuring intra-abdominal pressure. This measurement is to check if the intra-abdominal pressure exceeds a specified threshold since if such threshold is exceeded, there is a risk to the patient as discussed above and steps need to be taken to reduce the pressure such as draining additional fluid from the abdomen, opening the abdomen, etc.

The catheter 10 of the present invention can in some embodiments include an alarm or indicator to alert the user if pressure within the bladder, which correlates to pressure within the abdomen, rises to an unacceptable level, i.e., beyond a threshold or predetermined value (pressure). The indicator or alarm can be on the catheter or alternatively on an external device such as the monitor as discussed in more detail below. The alarm can also be connected via wireless connection to a phone or remote device to alert the appropriate personnel. The indicator or alarm can alternatively or in addition be activated if a change in pressure measurement exceeds a specified rate over a specified period of time.

Turning now to details of the catheter 10, which is also referred to herein as the device 10, and with initial reference to FIGS. 1A, 1B, 3 and 4 the catheter 10 of this embodiment has an elongated flexible shaft 12 having a lumen (channel) 14 extending within the shaft 12 and communicating at its distal region with balloon 16 to fluidly communicate with balloon 16 to inflate the balloon. Balloon 16 is utilized for monitoring pressure and is also referred to herein as the "pressure balloon." A fluid port 15 is positioned at a proximal region 17 of the catheter 10 for communication with an infusion source for infusion of gas, e.g., air, through the lumen 14 and into the balloon 16. The catheter 10 is shown in FIG. 1A with balloon 16 in the deflated condition (position) and in FIG. 1B with the balloon 16 in the inflated condition (position). The shaft 12 also includes a second lumen (channel) 20 and third lumen (channel) 24 extending therein (see also FIG. 5). In a preferred embodiment, the second lumen 20 is the largest lumen and is configured for continuous drainage of bodily contents from the bladder and can be connected to a drainage bag for collection of urine. Second lumen 20 has a side opening 22 at a distal portion, best shown in FIG. 3, communicating with the bladder. The third lumen 24 terminates at its distal end within balloon 26 to fluidly communicate with balloon 26 to inflate the balloon 26. The balloon 26 is inflatable to stabilize the catheter 10 to limit movement of the catheter 10 to keep it in place within the bladder and is also referred to herein as "the stabilizing balloon 26." A fluid port 28 is positioned at a proximal region 17 of the catheter 10 for communication with an infusion source for infusion of fluid through the lumen 24 and into the balloon 26. The balloon 26 can be filled with fluid, e.g., liquid such as water or saline, or a gas, e.g., air. In FIG. 1A, the balloon 26 is shown in the deflated condition and in FIG. 1B in the inflated condition.

Figure 5:
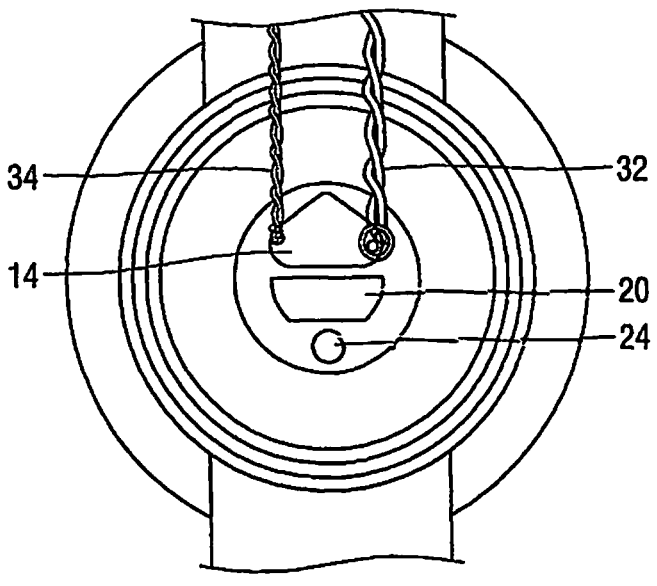
FIG. 5 is an enlarged transverse cross-sectional view of the catheter of FIG. 1.
Figure 6:
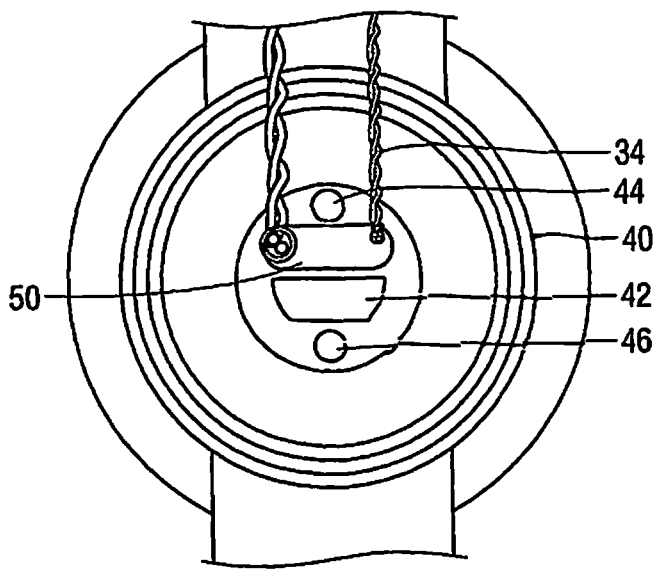
FIG. 6 is an enlarged transverse cross-sectional view of an alternate embodiment of a catheter of the present invention having four lumens.

Note FIG. 5 is a transverse cross-section of the catheter showing the three lumens of various shapes. These cross-sectional shapes of the lumens are provided by way of example as one or more of the lumens can be circular, oval or other symmetrical or asymmetrical shapes in transverse cross section. This also applies to the cross-sectional views of the other embodiments herein, e.g., FIGS. 6, 10B and 23, 30C, 45B, wherein the lumens can be shapes other than those shown. As noted above, preferably the drainage lumen is the largest lumen but in alternate embodiments one or more of the other lumens could be larger than the drainage lumen.

A sensor 30 is positioned within lumen 14 adjacent balloon 16. The wire(s) 32 are shown extending through lumen 14, the sensor 30 and wire(s) 32 being of sufficiently small size so as not to interfere with air flow though lumen 14. The sensor 30 measures pressure of the bladder. The sensor 30 is part of a transducer for converting the variation in pressure to an electrical signal for transmission to an external monitor. The pressure sensor also includes a temperature sensor to measure core temperature of the body as seen inside the bladder. Transmission wire(s) 34 of the temperature sensor extend adjacent wire 32 through lumen 14 and terminate external of the catheter 10 for connection to an external monitor. The transducer can be wired directly to the monitor or alternatively wired to a converter external of the catheter for converting the signal received by the transducer and transmitting a signal to the monitor, e.g., a bedside monitor, to display the pressure readings. This is shown schematically in FIG. 2. The readings can be displayed in quantitative form, graphical form or other displays to provide an indicator to the clinician of the bladder pressure. The monitor, or a separate monitor, will also display the temperature readings from sensor 30. Alternatively, the sensor/transducer can be connected to the monitor via a Bluetooth wireless connection.

Wires 32 and 34 can extend though lumen 14 and exit side port 15 for connection to a converter or monitor or alternatively can be inserted through the lumen 14, piercing the wall to enter the lumen 14 distal of the side port.

An alarm system can also be provided wherein the system includes a comparator for comparing the measured pressure (and/or temperature) to a threshold (predetermined) value, and if such threshold is exceeded, an indicator, e.g., an alarm, is triggered to indicate to the hospital personnel the excessive pressure and/or temperature. An alarm system can alternatively or in addition be activated if a change in pressure measurement exceeds a specified rate over a specified period of time. This would alert the staff to an imminent risk of ACS prior to intra-abdominal pressure exceeding a certain value, e.g., 20 mm hg, since due to this link, the relationship between intra-abdominal pressure and abdominal cavity volume is believed to be linear up to an intra-abdominal pressure of 12-15 mm hg and increasing exponentially thereafter.

Figure 2:
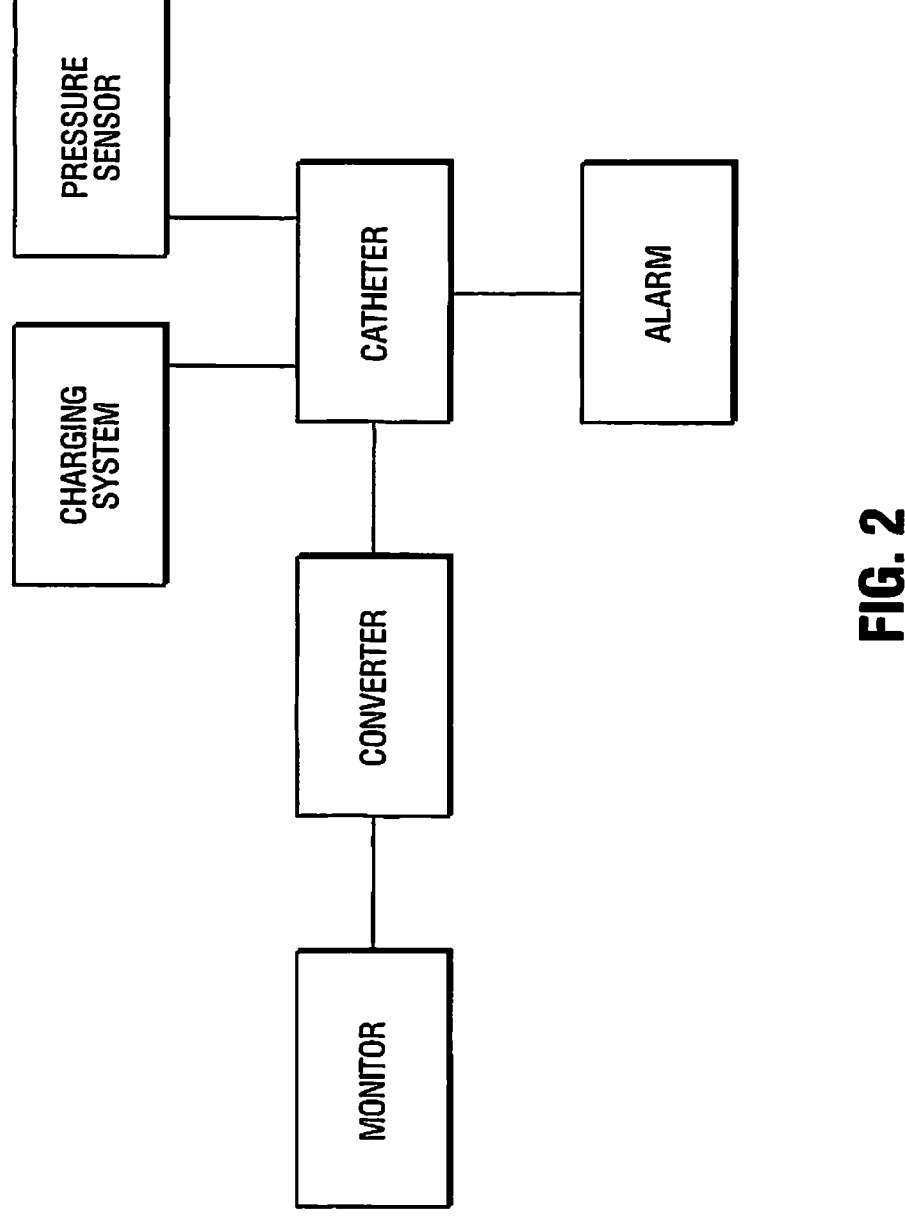
FIG. 2 is a schematic view of the system utilizing the catheter of FIG. 1A with an alarm system.

The alarm system can be part of the catheter (as shown in FIG. 2) or alternatively external to the catheter 10.

The lumen 14 and space 16a within balloon 16 together form a closed gas, e.g., air, chamber, i.e., the lumen 14 forming an air column. With the balloon 16 filled with air, pressure on the external wall of the balloon will force the balloon to deform inwardly, thereby compressing the air contained within the balloon space 16a and within the lumen 14. The pressure sensor 30 is located in a distal portion of the lumen 14 at the region of the balloon 16 and thus is positioned at the distal end of the air column. Therefore, the pressure is sensed at the distal region as the sensor 30 detects change in air pressure in lumen 14 due to balloon deformation. Placement of the sensor 30 at a distal location provides a pressure reading closer to the source which advantageously increases the accuracy because it reduces the risk of transmission issues by reducing the amount of interference which could occur due to water, air, clots, tissue, etc. if the transmission is down the air lumen (air column).

Additionally, the pressure measurement occurs about a more circumferential area of the balloon 16 providing a pressure reading of a region greater than a point pressure sensor reading. Also, average pressure over an area of the bladder wall can be computed. Thus, the area reading gleans information on pressure over more of the bladder wall. Stated another way, the balloon has a relatively large surface area with multiple reference points to contribute to average pressure readings of the surface around it by the sensor.

The air column is charged by insertion of air through the side port 15 which communicates with lumen 14. The side port 15 includes a valve to provide a seal to prevent escape of air from a proximal end. The balloon 16 can be composed of impermeable material, or in alternative embodiments, a permeable or semi-permeable material with an impermeable coating. This seals the air column at the distal end to prevent escape of air through the distal end, i.e., through the wall of the balloon 16. Thus, with the lumen sealed at the proximal and distal ends, a closed air system is provided, and without the requirement for repeated water insertion, a fully closed unit is provided.

In some embodiments, when the lumen 14 is air charged, the balloon 16 is not fully inflated. This improves the accuracy of the balloon 16 transmitting pressure from external the balloon to the interior of the balloon and into the lumen, i.e., air column, by ensuring the balloon has sufficient compliancy to prevent the balloon from introducing artifact into the pressure reading which would diminish its accuracy.

In some embodiments, the pressure balloon 16 is of a size to receive at least about 3 cc (3 ml) of fluid. However, other sizes/volumes are also contemplated such as about 2 cc or about 1 cc. Additionally, these volumes represent the maximum volume of fluid for the balloon, however, as noted above, in preferred embodiments, the pressure balloon 16 is not fully inflated so it would receive less than the maximum volume. Thus, with a balloon of X volume, the fluid would receive X-Y fluid, with Y representing the amount of desired extra space to achieved desired compliancy of the balloon while still enable sufficient inflation of the balloon to achieve its pressure induced deformation function.

Note in this embodiment, the stabilizing balloon 26 is positioned proximal of the pressure balloon 16. Also, in this embodiment, the stabilizing balloon 26 is larger than the pressure balloon 16. By way of example, the stabilizing balloon 26 can have a fully expanded diameter of about 23 mm and the pressure balloon 16 can have a fully expanded diameter of about 15 mm, although other dimensions or diameters for these balloons are also contemplated. By way of example, the stabilizing balloon 26 can have a capacity of about 10 cc (10 ml) of air, although other sizes/volumes are also contemplated. Note these sizes/volumes for both balloons are provided by way of example and other sizes are also contemplated. Alternatively, the stabilizing balloon can be the same size or smaller than the pressure balloon. Various shapes of the balloons are also contemplated.

Additionally, although the balloon 26 is positioned proximal of the balloon 16, it is also contemplated that the balloon 26 be positioned distal of balloon 16. The axial spacing of the balloons 16, 26 enable the stabilizing balloon 26 to engage the bladder wall to provide a sufficient radial force thereon for securing/mounting the catheter within the bladder without interfering with the function of balloon 16.

Figure 3:
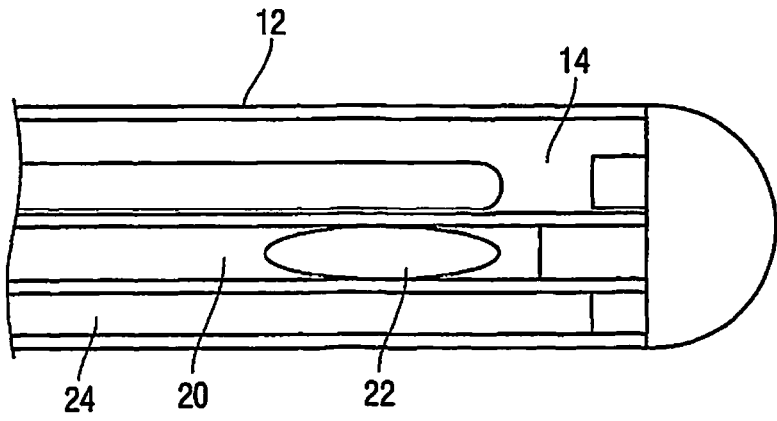
FIG. 3 is a close-up view of the tip of the catheter of FIG. 1A.
Figure 4:
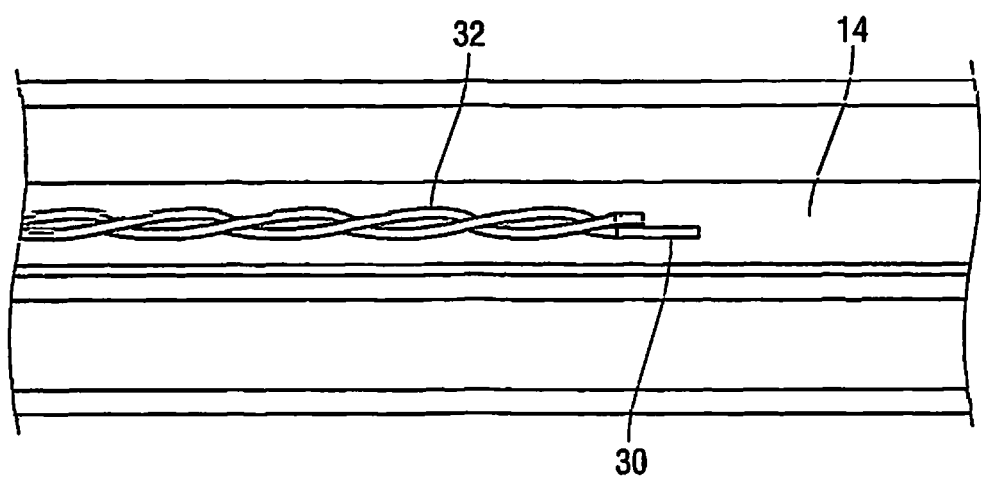
FIG. 4 is a close-up view of the sensor of FIG. 1A within the air lumen.
Figure 7:
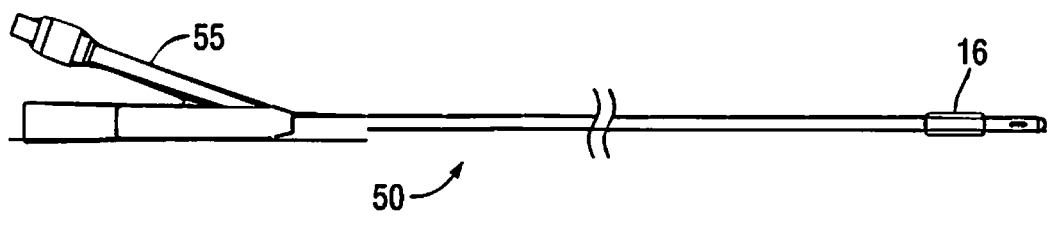
FIG. 7 is a side view of an alternate embodiment of the catheter of the present invention similar to FIG. 1A except having a single balloon, the balloon shown in the inflated condition.

It should be appreciated that although the stabilizing balloon is shown in the embodiment of FIG. 1, it is also contemplated as an alternative that the catheter and system of FIGS. 1 and 2 can be utilized without the stabilizing balloon 26 as shown for example in FIG. 7. Similarly, although the various embodiments (catheter) disclosed herein utilize a stabilizing balloon, it is also contemplated that alternatively the catheter of these various embodiments not include a stabilizing balloon. In the embodiment of FIG. 7, catheter 50 has two lumens: 1) a lumen for drainage of the bladder which has a side opening at a distal end to communicate with the bladder (similar to lumen 20 of FIG. 1A); and 2) an air lumen filling pressure balloon 16 via insertion of air through side port 55. The sensor 30 is positioned within the air lumen in the same manner as sensor 30 is in lumen 14 or in the alternative positions disclosed herein. Thus, the pressure and temperature sensing described in conjunction with FIG. 1 is fully applicable to the embodiment of FIG. 7. Besides the elimination of the stabilizing balloon and its lumen and side port, catheter 50 is the same as catheter 10, Note that although only one sensor is shown in FIG. 3, it is also contemplated that multiple sensors can be provided. Also, note that the sensor 30 is positioned in lumen 14 at a mid-portion of the balloon, i.e., just proximal where the opening in lumen 14 communicates with the interior 16a of the balloon 16. It is also contemplated that the sensor can be placed at another portion within the lumen 14, e.g., a more proximal portion, with respect to the lumen opening. Also, the lumen opening need not be at the mid portion of the balloon and can be at other regions of the balloon to communicate with the interior space 16a. Note if multiple sensors are provided, they can be positioned at various locations within the lumen 14.

As shown, the sensor 30 and its transmission wires are located in the same lumen 14 also used for initial inflation gas, e.g., air, for balloon 16 and for the air charged column. This minimizes the overall transverse cross-section (e.g., diameter) of the catheter 10 by minimizing the number of lumens since additional lumens require additional wall space of the catheter. However, it is also contemplated in an alternate embodiment that the sensor is in a dedicated lumen separate from the inflation lumen 14. This can be useful if a larger sensor or additional wires are utilized which would restrict the air lumen if provided therein. This is also useful if a specific sized lumen for the sensor and wires is desired to be different than the sized lumen for the air column. Provision of a separate lumen is shown in the cross-sectional view of FIG. 6 wherein in this alternate embodiment catheter 40 has four lumens: 1) lumen 42 for drainage of the bladder which has a side opening at a distal end to communicate with the bladder (similar to lumen 20 of FIG. 1); 2) lumen 44 for filling pressure balloon 16; 3) lumen 46 for filling stabilizing balloon 26; and 4) lumen 50 in which sensor 30 and its transmission wires 32 and temperature sensor wires 34 are contained. In all other respects catheter 40 is identical to catheter 10 and its balloons, air channel, sensor, etc. would perform the same function as catheter 10. Therefore, for brevity, further details of catheter 40 are not discussed herein as the discussion of catheter 10 and its components and function are fully applicable to the catheter 40 of the embodiment of FIG. 6. As noted above, the cross-sectional shapes of the lumens can be circular, oval, etc. or other shapes.

Turning now to the use of the catheter 10, the catheter 10 is inserted into the bladder. Note catheter 50 would be used in the same manner. The balloon 26 is inflated to secure the catheter 10 in place during the procedure by insertion of a fluid (liquid or gas) through side port 28 which is in fluid communication with lumen 24. The system is charged by inflation of the balloon 16, i.e., preferably partial inflation for the reasons discussed above, by insertion of air via a syringe through port 15 which is in fluid communication with lumen 14. As discussed above, the catheter 10 is a closed system with the balloon 16 sealed so that air inserted through lumen 14 and into balloon 16 cannot escape through balloon 16. Thus, a closed chamber is formed comprising the internal space 16a of the balloon 16 and the internal lumen 14 communicating with the internal space 16a of balloon 16. With the balloon 16 inflated, pressure monitoring can commence. When external pressure is applied to an outer surface 16b of the balloon 16, caused by outward abdominal pressure which applies pressure to the bladder wall and thus against the wall of balloon 16, the gas e.g., air, within the chamber is compressed. The sensor 30 at the distal end of lumen 14 provides continuous pressure readings, converted to an electrical signal by the transducer within the distal end of lumen 14, and then electrically communicates through wire(s) 32 extending through lumen 14, exiting through the proximal side port 15 and connected to an external monitor. Note the wire can terminate at the proximal end in a plug in connector which can be connected directly to the monitor or alternatively plugged into a converter to convert the signals from the transducer in the embodiments wherein the converter is interposed between the wires and monitor (see e.g., the system of FIG. 2) to provide the aforedescribed graphic display. Although, the system is capable of continuous pressure and temperature monitoring, it can also be adapted if desired for periodic monitoring so the pressure and temperature readings can be taken at intervals or on demand by the clinician.

In the embodiments wherein an indicator is provided, if the measured pressure exceeds a threshold value, and/or a change in pressure measurement exceeds a specific rate over a specific time period, the indicator would alert the clinician, e.g., via a visual indication or an audible indication that the threshold is exceeded. The indicator in some embodiments can include an audible or visual alarm (shown schematically in FIG. 2). In the embodiments having an indicator, the indicator can be provided on a proximal end of the catheter which extends out of the patient or the indicator can be part of an external component such as the monitor or a separate alarm system. A visual, audible, or other indicator can likewise be provided in any of the other embodiments disclosed herein to indicate if the measured temperature exceeds a predetermined value, and such indicator can include an alarm and can be part of the catheter or a separate component.

Figure 8A:
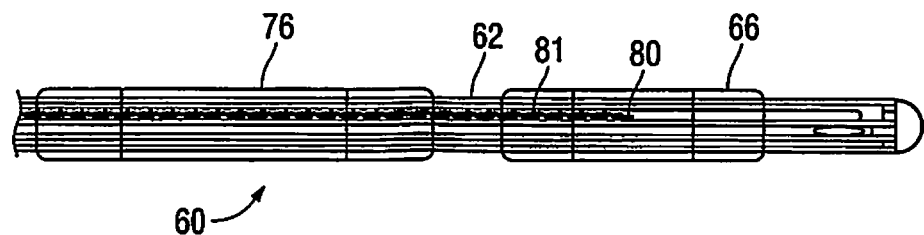
FIGS. 8A and 8B are side views of an alternate embodiment of the catheter of the present invention having two balloons and a pressure sensor and a separate temperature sensor in the air lumen, the two balloons shown in the deflated condition, with FIG. 8A showing the distal end and FIG. 8B showing the proximal end of the catheter.

In the embodiment of FIGS. 1-7, within the distal end of the air lumen 14 is a pressure transducer and pressure sensor 30 which also includes a temperature sensor. In the alternate embodiment of FIGS. 8A-10B, the temperature sensor is separate from the pressure sensor. More specifically, catheter 60 has an elongated flexible shaft 62 having a lumen (channel) 64 extending within the shaft 62 and fluidly communicating at a distal region with balloon 66 to inflate the balloon. Balloon 66 (also referred to as the pressure balloon) is utilized for monitoring pressure. A fluid side port 65 is positioned at a proximal region 67 of the catheter 60 for communication with an infusion source for infusion of gas e.g., air, through the lumen 64 and into the balloon 66. The catheter 60 is shown in FIG. 8A with balloon 66 in the deflated condition (position) and in FIG. 9 with the balloon 66 in the inflated condition (position). The shaft 62 also includes a second lumen (channel) 70 and third lumen (channel) 74 extending therein. The second lumen 70 is preferably the largest lumen and is configured for drainage of the bladder. Second lumen 70 has a side opening 72 at a distal portion communicating with the bladder. The third lumen 74 communicates at a distal region with stabilizing balloon 76 to fluidly communicate with balloon 76 to inflate the balloon. The stabilizing balloon 76 is inflatable to stabilize the catheter 60 to limit movement of the catheter 60 to keep it in place within the bladder. A side fluid port 75 is positioned at a proximal region 67 of the catheter 60 for communication with an infusion source for infusion of fluid through the lumen 74 and into the balloon 76.

Figure 9:
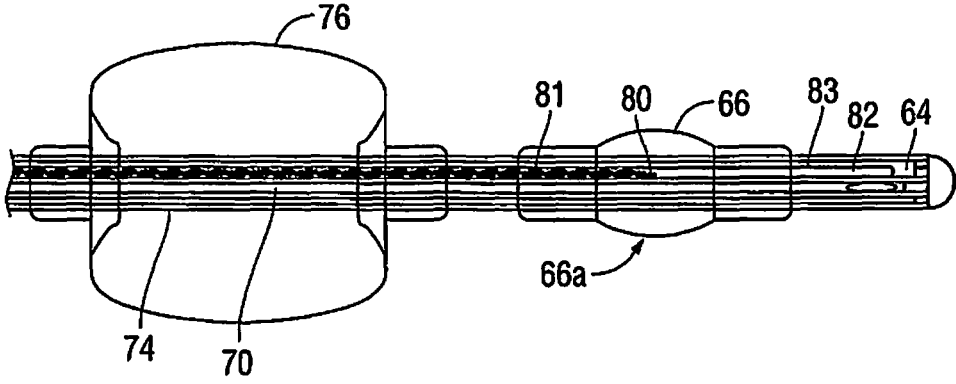
FIG. 9 is a side view similar to FIG. 8A showing the two balloons in the inflated condition.
Figure 10A:
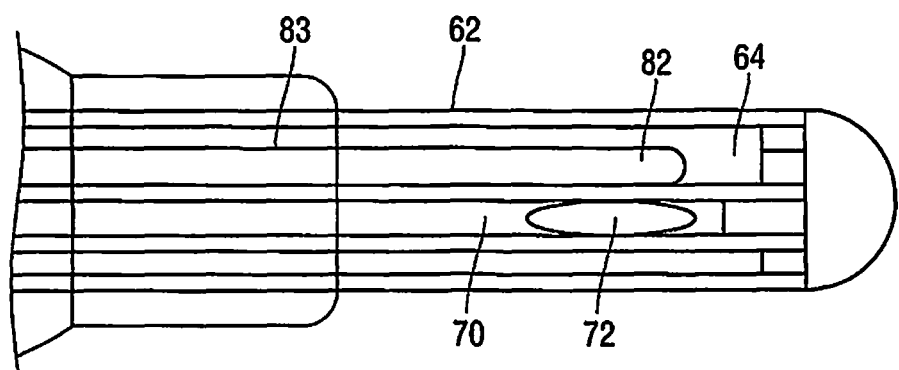
FIG. 10A is a close up view of the distal portion of the catheter of FIG. 8A.
Figure 10B:
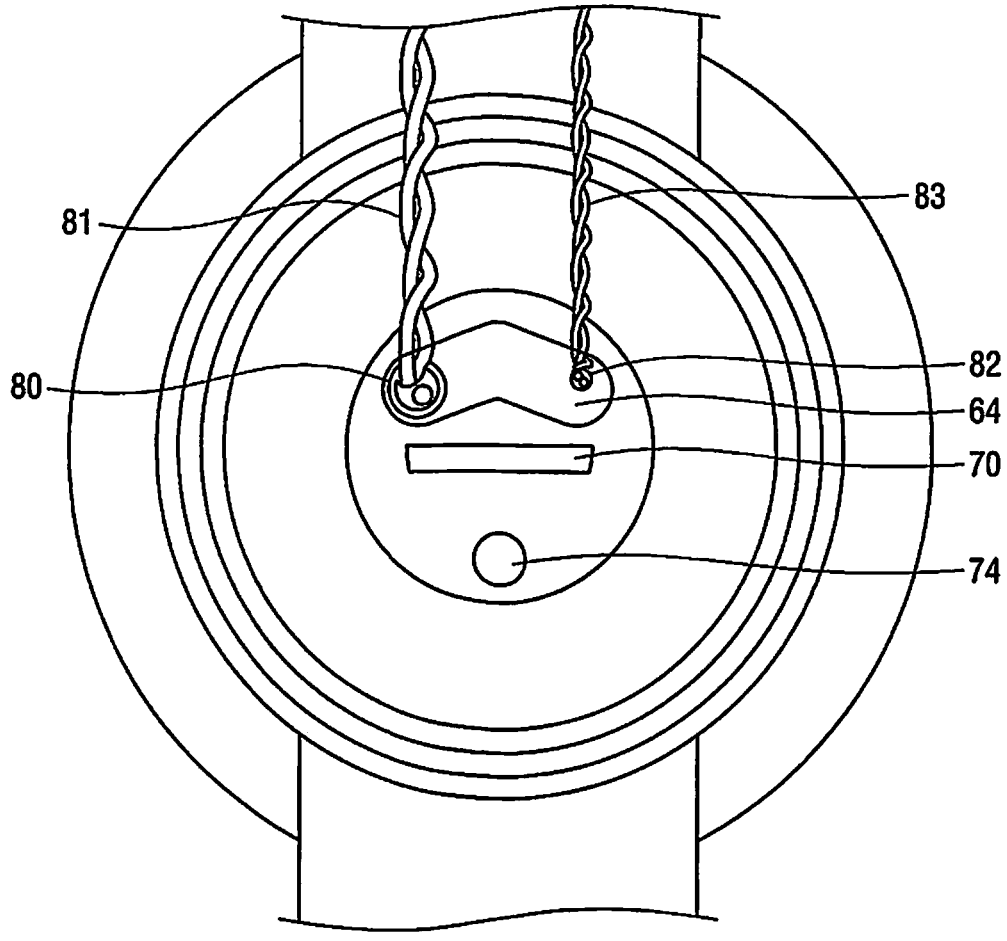
FIG. 10B is an enlarged transverse cross-sectional view of the catheter of FIG. 8A.

Sensor 80 is positioned in lumen 64 for sensing pressure in response to balloon deformation in the same manner as sensor 30. Sensor 82 is positioned in lumen 64 distal of sensor 80 for measuring core temperature. Temperature sensor 82 can be a thermocouple, a thermistor or other types of temperature sensors. As shown in FIG. 9, the temperature sensor is distal of the balloon 66 and its transmission wire(s) 83 extend proximally within lumen 64, exiting a proximal end (through side port 65) for communication with a monitor or alternatively a converter which communicates with the monitor. Wire(s) 81 of sensor 80 also extends through lumen 64, alongside wire 83, exiting through the side port 65 or a proximal end wall or a side wall of the lumen. It is also contemplated that alternatively one or both of sensors 80 and 82, and their associated wires 81, 83, can be positioned in a separate "fourth" lumen such as in the embodiment of FIG. 6 so that the "inflation lumen" and the "sensor lumen" are independent.

In use, catheter 60 is inserted into the bladder and stabilizing balloon 76 is inflated to secure the catheter 60 in place. The system is charged by inflation of the balloon 66, i.e., preferably partially inflated for the reasons discussed above, by insertion of gas, e.g., air, through port 65 which is in fluid communication with lumen 64 in a closed system formed by the internal space 66a of the balloon 66 and the internal lumen 64 communicating with the internal space 66a of balloon 66. With the balloon 66 inflated, pressure monitoring can commence as external pressure applied to an outer surface of the balloon 66 compresses the gas within the chamber. The sensor 80 at the distal end of lumen 64 provides continuous pressure readings, converted to an electrical signal by the transducer within the distal end of lumen, and then electrically communicates through wires 82 extending through lumen 64 to an external monitor either directly or via a converter. The sensor 82 at the distal end of lumen 64 provides continuous temperature readings via wires 83 communicating directly or indirectly with the monitor, Although, the system is capable of continuous pressure and continuous temperature monitoring, as with the other systems disclosed herein, it can also be adapted if desired for periodic monitoring so the pressure and/or temperature readings can be taken at intervals or on demand by the clinician.

Figure 8B:
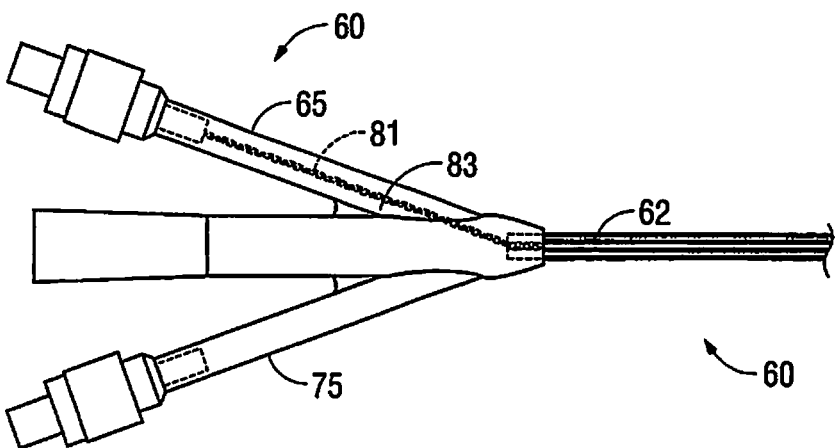
Figures 11, 12:
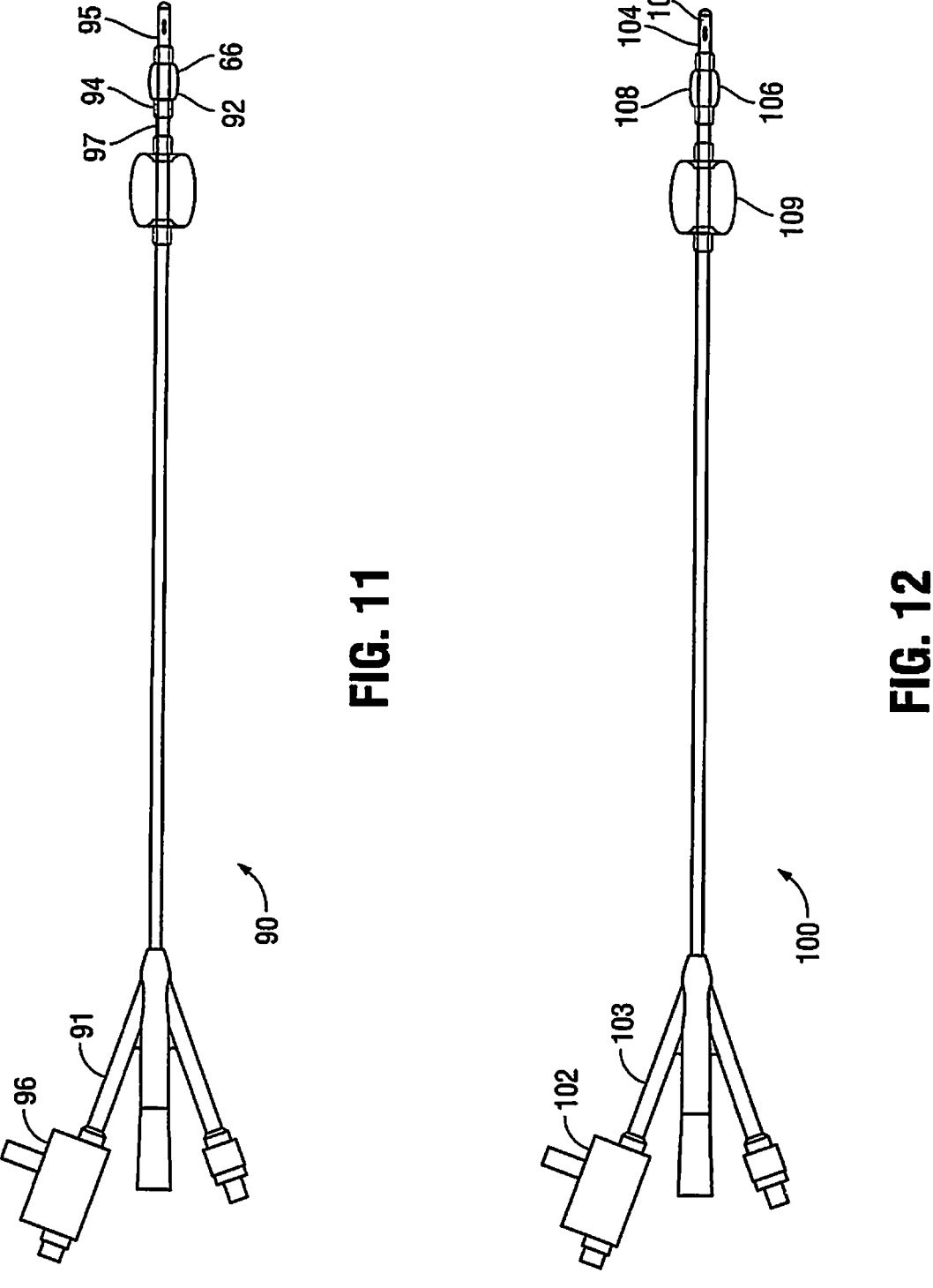
FIG. 11 is a side view of another alternate embodiment of the catheter of the present invention having two balloons, a sensor in the air lumen and an external transducer, the two balloons shown in the inflated condition.
FIG. 12 is a side view of another alternate embodiment of the catheter of the present invention having two balloons, a temperature sensor in the air lumen and the pressure sensor external of the catheter, the two balloons shown in the inflated condition.

In the alternative embodiment of FIG. 11, catheter 90 is identical to the catheter 60 of FIG. 8 except that the pressure transducer is positioned external of the catheter rather than in the air (or other gas) lumen. That is, instead of the pressure transducer including the sensor being positioned within the distal end of the air lumen, the pressure sensor 92 is positioned within lumen 94 at the distal end of the lumen and transmission wire(s) 93 connect the sensor 92 to the pressure transducer 96 positioned outside of the patient at a proximal region of catheter 90. As shown, the pressure transducer 96 can be positioned in a side port of catheter 90. In alternate embodiments, it is positioned outside the catheter. The temperature sensor 95 is positioned within lumen 94 along with transmission wire 97 in the same manner as temperature 82 and wires 83 are positioned in catheter 60 described above. The temperature sensor 95 can be a separate sensor positioned distal of the pressure sensor 92 as shown or alternatively it can be part of sensor 92 as in the embodiment of FIG. 1. In all other respects, catheter 90 is identical to catheter 60 and therefore for brevity further discussion is not provided since the structure and function of the balloons, the lumens, the positioning of the sensors in the lumens, the continuous pressure monitoring, etc., as well as the aforedescribed alternative arrangements of catheter 60, are fully applicable to the catheter 90.

In the alternative embodiment of FIG. 12, catheter 100 is identical to catheter 60 of FIG. 8 except that the pressure transducer and pressure sensor are positioned external of the patient at a proximal region of the catheter rather than in the air lumen. That is, instead of the pressure transducer sensor being positioned within and at the distal end of the air lumen, the transducer and pressure sensor 102 are positioned at a side port 103 of the catheter 100. In alternative embodiments, they are positioned outside the catheter. In yet other embodiments, the pressure sensor and/or pressure transducer can be positioned within the air (or other gas) lumen at a proximal end of the air lumen. The temperature sensor 107 is positioned within lumen 104 along with transmission wire(s) 108 in the same manner as temperature sensor 82 and wire 83 are positioned in catheter 60 described above. The system is charged by inflation of the balloon 106, i.e., preferably partially inflated for the reasons discussed above, by insertion of air via a syringe or other injection device through the side port 103 which is in fluid communication with lumen 104. The catheter 100 is a closed system with the balloon 106 sealed so that air inserted through lumen 104 and into balloon 106 cannot escape through balloon 106. Thus, a closed chamber is formed comprising the internal space of the balloon 106 and the internal lumen 104 communicating with the internal space of balloon 106. With the balloon 106 inflated, pressure monitoring can commence. When external pressure is applied to an outer surface of the balloon 106, caused by outward abdominal pressure which applies pressure to the bladder wall and thus against the wall of balloon 16, the gas (e.g., air) within the chamber of the balloon 106 is compressed. This compresses the air within the lumen 104 creating an air charged column along the lumen 104. The sensor 102 at the proximal end of catheter 100 measures pressure of the air column at its proximal end and can provide continuous pressure readings, converted to an electrical signal by the transducer at the proximal end or external of the catheter 100, and then electrically communicates through wire(s) to an external monitor. The balloon 106, like balloon 16, balloon 66 and the other pressure balloons described herein, is of sufficiently large size to provide a sufficient circumferential area for detection of pressure changes along several parts of the bladder wall, thereby providing an average pressure and enabling more accurate pressure readings. Balloon 109 is a stabilizing balloon like balloon 76 inflated through a separate lumen.

Note the wire(s) of the sensor 102 can terminate at the proximal end in a plug in connector which can be connected directly to the monitor or alternatively plugged into a converter to convert the signals from the transducer in the embodiments where the converter is interposed between the wires and monitor (see e.g. the system of FIG. 2) to provide the aforedescribed graphic display. Although, the system is capable of continuous pressure and temperature monitoring, it can also be adapted if desired for periodic monitoring so the pressure and/or temperature readings can be taken at intervals or on demand by the clinician. In all other respects, catheter 100 is identical to catheter 60 and therefore for brevity further discussion is not provided since the structure and function of the balloons, the continuous pressure monitoring, etc., as well as the aforedescribed alternative arrangements of catheter 60, are fully applicable to the catheter 100.

Figures 13A, 13B:
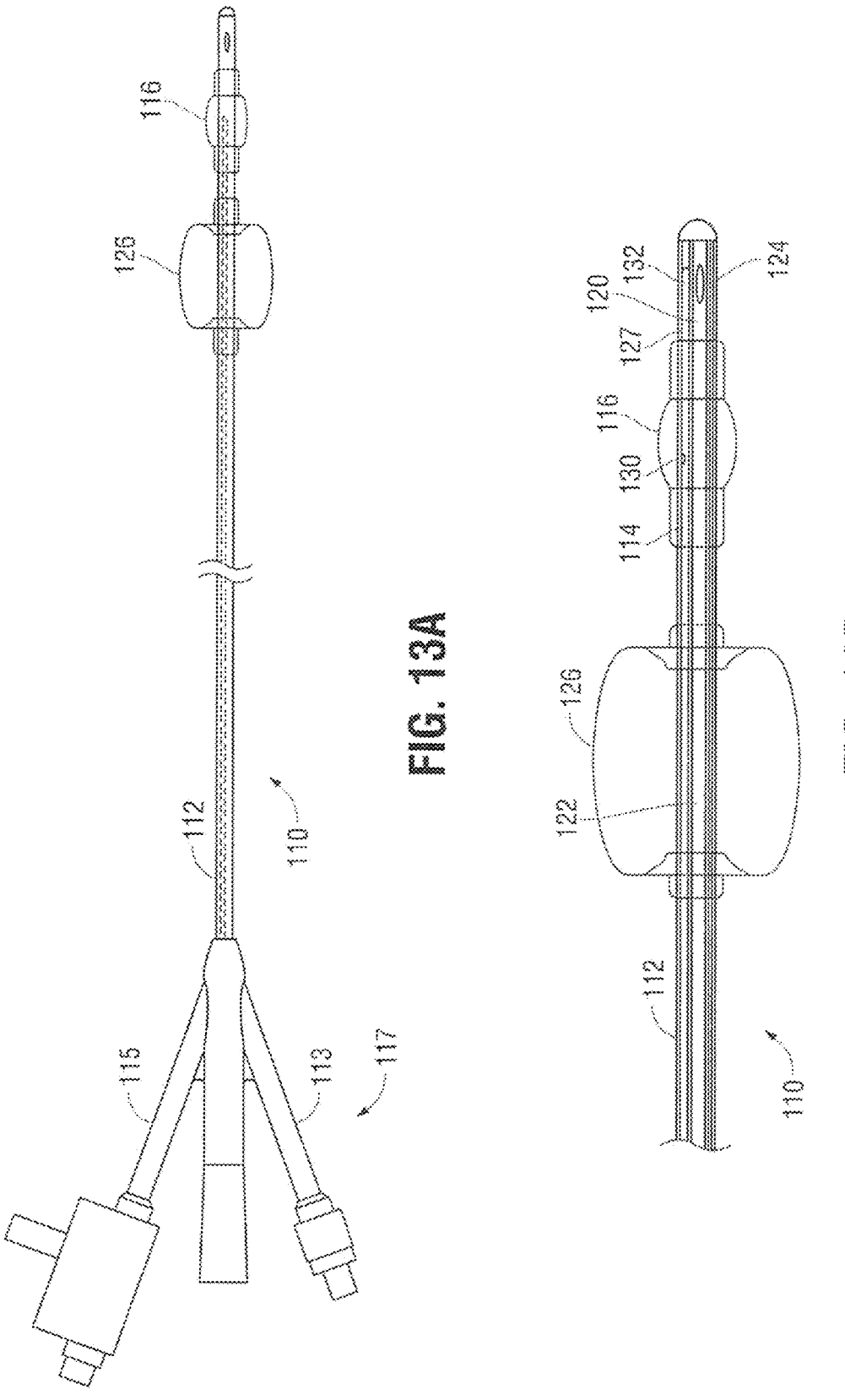
FIG. 13A is a side view of another alternate embodiment of the catheter of the present invention having two balloons and a pressure sensor positioned within the pressure balloon, the two balloons shown in the inflated condition.
FIG. 13B is an enlarged view of the distal portion of the catheter of FIG. 13A.

FIGS. 13A and 13B illustrate an alternate embodiment wherein catheter 110 includes a pressure sensor within the balloon. More specifically, catheter 110 has an elongated flexible shaft 112 having a lumen (channel) 114 extending within the shaft 112 and communicating at its distal region with balloon 116 to fluidly communicate with balloon 116 to inflate the balloon. Balloon 116 (also referred to as the pressure balloon) is utilized for monitoring pressure. A fluid side port 115 is positioned at a proximal region 117 of the catheter 110 for communication with an infusion source for infusion of gas through the lumen 114 and into the balloon 116. The shaft 112 also includes a second lumen (channel) 120 and third lumen (channel) 122 extending therein. Second lumen 120 has a side opening 124 at a distal portion communicating with the bladder. The third lumen 122 communicates at a distal region with stabilizing balloon 126 to fluidly communicate with balloon 126 to inflate the balloon to limit movement of the catheter 110 to keep it in place within the bladder for drainage. A fluid port 113 is positioned at a proximal region 117 of the catheter 110 for communication with an infusion source for infusion of fluid through the lumen 122 and into the balloon 126.

The pressure sensor 130 is carried by catheter 110 and positioned within the balloon 116 to measure pressure in response to deformation of the balloon in response to pressure exerted on an outer wall of balloon 116. The pressure transducer can include the sensor 130 or can be a separate component positioned at a proximal end of the catheter external of the catheter 110. The temperature sensor 132 can be positioned within the balloon 116, can be part of sensor 130, or alternatively positioned within lumen 114 (as shown in FIG. 13B), with its transmission wire(s) 127 extending within the gas, e.g., air, lumen 114 along with the wires of sensor 130 in the same manner as in catheter 60 described above.

In all other respects, catheter 110 is identical to catheter 60 and therefore for brevity further discussion is not provided since the structure and function of the balloons, lumens, continuous pressure monitoring, etc. as well as the aforedescribed alternative arrangements of catheter 60, are fully applicable to the catheter 110.

As discussed above, the pressure balloons disclosed herein have a large circumferential area (and large volume) to provide multiple reference points for pressure readings and to provide an average pressure to enable more accurate readings. Thus, the pressure balloon provides for gross measurement. In an alternate embodiment shown in FIG. 15, the pressure balloon for detecting pressure, designated by reference numeral 142, forms an outer balloon of catheter 140. Contained within the outer balloon 142 is an inner balloon 143. The inner balloon 143 provides a smaller diameter balloon and a smaller circumference (and volume) than the outer balloon 14. The inner balloon 143 together with the lumen 144 forms a smaller gas, e.g., air, column than in the embodiments discussed above where the larger balloon internal space communicates directly with the air lumen. This provides finer measurements. Thus, the compliant outer balloon 142 compresses the compliant inner balloon 143 which compresses the air within air lumen 144. The closed system is thereby formed by the internal space of the inner balloon 143 and the lumen 144. In certain instances, the smaller balloon air column can provide a more accurate reading from the average pressure determined by the larger outer balloon 142.

The inner balloon 143 and outer balloon 142 can be separately/independently inflated and closed with respect to each other so there is no communication, e.g. passage of gas or liquid, between the inner and outer balloons 143, 142.

The pressure transducer and pressure sensor 150 can be positioned within the lumen 144 in the same manner as sensor 30 of FIG. 1 and can function in the same manner. Alternatively, the pressure transducer can be at a proximal end of the catheter 140 as in the embodiment of FIG. 12 or external of the catheter. A temperature sensor can be part of sensor 150 as in the embodiment of FIG. 1 or alternatively it can be a separate component which can be positioned for example distal of the pressure sensor within the gas, i.e., air, lumen as in the embodiment of FIG. 8A. The transmission wires of the pressure sensor 150 and the temperature sensor extend through lumen 144.

The catheter 140 can optionally include a stabilizing balloon 145 similar to balloon 76 of FIG. 8. The catheter 140 would have a lumen, e.g., lumen 146, to inflate the stabilizing balloon 145. Lumen 148 with side opening 149 provides for drainage of the bladder. Lumen 144 which is used to inflate the inner balloon 143 and create the gas column has an opening at a distal region to communicate with inner balloon 143. A separate lumen 147 has an opening at a distal region to communicate with the outer balloon 142 to fill the outer balloon 142.

In use, catheter 140 is inserted into the bladder and stabilizing balloon 145 is inflated to secure the catheter 140 in place. The system is charged by inflation of the inner balloon 143, i.e., preferably partially inflated for the reasons discussed above, by insertion of air through a side port which is in fluid communication with lumen 144 in a closed system formed by the internal space 143a of the inner balloon 143 and the internal lumen 144 communicating with the internal space of inner balloon 143. Outer balloon 142 is filled, i.e., preferably partially inflated for the reasons discussed above, via injection of air through a separate lumen. With the outer balloon 142 inflated, pressure monitoring can commence as external pressure applied to the larger circumferential outer surface of the outer balloon 142 compresses and deforms the outer balloon 142 which compresses the inner balloon 143. As the inner balloon 143 is compressed and deformed in response to compression/deformation of the outer balloon 142 based on changes to bladder pressure, the sensor 150 at the distal end of lumen 144 provides continuous pressure readings, converted to an electrical signal by the transducer within the distal end of lumen 144, and then electrically communicates through wires 152 extending through lumen 144 to an external monitor either directly or via a converter. Although, the system is capable of continuous pressure and continuous temperature monitoring, as in the other embodiments disclosed herein it can also be adapted if desired for periodic monitoring so the pressure and/or temperature readings can be taken at intervals or on demand by the clinician.

Note that although separate lumens are provided for the inflation of inner balloon 143 and outer balloon 142, in an alternate embodiment, a single lumen can be utilized to inflate both balloons 143 and 142.

Figures 15, 16:
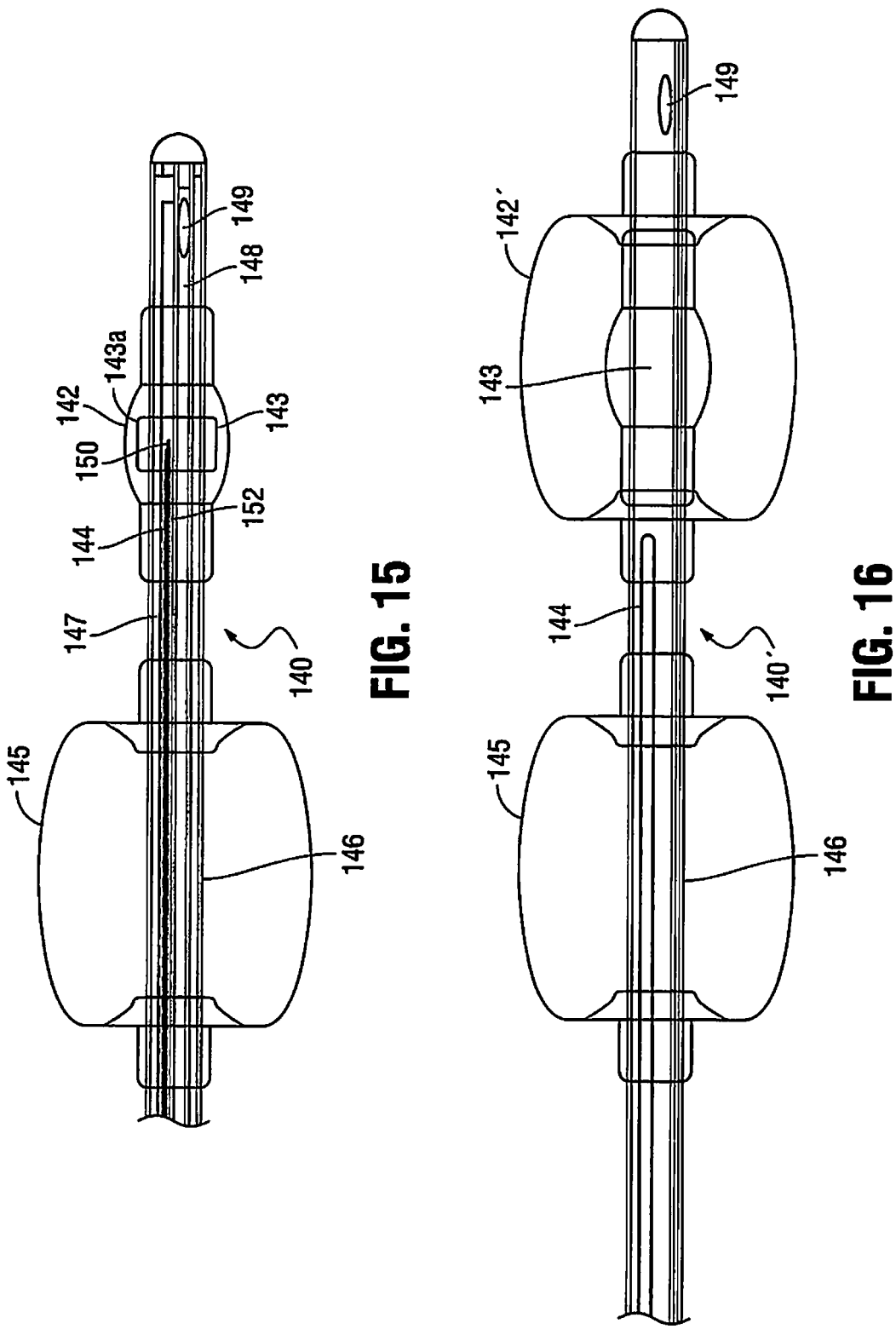
FIG. 15 is a side view of another alternate embodiment of the catheter of the present invention having an outer and inner pressure balloon and a stabilizing balloon, the balloons shown in the inflated condition.
FIG. 16 is a side view similar to FIG. 15 illustrating an alternate embodiment having a larger outer balloon.

FIG. 16 illustrates an alternate embodiment of catheter 140, designated by reference numeral 140'. Catheter 140' is identical to catheter 140 except a larger outer balloon 142' is provided to cover more surface area for pressure readings. In all other respects, catheter 140' is identical to catheter 140 and for brevity further discussion is not provided since the features and functions of catheter 140, and its alternatives such as single or two lumens for inner and outer balloon inflation, are fully applicable to catheter 140'. For ease of understanding, the components of catheter 140' which are identical to catheter 140 are given the same reference numerals as catheter 140.

Note that the larger balloon 142' can be used with the catheters of any of the embodiments described herein. Thus, a pressure balloon of the larger size balloon 142' can be used instead of the smaller pressure balloons illustrated in the drawings. Note the size of the balloons is provided by way of example and are not necessarily drawn to scale comparatively to the other components.

Figure 17A:
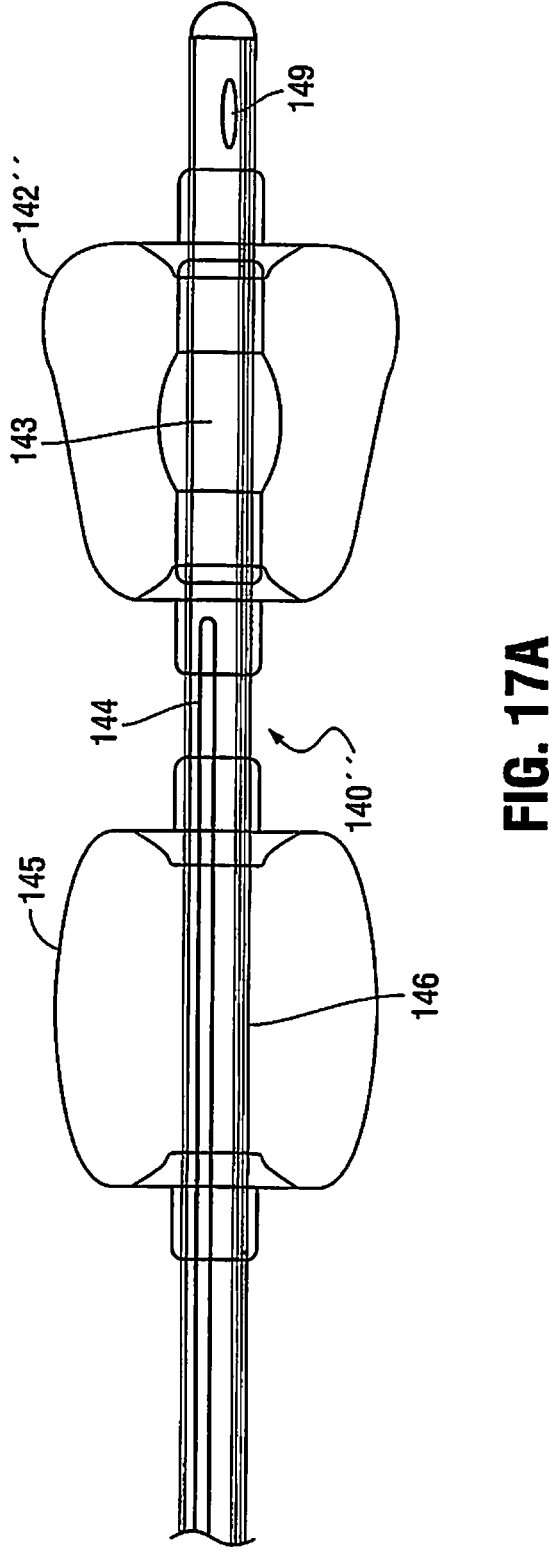
FIG. 17A is a side view similar to FIG. 15 illustrating an alternate embodiment having a pear-shaped outer balloon.
Figure 17B:
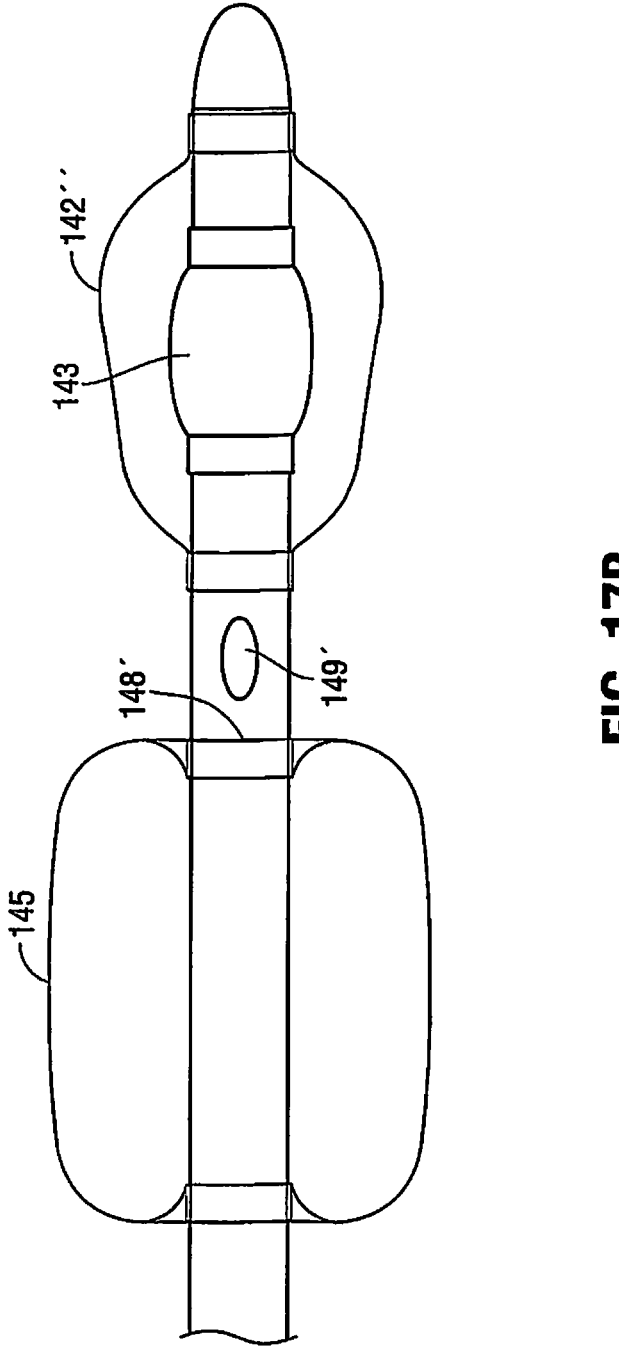
FIG. 17B is a side view similar to FIG. 17A showing an alternate embodiment wherein the drainage opening is between the two balloons.

FIG. 17A illustrates an alternate embodiment of catheter 140, designated by reference numeral 140". Catheter 140" is identical to catheter 140 except a pear shaped larger outer balloon 142" is provided. The larger balloon 142" covers more surface area for pressure readings. The pear shape could in certain applications decrease the risk of obstructing the ureter and provide more tactile continuity of the balloon to the bladder wall giving a better transmission of abdominal pressure to the internal sensor. In all other respects, catheter 140" is identical to catheter 140 and for brevity further discussion is not provided since the features and functions of catheter 140, and its alternatives such as single or two lumens for inner and outer balloon inflation, are fully applicable to catheter 140". For ease of understanding, the components of catheter 140" which are identical to catheter 140 are given the same reference numerals as catheter 140. FIG. 17B illustrates a catheter identical to catheter 140" with identical balloons, the only difference being that the side opening 149' is positioned proximal of the balloon 143 rather than distal of the balloon as in FIG. 17A. That is, opening 149', in communication with the catheter lumen 148' for drainage of the bladder, is positioned between the stabilizing balloon 145 and the inner and outer pressure (and inner) pressure balloon 142" (and 143). Thus, it is distal of the stabilizing balloon 145 and proximal of the outer balloon 142".

Note that the positioning of the side opening for drainage of FIG. 17B, which communicates with the drainage lumen of the catheter, can be utilized with any of the catheters disclosed herein. Thus, in the catheters disclosed in the various embodiments herein, instead of the drainage opening positioned distal of the pressure balloon(s), it can be proximal of the pressure balloon and distal of the stabilizing balloon so it is between the two balloons.

Note that the pear shaped balloon 142" can be used with the catheters of any of the embodiments described herein. Thus, a pressure balloon of the pear shape of balloon 142", and of larger size if desirable, can be used instead of the pressure balloons illustrated in the drawings.

FIGS. 18-25B illustrate an alternate embodiment of the catheter of the present invention. The pressure balloon for detecting pressure, designated by reference numeral 202, forms an outer balloon of catheter 200. Contained within the outer balloon 202 is an inner balloon 204. The inner balloon 204 provides a smaller diameter balloon and a smaller circumference (and volume) than the outer balloon 202. The inner balloon 204 together with the lumen 214, which communicates with the inner balloon 204 for inflation thereof, forms a smaller gas, e.g., air, column as in the embodiments of FIGS. 15-17. This provides finer measurements. Thus, the compliant outer balloon 202 fluid or wall compresses the outer wall 205 of the compliant inner balloon 204 which compresses the air (or other gas) within air lumen 214. The closed system is thereby formed by the internal space 204a of the inner balloon 204 and the lumen 214. The smaller balloon air column can in certain instances provide a more accurate reading from the average pressure determined by the larger outer balloon 202.

Figure 18A:
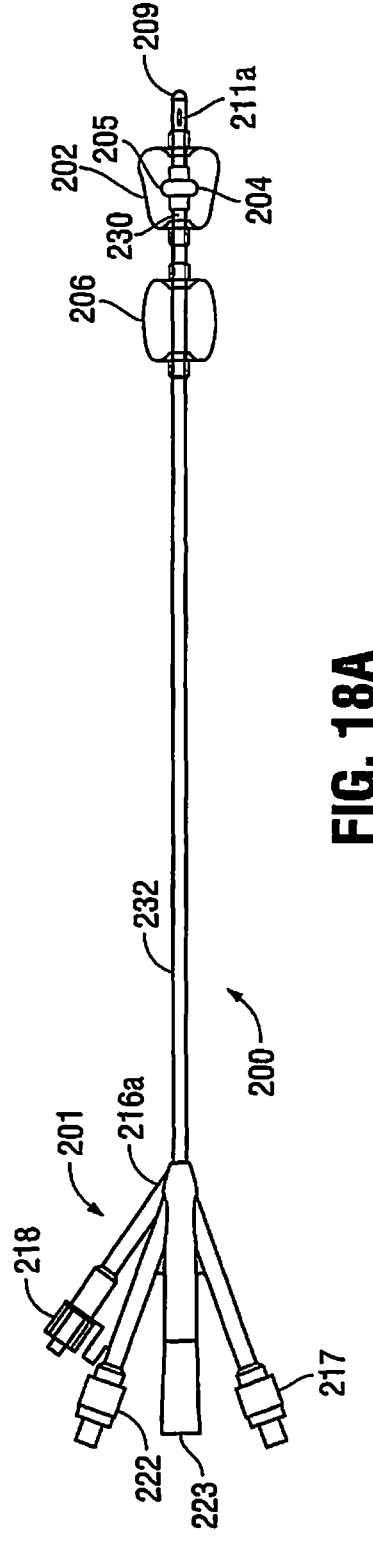
FIG. 18A is a side view of another alternate embodiment of the catheter of the present invention having a port for connection to an external pressure transducer and an outer and inner pressure balloon, the two balloons shown in the inflated condition.
Figure 18B:
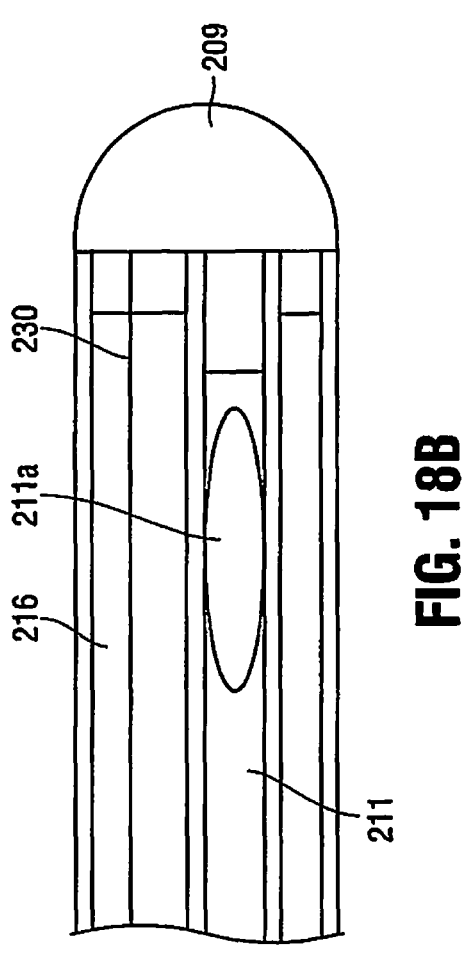
FIG. 18B is close up view of the distal end of the catheter of FIG. 18A.
Figure 19:
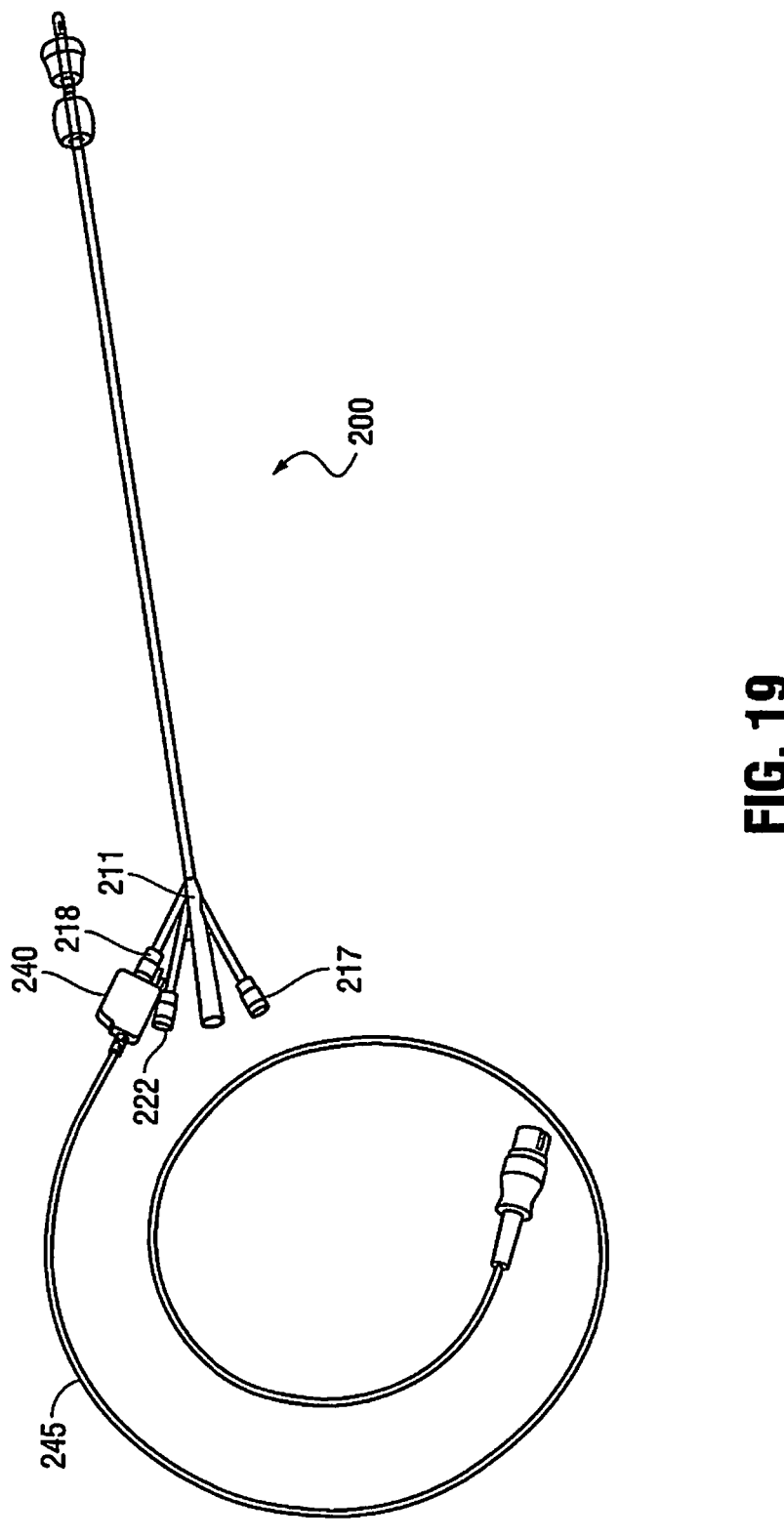
FIG. 19 is a perspective view of the catheter of FIG. 18A with a pressure transducer hub attached to the catheter.
Figure 24A:
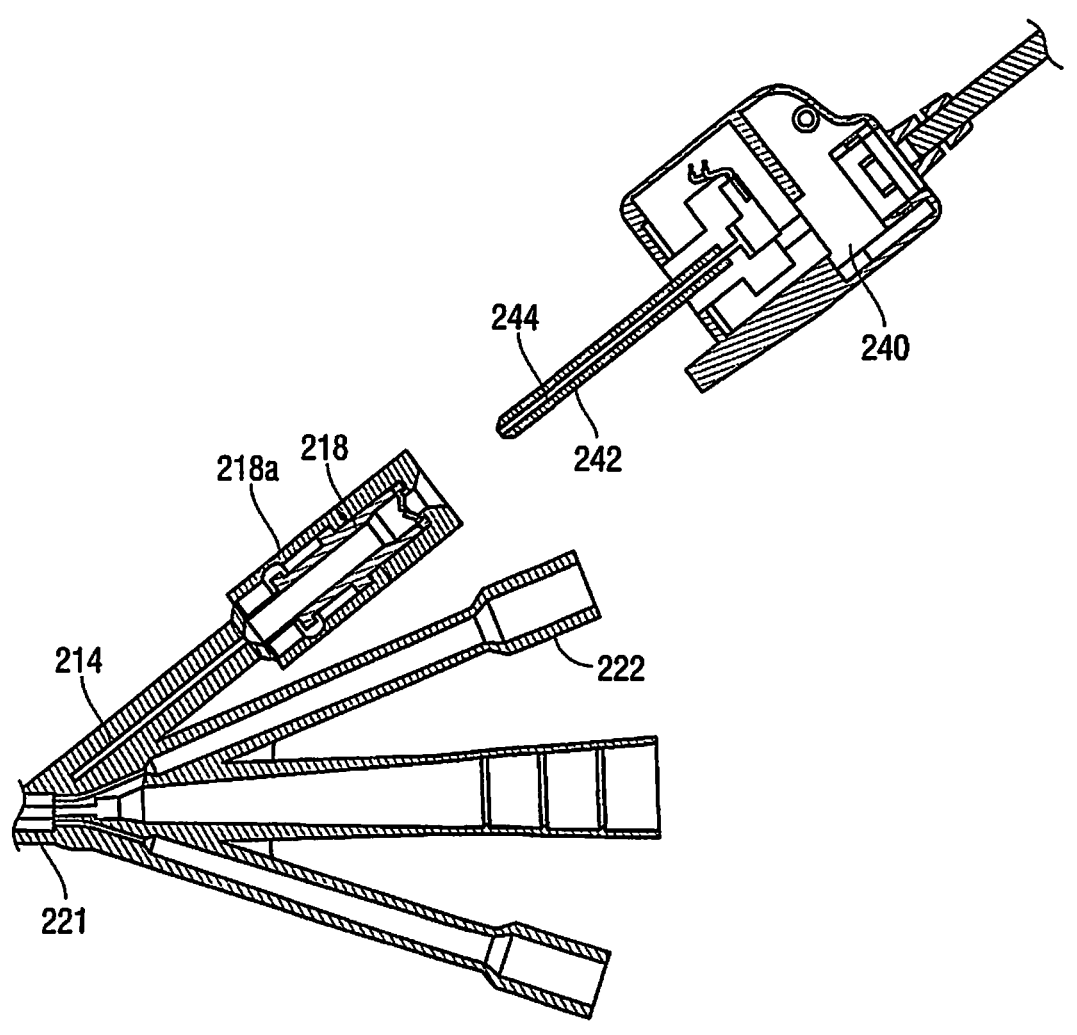
FIG. 24A is a cutaway side view showing the pressure transducer hub prior to connection to the catheter of FIG. 18A, a portion of the hub wall and catheter connector removed to show internal components.
Figure 24B:
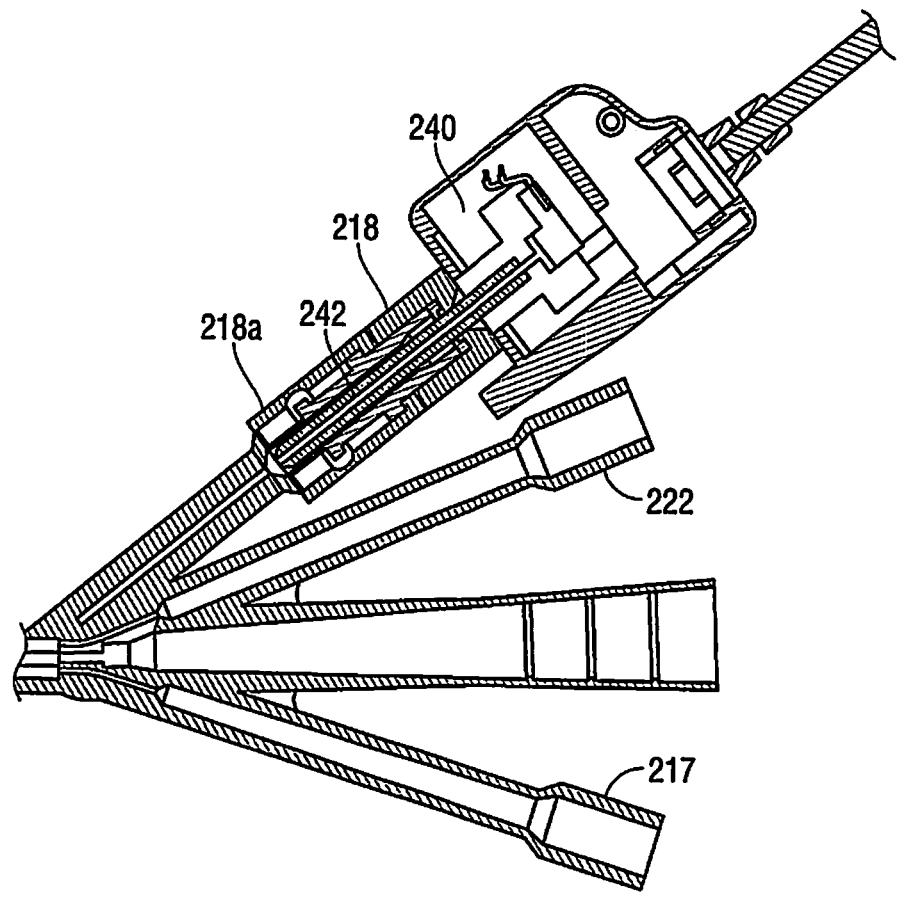
FIG. 24B is a side view similar to FIG. 24A showing the hub attached to the catheter.

The pressure transducer and pressure sensor are external to catheter 200 and mounted to port 218 at the proximal end 201 of catheter 200. More specifically, a transducer hub or housing, designated generally by reference numeral 240, contains the pressure transducer and sensor and is mounted to the angled side port 218. In the embodiment of FIG. 18A, the hub 240 is mounted over the port 218 and can be locked or secured thereto such as by a friction fit, snap fit, threaded attachment, a latch, etc., maintaining an airtight seal so the air is contained within the lumen 214 and balloon 204. The hub 240 has an elongated (rod-like) member or nose 242 extending distally therefrom (FIG. 24A) dimensioned to be inserted through the proximal opening in port 218 and into air lumen 214. (Note the air lumen 214 as in the other lumens extend into their respective angled side ports). The elongated member 242 also has a channel 244 extending therethrough to allow the pressure wave to travel through to the pressure sensor. Although in preferred embodiments no additional air needs to be injected into inner balloon 204 via lumen 214 after attachment of hub 240, it is also contemplated that a port or opening can be provided in hub 240 to receive an injection device for injection of additional air. Such additional air can communicate with and flow through channel 244 of elongated member 242, into lumen 214 and into inner balloon 204 for inflation, or alternatively, a side port or opening in angled port downstream of the elongated member 242 could be provided.

To charge the system, when the hub 240 is mounted to the side port 218, the elongated member 242 extends into lumen 214 to advance air through the air lumen 214 into inner balloon 204 to expand inner balloon 204. In some embodiments, 0.2 cc of air can be displaced/advanced by the member 242, although other volumes are also contemplated. Thus, as can be appreciated, mounting of the hub 240 to the catheter 200 automatically pressurizes the air lumen/chamber and expands the inner balloon 204. Note the inner balloon 204 can be partially or fully inflated (expanded), dependent on the amount of air advanced into the inner balloon 204. Further note that the lumen 214 is not vented to atmosphere when the transducer hub 240 is attached and air is advanced through the air lumen. The port 218 can include a closable seal through which the elongated member 242 is inserted but maintains the seal when the elongated member 242 remains in the lumen 214.

Lumen 214 which is used to inflate the inner balloon 204 and create the air column has an opening at a distal region to communicate with the interior of inner balloon 204. Lumen 212 of catheter has an opening at a distal region to communicate with the outer balloon 202 to fill the outer balloon 202. Angled port (extension) 222 at the proximal end of catheter 200 receives an inflation device to inflate, either fully or partially, the outer balloon 202.

Note as in the other embodiments disclosed herein, air is described as the preferred gas for creating the column and expanding the balloon, however, other gasses are also contemplated, for each of the embodiments herein.

The outer balloon 202 can be shaped such that a distal region 207a (FIGS. 20A-20C) has an outer transverse cross-sectional dimension, e.g., diameter, greater than an outer transverse cross-sectional dimension, e.g., diameter, of the proximal region 207b. A smooth transition (taper) can be provided between the distal region 207a and proximal region 207b. Note the balloon 202 can be pear shaped as shown in FIGS. 20B and 20C although other configurations are also contemplated. This pear shape in some applications is designed to conform to the shape of the bladder.

The inner and outer balloons 204, 202 can by way of example be made of urethane, although other materials are also contemplated such as silicone or EVA.

Figure 25A:
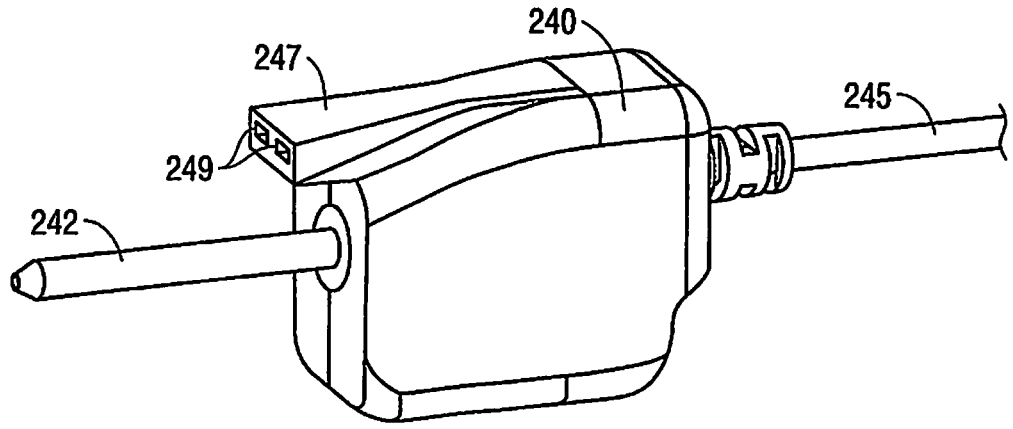
FIG. 25A is a perspective view of the transducer hub of FIG. 24A.
Figure 25B:
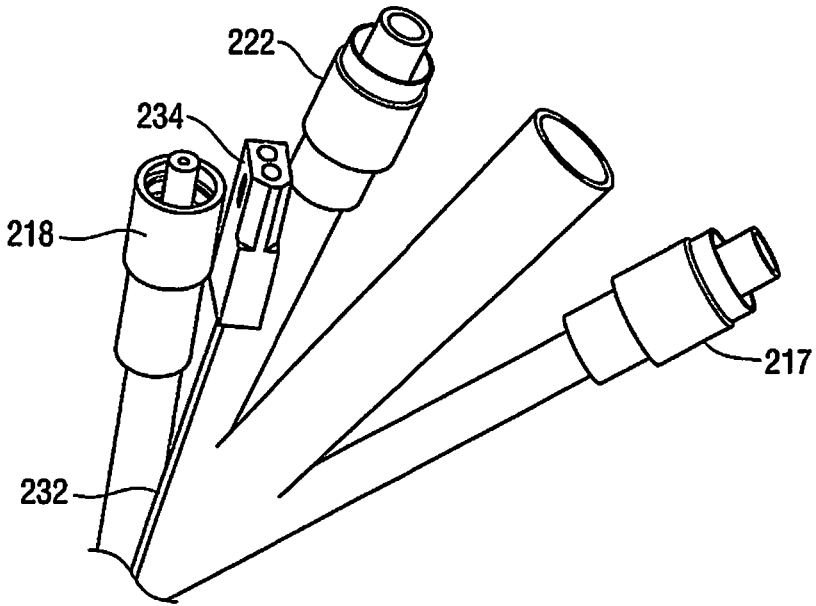
FIG. 25B is a perspective view of the proximal end of the catheter showing a connector for the thermocouple wire.

A temperature sensor 230 (FIG. 18B), such as a thermocouple, is positioned within the catheter 200 at a distal end to measure core body temperature. The sensor 230 is shown positioned in a lumen 216 separate from the lumens 214 and 212. One or more wires 232 extend from the sensor 230 through the lumen 216, exiting the lumen 216 and catheter 200 at a proximal end between the angled extensions/ports of the catheter 200, e.g., between the port 218 for the inner balloon 204 and the port 222 for the outer balloon 202. A connector 234, e.g., a male connector, is at the proximal terminal end of the wire 232 as shown in FIG. 25B. The transducer hub 240 includes a connector 247 with openings 249 (FIG. 25A) which receive the connector 234 of the wire 232. When the hub 240 is mounted to port 218 of catheter 200, the connector 234 of the wire is automatically connected to a connector carried by or within the hub 240 which is in communication with a temperature monitor. Note the connector, e.g., female connector, within or carried by the hub 240 can already be mounted to an external temperature monitor via a cable when the hub 240 is mounted to catheter 218 or alternatively the hub 240 can first be mounted to port 218 of the catheter 200 and then a cable is connected between the temperature monitor and catheter 200. In the illustrated embodiment of FIG. 25A, the wire connector 234 can plug into the openings 249 of connector 247 positioned on the hub 240. Note the connector 247 can also be internal of the hub 240 with an opening in the wall of the hub to enable access for the wire connector. Also note that alternatively the wire can include a female connector and the hub can have a male connector. Other types of connectors/connections are also contemplated.

As can be appreciated, connection of the transducer hub 240 to the catheter 200 (port 218) a) automatically connects the temperature sensor 230 to a connector for communication with a temperature monitor cable; and b) automatically advances air through the first lumen 214 to expand the inner balloon 204.

The catheter 200 can optionally include a stabilizing balloon 206 similar to balloon 76 of FIG. 8A. The stabilizing balloon 206 can be made of silicone, although other materials are also contemplated. If provided, the catheter 200 would have a lumen, e.g., lumen 210, to inflate the stabilizing balloon 206. Angled side port 217 can be provided in communication with lumen 210 for injection of a liquid or gas to expand the stabilizing balloon 206. The foregoing description of the stabilizing balloons in connection with other embodiments is fully applicable to balloon 206. Catheter 200 also includes a lumen 211 with a distal side opening 211*a* (FIG. 18B) to provide for drainage of the bladder as in the aforedescribed embodiments. In the illustrated embodiment, the side opening 211*a* is distal of outer balloon 202 and inner balloon 204 and distal of the stabilizing balloon 210 which as shown is proximal of outer balloon 202 and inner balloon 204. In alternate embodiments, the stabilizing balloon 206 can be distal of the outer balloon 202.

Thus, in the embodiment of FIG. 18A, catheter 200 has five lumens: 1) lumen 214 communicating with inner balloon 204 to inflate the inner balloon 204 and forming the air filled chamber; 2) lumen 212 communicating with outer balloon 202 for inflating outer balloon 202; 3) lumen 210 communicating with the stabilizing balloon 206 to inflate stabilizing balloon 206; 4) drainage lumen 211 having a side opening 211*a* at a distal end for drainage of the bladder; and 5) lumen 216 for the temperature sensor wire(s) 232. Catheter 200 also has three angled extensions/ports at its proximal end 201: 1) port 218 for access to lumen 214 to inflate the inner balloon 204; 2) port 222 for access to lumen 212 to inflate outer balloon 202; and 3) port 217 for access to lumen 210 to inflate stabilizing balloon 206. Drainage lumen 211 extends linearly terminating at region 223. Lumen 216 terminates proximally at the region of the angled ports 218, 222 through which wire 232 can exit from the catheter 200 for connection to a temperature monitor via hub 240. Note the location of the ports can vary from that illustrated in FIG. 18. Also, location of the lumens and the cross-sectional dimension and size of the lumen can vary from that shown in FIG. 23 as FIG. 23 provides just one example of the location and size, e.g., diameter, of the lumens as well as the shape/cross-sectional configuration and location. The catheter 200, as in the foregoing embodiments, can have an atraumatic tip 209.

In use, catheter 200 is inserted into the bladder and stabilizing balloon 206 is inflated to secure the catheter 200 in place. The system is charged by inflation of the inner balloon 204, i.e., preferably partially inflated for the reasons discussed above, by advancement of air through lumen 214 upon attachment of the pressure transducer 240 to the port 218 of catheter 200. Such attachment moves elongated member 242 into lumen 214 to displace the air (or other gas) already in the lumen 214 to expand the inner balloon 204. A closed system is formed by the internal space 204*a* of the inner balloon 204 and the internal lumen 214 communicating with the internal space 204*a* of inner balloon 204. In a preferred embodiment, additional air does not need to be added to the balloon 204/lumen 214. Outer balloon 202 is filled, i.e., preferably partially inflated for the reasons discussed above, via injection of air through the separate port 222 which communicates with lumen 212 of catheter 200. With the outer balloon 202 inflated, pressure monitoring can commence as external pressure applied to the larger circumferential outer surface of the outer balloon 202 compresses and deforms the outer balloon 202 which exerts a force on the outer wall of inner balloon 204 and compresses the inner balloon 204. As the inner balloon 204 is compressed and deformed in response to compression/deformation of the outer balloon 202 based on changes to bladder pressure, the pressure sensor within the external hub 240 attached at the proximal end of the catheter 200 provides continuous pressure readings, converted to an electrical signal by the transducer within the hub 240, and then electrically communicates through a connector, e.g. cable 245, to an external monitor either directly or via a converter to display pressure readings. Although, the system is capable of continuous pressure and continuous temperature monitoring, it can also be adapted if desired for periodic monitoring so the pressure and/or temperature readings can be taken at intervals or on demand by the clinician. Temperature readings are also taken during the procedure as temperature sensor 230 is connected to a temperature monitor via wire 232 connected to a connector of hub 240 which is connected to the temperature monitor to display temperatures. The temperature monitor can be separate from the pressure display monitor or alternatively integrated into one monitor. Cable 245 can connect to the temperature monitor as well (directly or via a converter) or a separate cable extending from the hub 240 could be provided for connection to the temperature monitor.

Note that although separate lumens are provided for the inflation of inner balloon 202 and outer balloon 204, in an alternate embodiment, a single lumen can be utilized to inflate both balloons 202 and 204. In such embodiment, catheter 200 can have one less angled port and one less lumen since inflation of the outer balloon 202 would be through port 218 and lumen 214.

The proximal and distal end of the inner balloon 204 in the illustrated embodiment are within the confines of the outer balloon 202, i.e., the proximal end of the inner balloon 204 is distal of the proximal end of the outer balloon 202 and the distal end of the inner balloon 204 is proximal of the distal end of the outer balloon 202. Thus, in this illustrated embodiment, the inner balloon 204 is fully encapsulated within the outer balloon 202.

With the inner/outer balloon arrangement, the larger outer surface of the outer balloon 202 takes gross measurements and then the forces are concentrated on the smaller inner balloon 204 to amplify/concentrate pressure on the small area of the inner balloon so small changes can be detected and waves transmitted to the pressure transducer (via the length of the lumen to a proximal transducer, e.g. an external pressure transducer).

As noted above, preferably no additional air needs to be added after mounting of hub 240. However, it is also contemplated that in alternate embodiments a port can be provided in communication with hub 240 to enable subsequent injection of air though lumen 214 and into inner balloon 204. Additionally, outer balloon 202 can in some embodiments receive additional fluid injection via port 222 during the procedure.

FIGS. 30A-34 illustrate an alternate embodiment of the catheter, designated generally by reference numeral 400. The catheter 400 differs from catheter 200 of FIG. 18A in the attachment of the inner and outer balloons to the catheter shaft. The catheter 400 also differs catheter 200 described above in the location of the drainage hole(s). In all other respects catheter 400 is the same as catheter 200 and thus the features and functions of catheter 200, and its alternatives disclosed herein, are fully applicable to catheter 400.

Catheter 400 has a shaft 402 having a distal region (portion) 402*a* terminating in a distal opening 402*b*. Distal opening 402*b* receives core pin 410 therein. Core pin 410, also referred to as a bonding pin or a connecting pin, has a proximal end 414*a* dimensioned for insertion in a press fit through opening 402*b* and into the lumen in distal region 402*a* of shaft 402. In the illustrated embodiment, the proximal end 414*a* has a non-circular shape, e.g., a triple lobe or Y shape, corresponding to the shape of the opening 402*b*. The distal end of the pin 410 has a reduced diameter cylindrical portion 414*b* which receives thereover a distal tip 412 (also referred to herein as a distal plug).

Catheter 400 further has a retention (stabilizing) balloon 404, an inner balloon 406 and an outer balloon 406. The retention balloon 404 is spaced proximally of the outer balloon 406 and inner balloon 408. The outer balloon 406 encapsulates the inner balloon 408 such that the inner wall 408c of the inner balloon 408 is contained within the outer balloon 406. The outer wall 408c of outer balloon 408 is exposed to the patient, e.g., the bladder. The retention balloon 404 functions in the same way as the retention (stabilizing) balloons described above and can of varying shapes as described herein. The inner and outer balloons 408, 406 function in the same way as the inner and outer balloons 204, 202 of catheter 200.

Figure 30A:
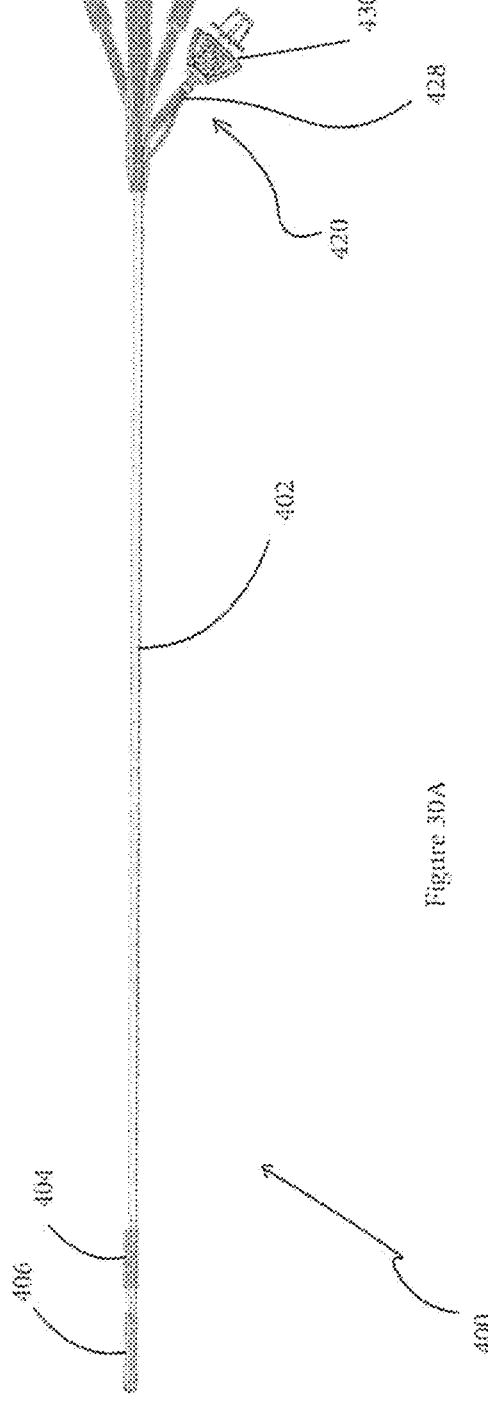
FIG. 30A is a side view of an alternate embodiment of the catheter of the present invention.
Figure 30B:
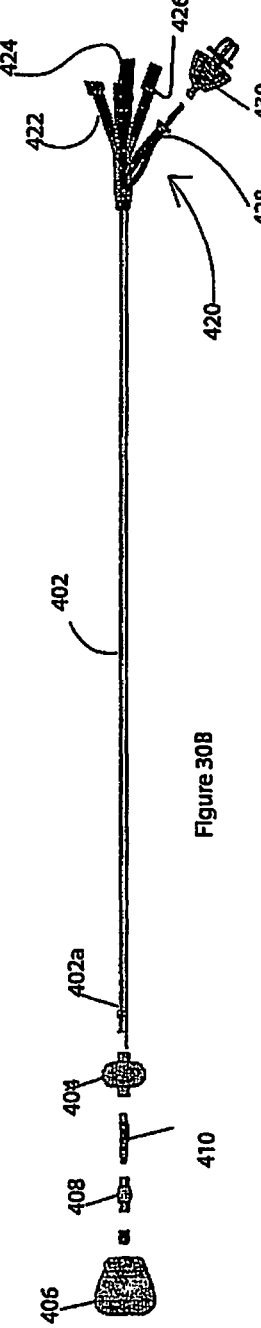
FIG. 30B is an exploded side view of the catheter of FIG. 30A.
Figure 30C:
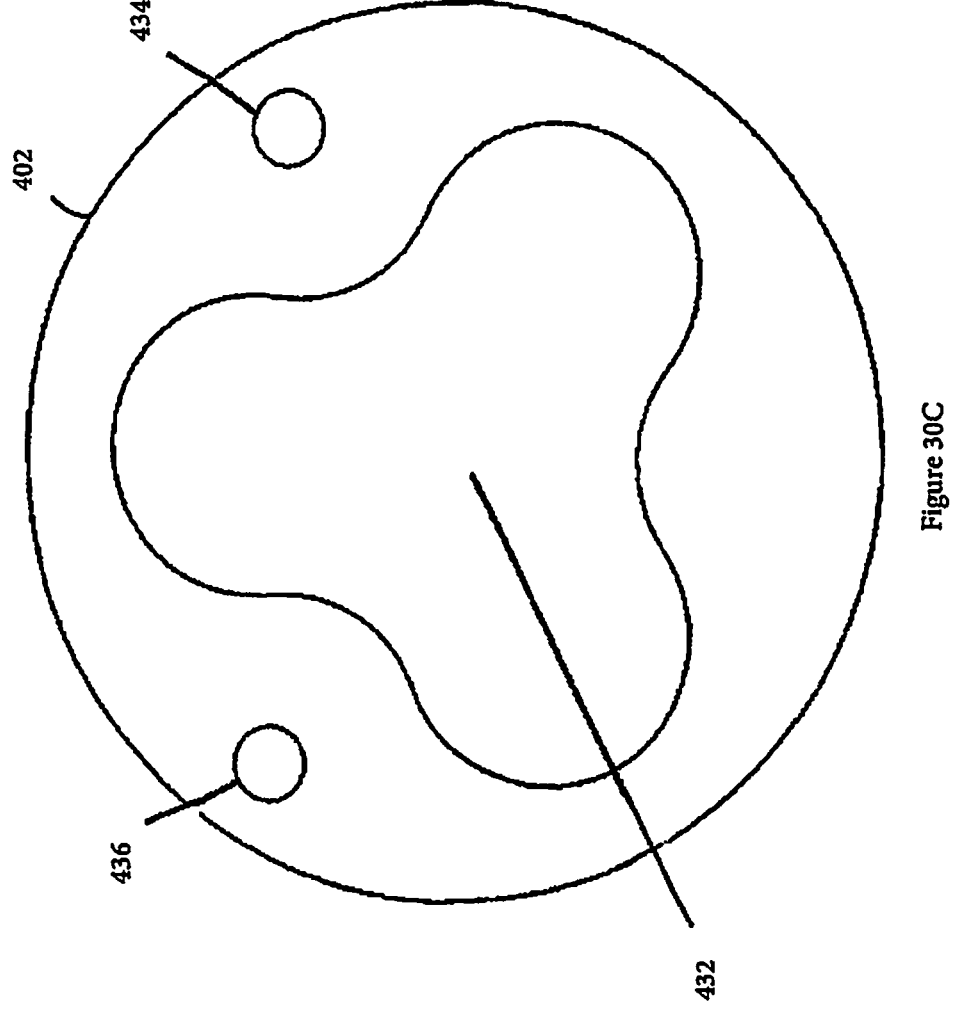
FIG. 30C is an enlarged transverse cross-sectional view of the catheter of FIG. 30A.
Figure 31:
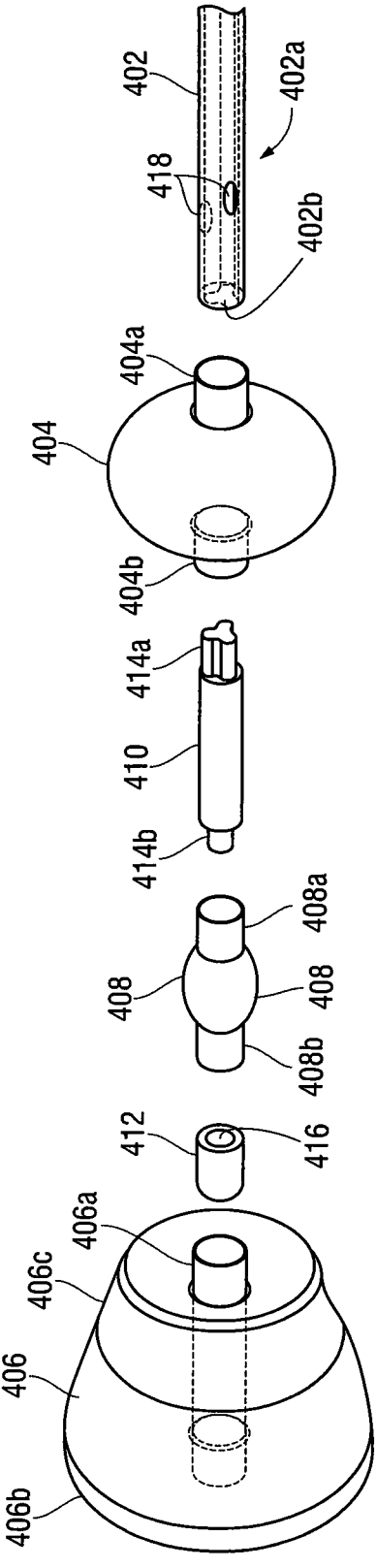
FIG. 31 is a close up exploded view of the distal end of the catheter of FIG. 30A.

As shown in the cross-sectional view of FIG. 30C, the catheter shaft 402 has four lumens: 1) lumen 438 communicating with inner balloon 408 to inflate the inner balloon 408 and forming the gas, e.g., air, filled chamber; 2) lumen 434 communicating with outer balloon 406 for inflating outer balloon 406; 3) lumen 436 communicating with the retention balloon 404 to inflate retention balloon 404; and 4) drainage lumen 432 having one or more side openings 418 (FIG. 32C) at a distal region of the catheter for drainage of the bladder. The lumens 438, 434 and 436 terminate inside of their respective balloons 402, 406 and 404. The side opening(s) 418 for drainage are positioned between the outer/inner balloon 406, 408 and the retention balloon 404 such that the outer balloon 406 and inner balloon 408 are distal of the side opening(s) 418 and the retention balloon 404 is proximal of the side opening(s) 418. Temperature sensor wires can be positioned in lumen 438, running parallel to the tubular portion (described below) of the inner balloon in embodiments where the balloon has the tubular portion, e.g., balloon 458, with the thermistor sensor located near the drainage holes 418. Alternatively, the temperature sensor wires can be positioned in the same lumen as the lumen for filling the outer balloon or the inner balloon or an additional lumen can be provided for the temperature sensor wire(s).

Catheter 400 also has three angled extensions/ports at its proximal end 420 (FIG. 30B): 1) port 428 for access to lumen 438 to inflate the inner balloon 408; 2) port 426 for access to lumen 434 to inflate outer balloon 406; and 3) port 422 for access to lumen 436 to inflate stabilizing balloon 404. Drainage lumen 432 extends linearly terminating at a distal region proximal of core pin 410 and terminating proximally at port 424. Note the location of the ports can vary from that illustrated in FIG. 30B. Also, the location of the lumens and the cross-sectional dimension and size of the lumens can vary from that shown in FIG. 30C as FIG. 30C provides just one example of the location and size, e.g., diameter, of the lumens as well as the shape/cross-sectional configuration and location.

Figure 32A:
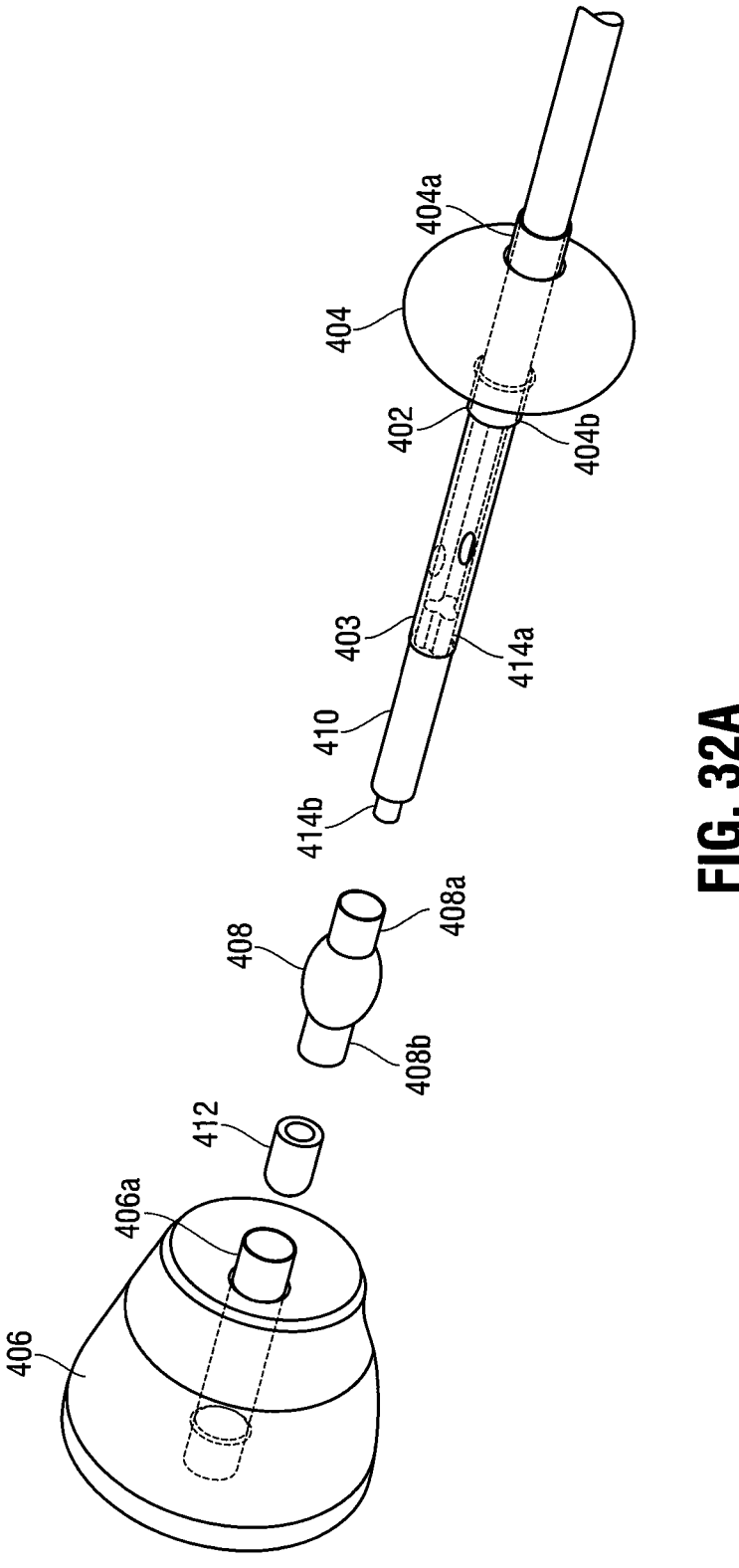

The steps of manufacture (assembly) of the balloons to the catheter will now be described with reference to FIGS. 32A-32C. The assembly steps are shown with the balloons inflated for ease of illustration but the assembly would preferably be made with the balloons deflated. In manufacture, the stabilizing balloon 404, which is identical in function and can be the same shape as the stabilizing (retention) balloons discussed above, such as a donut shape as shown, is placed over the outer shaft 402 and proximal and distal extensions 404a, 404b of balloon 404 are attached, e.g., welded, to the shaft 402. In the illustrated embodiment, the stabilizing balloon 404 is composed of the same material as the distal region 402a of shaft 402. In one embodiment by way of example, the material is silicone, although other materials are also contemplated. After the stabilizing balloon 404 is placed over the shaft 402, positioned proximal of the distal end of the shaft 402, and preferably after it is also attached to the shaft 402, the bonding pin 410 is inserted into the shaft 402. More specifically, proximal extension 414a extends into distal opening 402b of shaft 402, with a portion of the pin 410 including the distal extension 414b extending distally from and exposed from the shaft 402 as shown in FIG. 32A. The bonding pin 410 is preferably mechanically fixed, such as by a press fit into the lumen of the shaft 402. The shaft 402 contains small holes overlying the inserted pin 410 and the small holes are filled with material, e.g., silicone, to secure the pin 410 to the shaft 402.

Figure 32B:
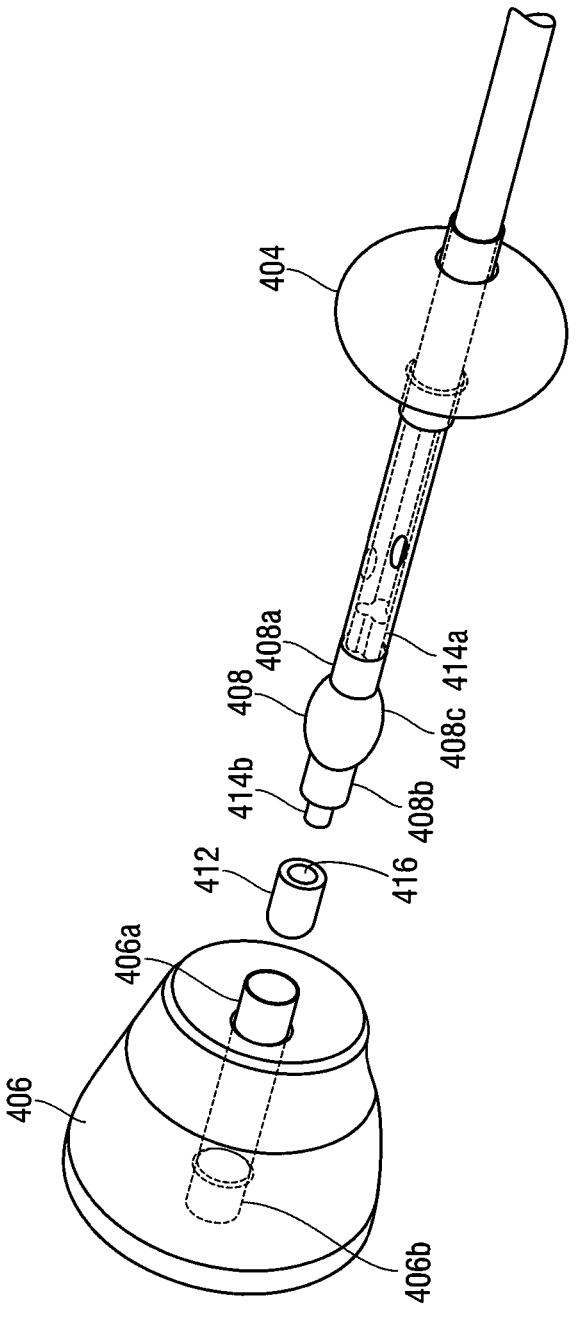
Figure 32C:
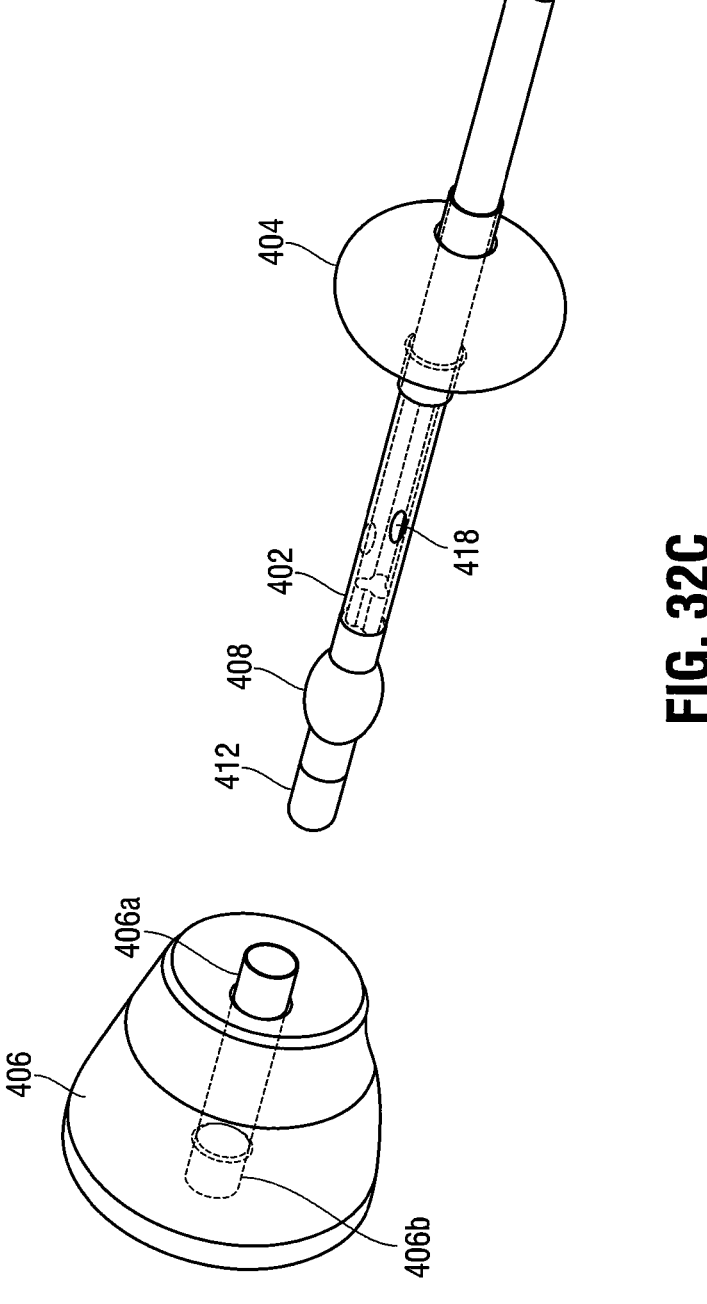
Figure 32D:
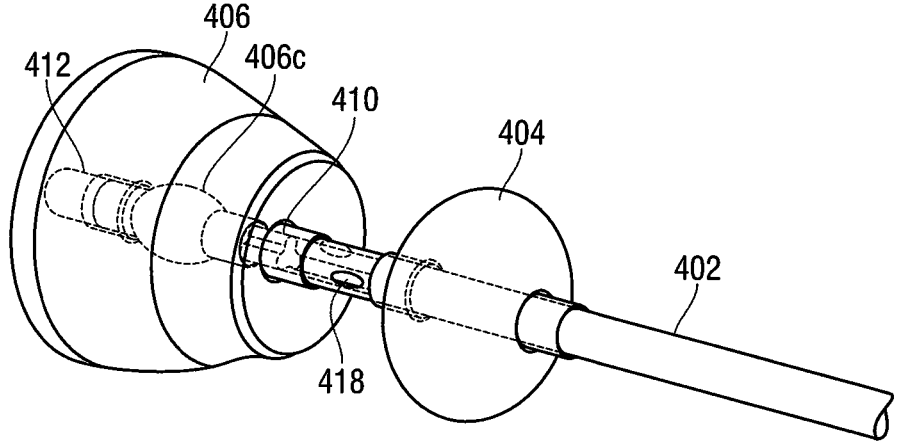
Figure 33:
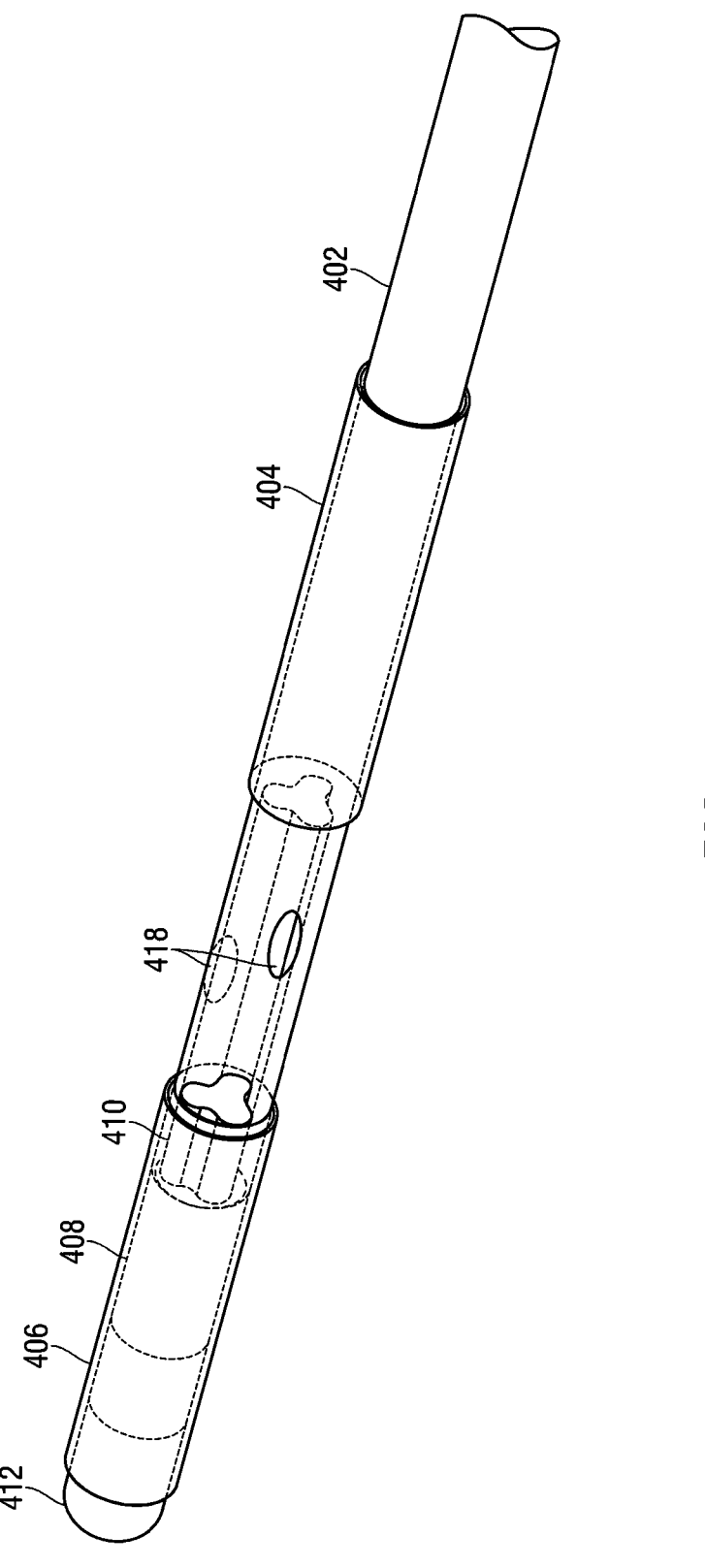
FIG. 33 is a side perspective of the distal end of the catheter of FIG. 30A showing the balloons in the deflated condition.

Next, with reference to FIG. 32B, the inner balloon 408 is placed over the bonding pin 410 and proximal and distal extensions 408a, 408b are attached, e.g., welded, to the bonding pin 410. The balloon 408 is attached to the center cylindrical region of the pin 410, leaving the proximal and distal extensions 414a, 414b exposed. In the illustrated embodiment, the inner balloon 408 is composed of the same material as the bonding pin 410 and both the bonding pin 410 and inner balloon 408 are composed of a different material than the distal region 402a of the shaft 402. (The distal region 402a can be the same material as the remainder or other portions of the shaft 402 or composed of a different material). After placement of the inner balloon 408 over the bonding pin 410, and either before or after attachment (e.g., welding) of the inner balloon 408 to the pin 410, distal tip or plug 412 is placed over distal extension 414b of pin 410 (FIG. 32C). Distal tip 412 has an opening 416 to receive extension 414b and is mechanically fixed, e.g., by a press fit, to the pin extension 414b. As shown, the tip 412 is spaced distally from the inner balloon 408. The tip 412 in some embodiments is composed of a different material than the core pin 410 and is preferably composed of the same material as the outer balloon 406, e.g., silicone, although other materials can be utilized. FIG. 32D illustrates the next step in assembly as the outer balloon 406 is inserted over the distal tip 412 and over the inner balloon 408 and bonded at a proximal extension 406a to the outer shaft 402 and at the distal extension 406b to the tip 412. Thus, as can be appreciated, in this embodiment, the outer balloon 406 is bonded at both ends to structure composed of the same material as the outer balloon 406; and the inner balloon 408 is bonded at both ends to structure composed of the same material as the inner balloon 408. Also, the retention balloon 404 is bonded at both ends to structure composed of the same material as the retention balloon 404. In other words, as can be appreciated, the embodiment of FIGS. 31-34 enables inner and outer balloons of different materials to be attached to the shaft of the catheter, e.g., materials that do not bond. Additionally, or alternatively, it enables a balloon of a different material than the shaft to be attached to the shaft. In one embodiment by way of example, the shaft is composed of silicone, the inner balloon is composed of EVA and the outer balloon is composed of silicone so EVA is bonded to EVA and silicone is bonded to silicone. In such embodiment, the core pin by way of example is composed of EVA. It should be appreciated that these materials are provided by way of example as other materials are also contemplated.

Figure 34:
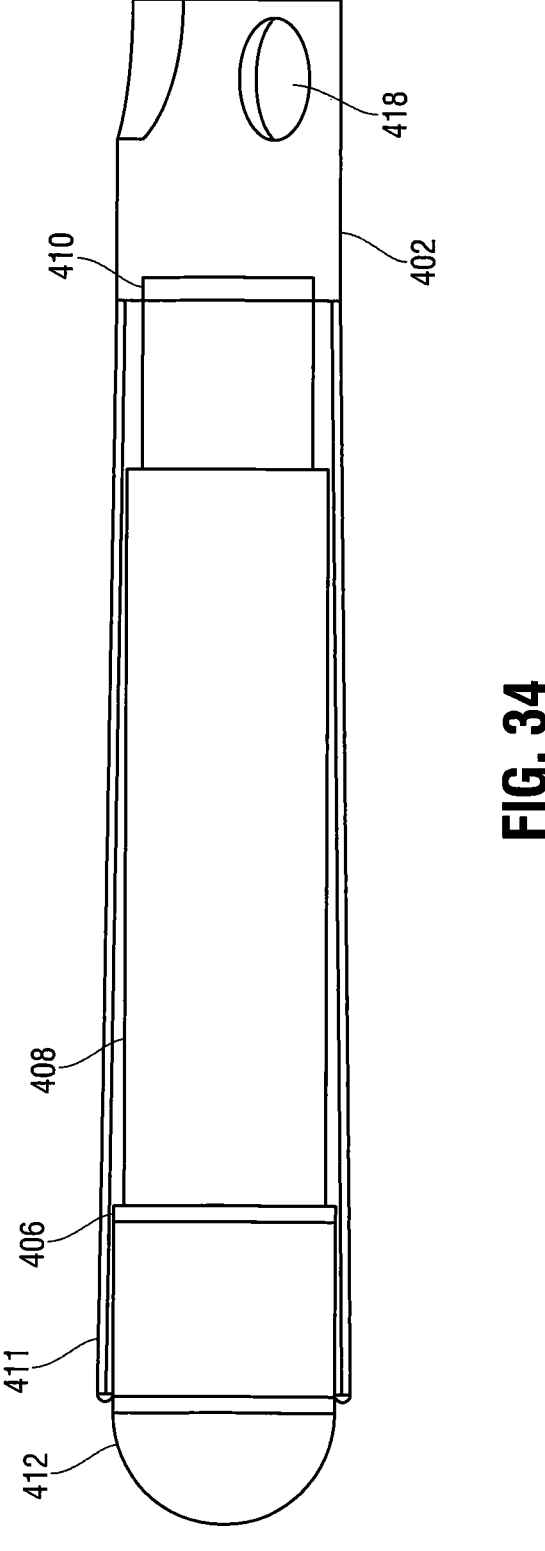
FIG. 34 is a close up view of the outer balloon of FIG. 33 in the deflated condition shown folded over itself.
Figure 35:
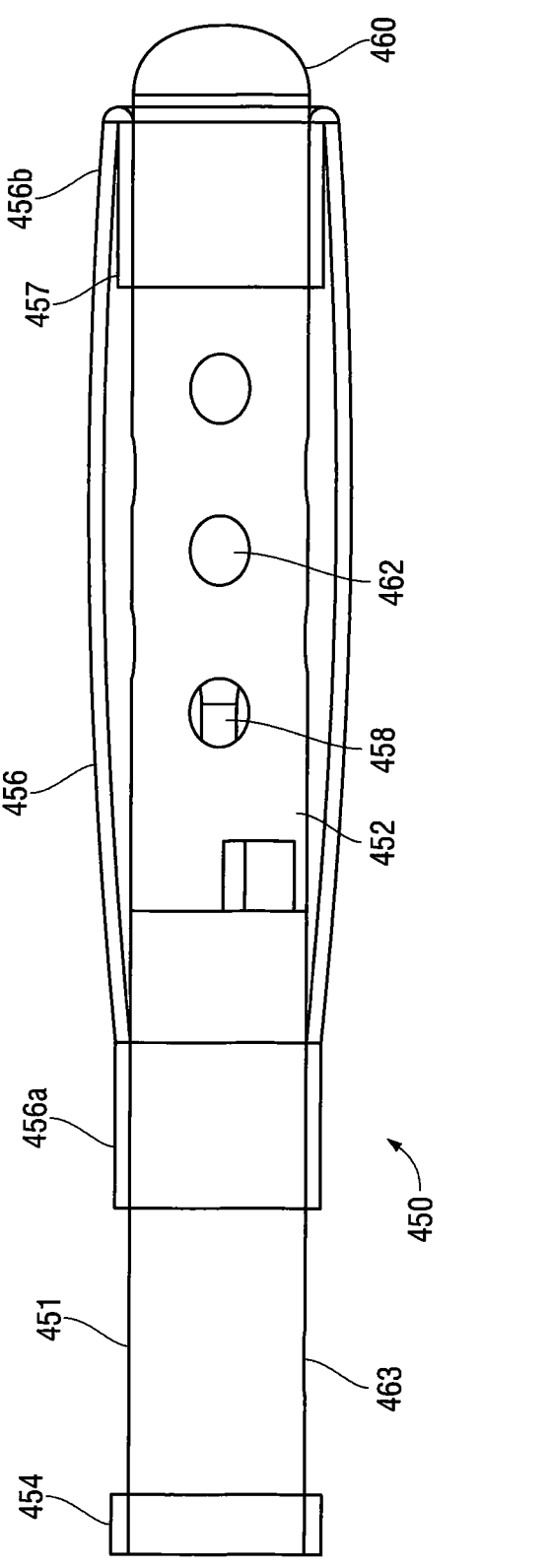
FIG. 35 is a side view of the distal region of the catheter of an alternate embodiment.
Figure 36:
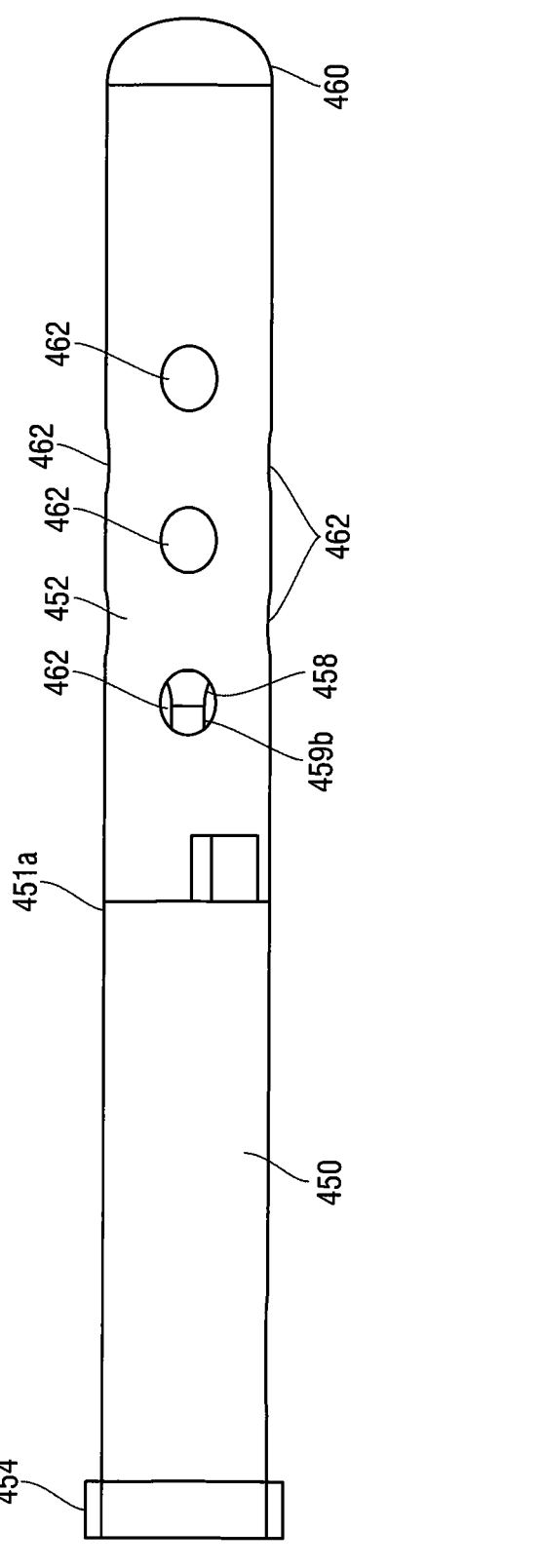
FIG. 36 is a view similar to FIG. 35 with the outer balloon removed for clarity.

In some embodiments, the outer balloon 406 is folded over itself as shown in FIG. 34 to allow the balloon 406 when inflated to extend out and fully cover the distal tip 412. Thus, the outer balloon 406 in its deflated condition has a distal cuff 411 which exposes the distal tip 412 for atraumatic insertion of the catheter 400, and expands to cover the distal tip 412 when inflated when the catheter 400 is fully inserted and placed at the target location. The balloons 404, 406 and 408 can be of the various shapes of the stabilizing, outer and inner balloons disclosed herein. In FIGS. 30A to 34 the outer balloon 406 by way of example is shown as pear shaped.

FIGS. 30A-34 illustrate the fully assembled catheter 400 which is used to measure pressure in the same manner as catheter 200 of FIG. 18A. Thus, a transducer hub 430, which can be any of the transducer hubs disclosed herein, such as hub 240 of FIG. 24A, hub 300 of FIG. 28A, etc., is attached to port 420 to advance gas, e.g., air through the lumen to inflate inner balloon 408. The lumens 438, 434 for inflation of the inner balloon 408 and outer balloon 406 are radially spaced from core pin 410 as core pin occupies the drainage lumen 432 (distal of side openings 418) and does not interfere with the balloon inflation lumens 434, 438.

Side opening(s) 418 in catheter 400 communicate with the drainage lumen 432 for draining the bladder. As shown, the drainage opening(s) 418 in this embodiment is positioned between the a) outer balloon 404/inner balloon 408 and b) retention balloon 404. More than one drainage opening can be provided. It should be appreciated that such location of the drainage opening(s) between the retention balloon and pressure balloon(s), rather than distal of the pressure balloon(s) can be utilized with any of the catheter embodiments disclosed herein.

As noted herein, the catheters of the present invention can be utilized for measuring other pressure in a patient and are not limited to intra-abdominal pressure nor limited to measuring bladder pressure.

In the foregoing embodiments, the inner balloon is positioned within the outer balloon and deformation of the outer balloon based on changes in pressure within the patient, e.g., within the bladder in response to abdominal pressure, causes deformation of the inner balloon as the fluid within the outer balloon (or wall) exerts a pressure against the wall of the inner balloon. This deforms the inner balloon to provide a pressure reading. In the alternate embodiment of FIGS. 35-41, the inner balloon is positioned within a chamber (or cage). This chamber forms an inner balloon encapsulating member as it encircles/encapsulates the inner balloon and is positioned between the inner balloon and outer balloon. Thus, the encapsulating member (chamber) separates the outer wall of the inner balloon from the interior of the outer balloon. However, the chamber has a series of openings so that the fluid within the outer balloon can pass through the chamber and apply a pressure against the outer wall of the inner balloon to deform the inner balloon to provide pressure readings in the same manner as the other embodiments disclosed herein.

With reference now to FIGS. 35-41, the catheter 450 has an elongated shaft 451. Note only the distal end of the catheter 450 is shown; the proximal end, hub, connector, etc. being the same as in the foregoing inner and outer balloon embodiments, e.g., catheter 200 of FIG. 18A. The catheter 450 has a retention balloon 454 identical to retention (stabilizing) balloon 206 of catheter 200 (or other stabilizing balloons disclosed herein), an inner balloon 458 and an outer balloon 456. In the gap (space) between the proximal end of the outer balloon 458 and the distal end of the retention balloon 454, is a drainage hole 463 (or multiple drainage holes) for draining the cavity, e.g., the bladder. A thermistor can be placed adjacent the drainage opening 463 for temperature readings, and the thermistor wire can extend through a lumen of the catheter 450, e.g., the drainage lumen, the pressure lumen or a separate lumen, for electrical connection to a temperature monitor. Catheter 450 has three lumens: 1) lumen 486 communicating with outer balloon 456 for inflating outer balloon 456; 2) a lumen communicating with the retention balloon 454 to inflate retention balloon 454; and 3) drainage lumen 484 having one or more side openings 463 at a distal region of the catheter for drainage of the bladder. In this embodiment, the tubular portion of the inner balloon 458 is positioned within the drainage lumen. In an alternate embodiment such as the embodiment of FIGS. 42-46 discussed below, a separate lumen can be provided to receive the tubular portion of the inner balloon.

The outer balloon 456 has a proximal end 456a attached to the shaft 451 and a distal end 456b attached to the chamber 452. The outer balloon 456 can include a cuff 457 like cuff 411 of outer balloon 406 of FIG. 34 wherein it is folded over itself to expose the atraumatic tip 460 of the catheter 450 (the atraumatic tip of the chamber 452) and when expanded covers the tip 460. In one embodiment, the spacing between the proximal end of the outer balloon 456 and the distal end of the retention balloon 454 is about 20 cm but other spacings/distances are also contemplated.

Figure 37:
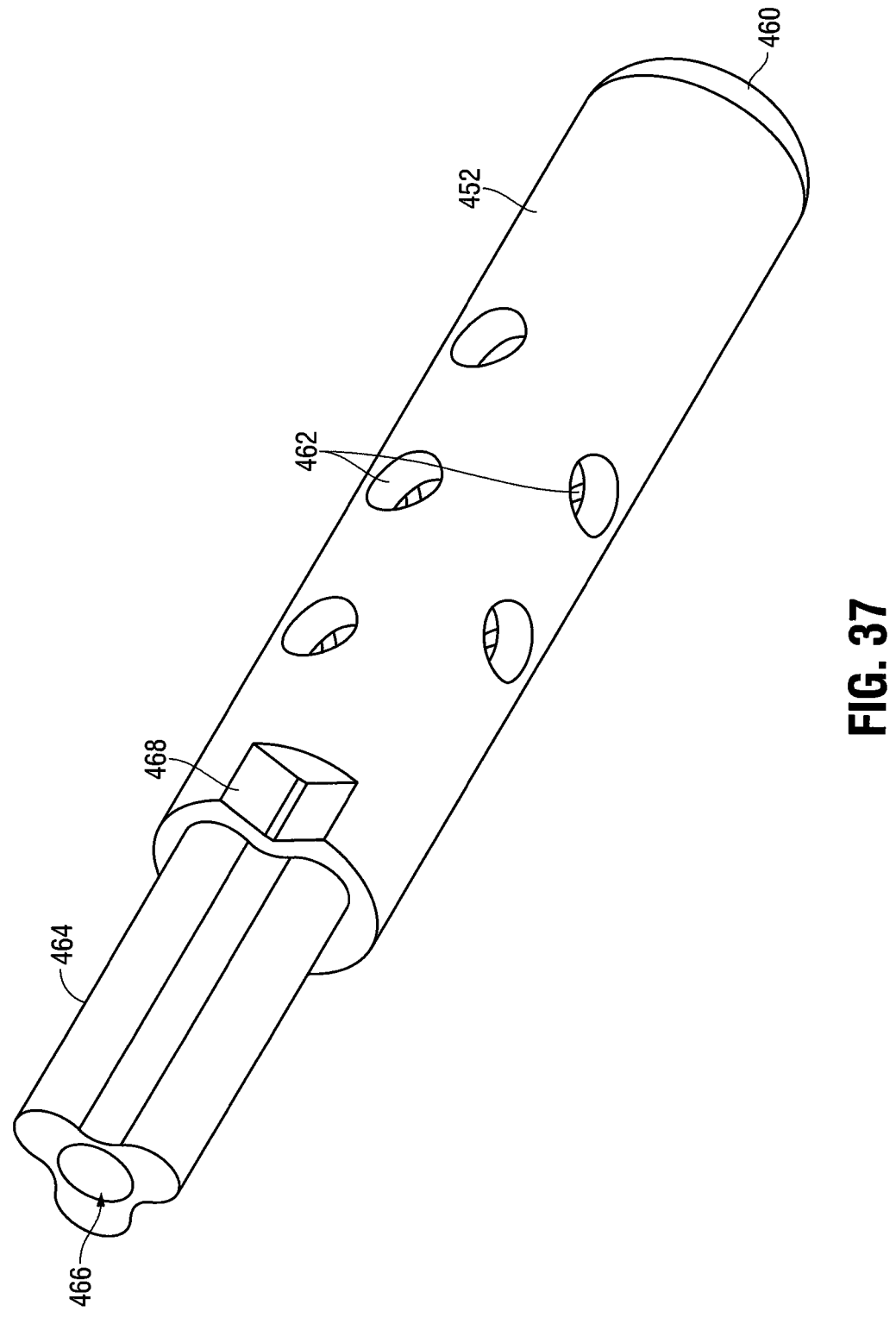
FIG. 37 is a perspective view of the inner balloon chamber of the catheter of FIG. 35.
Figure 38:
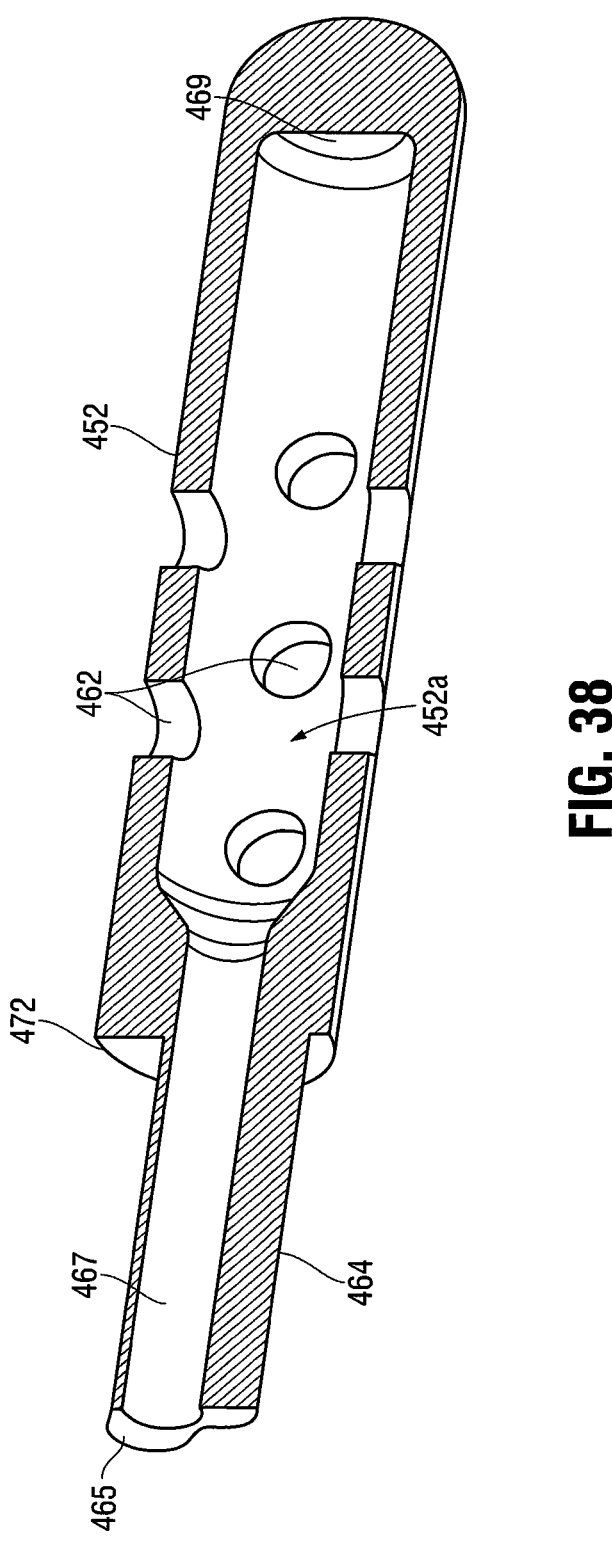
FIG. 38 is a cutaway view of the chamber of FIG. 37.
Figure 39:
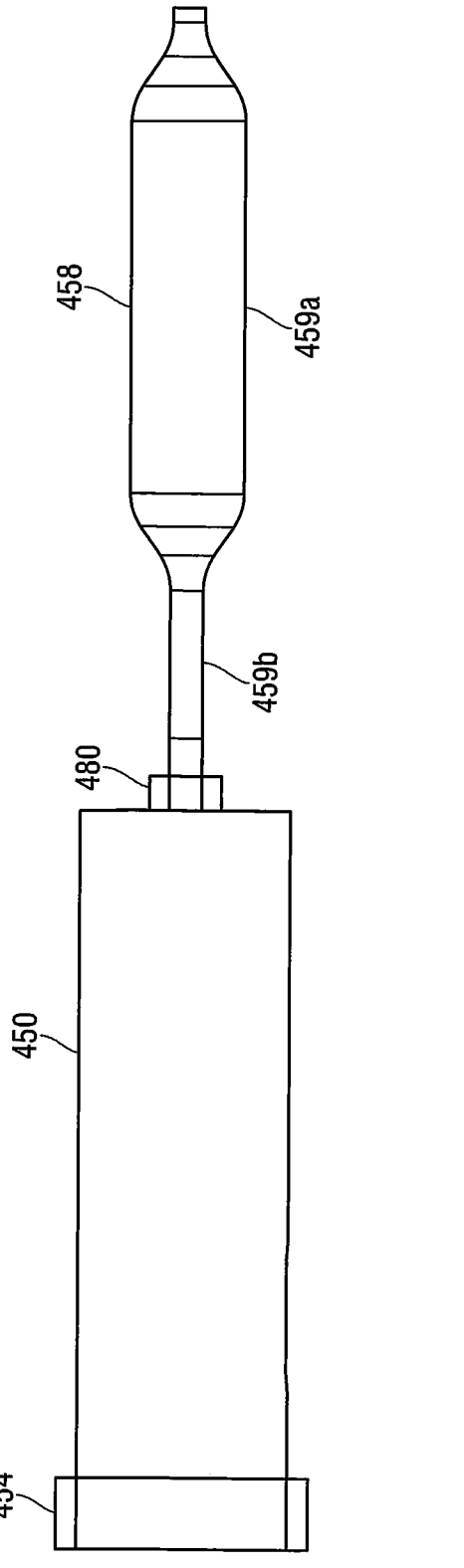
FIG. 39 is a view similar to FIG. 35 with the outer balloon and chamber removed for clarity.
Figure 40:
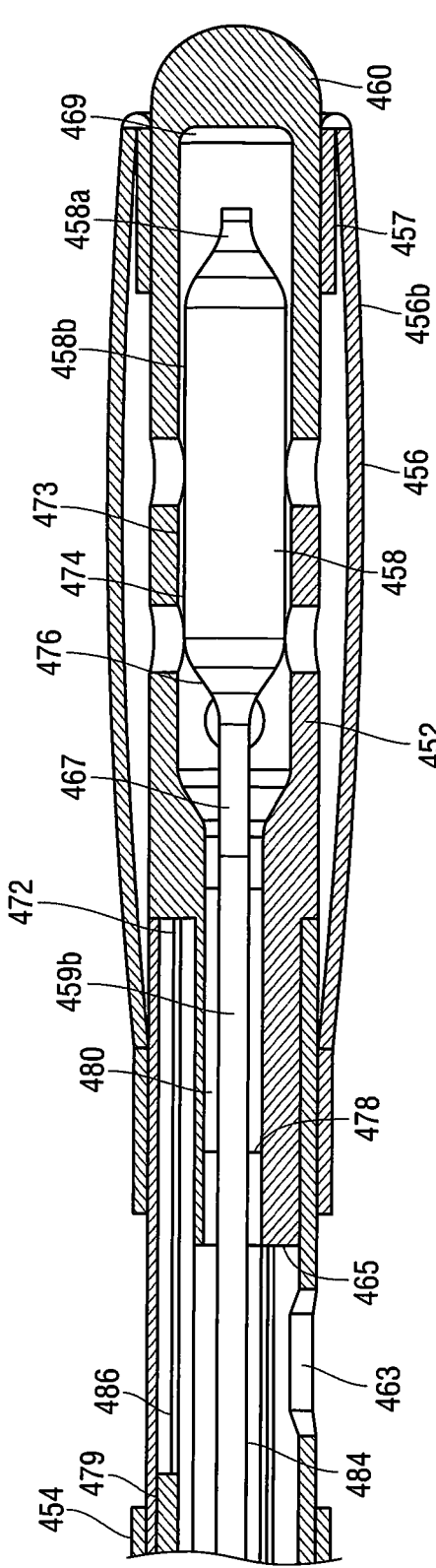
FIG. 40 is a cutaway view of the catheter of FIG. 35.
Figure 41:
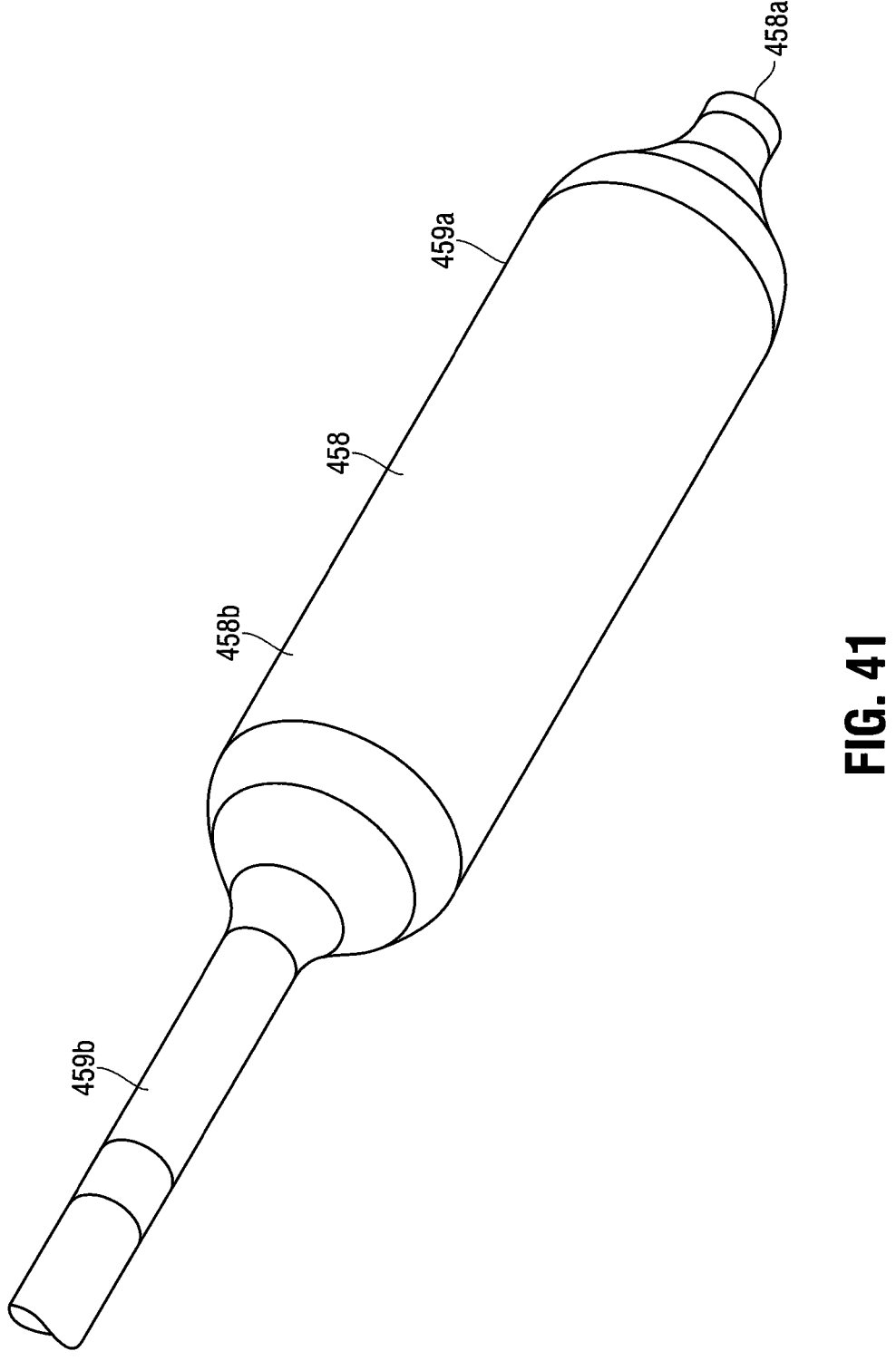
FIG. 41 is a perspective view of the inner balloon of the catheter of FIG. 35.
Figure 42:
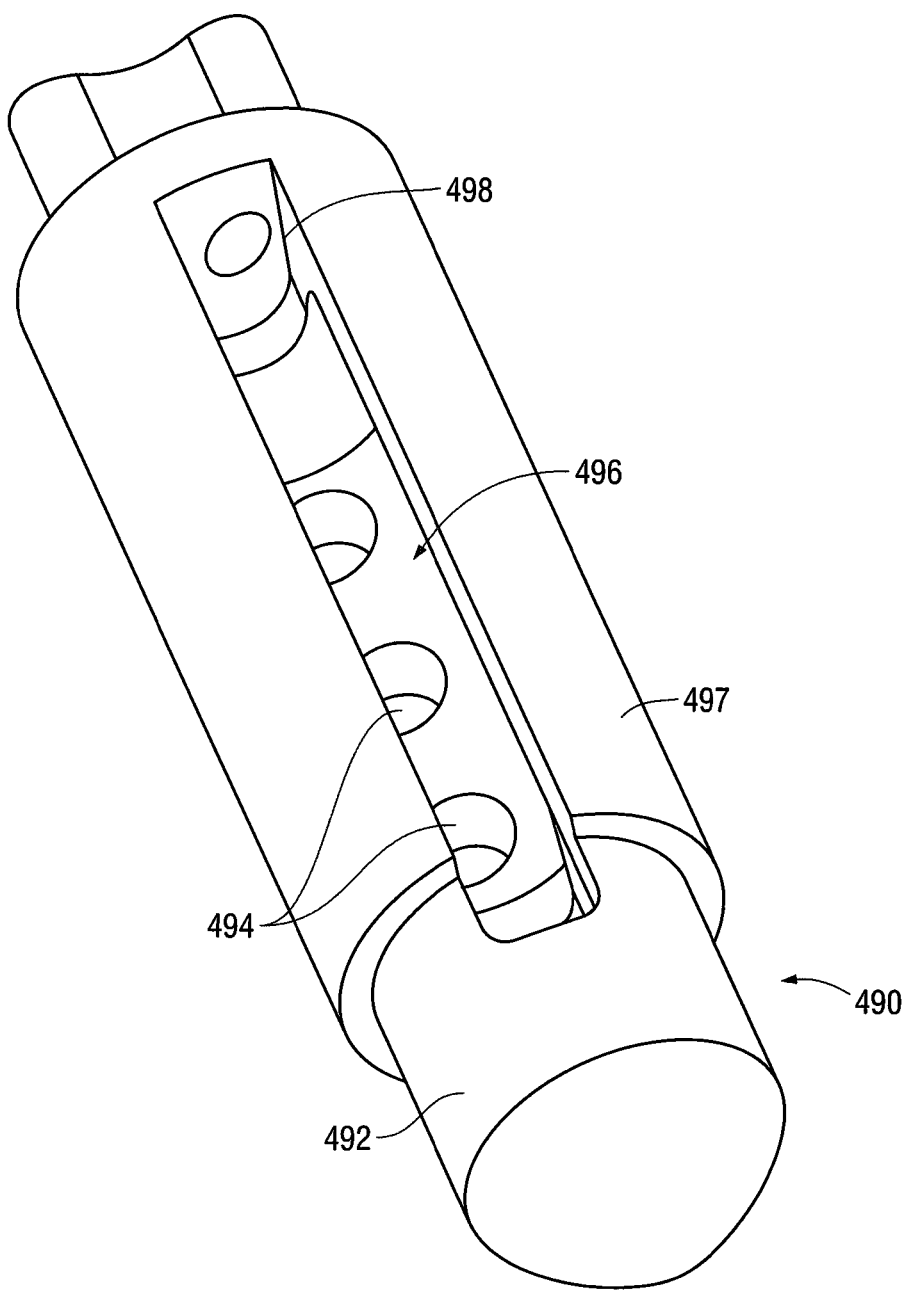
FIG. 42 is a perspective view of an alternate embodiment of the inner balloon chamber.
Figure 43:
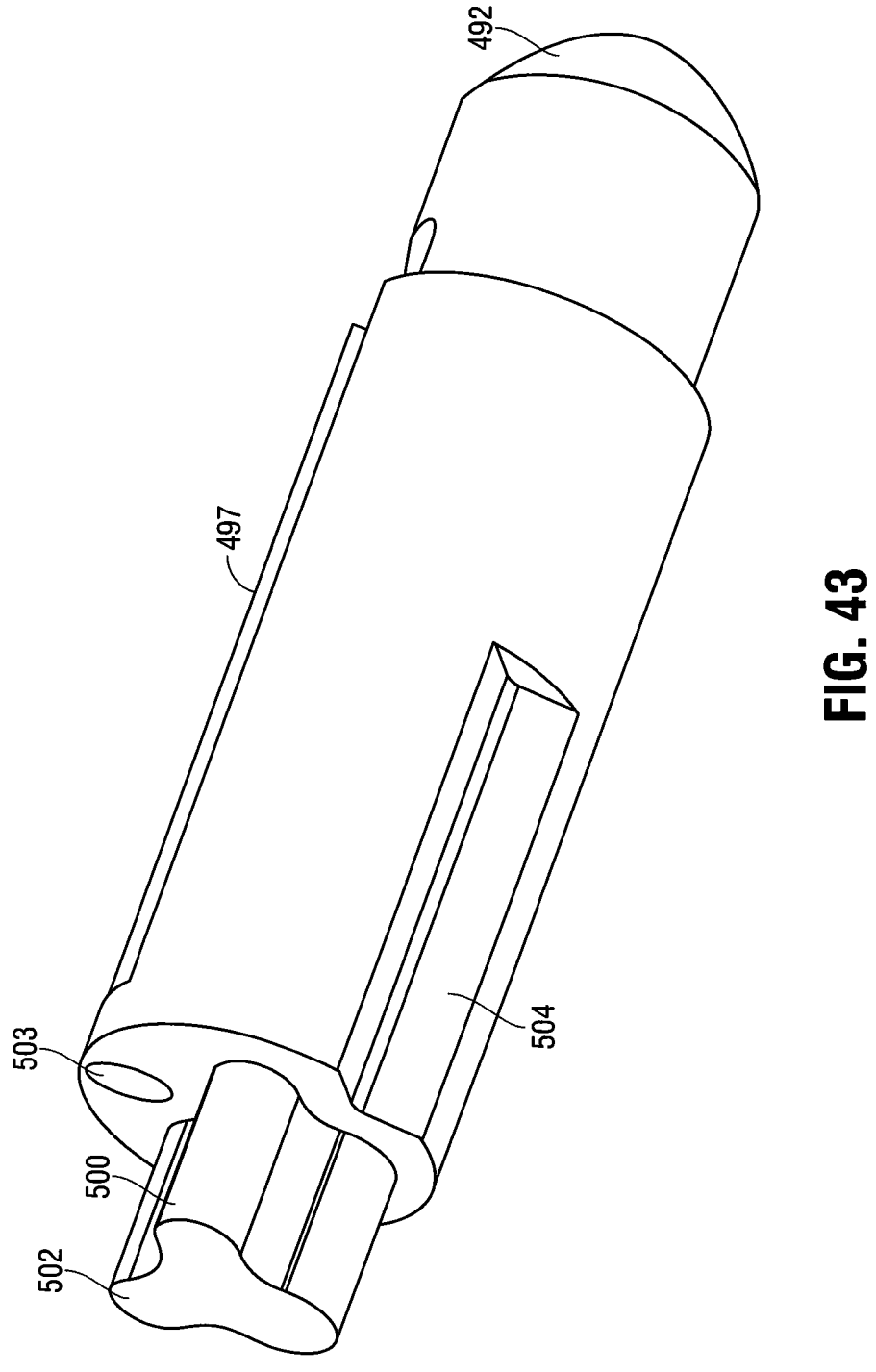
FIG. 43 is a perspective view of the chamber of FIG. 42 from the other side.
Figure 44:
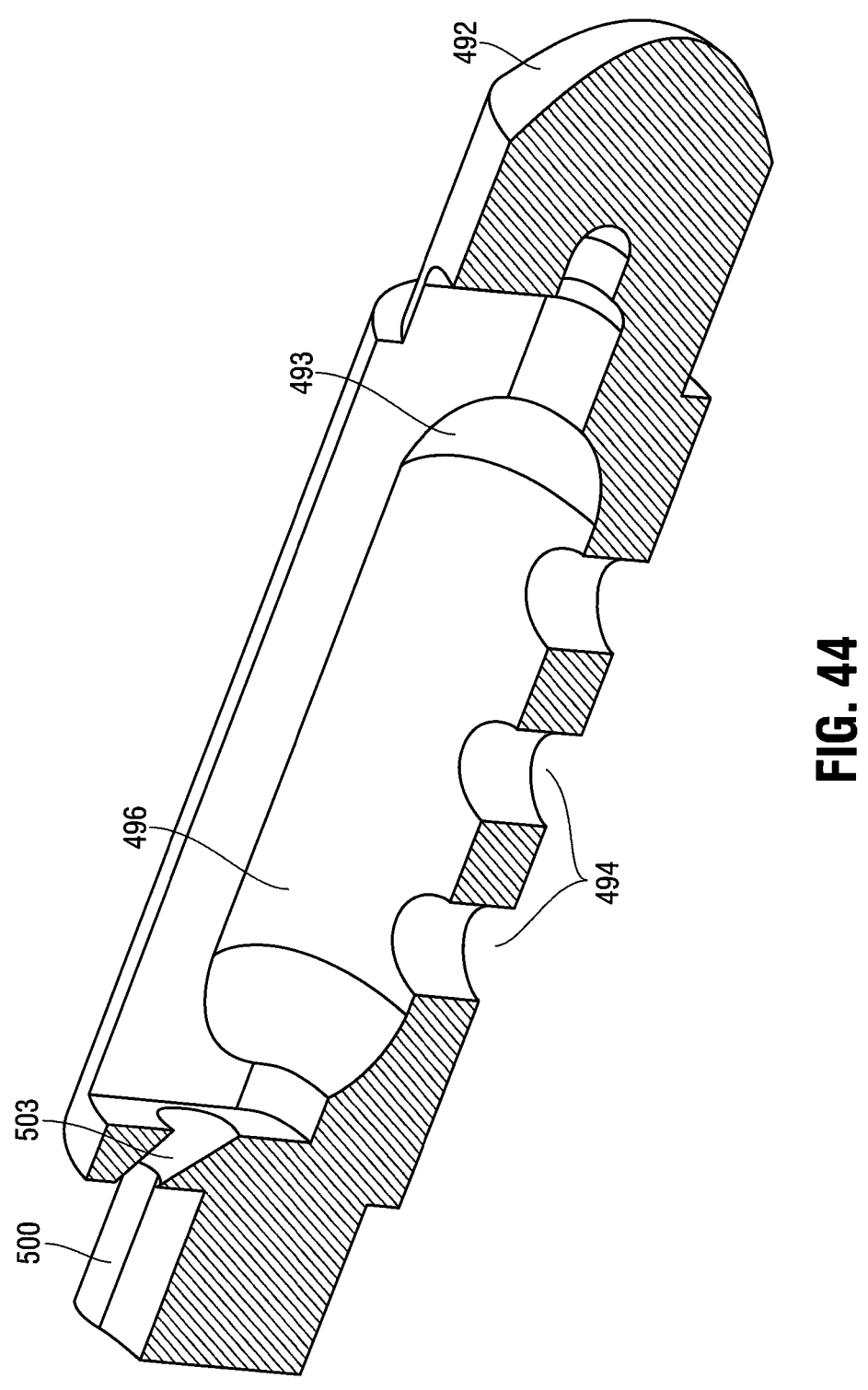
FIG. 44 is a cutaway view of the chamber of FIG. 43.
Figure 45A:
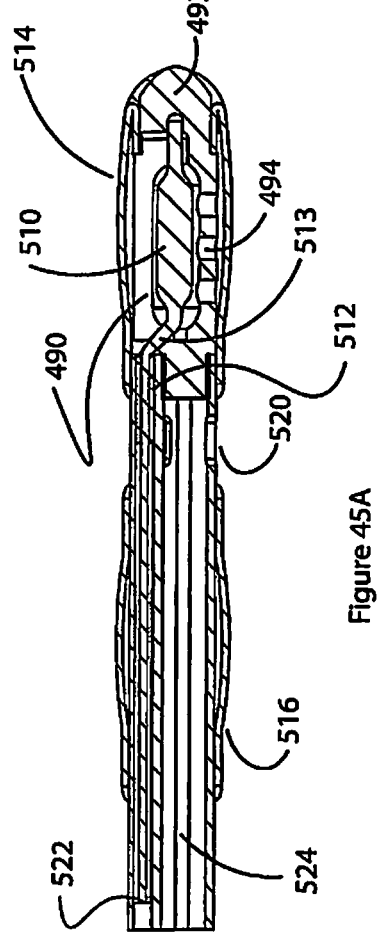
FIG. 45A is a longitudinal cross-sectional view of the distal region of a catheter containing the chamber of FIG. 42.
Figure 45B:
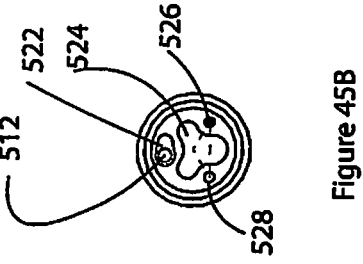
FIG. 45B is a transverse cross-sectional view taken along line A-A of FIG. 45A.
Figure 46A:
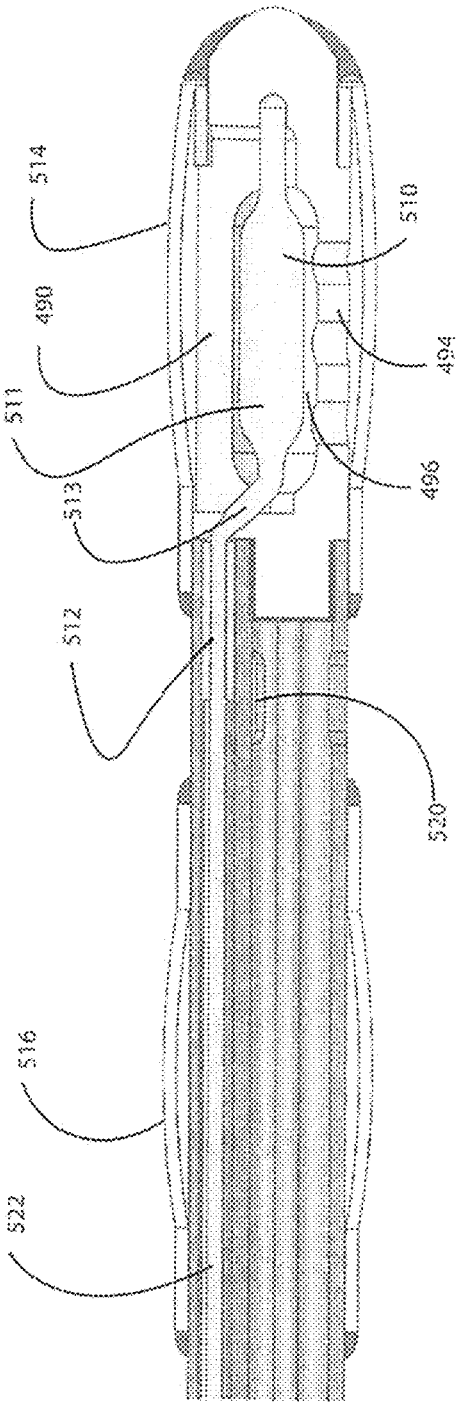
FIG. 46A is a cutaway view similar to the cross-sectional view of FIG. 45.
Figure 46B:
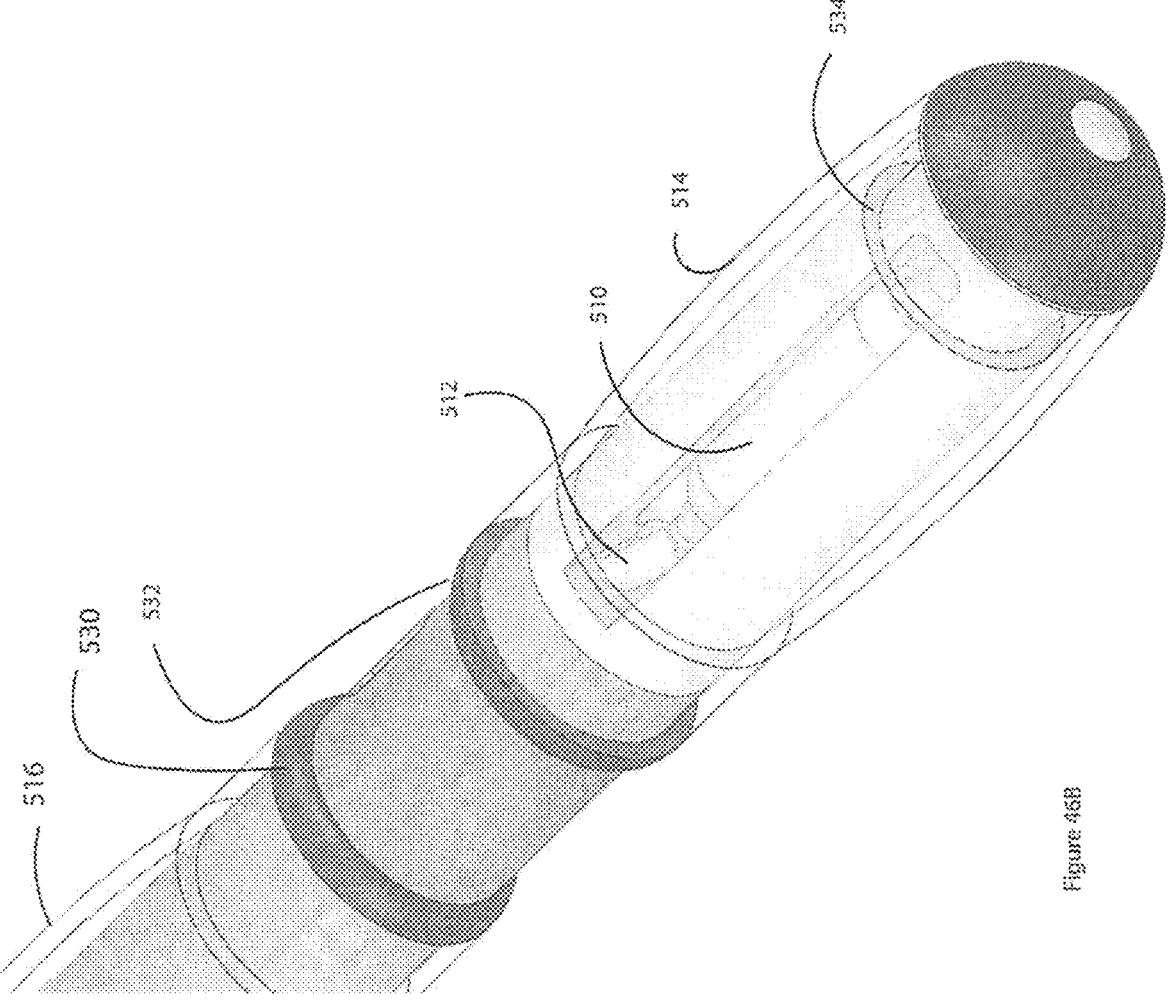
FIG. 46B is a perspective view of the distal end of the catheter of FIG. 46.

The chamber 452 forms the distal end region of the catheter 450 as it extends distally from the distal edge 451a of shaft 451. With reference to FIGS. 37 and 38, chamber 452 has a reduced diameter proximal extension 464 for press fit and attachment within the distal end of shaft 451. Opening 466 in chamber 452 communicates with lumen 467 which extends through proximal extension 464, terminating at cavity 452a of chamber 452. Opening 468 lines up with outer balloon inflation channel for inflating the outer balloon. Chamber 452 has a wall 472 forming a shoulder for abutment with distal wall 459 of shaft 451 (see FIG. 40). Cavity 452a is dimensioned to receive the inner balloon 458 in the deflated condition as well as in the inflated condition. As shown in FIG. 40, in the inflated condition, a small gap 473 exists between the outer wall 458b of the inner balloon 458 and the inner wall 474 of the chamber 452. In some embodiments, the gap is about 0.020 inches although other sized gaps (spacing) are also contemplated. Cavity 452a terminates distally at wall 469. In some embodiments, a wire can extend through the inner balloon 458 and be embedded in wall 469 (pierces the wall 469) to help stabilize and center the inner balloon 458. Such wire can extend proximally from wall 469, through cavity 452a and through lumen 467 and extend through a lumen in the catheter, extending through the entire, or alternatively, a partial, length of the catheter.

Chamber 452 also includes a plurality of openings 462 (only some of which are labeled for clarity) to provide fluid (liquid or gas) flow from the outer balloon 456 against the outer wall 458b of the inner balloon 458 retained within the chamber 452. Thus, the chamber 452 separates the outer wall 458b of the inner balloon 458 from the interior of the outer balloon, except for the communication through the openings 462 in the chamber 452. (The inner and outer balloons are sealed from each other so they are not in fluid communication with each other). One arrangement of chamber openings is shown by way of example in FIGS. 37 and 38, with two rows of three longitudinally aligned openings (holes) and two rows of two longitudinally aligned openings, each row spaced apart radially around the circumference of the chamber 452. The rows are shown equidistantly spaced but other arrangements are also contemplated. Also, a fewer or greater number of rows can be provided and a different number of holes than the number shown can be provided. Holes of different sizes than shown, as well as holes of varying size in the chamber 452, are also contemplated. The chamber 452 can be made of silicone, although other materials are also contemplated.

The inner balloon 458 has balloon portion 459a and a tube portion 459b. The tube portion 459b extends through lumen 467 of chamber 452 and through lumen 484 in the catheter shaft 451. The tube portion 459b can extend the entire length of the catheter 450 such that it terminates adjacent the inflation port; alternatively, it can terminate within the lumen 484 of the shaft 451 or within the lumen 467 of the chamber 452 in which case inflation fluid, e.g., gas such as air, would flow through the shaft lumen (and through lumen 467 in the latter embodiment) for a certain length where it would then enter an opening in the tubular portion 459b for flow into the inner balloon 458. The inner balloon 458 can be made of polyamide such as nylon, although other materials are also contemplated, such as EVA. The inner balloon 458 can be made of various dimensions, and in one embodiment by way of example the full balloon diameter is about 3.5 mm, the balloon length is about 10 mm and the wall thickness is about 0.05 mm. By way of example, the inner diameter tubular portion 459b of the inner balloon 458 could be about 0.2 mm. Other balloon dimensions are also contemplated. A wire could be provided to fill the gap to reduce the air column. The distal end of the inner balloon 458 can be welded or soldered or sealed by other methods.

A sealant or plug 480 can be provided, the plug 480 positioned around the tubular portion 459b of the inner balloon 458 which closes off the lumen 467 distal of the drainage hole 463. The plug 480 could also help maintain the centering of the tubular portion 459b. Plug 480 abuts inner wall 478 of chamber 452 as shown in FIG. 40. The plug in one embodiment is made of RTV silicone.

A thermistor can be positioned adjacent the drainage opening(s) 463 and the temperature sensor wires can be positioned in lumen 484, running parallel to the balloon tubular portion 459b. Alternatively, the temperature sensor wires can be positioned in the same lumen as the lumen for filling the outer balloon or alternatively an additional lumen can be provided for the temperature sensor wire(s).

The outer balloon 456 could include a coating such a parylene to change the modulus of the balloon. That is, such coating could stiffen the balloon so it is not to continuously expanding under pressure, which could cause a reduced pressure reading. The coating can also cover all or part of the catheter which could add lubricity.

The inner and outer balloons disclosed herein can be filled to various volumes. In one example, the inner balloon can be filled to a volume of about 0.16 cc and the outer balloon can be filed to about 10 cc.

As noted herein, the catheters of the present invention can be utilized for measuring other pressure in a patient and are not limited to intra-abdominal pressure nor limited to measuring bladder pressure. Thus, the double balloon/chamber structure of FIGS. 35-41 can be used for example with catheters to measure maternal uterine contraction pressure by measuring bladder pressure as in co-pending application Ser. No. 15/949,022, filed Apr. 9, 2018, the entire contents of which are incorporated herein by reference, and with catheters to measure the intrauterine pressure in the uterus and the fallopian tubes during HSG, SHG, HyCoSy, or SIS procedures or other procedures, as in co-pending application Ser. No. 15/978,072, filed May 11, 2018, the entire contents of which are incorporated herein by reference.

Catheter 450 can be used in the same manner as the catheters described above, and such aforedescribed use(s) are fully applicable to catheter 450, the difference being the caged inner balloon. Thus in use, catheter 450 is inserted into the cavity, e.g., bladder, and stabilizing balloon 454 is inflated to secure the catheter 450 in place. The system is charged by inflation of the inner balloon 458, i.e., preferably partially inflated for the reasons discussed above, by insertion of air through a side port which is in fluid communication with tubular portion 459b, or by mounting of the transducer hub as described herein, in a closed system formed by the internal space of the inner balloon 458 and the internal lumen and/or tubular portion 459b communicating with the internal space of inner balloon 458. Outer balloon 456 is filled, i.e., preferably partially inflated for the reasons discussed above, via injection of fluid such as air or saline through a separate lumen. With the outer balloon 458 inflated, pressure monitoring can commence as external pressure applied to the larger circumferential outer surface of the outer balloon 458 compresses and deforms the outer balloon 456 which forces fluid within the outer balloon 458 through openings 462 in chamber 452 against the outer wall of the inner balloon 458, compressing the inner balloon 458. As the inner balloon 458 is compressed and deformed in response to compression/deformation of the outer balloon 456 based on changes to bladder pressure, the sensor provides continuous pressure readings, communicated to an external monitor. Although, the system is capable of continuous pressure and continuous temperature monitoring, as in the other embodiments disclosed herein it can also be adapted if desired for periodic monitoring so the pressure and/or temperature readings can be taken at intervals or on demand by the clinician.

An alternate embodiment of the chamber (cage) is illustrated in FIGS. 42-46B and designated by reference numeral 490. Chamber 490 differs from chamber 452 in that it has a slot 496 for ease of assembly and has an angled channel 503 for receipt of the tubular portion of the inner balloon. More specifically, elongated slot 496 extends through an outer wall of the chamber 490 and allows the inner balloon 510 to be placed, e.g. top loaded, into the cavity 496 of the chamber 490. The inner balloon 510 is identical to inner balloon 458 described above except that the tubular portion 512 extending proximally from balloon portion 511 is angled at portion 513 so that the tubular portion 512, rather than being placed in the drainage lumen as in FIG. 40, is placed in a separate lumen 522. Angled channel 503 in chamber 490 receives the angled portion 513 of balloon 510.

Like chamber 452, chamber 490 has a series of openings 494 to provide fluid (liquid or gas) flow from the outer balloon 510 against the outer wall of the inner balloon 510 retained within the chamber 490. Thus, the chamber 490, like chamber 452, separates the outer wall 458b of the inner balloon 458 from the interior of the outer balloon 514, except for the communication through the openings 494 in the chamber 490. One arrangement of chamber openings is shown by way of example in FIG. 42, with one row of three openings (holes), however, other arrangements are also contemplated. Also, a greater number of rows can be provided and a different number of holes than the number shown can be provided as well as holes of different sizes than shown and holes of varying size in the chamber 490. The chamber 490 can be made of silicone, although other materials are also contemplated.

Chamber 490 has a reduced diameter proximal extension 502 for press fit and attachment within the distal end of the catheter shaft. Slot 504 in chamber 490 communicates, i.e., aligns, with lumen 528 for inflating outer balloon 514. A wire can extend through the inner balloon 510 and be embedded in a wall 493 (pierces the wall 493) to help stabilize and center the inner balloon 510.

The catheter has four lumens: 1) lumen 522 receiving the tubular portion 512 of the inner balloon 510; 2) lumen 528 communicating with outer balloon 514 for inflating outer balloon 514; 3) lumen 526 communicating with the retention balloon 516 to inflate retention balloon 516; and 4) drainage lumen 524 having one or more side openings 520 at a distal region of the catheter for drainage of the bladder. In this embodiment, the tubular portion 512 of the inner balloon 510 is positioned in a separate lumen as shown. Except for the angled portion 513, the inner balloon 510 is identical to the inner balloon 458 of FIG. 41. The outer balloon 514 and retention balloon 516 function in the same manner as outer balloon 456 and retention balloon 454 of FIG. 40. The balloons can be of the various configurations described herein, or alternatives thereof. A thermistor can be positioned in lumen 522 or in another lumen. In all other respects, the catheter of FIGS. 43-47 functions in the same manner as catheter 450. Therefore, the discussion of the structure, features and function of catheter 450 is fully applicable to the catheter of FIGS. 43-47.

Figures 47A, 47B:
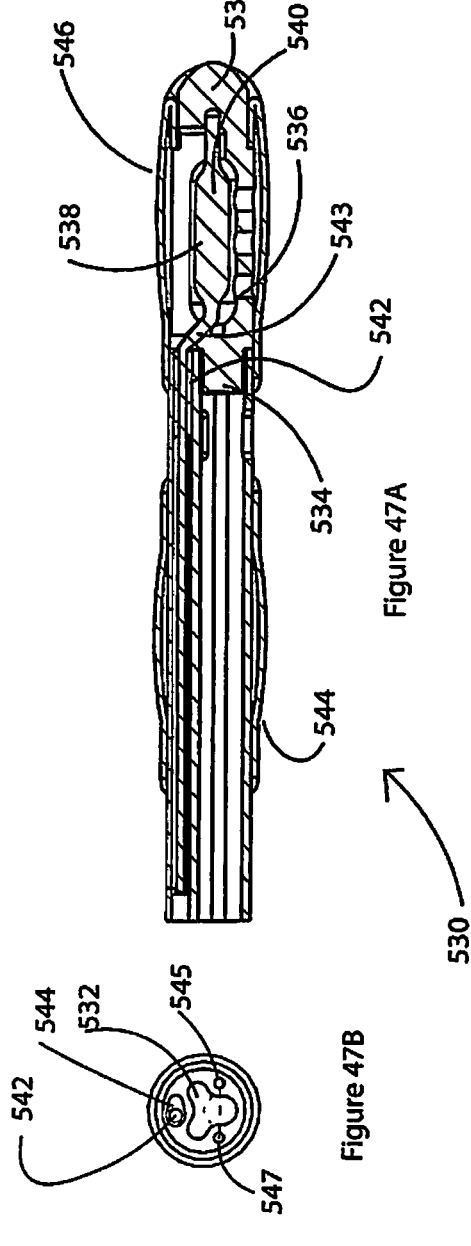
FIG. 47A is a longitudinal cross-sectional view of the distal region of an alternate embodiment of the catheter of the present invention.
FIG. 47B is a transverse cross-sectional view taken along line A-A of FIG. 47A.
Figure 47C:
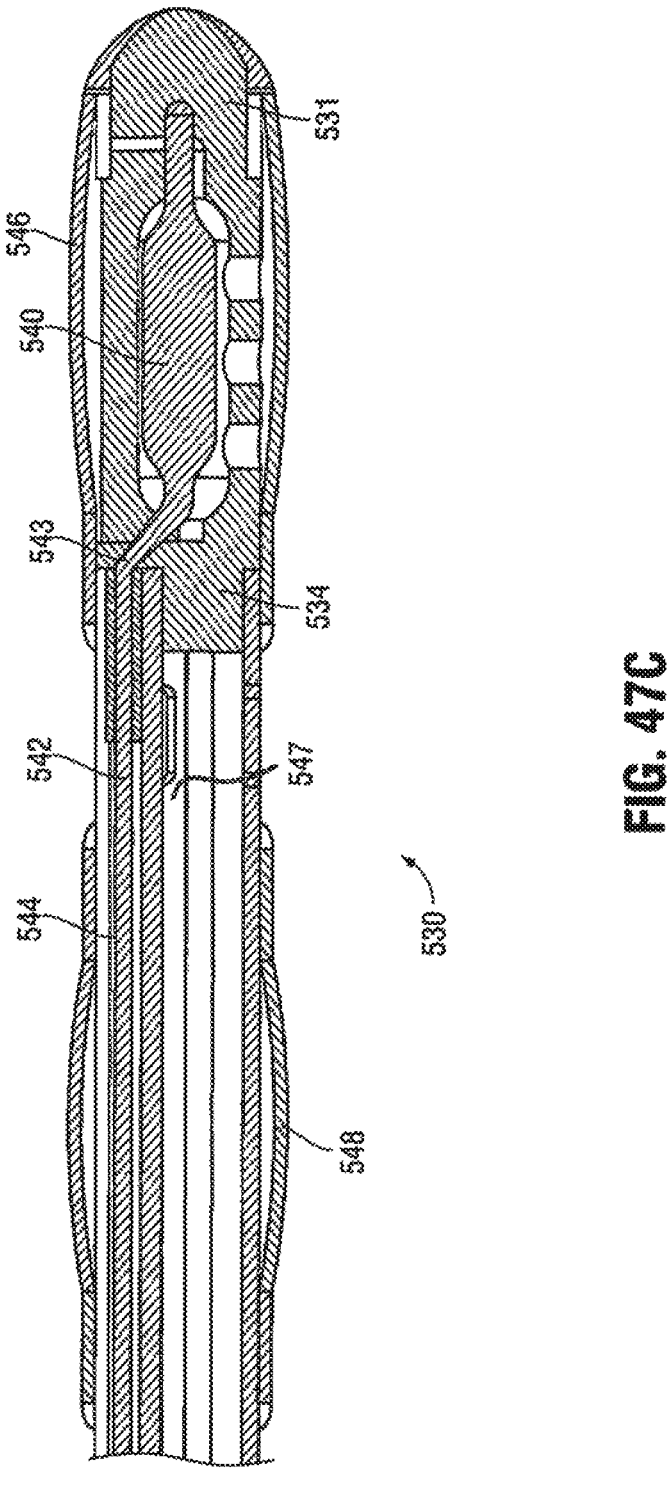
FIG. 47C is a cutaway view similar to the cross-sectional view of FIG. 47A.
Figure 48A:
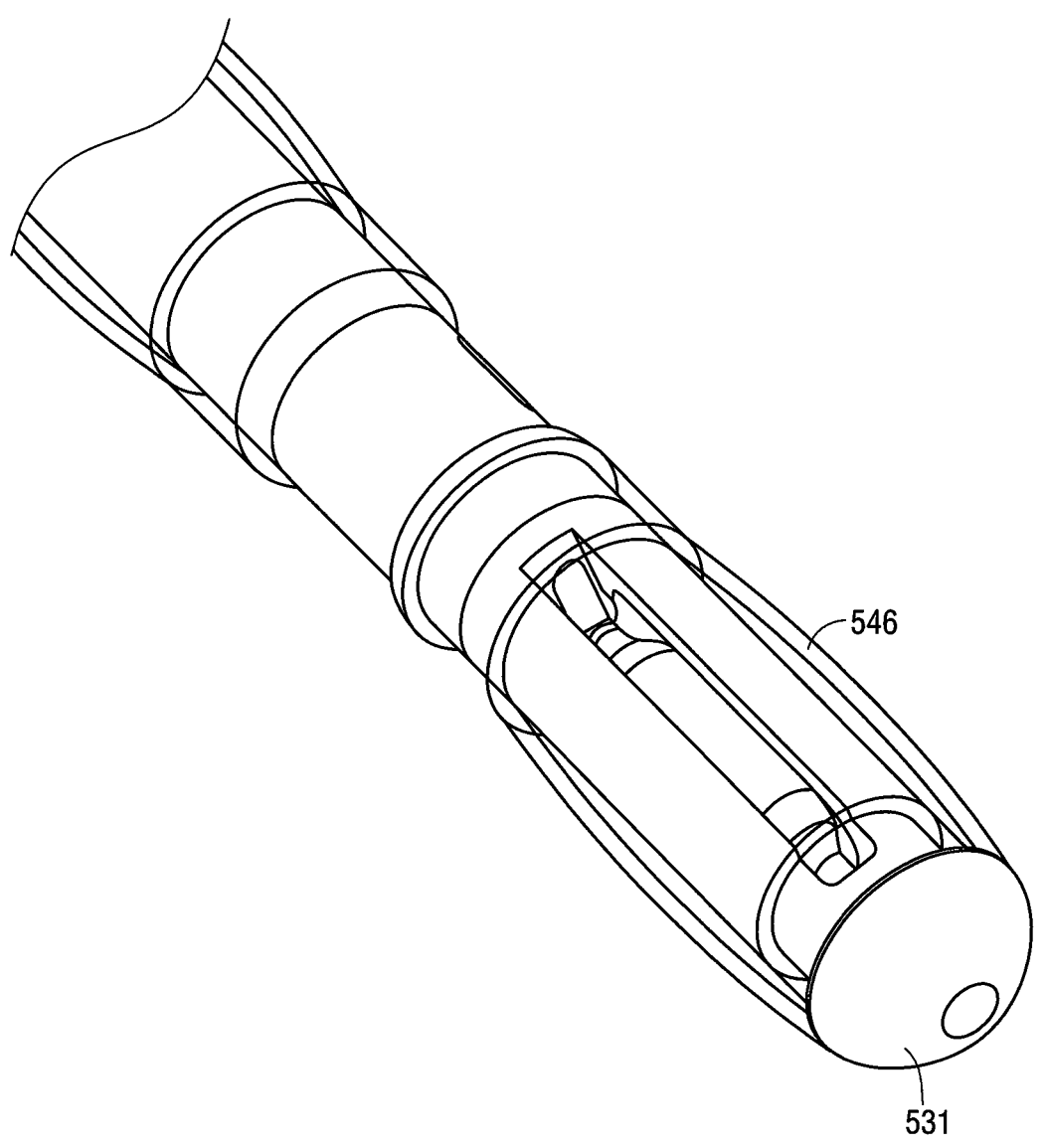
FIG. 48A is a perspective view of the distal end of the catheter of FIG. 47A.
Figure 48B:
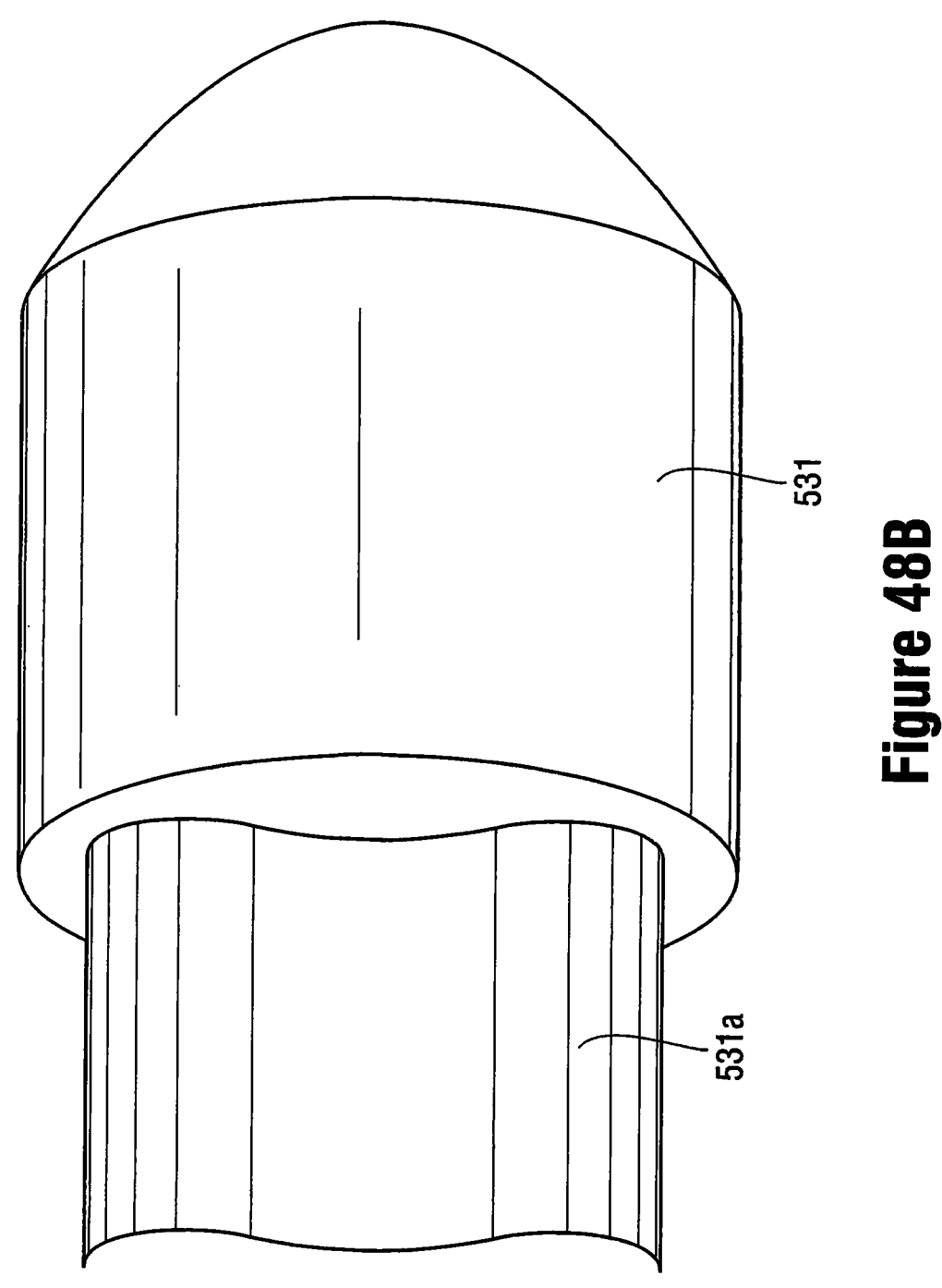
FIG. 48B is a perspective view of the distal tip of the catheter of FIG. 48A.
Figure 48C:
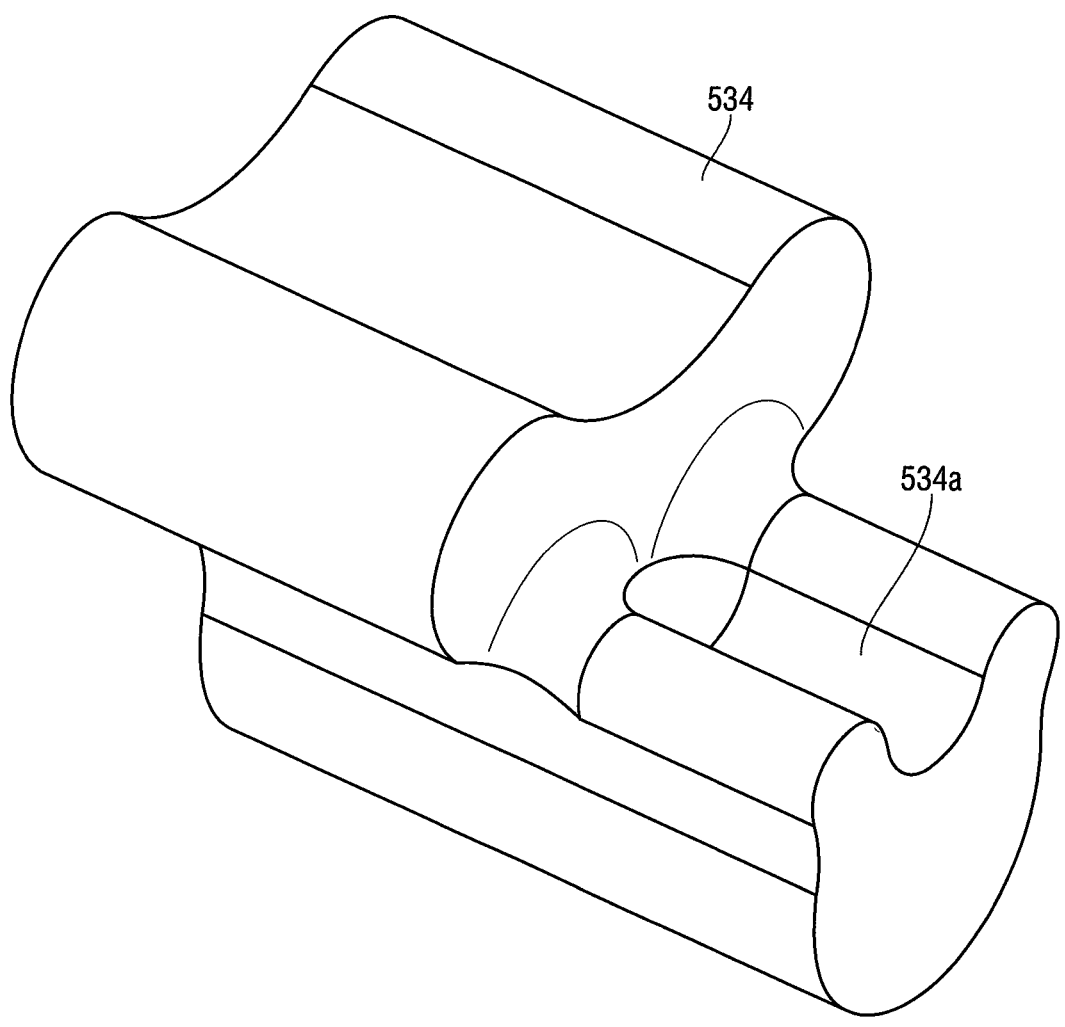
FIG. 48C is a perspective view of the plug of the catheter of FIG. 47A.
Figure 49:
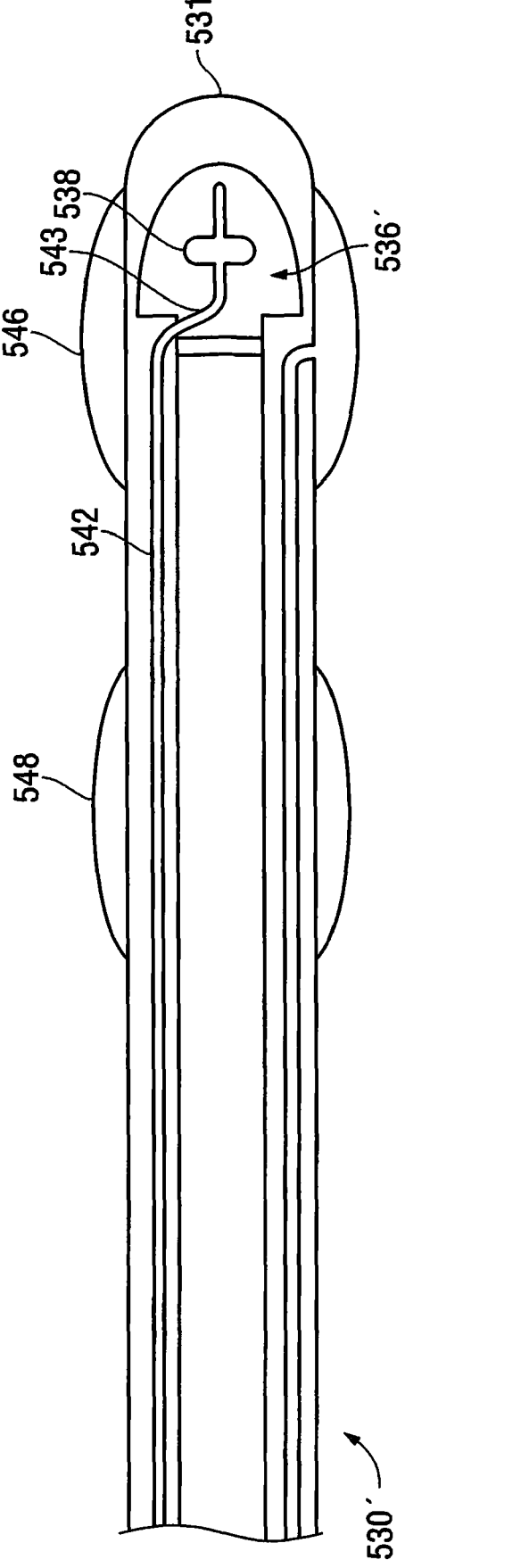
FIG. 49 is a side view of an alternate embodiment of the catheter of the present invention.

FIGS. 47A and 48B illustrate an alternative embodiment of the catheter of the present invention. In these embodiments, the catheter does not include the cage. Catheter 530 has an inner drainage lumen 532 having a distal plug or seal 534 which seals the drainage lumen 532 distal of the plug 534 to form a distal region or area of 536 sealed from the drainage lumen 532. Positioned within the sealed off region 536 is inner balloon 538. Inner balloon 538 has a balloon region 540 and a tubular region 542 extending proximally therefrom. The plug 534 has a recess 534a (FIG. 48C) to receive tubular region 542 of the inner balloon 538. Tubular region 542 has an angled region 543 so that the tubular region 542 is positioned in a separate lumen (lumen 544) than the drainage lumen 532. The distal region 536 can be of the same diameter as the drainage lumen 532 as shown in FIG. 48A or alternatively, can be larger (wider) than drainage lumen 532 as in the embodiment of FIG. 48B showing widened sealed region 536' of catheter 530'. In all other respects, catheter 530' is identical to catheter 530 so like reference numerals are used for like parts. A plurality of openings are provided in distal region 536 for fluid communication from the outer balloon through the openings and against the outer wall of the inner balloon 538 to deform the inner balloon 538 as in the embodiments of FIGS. 35-47. The catheter can have a cap 531 at the distal end to provide a blunt tip for the catheter. The cap 531 has a recess 531a (FIG. 48B) to receive a distal extension of the balloon 538.

Inner balloon 538 functions in the same manner as inner balloon 458. Catheter 530 has an outer balloon 546 and a retention (stabilizing) balloon 548 which function in the same manner as outer balloon 456 and retention balloon 454 of FIG. 40 with inflation lumens 545, 547 (FIG. 47B). The balloons can be of the various configurations described herein, or alternatives thereof. A thermistor can be positioned in lumen 544 or in another lumen. Catheter 530 of FIGS. 48a and 48B function in the same manner as catheter 450 and has e.g., a drainage lumen, a lumen for inflation of the outer balloon and a lumen for inflation of the retention balloon. Therefore the discussion of the structure, features and function of catheter 450 is fully applicable to the catheter 530 and 530'.

FIGS. 50A-63B illustrate an alternative embodiment of the catheter of the present invention that does not include the cage. By placement of the inner balloon within the lumen of the catheter without a cage, it reduces the stiffness of the catheter and reduces cost. This embodiment also has the advantages of keeping the inner pressure balloon centered to prevent false pressure readings. This embodiment also includes an intermediate balloon forming an inner liner within the outer balloon, discussed in detail below.

Catheter 600 has a retention balloon 604 identical to retention (stabilizing) balloon 206 of catheter 200 (or other stabilizing balloons disclosed herein), an inner balloon 608 and an outer balloon 606. An intermediate balloon 614 is positioned within the outer balloon 606 and external of the inner balloon 608.

Turning to FIGS. 56-58D, catheter 600 has four lumens: 1) lumen 644 in which inner balloon 608 is positioned (the inner balloon 608 forming the gas, e.g., air filled chamber); 2) lumen 642 communicating with intermediate balloon 614 via opening 642a for inflating the intermediate balloon 614 and thus expanding outer balloon 606; 3) lumen 640 communicating with the stabilizing balloon 604 to inflate stabilizing balloon 604; and 4) drainage lumen 646 having one or more side openings 610 at a distal end for drainage of the bladder. The side opening(s) is positioned between the outer balloon 606 and retention balloon 604, i.e., between the expanded portions of the balloons 606, 604. The lumen 644 is also sized to receive thermistor wires for temperature sensing.

Catheter 600 also has a hub portion with three angled extensions/ports (FIG. 50C) at its proximal end: 1) port 620 for access via opening 623 to inflate the inner balloon 608; 2) port 622 for access via opening 625 to lumen 642 to inflate intermediate balloon 614; and 3) port 626 for access to lumen 640 via opening 629 to inflate stabilizing balloon 604 via opening 629. Drainage lumen 646 extends linearly terminating at proximal region 624 in opening 627. Thermistor wires (discussed below) can exit from the catheter port 620 for connection to a temperature monitor via hub 330 (discussed below). Note the location of the catheter angled ports can vary from that illustrated in FIG. 50A. Also, the location of the lumens and the cross-sectional dimension/ size of the lumens can vary from that shown in FIGS. 58B-58D as these provide just one example of the location and size, e.g., diameter, of the lumens as well as one example of the shape/cross-sectional configuration and location.

Figure 50A:
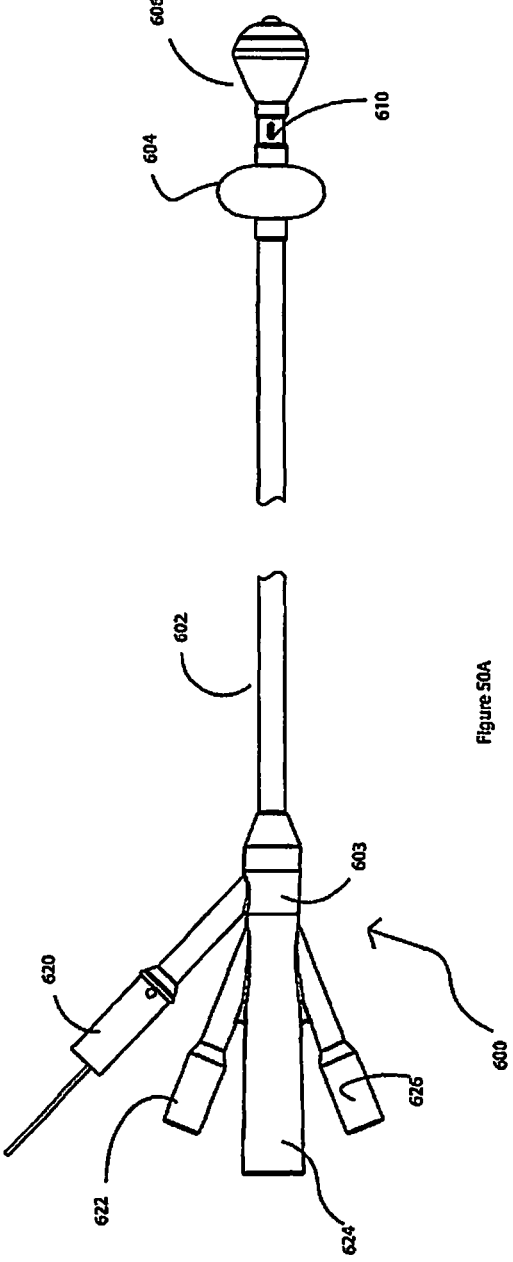
FIG. 50A is a side view of an alternate embodiment of the catheter of the present invention showing the balloons in the inflated condition.
Figure 50B:
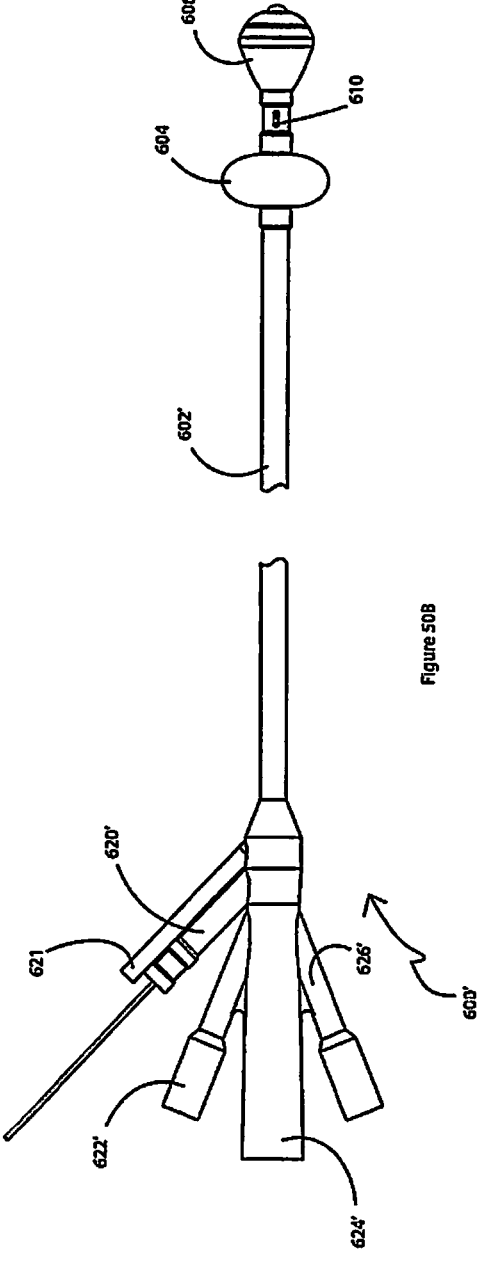
FIG. 50B is a side view of an alternate embodiment of the catheter of FIG. 50A having an additional port for the thermistor wires.
Figure 50C:
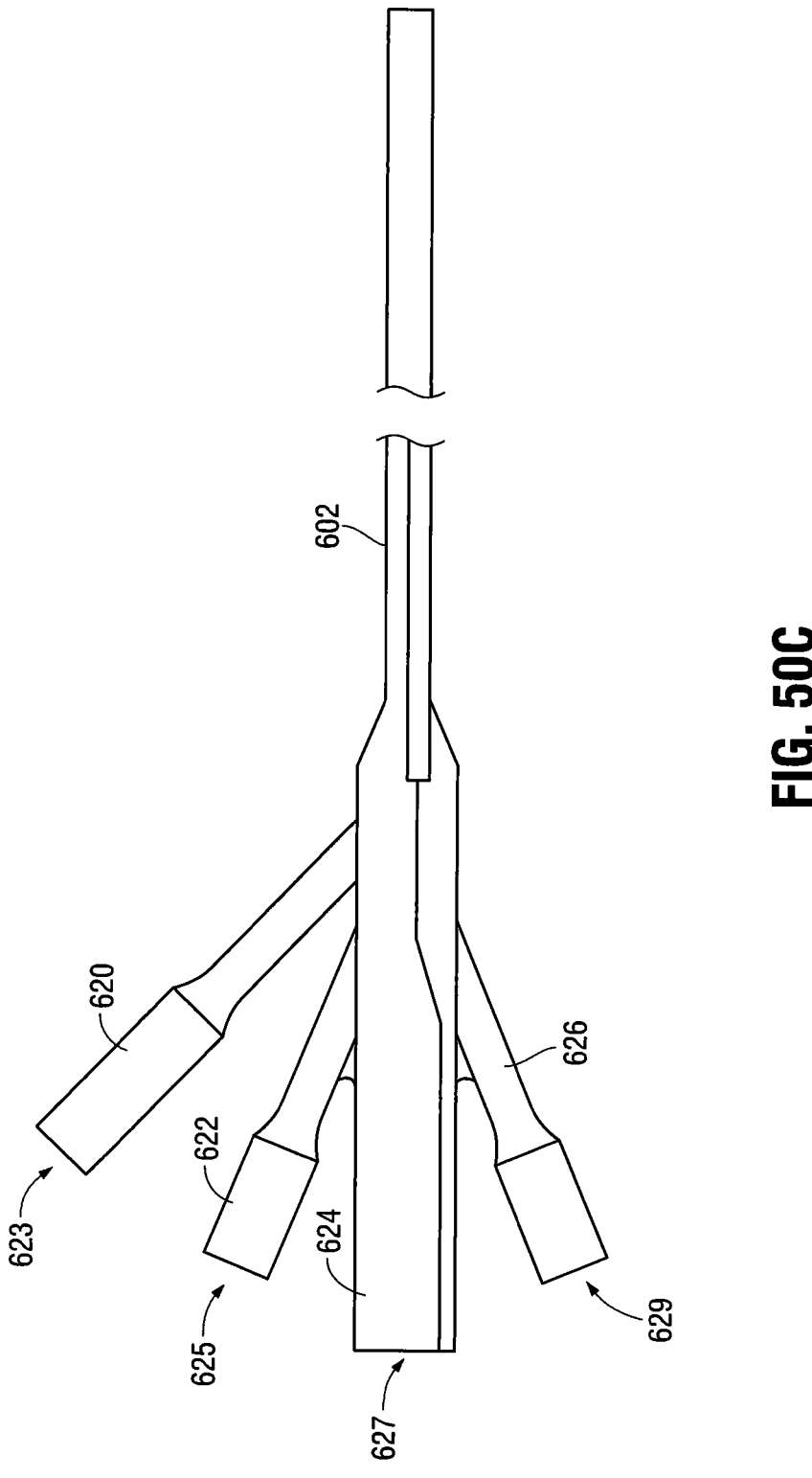
FIG. 50C is a side view of the proximal portion of the catheter of FIG. 50A.
Figure 51:
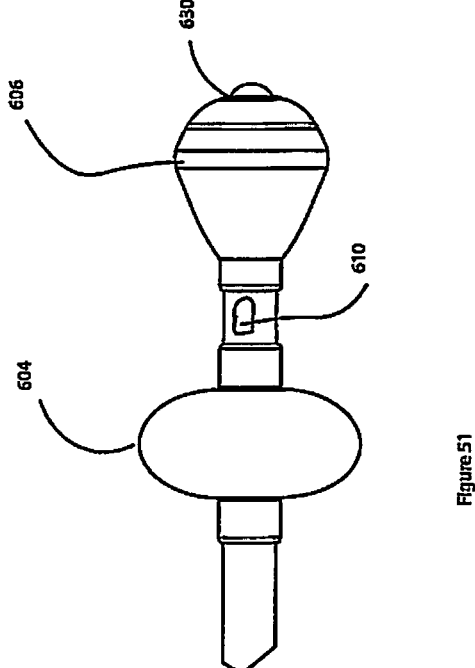
FIG. 51 is a close up view of the distal end of the catheter of FIG. 50A with the balloons in the inflated condition.
Figure 53:
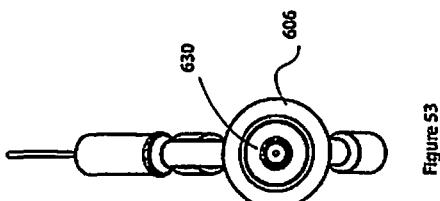
FIG. 53 is a front view of the catheter of FIG. 50A.
Figure 52:
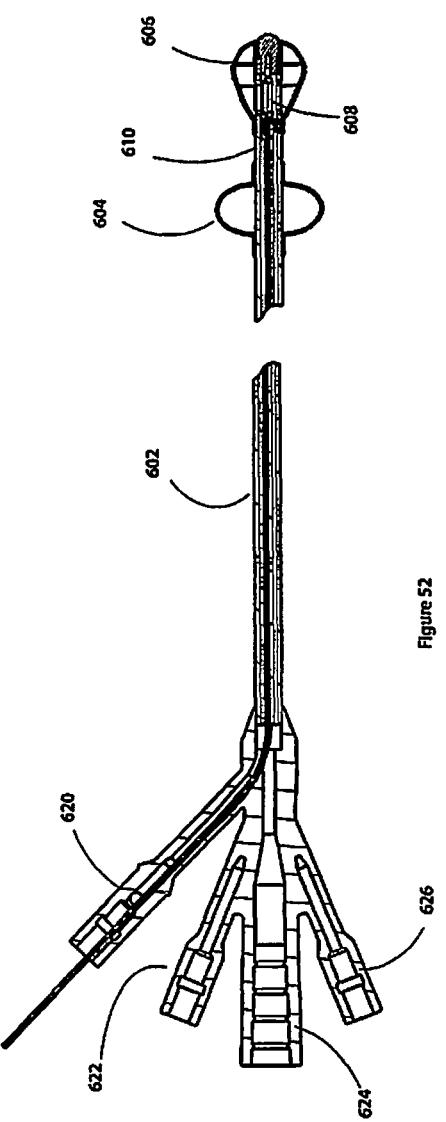
FIG. 52 is a cross-sectional view of the catheter of FIG. 50A.

In the alternate embodiment of FIG. 50B, catheter 600' is different from catheter 600 of FIG. 50A in that four angled ports are provided. Ports 626', 624' and 622' of catheter 600' are identical to ports 626, 624 and 622 of catheter 600 of FIG. 50A and therefore similar components are labeled with "prime" reference numerals. In this embodiment, an additional port 621 is provided for the thermistor wires as they do not extend through port 620' as they do in port 620 of FIG. 50A. Otherwise catheter 600' is identical to catheter 600, e.g. it has the retention, outer, intermediate and inner balloons. Note the thermistor wires extending through port 621 can extend through a separate lumen within catheter shaft 602', or alternatively, can extend through the same lumen as the lumen for the inner balloon, but separate at a proximal end to extend through port 621.

A thermistor can be placed adjacent the drainage opening 610 of catheter 600 for temperature readings, and the thermistor wire(s) can extend through a lumen of the catheter 600 such as lumen 644 for the inner balloon as in catheter 600 or alternatively through the drainage lumen or through a separate lumen, for electrical connection to a temperature monitor.

Catheter 600 has an inner drainage lumen 646 having a plug or seal 662 (FIG. 54) positioned therein which seals the drainage lumen 646 distal of the plug 662. A distal plug 630 is distal of the drainage side opening(s) 610 so as to not interfere with drainage of the bladder. The distal plug 630 also forms a cap at the distal end of the catheter 600 to provide a blunt tip.

Figure 54:
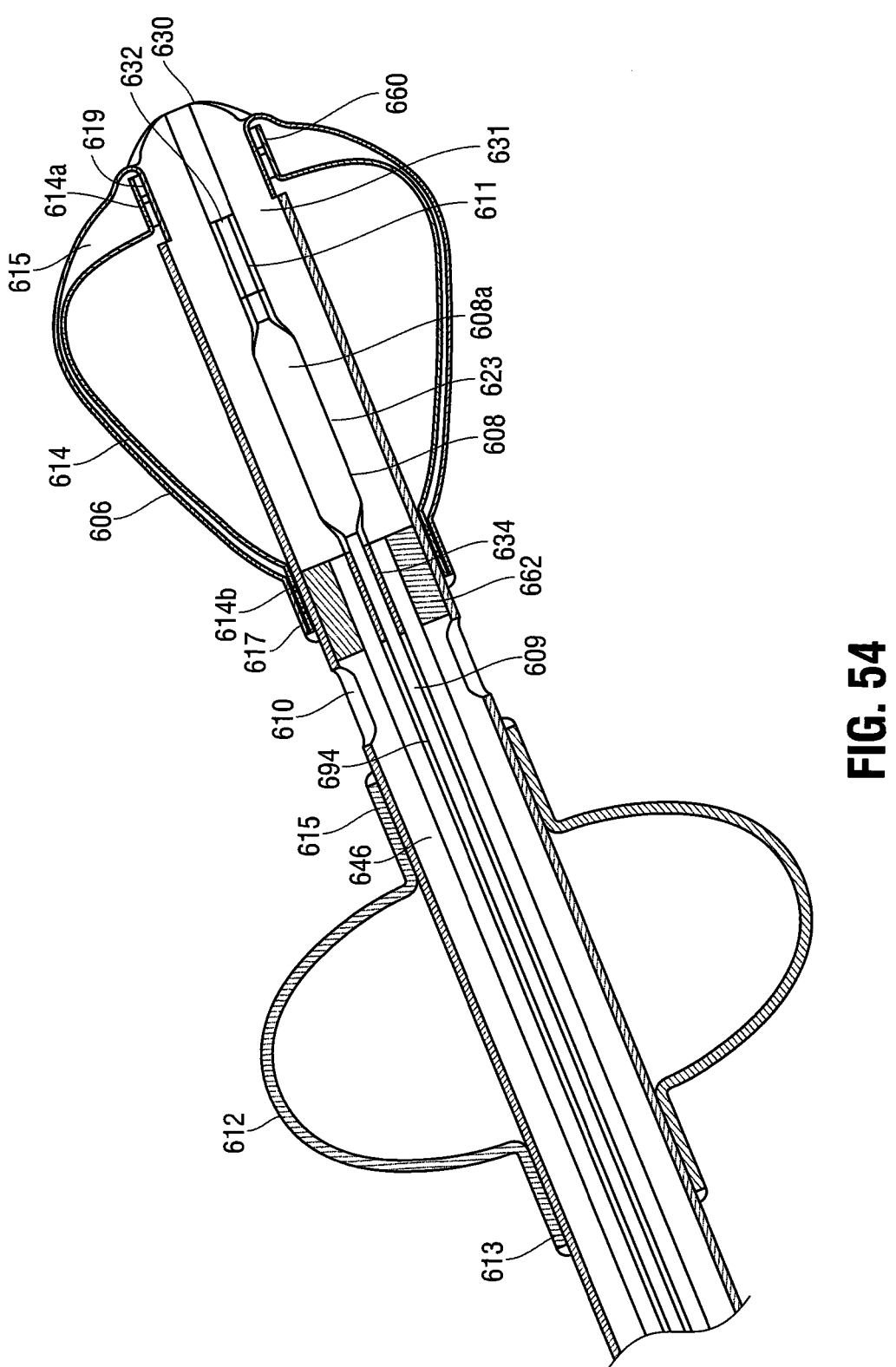
FIG. 54 is a cutaway side view illustrating the inside of the catheter similar to the catheter of FIG. 50A.
Figure 55:
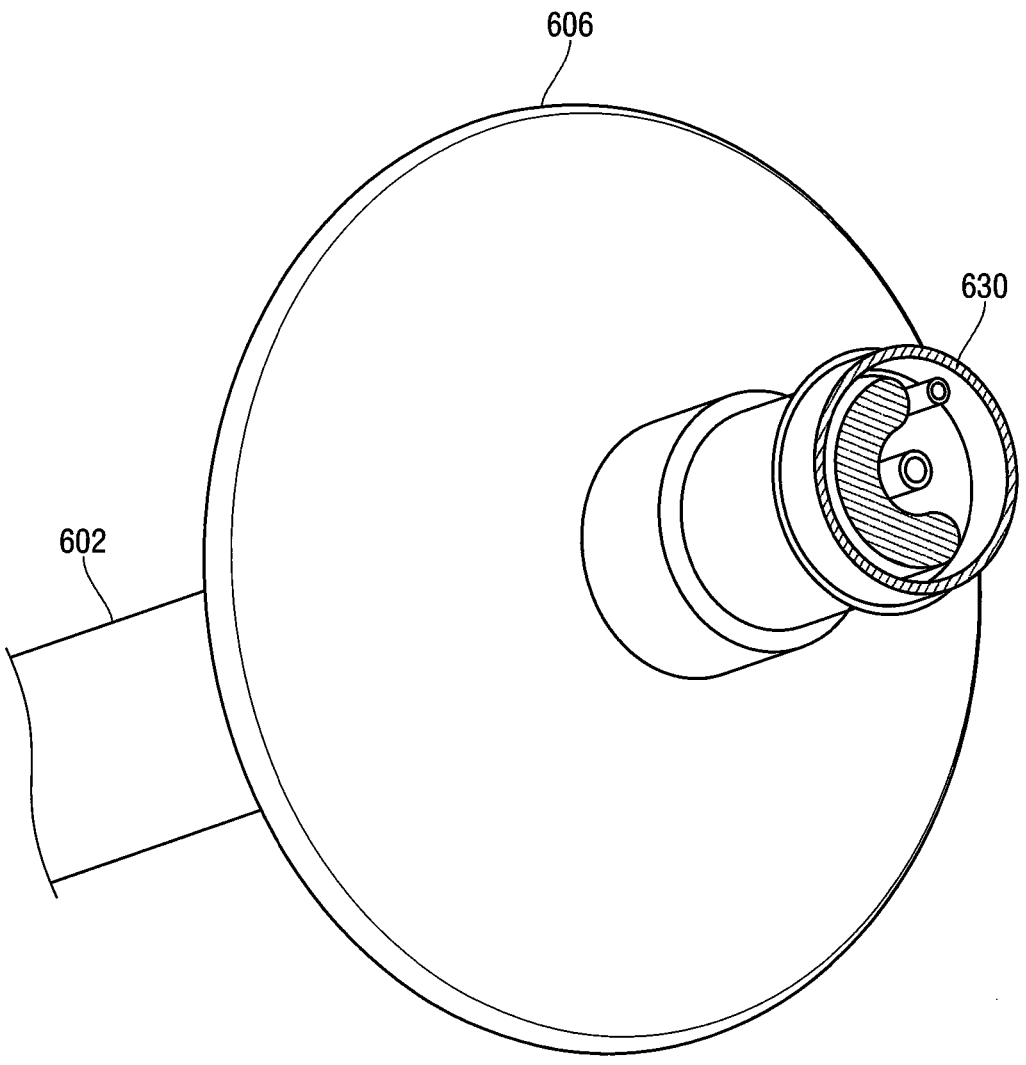
FIG. 55 is an enlarged view of the distal tip of the catheter of FIG. 50A.
Figures 56, 57, 58A, 58B, 58C, 58D:
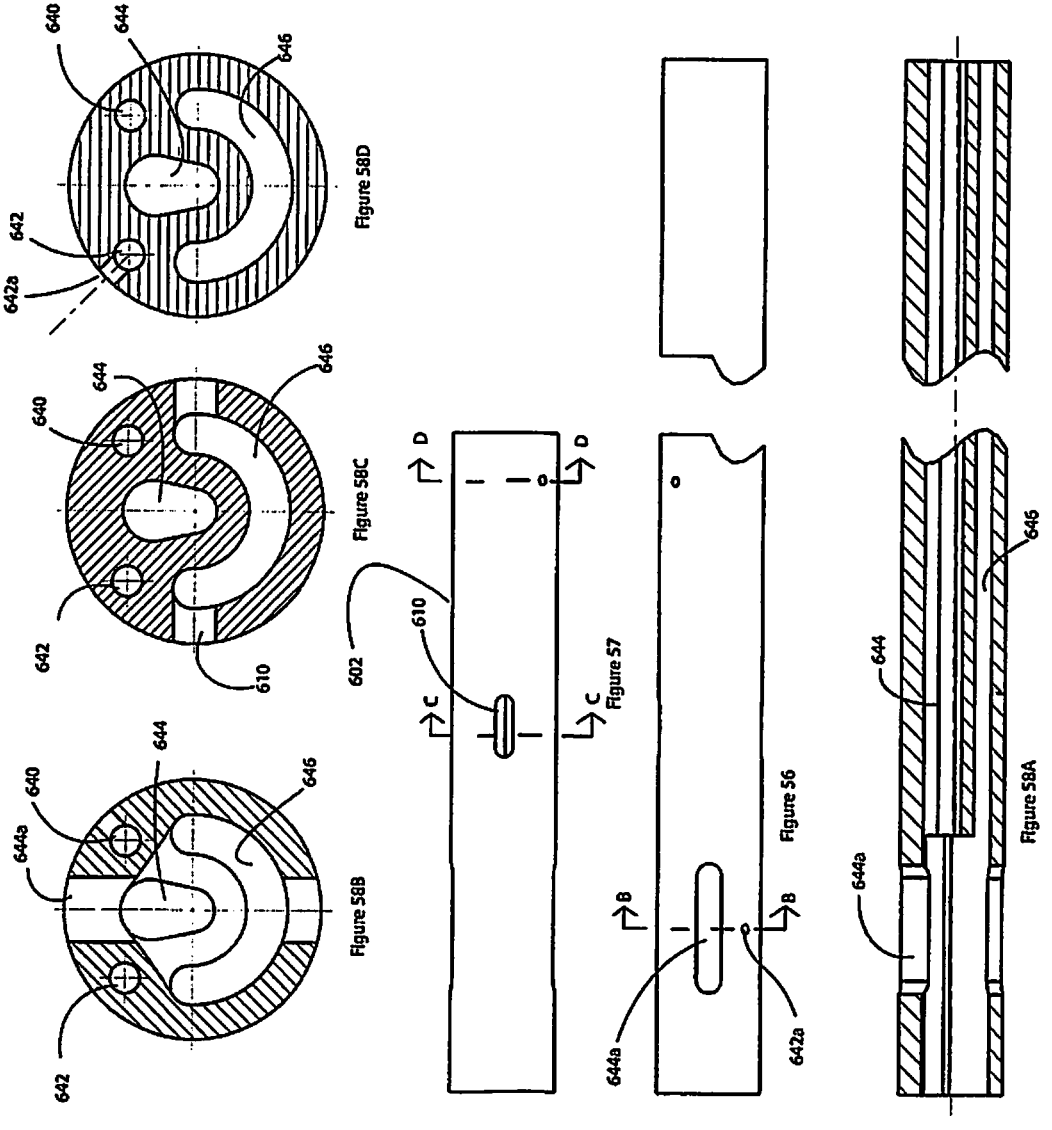
FIG. 56 is a side view of a portion of the shaft of the catheter of FIG. 50A showing the openings for communicating with the outer wall of the inner balloon.
FIG. 57 is a side view of a portion of the shaft of the catheter of FIG. 50A showing the drainage opening.
FIG. 58A is a longitudinal cross-sectional view of the catheter shaft of FIG. 56.
FIG. 58B is a transverse cross-sectional view taken along line B-B of FIG. 56.
FIG. 58C is a transverse cross-sectional view taken along line C-C of FIG. 57.
FIG. 58D is a transverse cross-sectional view taken along line D-D of FIG. 57.
Figure 59A:
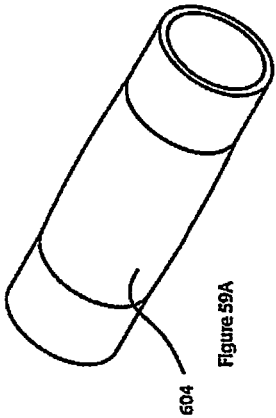
FIG. 59A is a perspective view of the retention balloon of the catheter of FIG. 50A.
Figure 59B:
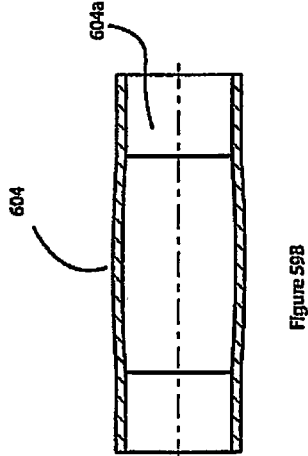
FIG. 59B is a cross-sectional view of the retention balloon of FIG. 59A.

Distal of plug 662 is a distal region or area 623 which forms an enlarged area of the lumen 644 which receives the inner balloon 608. Inner balloon 608 has a balloon region 608a and a tubular region 609 extending proximally therefrom. Tubular region 609 extends within lumen 644 which is separate (independent) from the drainage lumen 646. Thermistor wires discussed below can also extend through lumen 644. FIG. 54 shows the enlarged region 623 of lumen 644 which forms a chamber for the balloon 608. A plurality of openings 644a (FIGS. 56 and 58B) are provided within the catheter 600 at the distal region 623 for fluid communication from the intermediate balloon 614 through the openings 644a and against the outer wall of the inner balloon 608 to deform the inner balloon 608. Thus, the openings 644a communicate with the chamber 623. The openings 644a can be oval shaped as in FIG. 56, or alternatively others shapes and sizes. In the illustrated embodiment, two openings are provided, however, additional openings can be provided. These openings provide a passageway for fluid, e.g., gas such as air or saline, from inside the inflated intermediate balloon 614 into contact with the outer wall of the inner balloon 608 to deform the inner balloon 608 to provide finer pressure measurements.

The inner balloon 608 has an elongated shape (FIGS. 54 and 60A) with tubular portion 609 extending proximally from the expanded portion 608a. As noted herein, the elongated tubular portion 609 can extend along the length of the lumen 644 and through the side port 620, terminating at a proximal end in the catheter connector, and attached thereto, as discussed below. For example, the tubular portion 609 in some embodiments can have a length of about 600 mm and the expandable portion 608a can have a length of about 10 mm, although other dimensions are also contemplated. Inner balloon 608 has a distal extension 611 attached within opening 631a (FIG. 61B) in distal extension 631 of distal plug 630 via sealing material 632 (FIG. 54), such as silicone. A proximal plug 662 is positioned within the lumen 644, adjacent to but proximal of the expandable portion 608a of balloon 608 to attach the tubular portion 609 of balloon 608 within opening 644 via sealing material 634 such as silicone. Thus, distal and proximal plugs 630 and 662 securely retain the balloon 608 at different sides so it is maintained within the enlarged region 623 centered within the region. That is, in preferred embodiments, the inner balloon 608 is kept spaced from the wall of the distal region 623 so as not to interfere with flow through the openings 644a which could cause false pressure readings. Inner balloon 608 is preferably composed of a thermoplastic material, such as PET, which is impermeable to air and not water soluble, but has relative stiffness. Other materials are also contemplated such as EVA.

In an alternate embodiment, the inner balloon can include an inner component 639 placed within the inside diameter. The inner component 639 (FIG. 60D) is a bead-mandrel which is utilized to decrease the amount of air charge in the inner sensing balloon 608. Such inner component can increase the sensitivity of the sensor capabilities. That is, if there is less air in the inner balloon 608, the balloon is more responsive to changes in pressure. Thus, by eliminating dead space, it makes it more sensitive. The component 639 can extend the length of the balloon, i.e., starting at the proximal end of the tubular portion 609 and extending to the distal tip of balloon 608, or alternatively can extend only along a partial length of the inner balloon 608, e.g., extending only in a portion of the tubular portion 609 and/or the expanding portion 608. In some embodiments, the inner component 639 can have for example a length of about 19 to about 20 inches and an outer dimeter of about 0.02 inches, although other lengths and diameters are also contemplated.

Figure 60A:
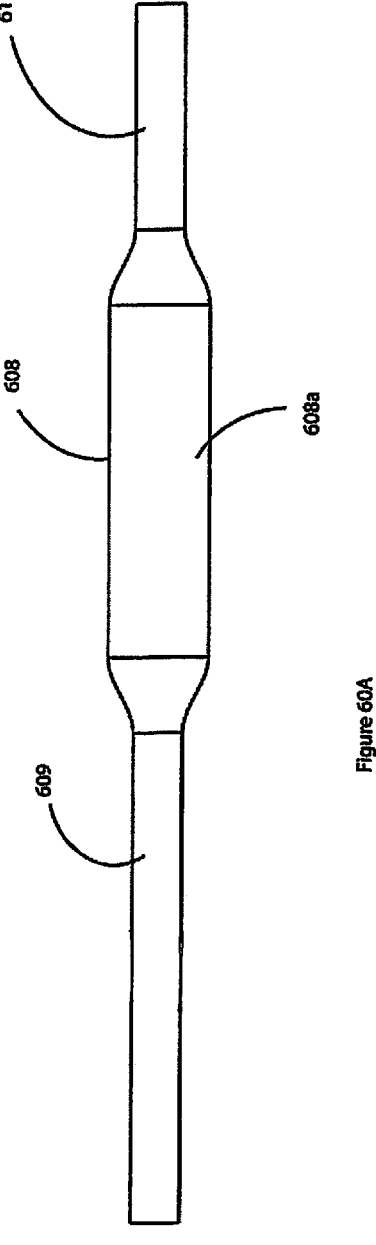
FIG. 60A is a side view of the inner balloon of the catheter of FIG. 50A.
Figure 60C:
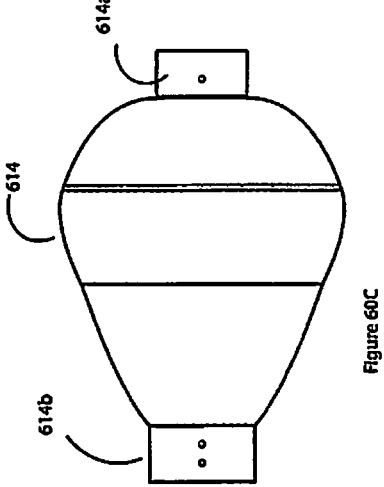
FIG. 60C is a side view of the intermediate balloon (inner liner) of the catheter of FIG. 50A.
Figure 61B:
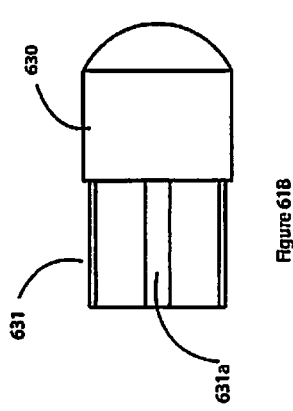
FIGS. 61A and 61B are side views of the distal tip of the catheter of FIG. 50A.
Figure 60B:
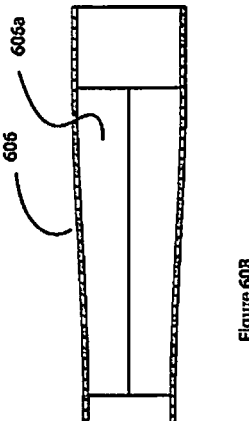
FIG. 60B is a side view of the distal outer balloon of the catheter of FIG. 50A.
Figure 61A:
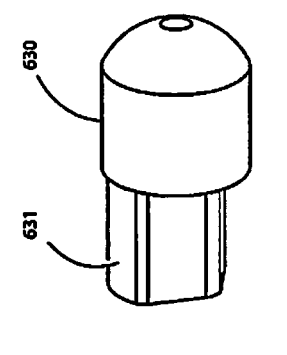
Figure 60D:
FIG. 60D is a side view of an insert for the inner balloon in accordance with an alternate embodiment.

The intermediate balloon 614 can be "pear shaped" or "liberty bell shaped" as shown in FIGS. 54 and 60C. Proximal extension 614b is attached to an outer surface of catheter 600 at region 617 and distal extension 614a is attached to an outer surface of catheter 600 at region 619. The intermediate balloon 614 is positioned within outer balloon 606. In the embodiment of FIG. 54, the intermediate balloon 614 is shaped to form a gap 615 at a distal region between the outer wall of the balloon 614 and inner wall of the outer balloon 606, however, in alternate embodiments, the intermediate balloon 614 could more closely follow the full contour of the outer balloon 606 so that no gap or a smaller gap would be provided. The distal end of the outer balloon 606 can wrap underneath the end of the intermediate balloon 614 for attachment to the catheter outer surface as shown in FIG. 54, with a distal sleeve 660 positioned over the two ends of the balloons. Alternatively, the outer balloon distal end can remain atop the intermediate balloon distal end in the same manner it does at the proximal attachment at region 617 shown in FIG. 54. In alternate embodiments, the intermediate balloon 614 can also wrap in the same manner as the outer balloon 606 of FIG. 54. In an alternate embodiment, the outer balloon 606 can have one side larger so it inverts on itself such that it would not stick out of the distal end of the catheter shaft.

The intermediate balloon 614 forms an inner liner of the outer balloon 606 to therefore act a like a coating to stiffen the outer balloon 606. The intermediate balloon 614 is composed of a material, e.g., a thermoplastic material, that is less compliant than the outer balloon 606. For example, the intermediate balloon 614 can be composed of EVA which would counteract expansion of the more compliant outer balloon 606. The outer balloon 606 is composed of a more compliant material such as silicone. With a compliant balloon, it would continue to expand (stretch) so the pressure would drop. The inner liner prevents this. Note that outer balloon 606 preferably has a smoother surface to shield the thermoplastic intermediate balloon 614 during insertion and use to reduce patient discomfort. The intermediate balloon 614 in some embodiments has a wall thickness less than the wall thickness of the outer balloon 606. Note that other compliant/non-compliant materials are also contemplated.

In an alternate embodiment, upon inflation of the intermediate balloon 614, the outer balloon 606 would peel back. Therefore, the outer balloon 606 would act as a sheath.

In use, the intermediate balloon 614 is expanded via injection of fluid, e.g. air saline, etc. through the port 622. Expansion of the intermediate balloon 614 causes expansion of the outer balloon 606. Deformation of the outer balloon 606 based on changes in pressure within the patient, e.g., within the bladder in response to abdominal pressure, causes deformation of the intermediate balloon 614. As the intermediate balloon 614 is deformed, fluid within the intermediate balloon 614 passes through the opening(s) 644a within the catheter to apply a pressure against the outer wall of the inner balloon 606 to deform the inner balloon 606 to provide pressure readings in the same manner as the other embodiments disclosed herein.

Alternate Catheter Hub Attachments

Figure 26:
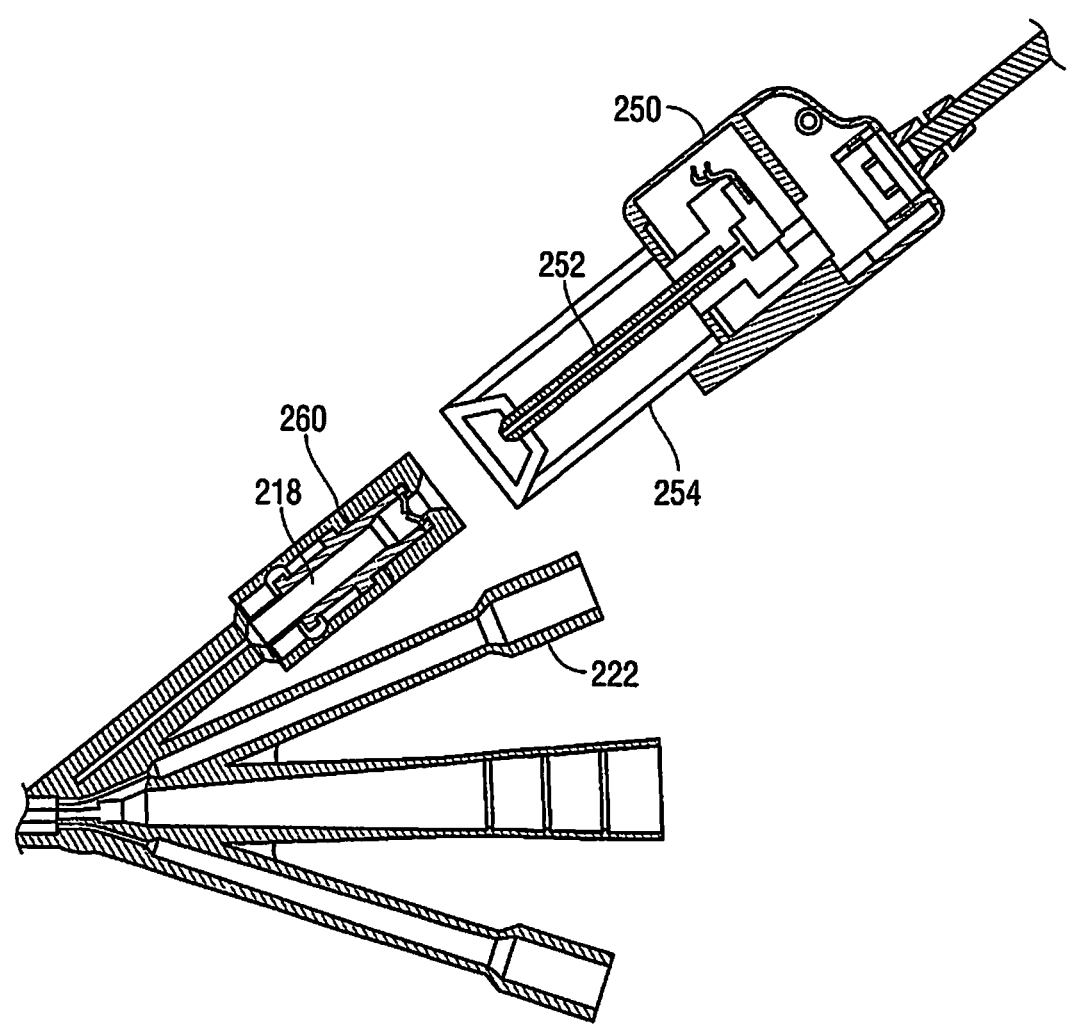
FIG. 26 is a side view of alternate embodiment of the pressure transducer hub having a shroud over the elongated member for snap fitting onto the catheter.

Turning back to the transducer hubs mountable to the catheter, FIG. 26 illustrates an alternate embodiment of the pressure transducer hub. In this embodiment, hub 250 has a shroud 254 (shown schematically) positioned over elongated member 252. This helps protect/shield the elongated member 252. When the transducer 240 is mounted to the port 260 of the catheter, the shroud 254 fits over cover 260 of port 218 and is retained by a snap fit or by other methods of securement.

Figure 27:
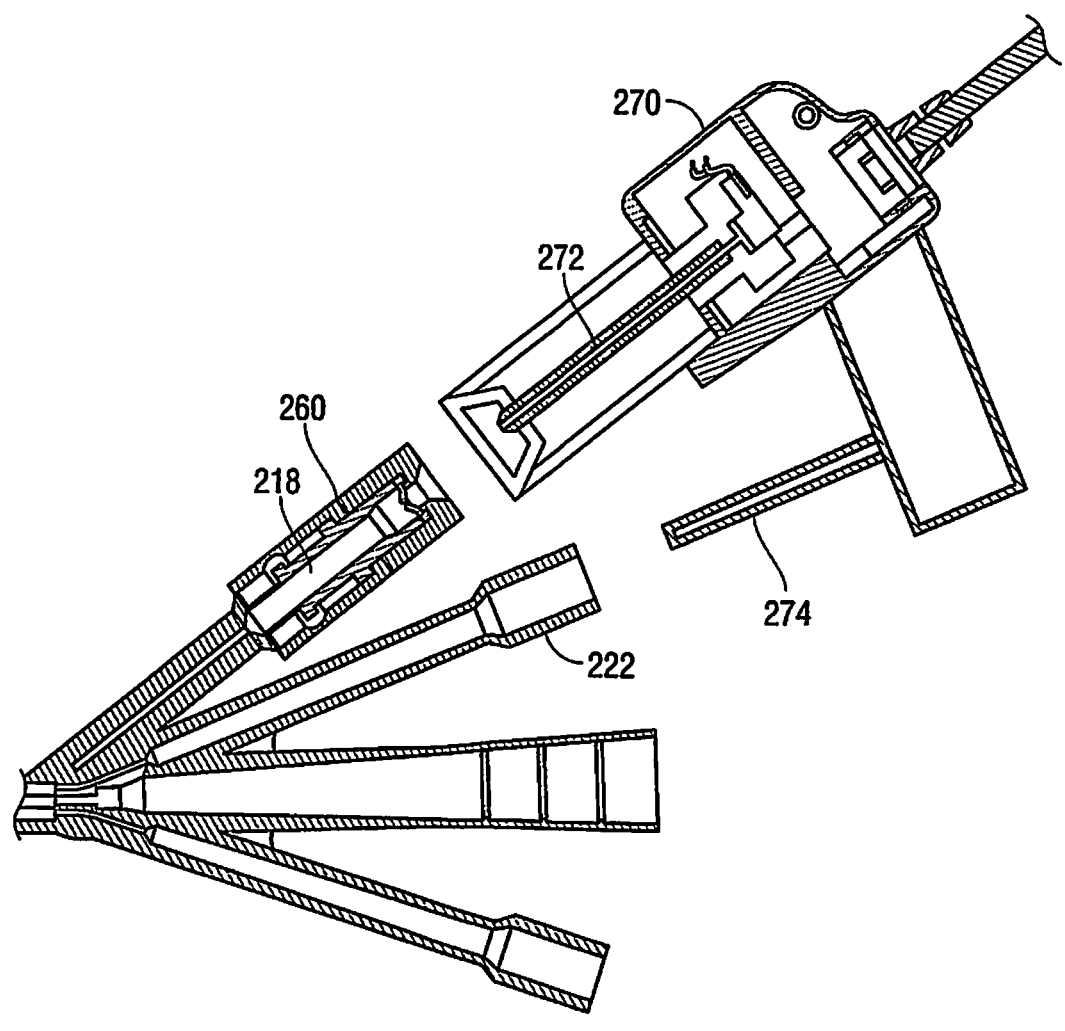
FIG. 27 is a schematic view of an alternate embodiment of the pressure transducer hub extendable into two side ports of the catheter.

In the aforedescribed embodiments, mounting of the transducer hub a) automatically connects the temperature sensor to a connector for communication with a temperature monitor cable; and b) automatically advances air through the first lumen to expand the inner balloon. In the embodiment of FIG. 27, the pressure transducer hub 270 has a second elongated member 274 extending therefrom. When transducer hub 270 is mounted to the catheter, e.g., port 218, elongated member 272 enters the air lumen in the same manner as elongated member 242 of FIG. 24A. Additionally, elongated member 274 automatically enters the lumen 210 at port 222 which communicates with the outer balloon 202. Therefore, in this embodiment, mounting of the transducer hub 270 a) automatically connects the temperature sensor to a connector for communication with temperature monitor cable as in the embodiment of FIGS. 18-25B; b) automatically advances air through the first lumen to expand the inner balloon as in the embodiment of FIGS. 18-25B; and c) automatically advances air through lumen 210 communicating with the outer balloon 202 to inflate (expand) the outer balloon 202. The catheter of FIG. 27 (and FIG. 26) is otherwise identical to catheter 200 of FIG. 18A so for brevity further discussion is not provided since the description of the function and elements of catheter 200 are fully applicable to the catheter of FIG. 27 (and to the catheter of FIG. 26).

FIGS. 28A-28D show an alternate embodiment of the hub/connector. The pressure transducer is external to catheter 280 and mounted to port 282 at the proximal end 281 of catheter 280 via connector (housing) 290. Catheter 280 is identical to catheter 200 of FIG. 18A except for the connector and transducer hub temperature sensor connection.

Figure 28A:
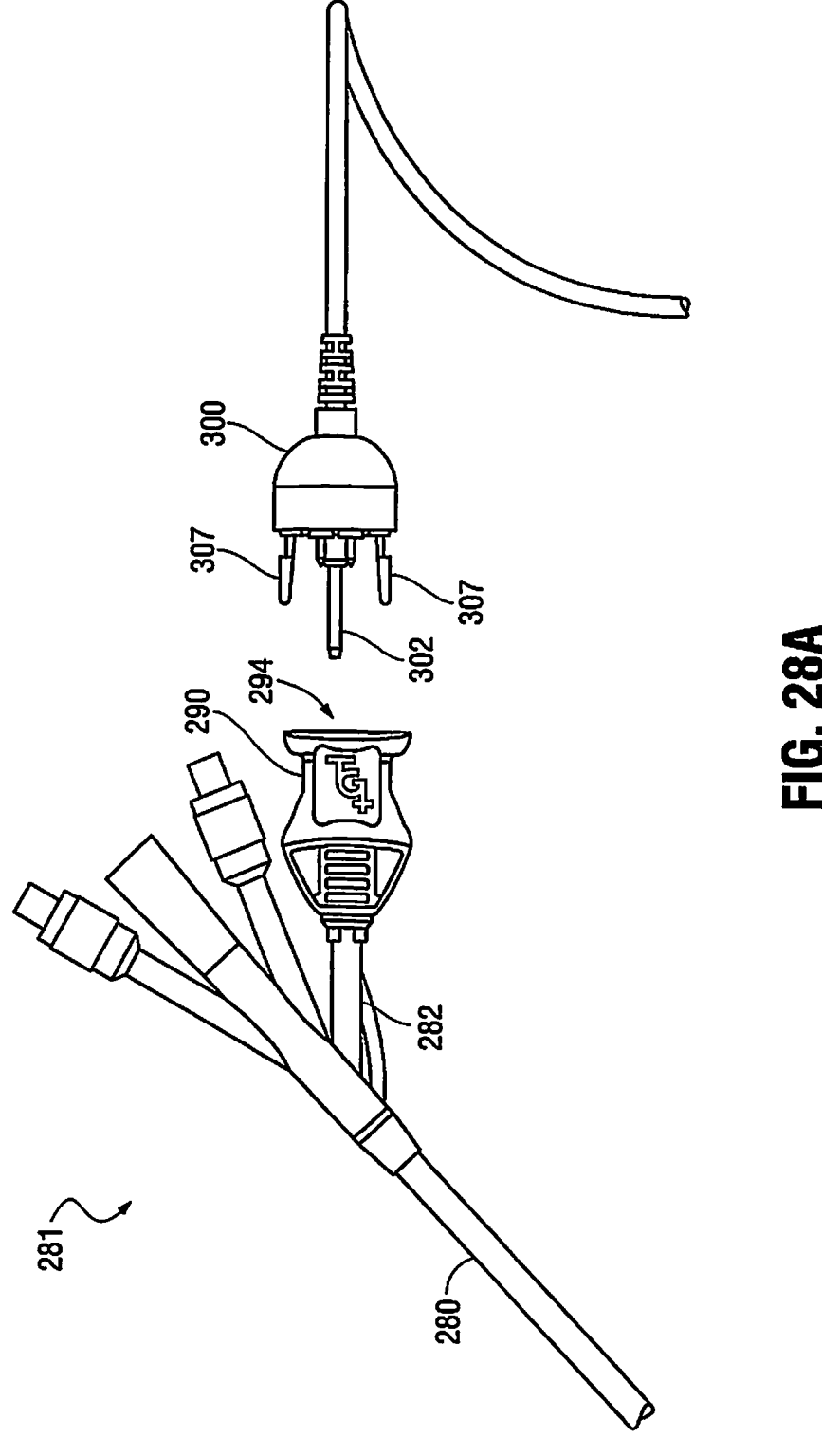
FIG. 28A is a perspective view of an alternate embodiment of the transducer hub and connector.
Figure 28B:
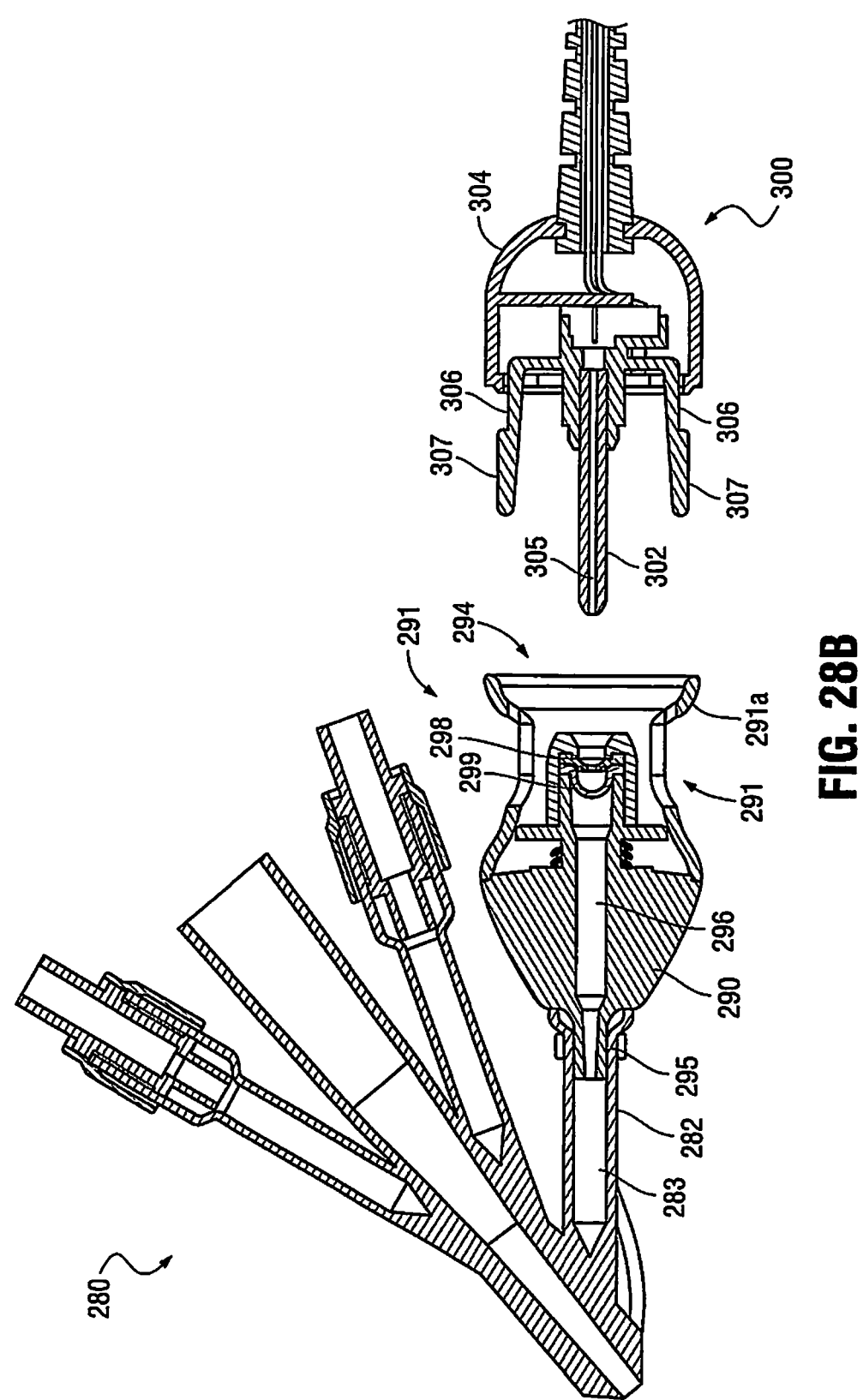
FIG. 28B is a cutaway side view of the hub and connector of FIG. 28A showing the pressure transducer prior to connection to the catheter of FIG. 18A, a portion of the hub wall and connector removed to show internal components.
Figure 28C:
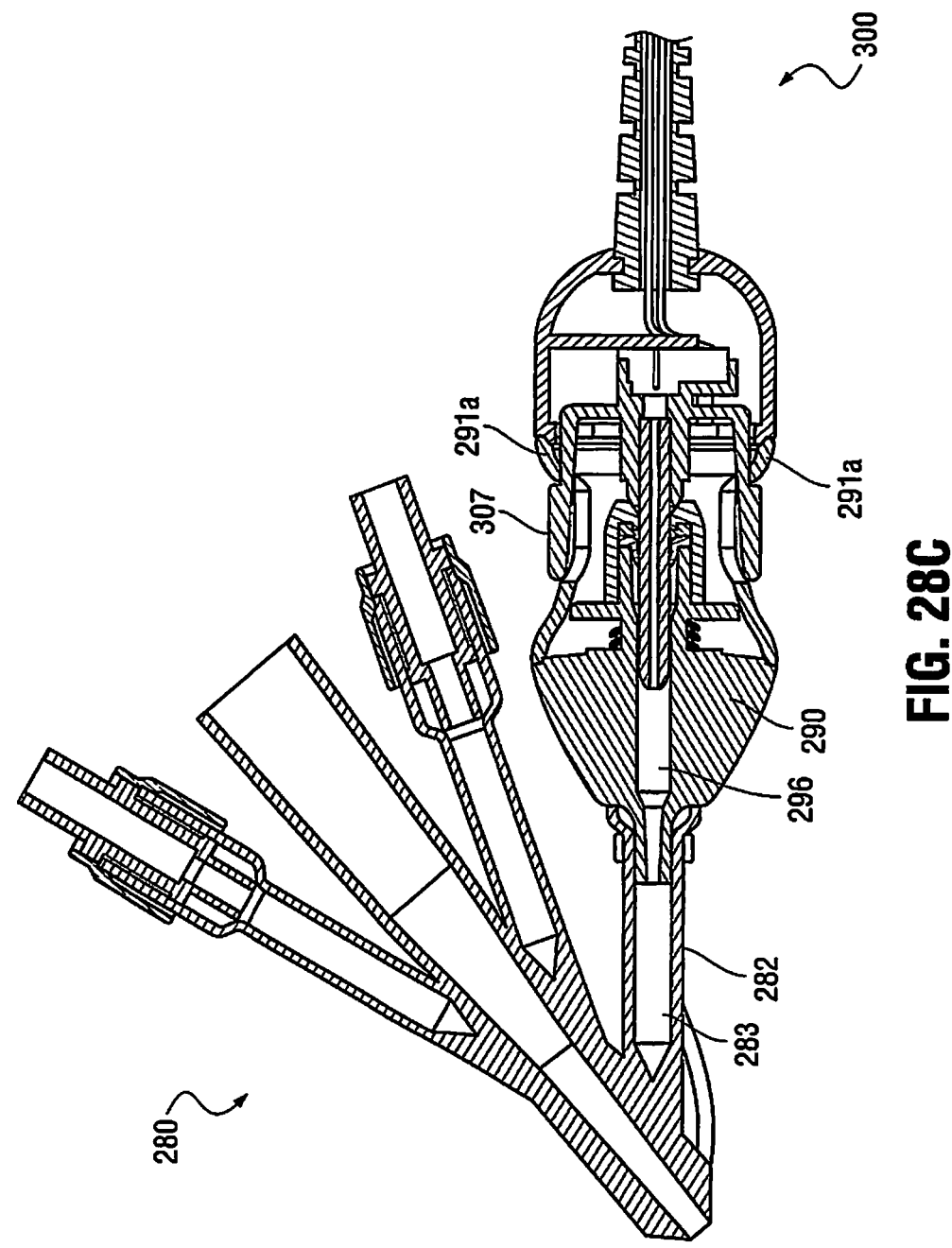
FIG. 28C is a cutaway side view similar to FIG. 28B showing the hub attached to the catheter.

More specifically, transducer hub or housing, designated generally by reference numeral 300, contains the pressure transducer and sensor 309 and is mounted to the angled side port 282. In the embodiment of FIG. 28A, the hub 300 is mounted to the catheter 280 by connection to housing 290. Housing 290 is connected to port 282 via a barbed fitting 295 providing an interference fit with the port 282. The hub 300 is locked or secured to connector 290 such as by a snap fit provided by the latch arms discussed below, although other attachments are also contemplated such as a friction fit, threaded attachment, other form of latch, etc., as well as other types of snap fits to provide an attachment that maintains an airtight seal so the air is contained within the air lumen and balloon 202 of the catheter 280. (As noted above catheter 280 is identical to catheter 200 except for its connector so catheter 280 includes (not shown) the inner and outer pressure balloons, stabilizing balloon, temperature sensor, etc. The catheter 280 can also have a single pressure balloon as in the aforementioned embodiments.

The housing 290 attached to catheter 280 has a proximal opening 294 and a channel (lumen) 296 to receive an elongated (rod-like) member or nose 302 extending distally from transducer hub 300. As shown channel 296 has a first diameter region 296*a* to match with the lumen 283 of the port 282, a second larger diameter region 296*b* proximal of region 296*a* to receive the male rod 302 of the hub 300, and a still larger diameter region 296*c* proximal of region 296*b* to receive the valve 299 and valve 298 and allow expansion thereof. As shown, valve 298 is dome shaped and is distal of valve 299. Conical cap 293, proximal of valve 299, provides a lead in to the valve 299 for the rod 302. Thermistor pins 292 receive thermistor connectors 308. Note valves 288, 299 are one example of valves that can be provided as other valves to provide an airtight seal are also contemplated. A single valve is also contemplated.

Hub 300 is mounted to connector 290 and includes a housing 304 from which a pair of distally extending snap fit connector arms 306 extend. The latch arms 306 are sufficiently flexible to enable attachment and have an enlarged distal portion 307, illustratively shown as arrow shaped although other enlarged shapes could be provided. The elongated member 302 extends between the latch arms 306. When the hub 300 is mounted to the connector 290, the elongated member 302 extends into the channel 296 to advance air to inflate the inner balloon. The enlarged ends 307 of latch arms 306 enter recesses 291 and engage shoulders 291*a* to retain the hub 300. Note to release (disconnect) the hub 300, the ends 307 are pressed radially inwardly to disengage from shoulder 291*a* and the hub 300 is pulled proximally. Note that alternatively a different number of latch arms could be provided.

The housing (connector) 290 has a lumen 296 for communication with the lumen 283 in the side port 282 of catheter 280 which communicates with the air lumen and inner balloon of the catheter 280. As noted above, the lumen 296 is dimensioned to receive the elongated rod 302 of transducer hub 300. The wire for the sensor extends in housing 300. When transducer hub 300 is attached to connector 290, such attachment inserts the elongated rod 302 into lumen 296 to advance air though the air lumen in the catheter and into the balloon 204. (Note the air lumen extends into its angled side port 282). The elongated member 302 also has a channel or lumen 305 extending therethrough to allow the pressure wave to travel through to the pressure sensor. Although in preferred embodiments no additional air needs to be injected into balloon 204 after attachment of hub 300, it is also contemplated that a port or opening can be provided in hub 300 to receive an injection device for injection of additional air. Such additional air can communicate with and flow through channel 305 of elongated member 302, into the air lumen and balloon 204 for inflation, or alternatively, a side port or opening in the angled port downstream (distal) of the elongated member 302 could be provided. Attachment of hub 300 to housing 290 also automatically connects thermistor connectors 308 to thermistor pins 292 to automatically connect the temperature sensor to the hub 300 for communication via a cable to a temperature monitor.

To charge the system, when the hub 300 is mounted to the side port 282 via attachment to connector 290, the elongated member 302 extends into lumen 296 to advance air through the air lumen into balloon 204 (or the pressure balloon in the embodiments with a single pressure balloon) to expand the balloon 204. That is, connection of the transducer hub 300 to the catheter 280 (port 282) automatically advances air through the connector lumen 296, the port lumen 283 and the first lumen 214 to expand the balloon 204. (Such connection also automatically connects the temperature sensor to the hub 300). In some embodiments, 0.2 cc of air can be displaced/advanced by the member 102, although other volumes are also contemplated. Thus, as can be appreciated, mounting of the hub 300 to the catheter 280 automatically pressurizes the air lumen/chamber and expands the balloon. Note the balloon can be partially or fully inflated (expanded), dependent on the amount of air advanced into the balloon. Further note that preferably the lumen is not vented to atmosphere when the transducer hub 300 is attached and air is advanced through the air lumen. The port 282 includes a closable seal, e.g., valves 298 and 299, through which the elongated member 302 is inserted but maintains the seal when the elongated member 302 remains in the lumen 296. Note that catheter 280 is identical in all other respects to catheter 200 so that the description of catheter 200 and its components and function (and alternatives) are fully applicable to catheter 280, the difference being the connector 290 of catheter 292 to receive transducer hub 300. The transducer hub is also different, e.g., has latch arms and a different configuration.

Figure 29A:
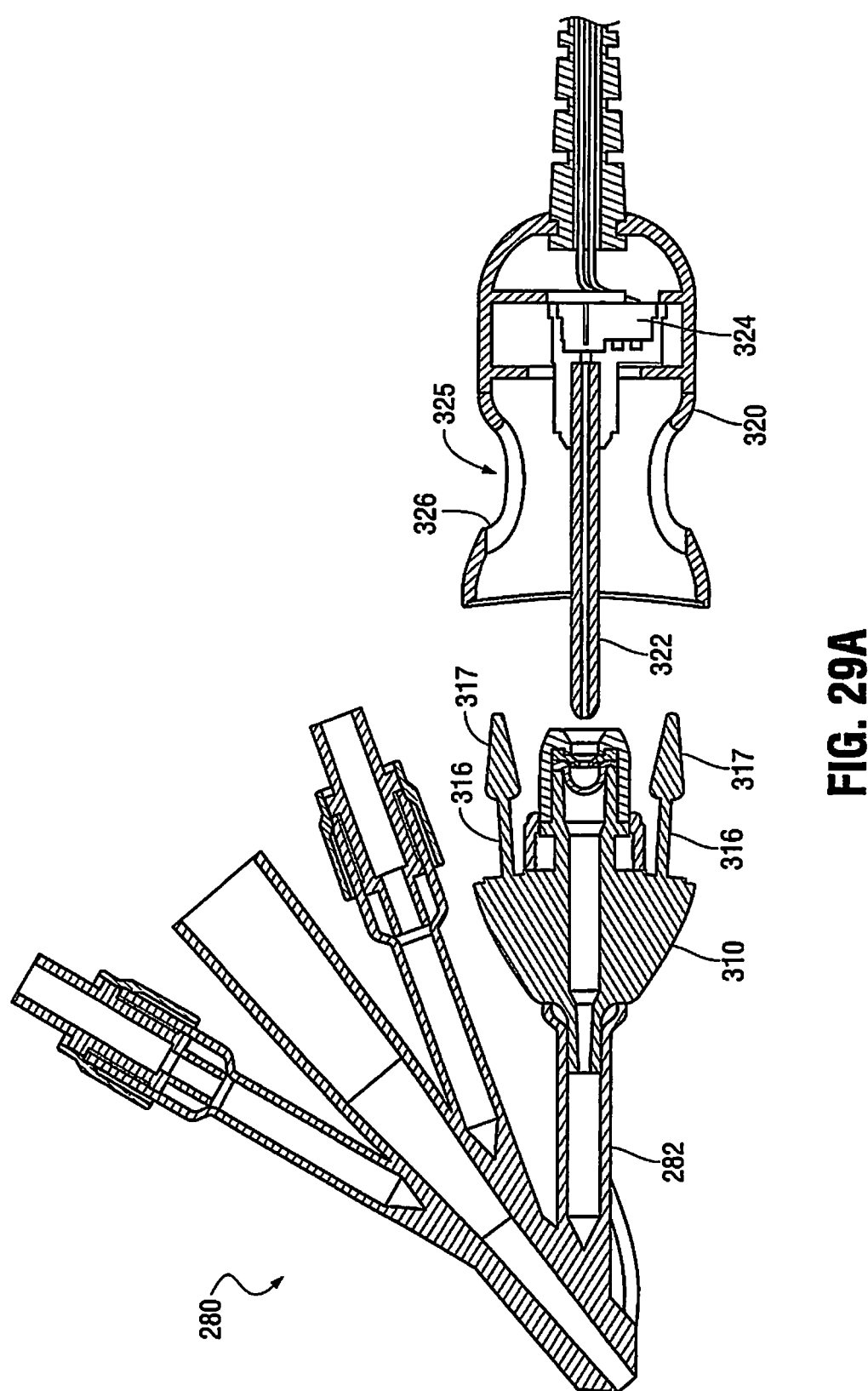
FIG. 29A is a cutaway side view of the hub and connector of an alternate embodiment showing the pressure transducer prior to connection to the catheter of FIG. 18A, a portion of the hub wall and catheter connector removed to show internal components
Figure 29B:
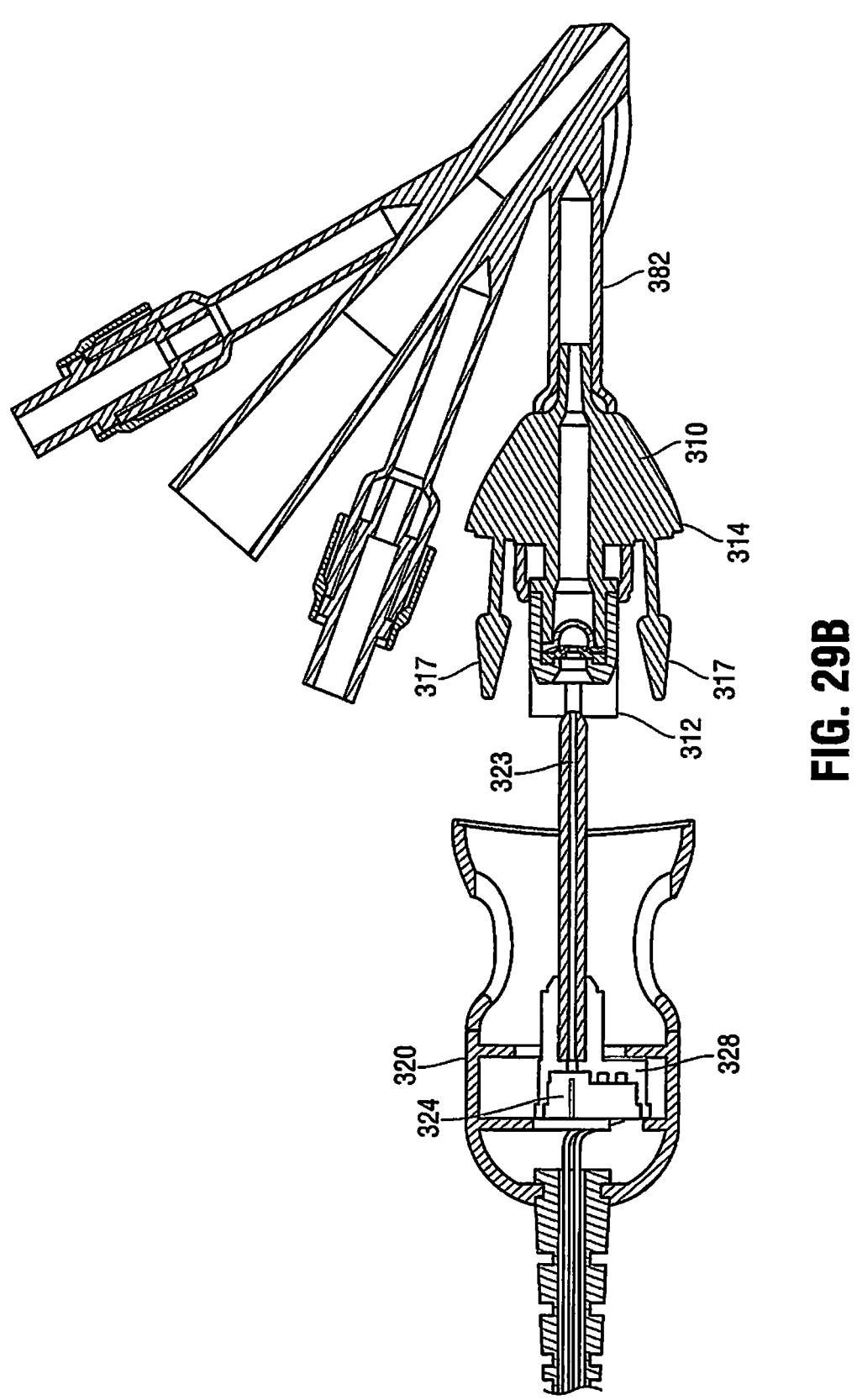
FIG. 29B is a cutaway side view of the hub and connector of FIG. 29A.
Figure 29C:
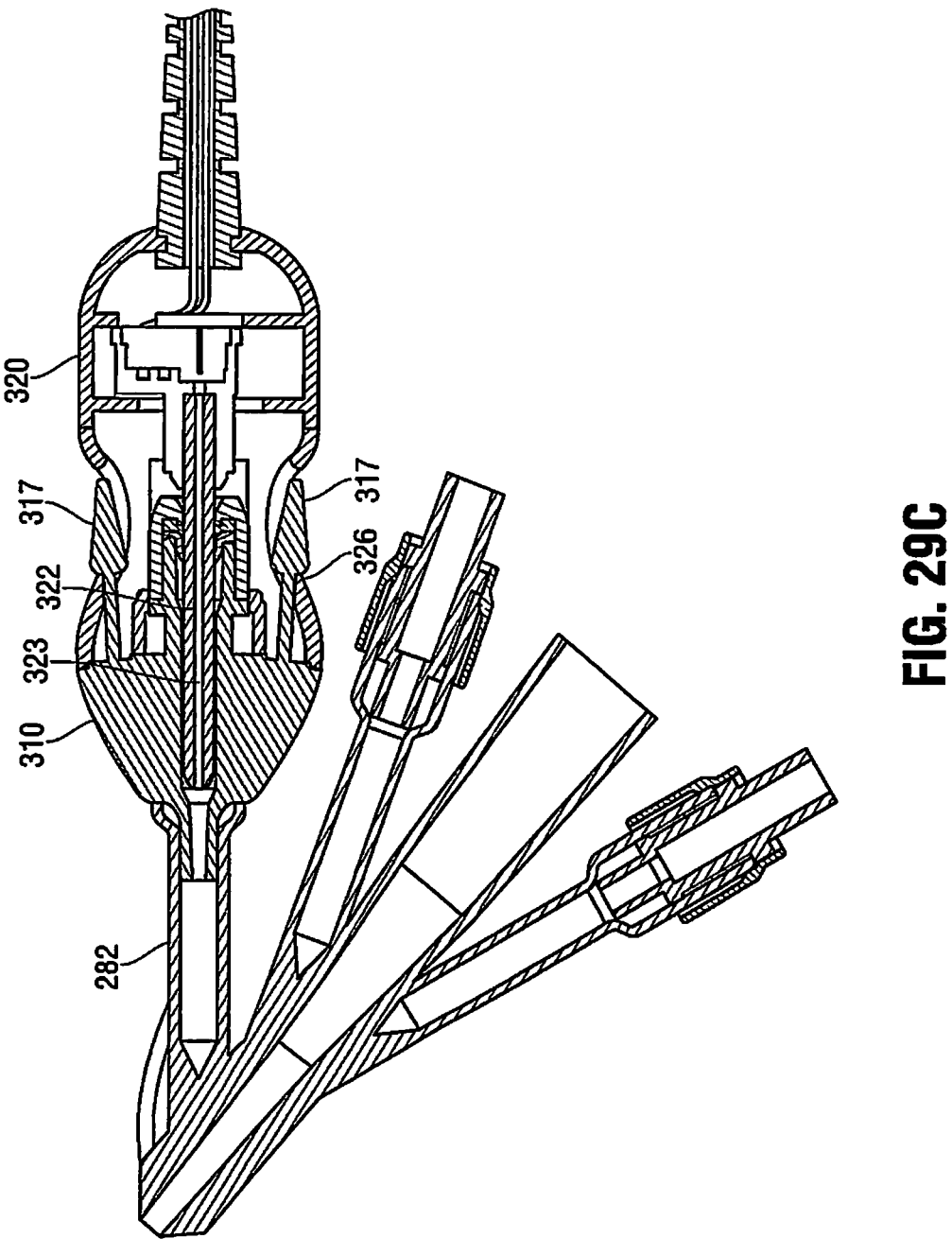
FIG. 29C is a cutaway view similar to FIG. 29B showing the hub attached to the connector of FIG. 29A when attached.

In the alternative embodiment of FIGS. 29A-29C, the latch arms are reversed so that they are located on the connector rather than on the transducer hub as in FIG. 28A. More specifically, transducer hub (housing), designated by reference numeral 320, has an elongated member 322 with a channel 323 and is identical to elongated member 302 of FIG. 28A for advancing air through the lumen and into the pressure balloon. Pressure transducer 324 is contained within the housing 320. Recesses 325 are dimensioned to receive the latch arms 317 of the connector or housing 310 which is connected to the side port 282 of catheter 280. (Catheter 280 is the same as catheter 280 of FIG. 28A except for connector 310). Extending proximally from housing 310 are two latch arms 16 with enlarged region 317 which engage the shoulders 326 formed by recesses 325 in hub 320 in a similar manner as latch arms 306 of FIG. 28A engage in recesses 291 and shoulder 291a. Connectors 328 in hub 320 engage thermistor pins 312 of connector 310 for connection of the temperature sensor. Connection of the hub 320, like hub 300, automatically advances air to inflate the pressure balloon and automatically connects the temperature sensor.

To disconnect (release) the hub 320, ends 317 of latch arms 316 are pressed radially inwardly to disengage from shoulder 326 so hub 320 can be pulled proximally out of connector 310.

In the alternate embodiment of FIGS. 64-69, the transducer hub or housing, designated generally by reference numeral 330, contains the pressure transducer and sensor and is mounted to the angled side port 620 of catheter 600. The hub 330 is mounted to the catheter 600 by connection to housing (connector) 670. Housing 670 is connected to port 620 via a barbed fitting 677 (FIG. 66A) providing an interference fit within the port 620. The hub 330 is locked or secured to connector 670 such as by a snap fit provided by the latch arms 332 discussed below, although other attachments are also contemplated such as a friction fit, threaded attachment, other forms of latch, etc., as well as other types of snap fits to provide an attachment that maintains an airtight seal so the air is contained within the air lumen and balloon of the catheter 600.

The housing (connector) 670 attached to catheter 600 has a proximal opening 672 and an internal channel (lumen) 680 (FIG. 65) to receive an elongated (rod-like) member or nose 334 extending distally from transducer hub 330. As shown, channel 680, which communicates with lumen 620a of port 620 has a first diameter region 680b, a second larger diameter region 680a proximal of region 680b to receive the male rod 334 of the hub 330, and a still larger diameter region 680c (FIG. 69) proximal of region 680a to form a receptacle for O-ring 682. This configuration of channel 680 provides a region larger than the OD of the rod 334 so it is not a one-one ratio. In a one-one ratio, a small pressure drop in the balloon would result in a large pressure drop in the system. Thus, the channel 680 is configured/sized to provide extra volume to act as a capacitor to slow down the percentage pressure loss and stabilize the pressure readings due to loss of air when compressed. The channel 680 has a distal larger diameter region 680d extending from narrowed region 680b to form a funnel for entry of the tubular portion 609 of the inner pressure balloon 608. The tubular portion 609 of the inner balloon 608 in manufacture is slid into/pressed into the funnel 680d until it cannot go in any further due to the reduced channel portion 680b. The tubular portion 609 of balloon 608 can be glued into place within region 680d. Note that in the illustrated embodiment, the tubular portion 609 of inner balloon 608 would extend into and through side port 620 into connector 680d. However, in alternate embodiments, the tubular portion 609 of balloon 608 could terminate further distally within angled port 620, and in some embodiments could terminate even further distally, i.e., within catheter lumen 644 so that air would be advanced by rod 334 through lumen 644 and then into the tubular portion 609 through a proximal opening in tubular portion 609 communicating with lumen 644.

Figure 28D:
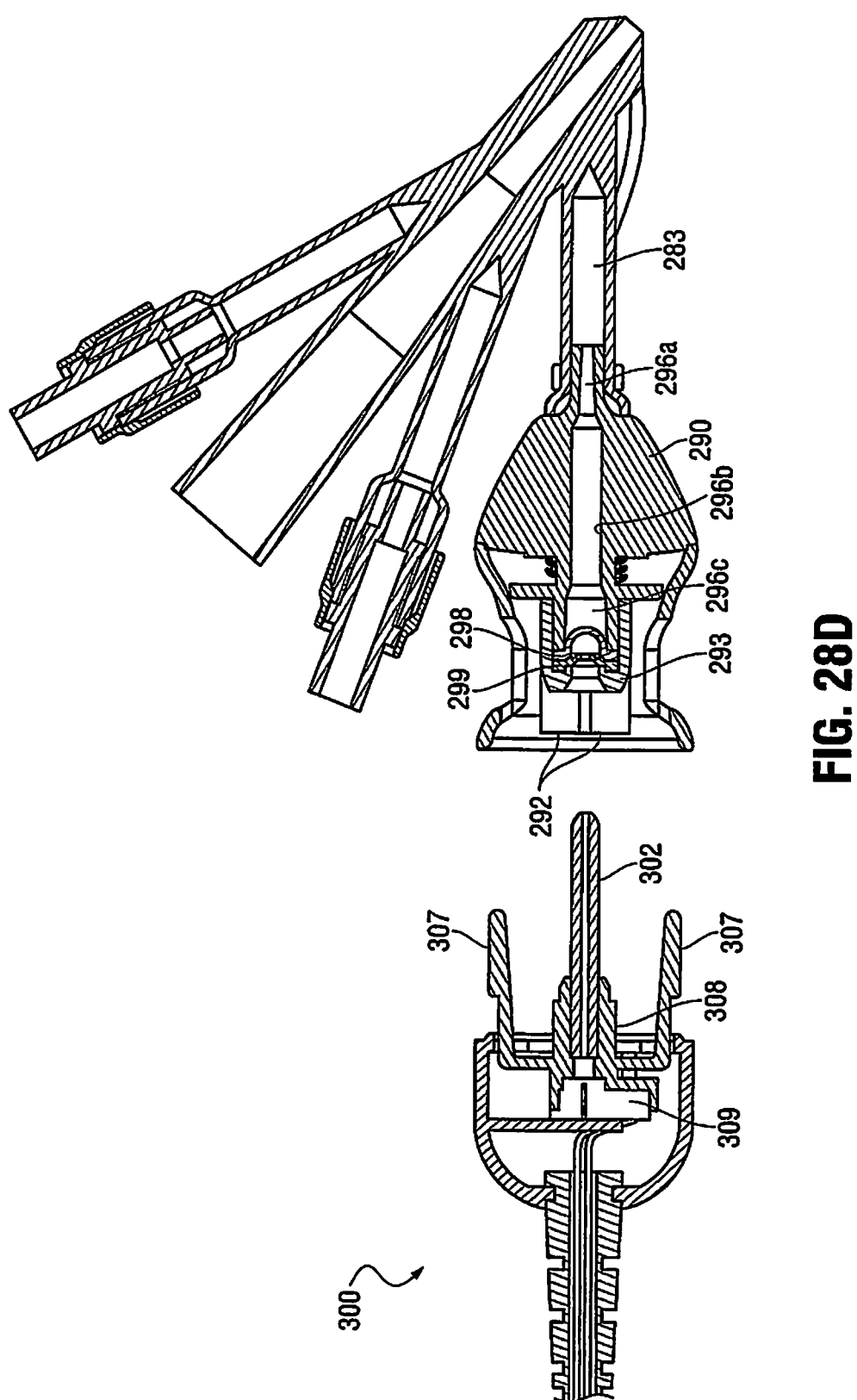
FIG. 28D is a cutaway side view similar to FIG. 28B from the other side.

Instead of valves as in the embodiment of FIG. 28D, two O-rings 684, 682 are seated within connector 670 with O-ring 682 positioned in support or cup 676 and O-ring 684 positioned distal of support 676 in a recess in connector 670. Thermistor barrel shape receptacles 678 (FIGS. 66C, 67 and 68) receive thermistor connectors or pins 335 (FIG. 64), and a metal piece (receptacle) is positioned within each plastic barrel 678, each forming a female receptacle for the male pin(s) 335. The thermistor wires 679, shown in FIGS. 66B and 66C, extend from the thermistor, positioned in the catheter 600 adjacent the drainage lumen, through lumen 644 and through side port 620. (Alternatively, the wires can extend through a separate lumen in the catheter). The two wires 679 extend through an elongated groove 673a and slot 673c in conical connector part 673, and are then wrapped (spooled) around shaft 681 and retained by flange 673b. The wires 679 extend through the flange 673b and are split to each electrically connect with a metal piece (receptacle) in one of the female connector barrels 678. C-shaped extension 671a of cover 670 is inserted into slot 673c covering the wires 679. When cover 671 is placed over holder 673, the wires 679 are hidden to protect the wires. Thus, as can be appreciated in the view of FIG. 64, once assembled, the wires 679 are not visible.

Hub 330 is mounted to connector 670 and includes a housing 331 from which a pair of distally extending snap fit connector arms 332 extend. The latch arms 332 are sufficiently flexible to enable attachment and have an enlarged distal portion 332a, illustratively shown as arrow shaped although other enlarged shapes could be provided. The elongated member 334 extends between the latch arms 332. When the hub 330 is mounted to the connector 670, the elongated member 334 extends into the channel 680 of connector 670 to advance air though inner balloon tubular portion 609 to inflate the inner balloon 608. The enlarged ends 332a of latch arms 332 enter recesses 674 and engage shoulders 674a to retain the hub 330. The arrowhead tips of the latch arms 332 are at an acute angle to create a positive lock so that once engaged with the shoulder 674a, the hub 330 cannot be pulled proximally unless the latch arms 332 are released. To release (disconnect) the hub 330, the ends 332a are pressed radially inwardly to disengage from shoulder 674a and the hub 330 is pulled proximally. Note that alternatively a different number of latch arms could be provided. The distally extending thermistor pins 335 engage thermistor connectors within barrels 678 of connector 670 which have an interior stop to limit insertion of hub 330.

This connection of the hub 330 and connector 670 limit lateral and longitudinal movement to ensure accurate pressure readings as lateral movement, for example, could change the pressure. The longitudinal movement is restricted in a proximal direction by the latch arms/shoulder engagement and in a distal direction by the full insertion of the thermistor pins 335 or alternatively by engagement of the hub 330 and housing 670 distal and proximal surfaces. The O-ring engagement of the elongated rod 334 limits lateral movement of the rod 334 and therefore restricts lateral movement of the hub 330.

Printed circuit board 336 containing the pressure sensor is mounted within hub 330. It can be bonded to a support within the hub. Note a digital pressure sensor can be used instead of an analog sensor in this embodiment as well as the other embodiments disclosed herein.

When transducer hub 330 is attached to connector 670, such attachment inserts the elongated rod 334 into lumen 680 to advance air though the tubular portion 609 of the inner balloon 608 and into the inner balloon 608 to inflate the balloon 608. The elongated member 334 also has a channel or lumen 337 (FIG. 63) extending therethrough to allow the pressure wave to travel through to the pressure sensor of PCB 336. Although in preferred embodiments no additional air needs to be injected into balloon 608 after attachment of hub 330, it is also contemplated that a port or opening can be provided in hub 330 to receive an injection device for injection of additional air. Such additional air can communicate with and flow through channel 337 of elongated member 334, into the tubular portion 609 and inner balloon 608 for inflation, or alternatively, a side port or opening in the angled port downstream (distal) of the elongated member 334 could be provided. Attachment of hub 330 to housing 670 also automatically connects thermistor connectors (within barrels 678) to thermistor pins 335 to automatically connect the temperature sensor (within the catheter) to the hub 330 for communication via a cable to a temperature monitor.

In use, to charge the system, when the hub 330 is mounted to the catheter side port 620 via attachment to connector (housing) 670, the elongated member 334 extends into lumen 680 to advance air through the lumen into balloon 608 to expand the balloon 608. That is, connection of the transducer hub 330 to the catheter 600 (port 620) automatically advances air through the connector lumen 680 and tubular portion 609 to expand the inner balloon 608. Such connection also automatically connects the temperature sensor to the hub 330. In some embodiments, 0.2 cc of air can be displaced/advanced by the member 334, although other volumes are also contemplated. Thus, as can be appreciated, mounting of the hub 330 to the catheter 600 automatically pressurizes the air lumen/chamber and expands the balloon. Note the balloon can be partially or fully inflated (expanded), dependent on the amount of air advanced into the balloon. Further note that preferably the lumen is not vented to atmosphere when the transducer hub 330 is attached and air is advanced through the air lumen.

Note the lumen which is used to inflate the pressure balloon and create the air column has an opening at a distal region to communicate with the interior of the pressure balloon. If an outer balloon is provided, an additional lumen can be provided in the catheter to communicate with the outer balloon to fill the outer balloon and an additional angled port (extension) at the proximal end of the catheter would receive an inflation device to inflate, either fully or partially, the outer balloon.

Note in each of the embodiments disclosed herein, air is described as the preferred gas for creating the column and expanding the balloon, however, other gasses are also contemplated for each of the embodiments.

The pressure balloons of the embodiments herein can be symmetrically shaped as shown or alternatively shaped such that a distal region has an outer transverse cross-sectional dimension, e.g., diameter, greater than an outer transverse cross-sectional dimension, e.g., diameter, of the proximal region. A smooth transition (taper) can be provided between the distal region and proximal region, although other configurations are also contemplated. The inner (and outer) balloon can by way of example be made of urethane, although other materials are also contemplated.

The wire connector of the foregoing embodiments can plug into the openings of a connector positioned on or in the hub. The wire connector can be internal of the hub with an opening in the wall of the hub to enable access for the wire connector. Also note that alternatively the wire can include a female connector and the hub can have a male connector. Other types of connectors/connections are also contemplated.

In alternate embodiments, any of the catheters disclosed here can include a pulse oximetry sensor to measure oxygen saturation in the urethral or bladder tissue. The sensor can be located either proximal or distal to the pressure balloon and/or stabilizing balloon. It could also alternatively be mounted within one of the balloons.

Figures 14A, 14B:
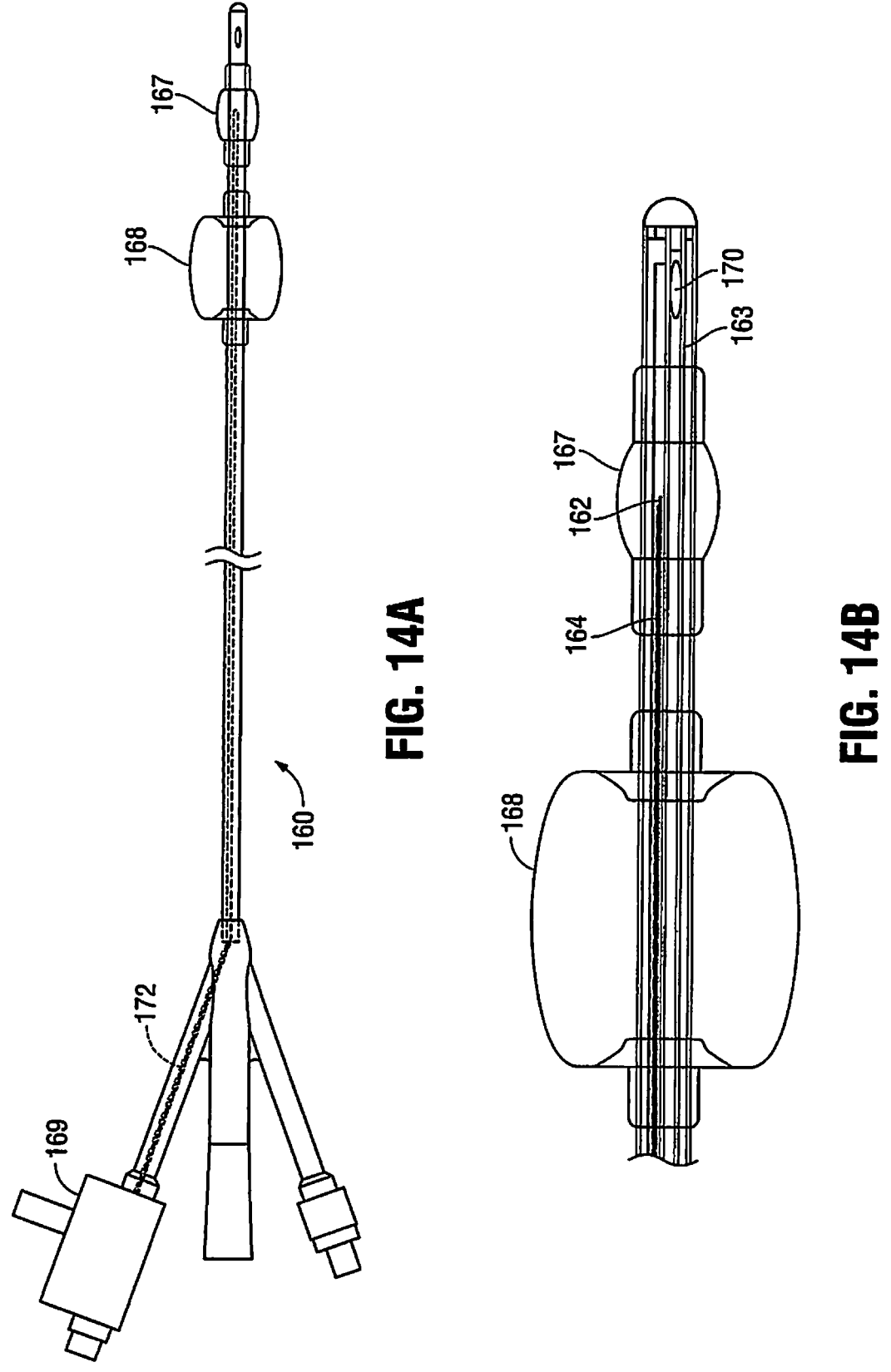
FIG. 14A is a side view of another alternate embodiment of the catheter of the present invention having dual pressure sensors, the first sensor positioned within the air lumen and the second sensor positioned external of the catheter, the two balloons shown in the inflated condition.
FIG. 14B is an enlarged view of the distal portion of the catheter of FIG. 14A.

It is also contemplated that in some embodiments a backup system be provided to determine pressure. The backup system can provide a double check of pressure readings to enhance accuracy. Such backup system can be used with any of the embodiments disclosed herein to provide a second pressure reading system. One example of such backup system is disclosed in FIGS. 14A and 14B. In this embodiment, catheter 160 has the pressure transducer/pressure sensor 162 like sensor 30 of FIG. 1 within the air (or other gas) lumen 164 communicating with pressure balloon 167, forming a "first system", plus a pressure transducer/pressure sensor 169 at a proximal end of the catheter as in FIG. 12 or external of the catheter forming a "second system". Thus, the pressure sensor 162 is at a distal end of the air charged lumen 164 and pressure sensor 169 is at proximal end of the air charged lumen 164. Both sensors 162 and 169 are electrically connected to a monitor which provides a graphic display of pressure readings. The catheter 160 also includes a temperature sensor either as part of the sensor 162 or a separate component that can be positioned for example in the lumen 164 distal of sensor 162 as in the embodiment of FIG. 8. A stabilizing balloon 168 and an inflation lumen to inflate balloon 168 can also be provided. Lumen 163, having a side opening 170 at its distal end, is configured to drain the bladder similar to lumen 20 and side opening 22 of the embodiment of FIG. 1.

In use, catheter 160 is inserted into the bladder and stabilizing balloon 168 is inflated to secure the catheter 160 in place. The system is charged by inflation of the balloon 167, i.e., preferably partially inflated for the reasons discussed above, by insertion of air through side port 172 which is in fluid communication with the air lumen in a closed system formed by the internal space of the balloon 167 and the internal lumen 164 communicating with the internal space of balloon 167. With the balloon 167 inflated, pressure monitoring can commence as external pressure applied to an outer surface of the balloon 167 compresses the air (or other gas) within the chamber. The sensor 162 at the distal end of lumen 64 provides continuous pressure readings, converted to an electrical signal by the transducer within the distal end of lumen, and then electrically communicates through its transmission wires extending through the air lumen to an external monitor either directly or via a converter. Additionally, pressure within the air charged column is measured at a proximal region by sensor 169 within side port 172 of catheter 160. The sensor 162 at the distal end of lumen 164 provides continuous pressure readings, and such pressure readings can be confirmed by the proximal sensor. Such pressure readings can be performed continuously (along with continuous temperature monitoring) or alternatively can also be adapted if desired for periodic monitoring so the pressure and/or temperature readings can be taken at intervals or on demand by the clinician. Thus, air pressure readings at a proximal end plus microtip pressure readings at the distal end are provided. The sensors 162 and 169 can electrically communicate with an external monitor to display both pressure readings from sensors 162, 169, or alternatively, if the pressure readings are different, they can be averaged to display a single measurement. Clearly, other displays of information can be provided to display the information from the two sensors 162, 169.

The sensors disclosed herein can be microtip sensors within the air (or other gas) lumen or balloon. In alternative embodiments, fiber optic sensors within the air (or other gas) lumen or balloon can by utilized to transmit circumferential/area pressure. The pressure transducers can be housed within the catheter or alternatively external to the catheter. Additionally, core temperature sensors can be part of the pressure sensor or a separate axially spaced component.

The multi-lumen catheters disclosed herein provide an air (or other gas) charged balloon giving precise readings of intra-abdominal pressure and the systems are charged via insertion of air through a side port. The multi-lumen catheters are easily inserted into the bladder in the same manner as standard bladder drainage catheters and enable continuous drainage of urine while continuously recording IAP without interrupting urine flow and without requiring retrograde filling of the bladder with water. Thus, these catheters provide a closed system. The catheters also have a balloon providing a large reservoir (large capacity) and large circumferential area/interface for obtaining more information from the bladder over multiple reference points (rather than a single point sensor) that provides an average pressure to provide a more accurate assessment of the surrounding environment as pressure measurement is not limited to one side of the bladder but can determine measurements on the opposing side as well.

As noted above the catheters in some embodiments can be connected to a bedside monitor through either a wire or blue-tooth wireless connection. The system can also in some embodiments include an indicator or alarm system to alert the staff at the site as well as remote staff through wired or wireless connections to external apparatus, e.g., hand held phones or remote monitors.

As noted above, an alarm or indicator can be provided in some embodiments to alert the staff. The indicator can be a visual indicator such as a light, LED, color change, etc. Alternatively, or additionally, the indicator can be an audible indicator which emits some type of sound or alarm to alert the staff. The indicator can be at the proximal region of the catheter or at other portions of the catheter, e.g., at a distal end portion, where known imaging techniques would enable the user to discern when the indicator is turned on. It is also contemplated that in addition to providing an alert to the user in some embodiments, the pressure monitoring system can be tied into a system to directly reduce abdominal pressure so that if the pressure exceeds a threshold level (value), the abdominal pressure can automatically be reduced. In such systems, an indicator can be provided on the proximal portion of the catheter, e.g., at a proximal end outside the patient's body, or separate from the catheter. The sensor can be in communication with the indicator, either via connecting wires extending through a lumen of the catheter or a wireless connection. The sensor can be part of a system that includes a comparator so that a comparison of the measured pressure to a predetermined threshold pressure value is performed and a signal is sent to the indicator to activate (actuate) the indicator if the measured pressure exceeds the threshold pressure to alert the clinician or staff that pressure within the abdomen is too high and a signal is also sent to a device or system to automatically actuate the device or system to reduce the abdominal pressure. If the measured temperature is below the threshold, the indicator is not activated. A similar system can be used for temperature measurement and indication.

It is also contemplated that a micro-air charged sensor could be provided in the retention (stabilizing) balloon.

It is also contemplated that microtip sensors and/or fiber optic sensors can be utilized to measure pressure, and these sensors can be utilized instead of or in addition to the air pressure readings utilizing the aforedescribed balloon(s) for measuring pressure.

Pulse oximeters for measuring oxygen levels (oxygen saturation) in the urethral and/or bladder tissue could also be provided. In some embodiments, the pulse oximetry sensors can be positioned on the catheter proximal to the retention balloon. Alternatively, the sensors can be positioned within the retention balloon, on the catheter distal to the pressure balloon or on other regions of the catheter. Another channel in the catheter can be provided for the sensor and its connector to external devices, e.g. readers.

The catheters disclosed herein are designed for insertion into the bladder. However, it is also contemplated that they can be adapted for insertion into the rectum, colostomy pouch, stomach, supra-pubic bladder drain, or other orifice directly connected with the abdominal cavity.

Smart Cable

The smart cable of the present invention, which connects at one end to the pressure monitor and at the other end to one of the pressure sensing/measuring catheters disclosed herein, has one or more of the following features: a) a filter system to enable collection and analysis of data at a particular point in the patient's respiratory cycle (referred to below as "feature a"); b) a temperature adjustment feature to adjust pressure values in response to temperature changes (referred to below as "feature b"); c) the capability of storing an initial sensing balloon pressure value to facilitate shift changes (referred to below as "feature c"); and or d) the capability to adjust for pressure changes caused by patient movement (referred to below as "feature d"). Each of these features a, b, c and d is discussed in detail below. Note that the cable of the present invention can have only one of these features, two of these features, three of these features or all of these features. Furthermore, the cable of the present invention can be used with any of the catheters disclosed herein or alternatively used with other catheters. By providing these features in the cable itself, the cable can be used with standard monitors having pressure sensing capability and zeroing function, e.g. Philips or GE monitors. These generic monitors are used for measuring pressure, such as blood pressure, which are adapted for measuring abdominal pressure using the catheter and connector of the present invention.

The cable is disclosed herein for use with a pressure sensing catheter insertable into the bladder for measuring abdominal pressure via measuring bladder pressure as disclosed herein and also disclosed in commonly assigned patent publication 2018/0344234 and publication 2020/0164184, the entire contents of these applications are incorporated herein by reference. However, it should be understood that the cable can be used to connect to the monitor other pressure sensing catheters such as by way of example a) a catheter for measuring bladder pressure to determine uterine contraction pressure as disclosed in commonly assigned U.S. publication 2018/0344250 or b) a catheter for measuring intra-abdominal pressure in a pregnant woman to assess occurrence or likelihood of pre-eclampsia as disclosed on commonly assigned provisional application Ser. No. 62/803,284, filed Feb. 8, 2019 or c) a catheter for measuring intramuscular pressure as in commonly assigned U.S. publication 2018/0344184 or d) a catheter for measuring the intrauterine pressure in the uterus and the fallopian tubes during HSG, SHG, HyCoSy, or SIS procedures as disclosed in commonly assigned U.S. publication 2018/0344183. The entire contents of each of the applications are incorporated herein by reference.

The cable of the present invention can be utilized, e.g., plugged into various pressure monitors such as the GE Dash or Marquette monitor or the Phillips Intellivue. By way of example, cable 700 of FIGS. 70-73 is shown for use for connection to a Phillips vessel pressure monitor with connectors for the monitor shown in FIG. 73.

With regard to feature (a), currently pressure readouts are in the form of a square wave where the high and low pressure readings (peaks and valleys) of the pressure readings are all displayed. It is up to the clinician to discern the lower values or assess the median value. In the cable of the present invention, the filter system collects and analyzes all the data input and filters out the upper values and takes the lowest values over specific periods of time. That is, over a period of time X, the cable, via its software, takes Y samples representative of the lowest value and calculates an average Z. This is repeated during the period of pressure monitoring and the average is then displayed on the monitor as a line readout. This provides an easily discernable readout (e.g., at a glance) of the lowest pressure values. By way of example, the software can filter out the higher values and take 4 samples (Y) in a 6 second time period (X) and calculate the average value (Z) in the 6 second time period. Clearly, a different number of samples and/or a different time period is also contemplated. In some embodiments, the filtering function can be selectively turned on by a button or switch on the cable. In this manner, if the standard wave pattern readout is desired, the filtering function is not activated; if the filtering function for the straight line readout of low pressure values is desired, the filtering function is activated. Note either the filtering function or the non-filtering function can be the default function and thus activated accordingly.

With regard to feature (b), in some embodiments, the cable reads temperature so the pressure values can be adjusted for temperature. For example, if there is an increase in temperature within the patient's body, pressure would increase. Similarly, if there is an increase in room temperature, pressure would likewise increase. Such temperature changes could therefore undesirably effect pressure reading and provide inaccurate pressure readings. In this embodiment, the temperature readings are evaluated by the printed circuit within the cable and the pressure value is adjusted accordingly so the pressure reading remains accurate. Thus, by adjusting for temperature changes, the accuracy of pressure readings is improved. In another embodiment, a barometric sensor is provided and the cable reads barometric pressure to accommodate for changes in barometric pressure. Changes in barometric pressure, such as caused by a rainstorm, could cause a change in pressure which could lead to inaccurate pressure readings. Barometric pressure and the sensing balloon pressure are inversely related so that an increase in barometric pressure will cause a decrease in pressure and a decrease in barometric pressure (such as by a rain storm) will cause an increase in pressure, the cable software making the adjustments accordingly to maintain the accuracy of the pressure readings of the sensing balloon. Thus, in this embodiment, the cable will adjust the pressure value to take into account barometric pressure changes, thereby improving the accuracy of the pressure reading. The pressure adjustment to accommodate barometric measurement can be used instead of or in addition to the pressure adjustment to accommodate temperature measurement changes. Thus, in these embodiments, in use, at the start of the procedure, temperature readings would be provided. During the pressure monitoring, if the temperature changes, e.g., changes beyond a threshold amount, the pressure readings would be adjusted. This could be to accommodate any change in temperature, or alternatively, can be in response to a change in temperature exceeding a predetermined change. Similarly, during pressure monitoring adjustments can be made to accommodate any change in barometric pressure, or alternatively, can be in response to a change in barometric pressure exceeding a predetermined change. Consequently, as can be appreciated the accuracy of pressure reading and thus pressure monitoring is increased as a result of the cable software.

Feature c enables the tare function to be stored in the cable so the initial pressure value is remembered for calibration of the sensor. Tare is used to monitor pressure change or relative pressure. The tare function sets a new 0 point (at the current reading) providing a baseline for measuring relative pressure. When the new 0 point is set for relative pressure measurement, the output adjusts to that new 0 point. Tare function in effect calls whatever output the sensor is reading to a zero without changing the true zero point.

At set up, the outer balloon is inflated and pressure sensor zeroed (tare function) and stored within the cable. (Note the cable connection also inflates the inner balloon due to insertion of the pin, e.g., pin/rod 334 of FIG. 64 into the air lumen). During a shift change, the clinician disconnects the cable connector from the catheter. Without the stored value, the balloon would need to be deflated, the catheter withdrawn, and then the balloon re-inflated for calibration. (Note the balloon cannot be calibrated when within the body because movement of the patient, or other variable, will impact measurement). By storage of the tare value in the cable, the catheter can remain in the patient, with the balloon inflated, while the connector is disconnected to the catheter and reconnected. Thus, there is no need to recalibrate pressure in the balloon. Note the shift changes typically occur at 12 hour intervals and are dictated by hospital or health clinic policy. The steps of zeroing the pressure sensor and storing the tare value are discussed below in conjunction with the discussion of the use of the system and depicted in the charts and diagrams of FIGS. 74-78.

The cable of the present invention can also have the capability to adjust for pressure changes caused by patient movement (feature d identified above). The patient is typically in the supine position. If the patient moves, e.g., sits up, this could affect pressure readings, e.g., the pressure can increase due to the higher elevation and pressure (e.g., squeezing) applied by the body, The cable therefore can have a movement adjustment feature. In the lying position, the pressure measurement is stored in the cable. When the patient is elevated, e.g., moved to a sitting position, the change in pressure is detected, and this difference is subtracted from the new seated pressure reading. By way of example, assuming in the supine position, the pressure measurement is 8 mmHg and when the patient is in a seated position, the pressure changes to 15 mmHg. The cable would accommodate for this differential by subtracting 7 mmHG from the measurement value. One way to achieve this would be for the clinician to push a button when the patient is in the supine position to store the pressure value in memory in the cable PCB. Once seated, another button on the cable would be pressed to remove the delta function.

Turning now to FIGS. 70-73, details of the cable system are illustrated. The smart cable of the present invention is designated generally by reference numeral 700 and has a monitor connection end 721a at a proximal region and a catheter connection end 721b at a distal region distal of housing 720. Housing (hub) 720 contains a printed circuit board 721.

Figure 64:
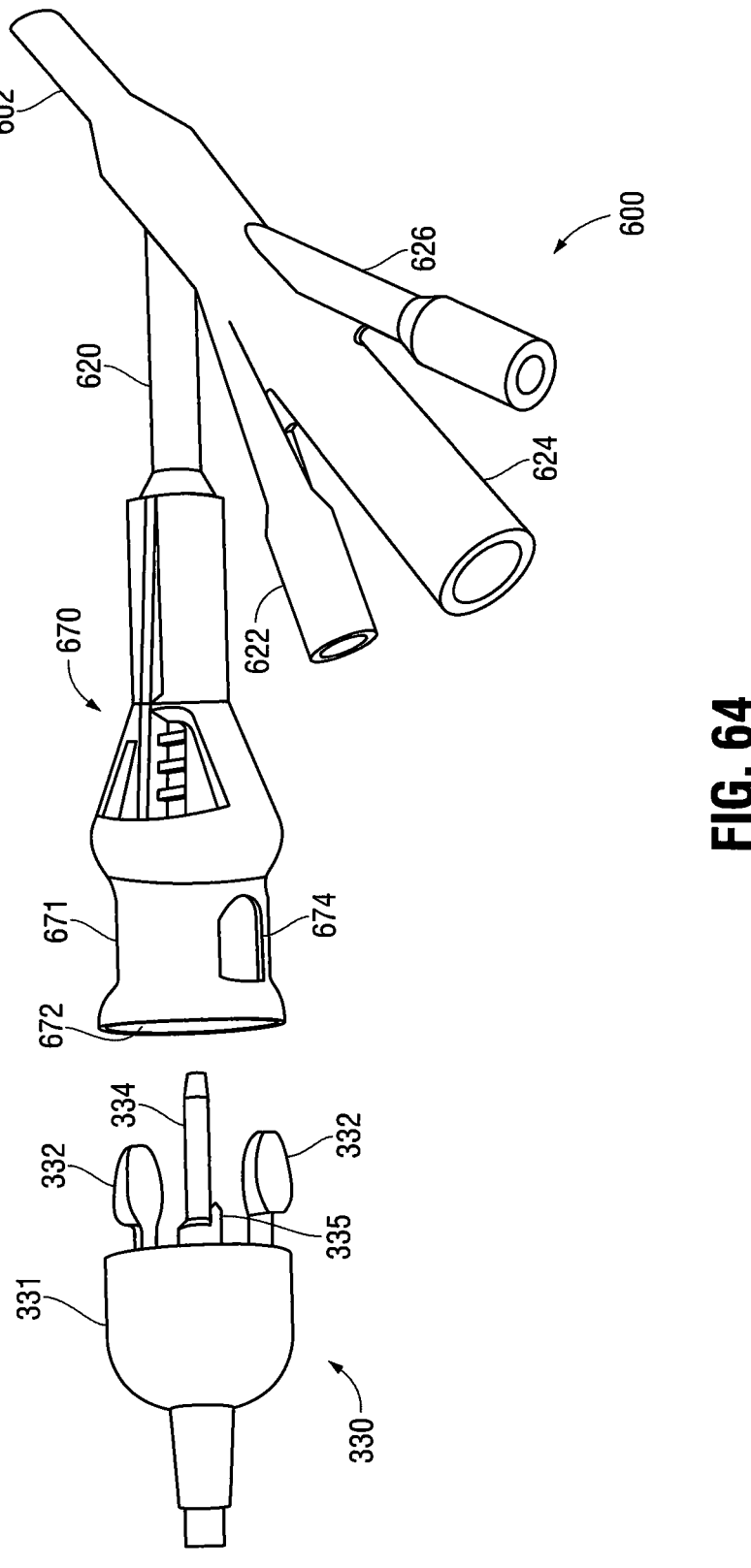
FIG. 64 is a perspective view of an alternate embodiment of the hub and connector of the present invention.
Figure 65:
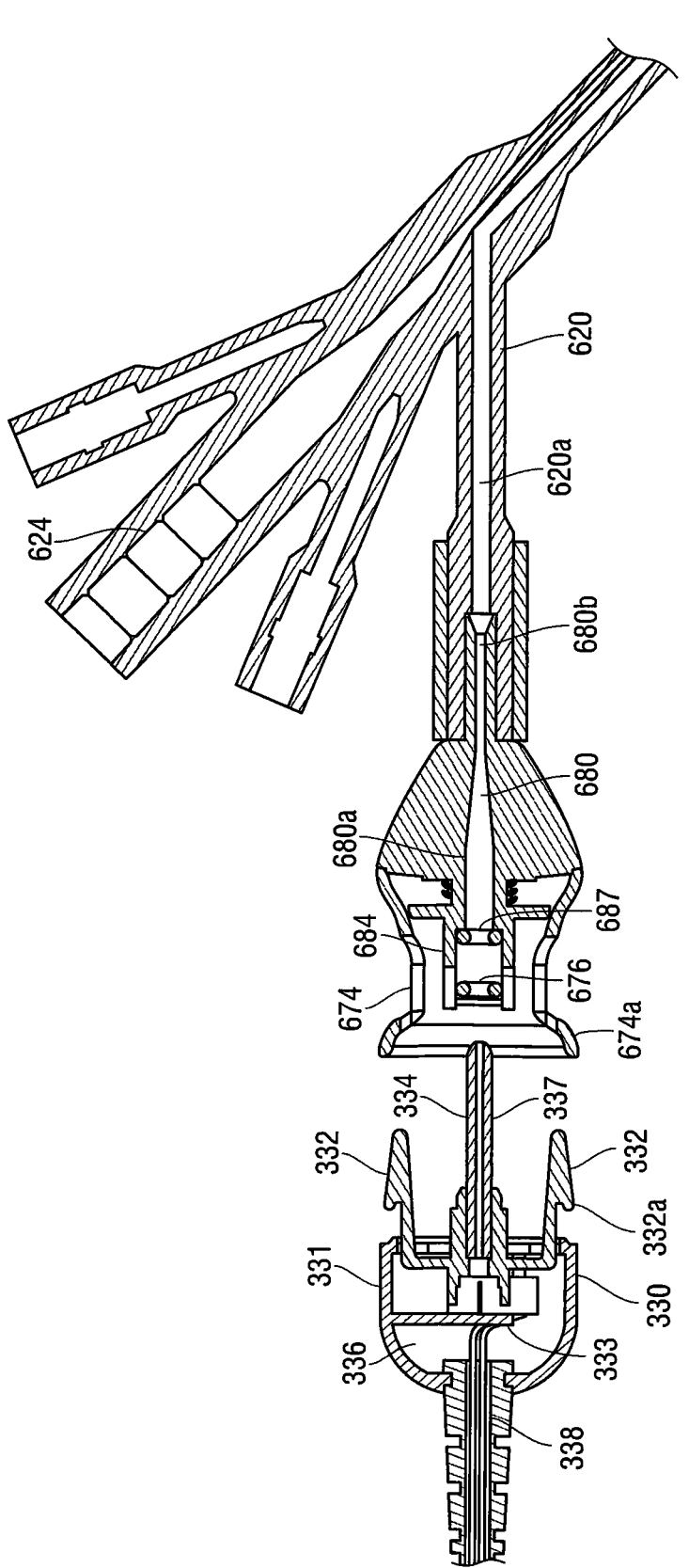
FIG. 65 is a cutaway side view of the hub and connector of FIG. 64.
Figure 66A:
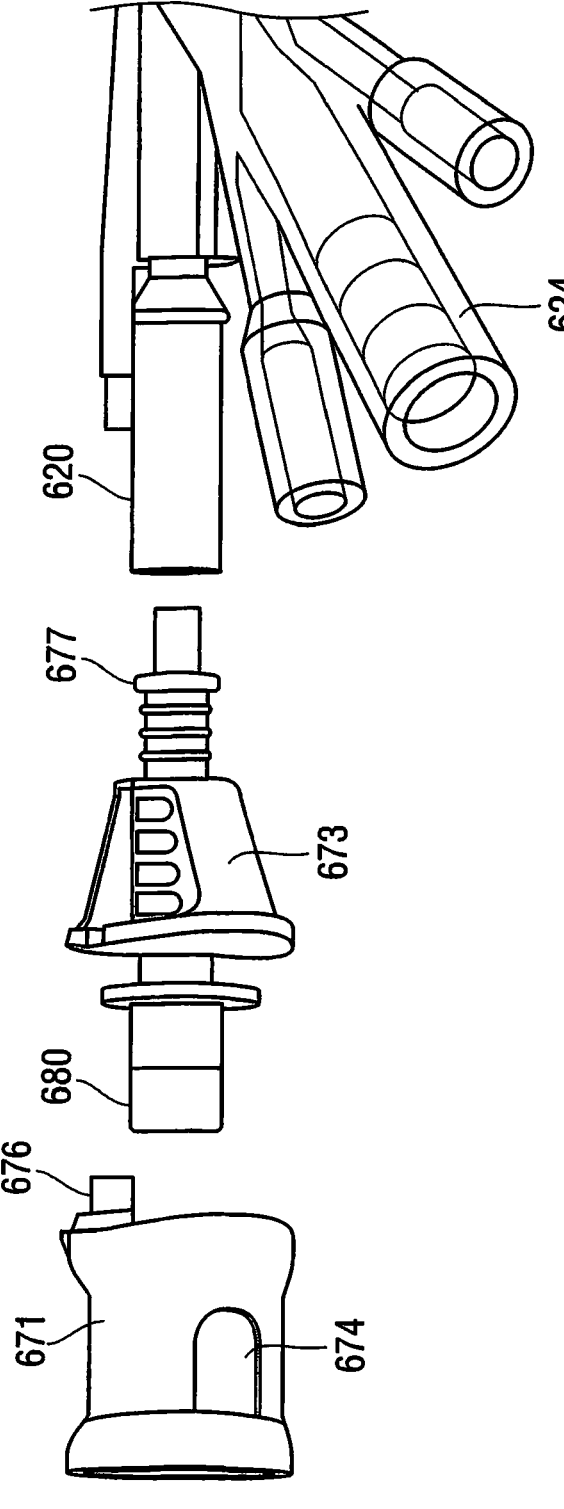
FIG. 66A is an exploded perspective view of the hub and connector of FIG. 64.
Figure 66B:
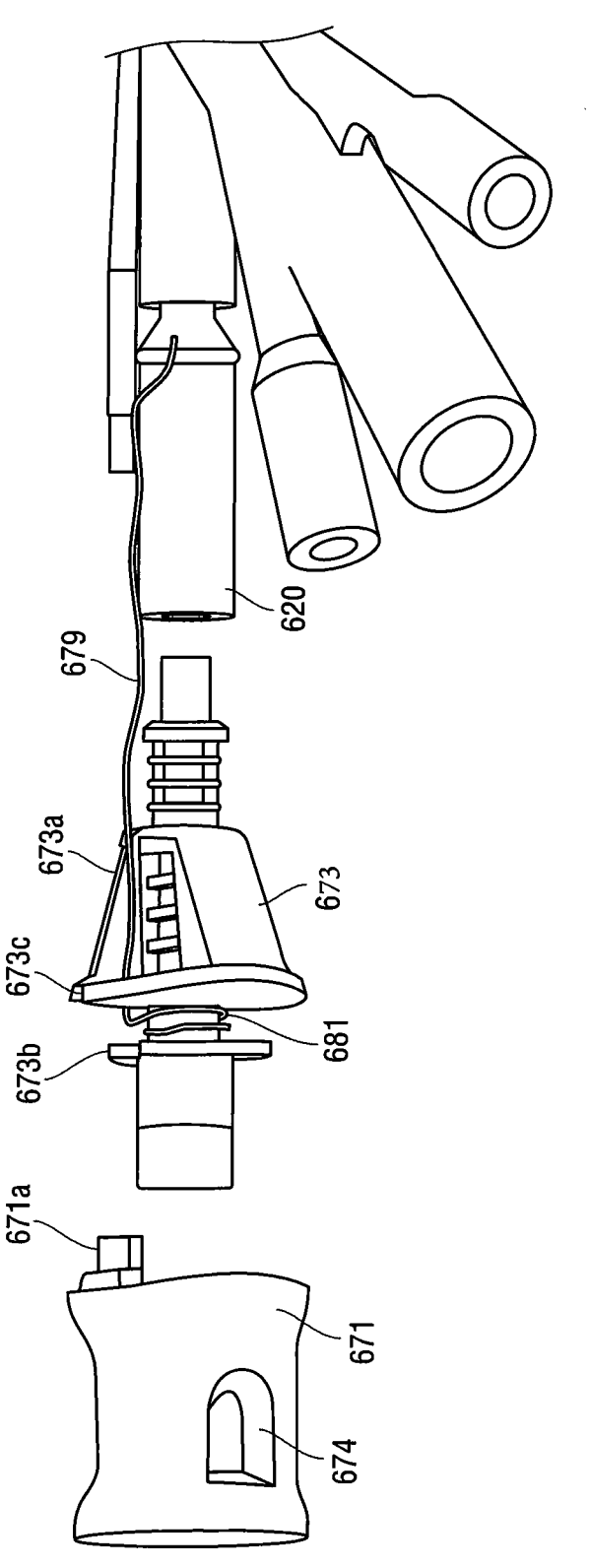
FIG. 66B is an exploded perspective view of the connector showing the thermistor wires.
Figure 66C:
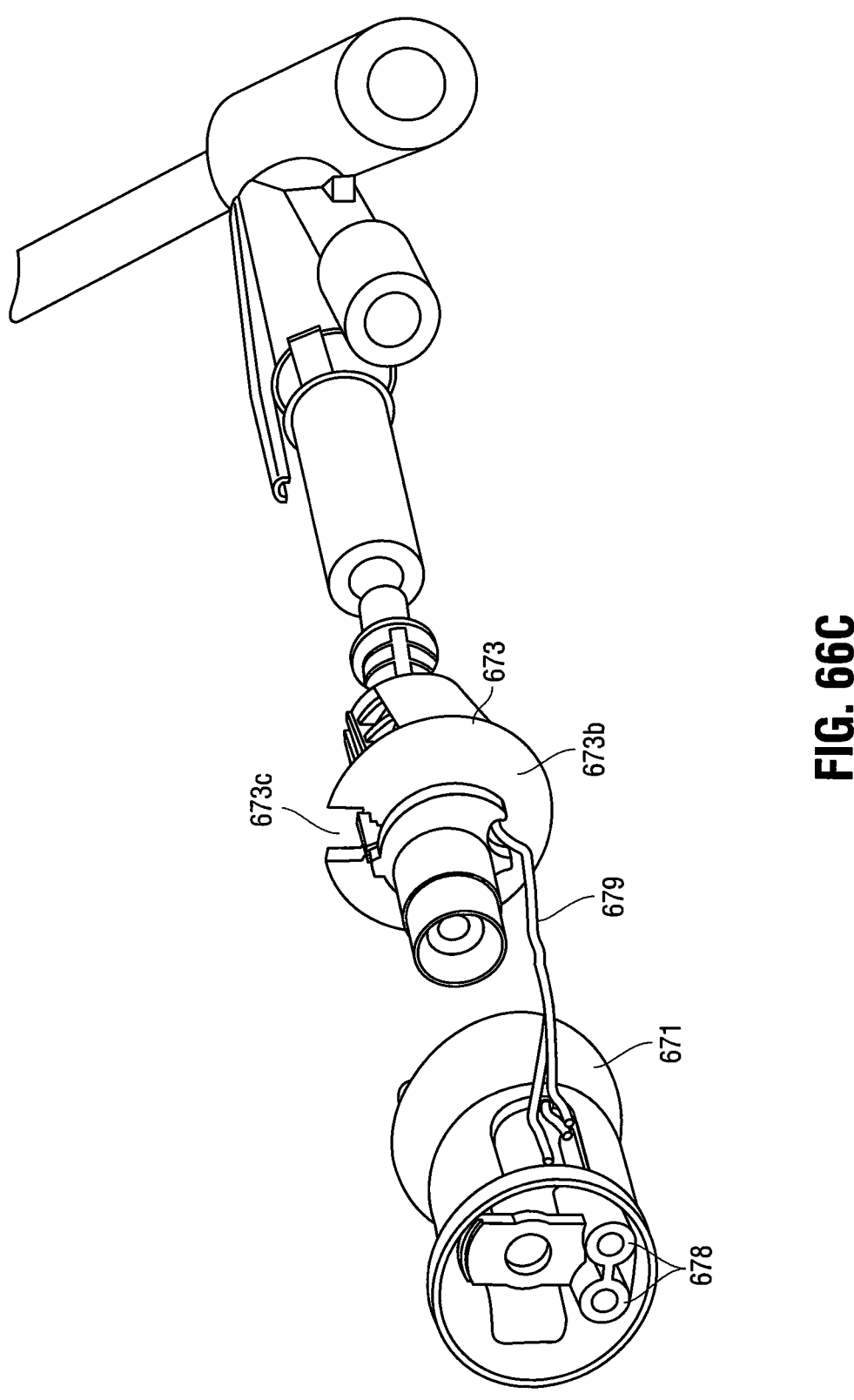
FIG. 66C is an exploded perspective of the connector of FIG. 64 showing the thermistor wires.
Figure 67:
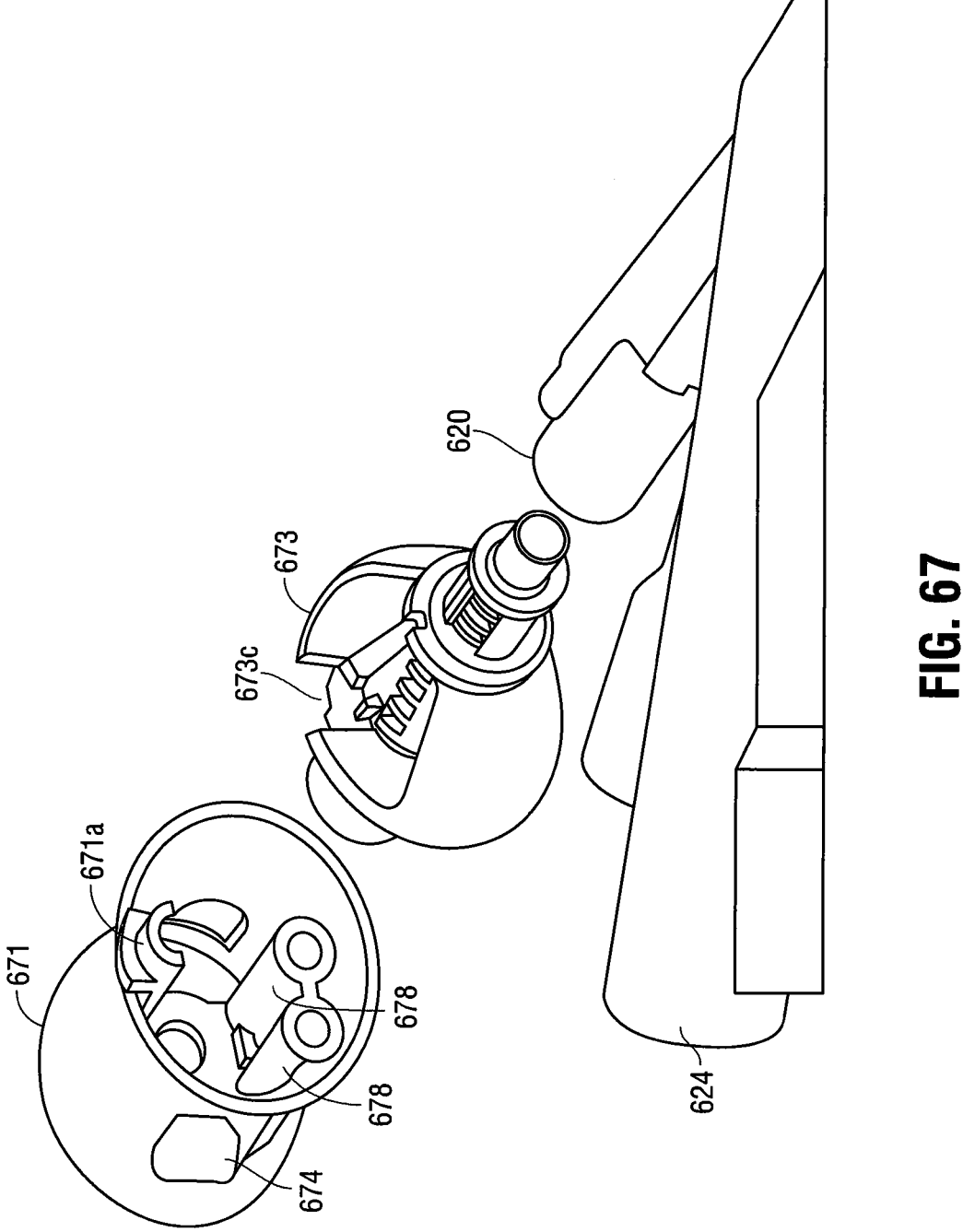
FIGS. 67 and 68 are exploded perspective views of the hub and connector of FIG. 64.
Figure 68:
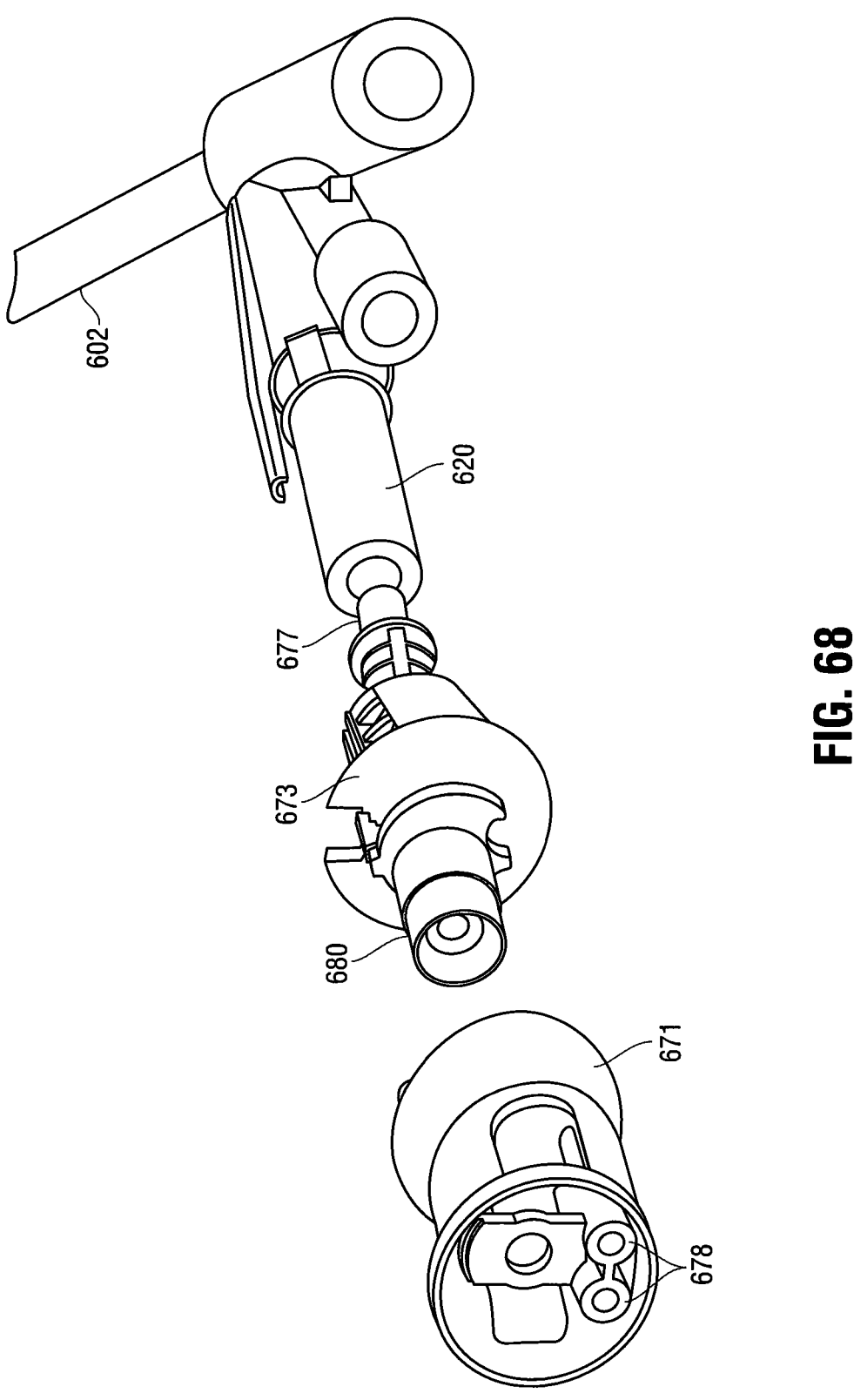

At catheter connection end, wires extend for connection of the pressure sensor board to the connector/hub of the catheter, e.g., hub 670 of FIG. 64 and for connection to the thermistor.

Figure 70:
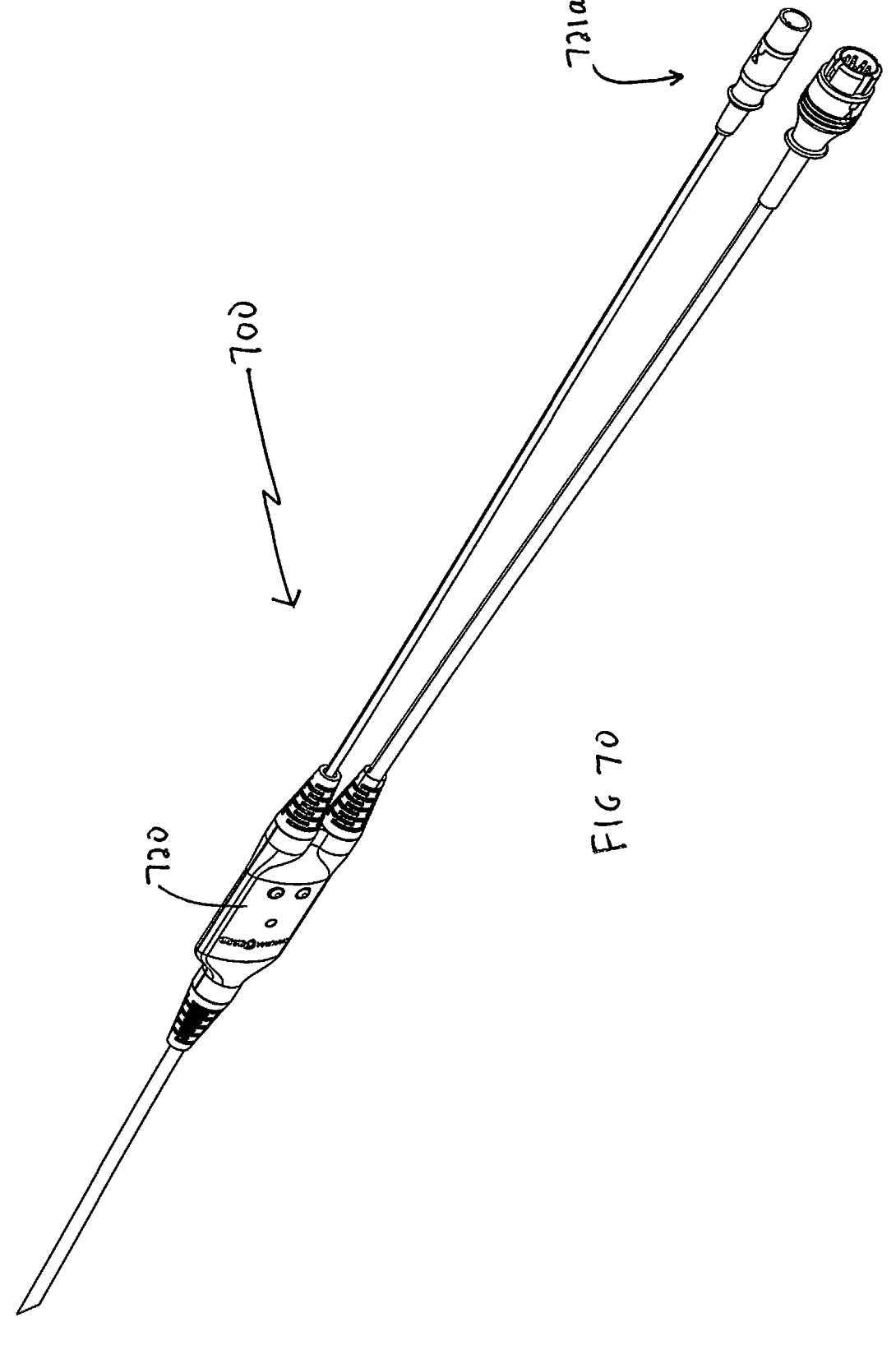
FIG. 70 is a perspective view of one embodiment of the smart cable of the present invention.

Emerging from the housing 720, the cable 700 splits so that thermistor wires connect within proximal housing (strain relief) 714 of thermistor housing 702, terminating at proximal housing 704 from which thermistor monitor connector 708 extends. Also emerging from the housing 720 are the pressure sensor wires that connect within proximal housing (strain relief) 716 of thermistor housing 702, terminating at proximal housing 710 from which pressure monitor connector 712 extends. As shown in FIG. 73, thermistor monitor connector 708 has two pins forming the male connection to the monitor such as a Phillips Intellivue monitor; pressure monitor connector 712 has twelve pins forming the male connection to the monitor such as the Phillip Intellivue monitor. Note the connectors 708 and 712 are configured for compatibility with the Phillips Intellivue monitor. For connection to other monitors, a different connector configuration, e.g., a different number of pins, a female receptacle rather than male pins, etc., can be provided. As can be appreciated, the split cable extends to the housing 720 and merges into a single housing 720 as shown in FIGS. 70 and 71 for a single connection to the catheter.

The wiring for the sensors is shown in FIG. 72 with reference numeral 728 designating the input end (from the catheter) and reference numeral 730 designating the output end (to the monitor). The following table identifies the function of the seven wires of FIG. 72, with paired + and − pressure and temperatures signals for pressure and temperature measurement, respectively.

| SIGNAL | FUNCTION | REFERENCE NUMERAL |
|---|---|---|
| V+ (5 V) | Power | 732 |
| S+ | Pressure | 734a |
| S− | Pressure | 734b |
| V− | Ground | 740 |
| T+ | Temperature | 736b |
| T− | Temperature | 736a |
| SH | Drain | 738 |

Figure 77A:
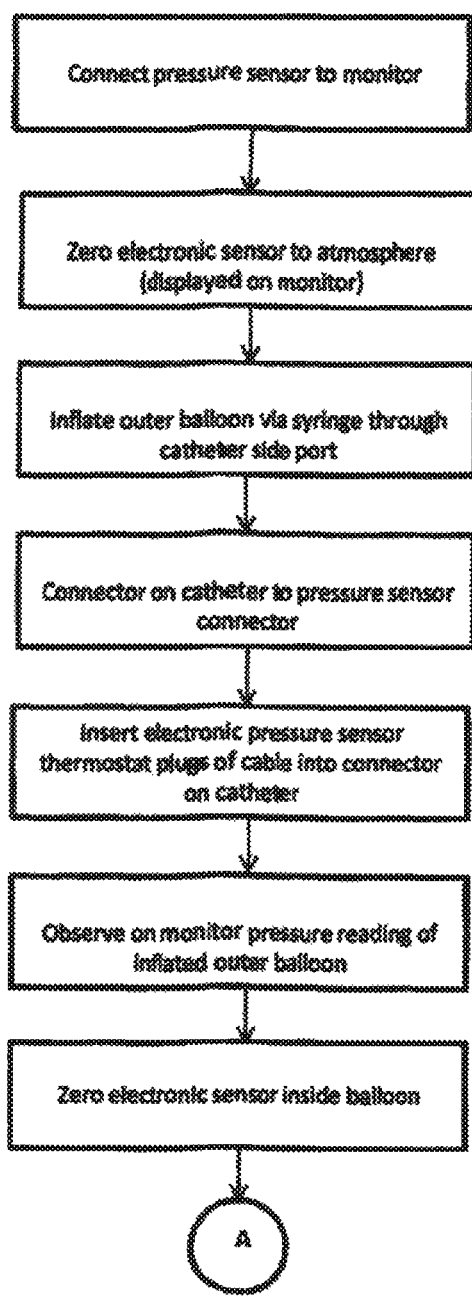
FIGS. 77A, 77B and 77C show a flow chart showing use of the smart cable of FIG. 70, the flow chart continuing on three pages as identified by "A" and "B"
Figure 77B:
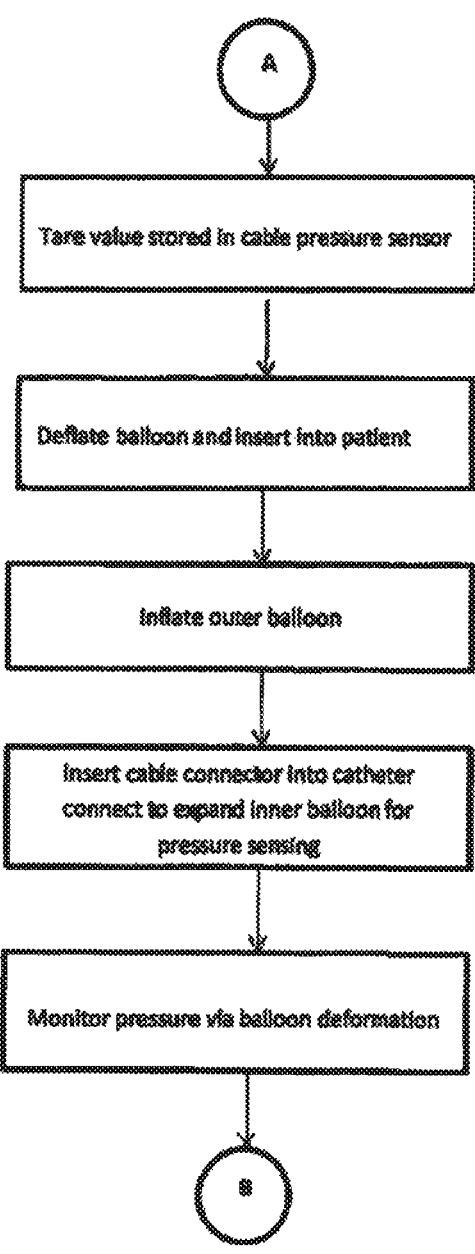
Figure 77C:
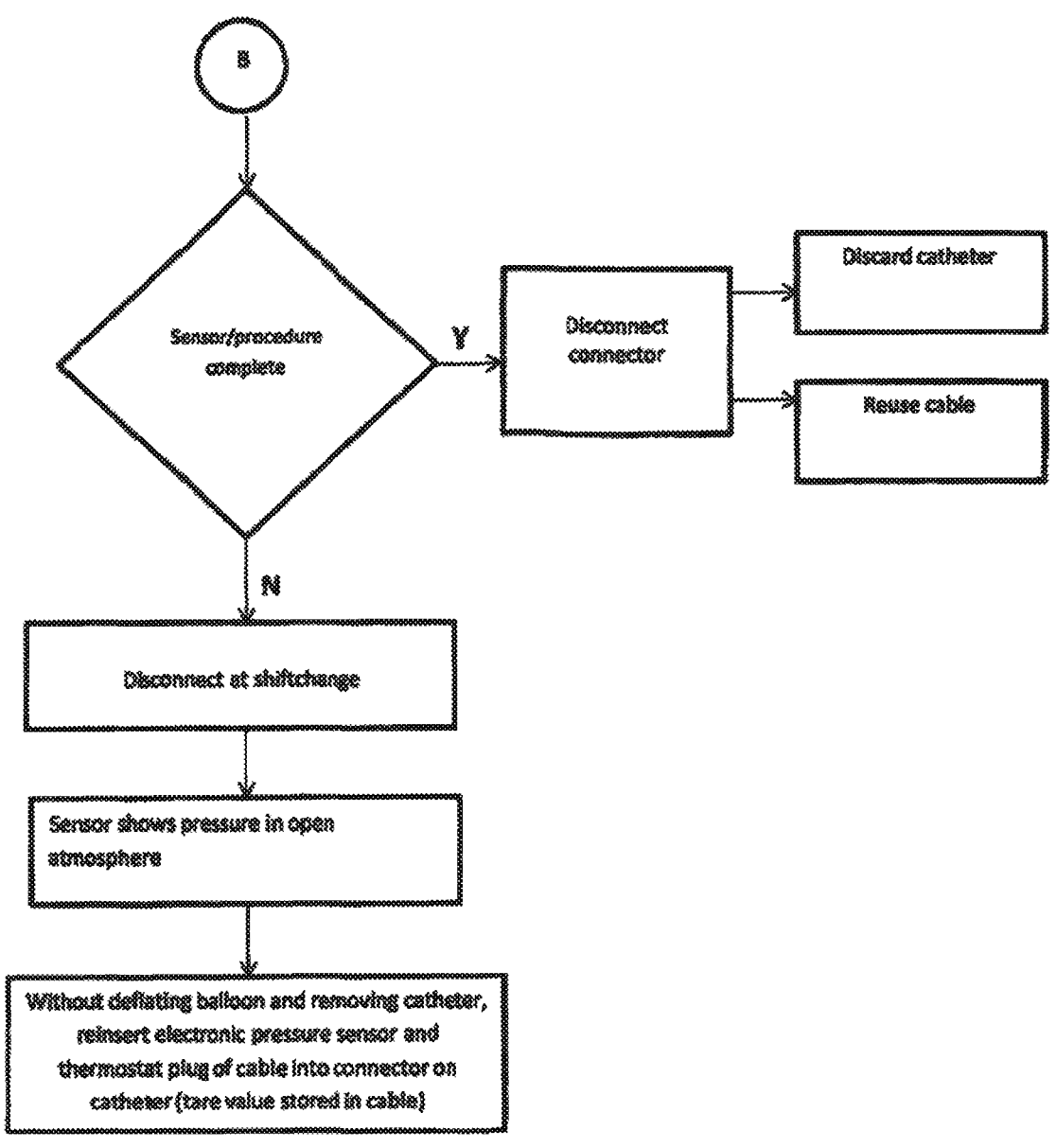

S in accordance with one embodiment will now be described with reference to the flow chart of FIG. 77A-77C.

In the first step, the cable connector (the electronic pressure sensor) 700 is attached (at its proximal end 721a) to a conventional monitor such as a Philips or GE monitor identified above which provides a graphical display of pressure sensing values. The balloons of the catheter are uninflated. Next the calibrate (zero) button on the monitor is pressed (activated) to zero the electronic sensor to atmosphere.

In the next step, the outer pressure sensing balloon of the catheter is inflated via infusion of a fluid such as saline or air. The connector 700 is then connected to the hub of the catheter to connect the thermistor pins and electronic pressure sensor of the distal end of cable 700 to the hub connector receptacle on the proximal end of the catheter. For example, the distal end of the cable can have the form/structure of 330 of FIG. 64 and the catheter receptacle can be of the form of housing 670 of FIG. 64. After the cable connector and catheter connector are aligned and attached, the balloon pressure is displayed on the monitor, e.g. 89 or 90 mmHg. Next the electronic sensor is now zeroed inside the balloon, providing a display of 0 pressure on the monitor. This tared value is stored in the cable 700 PCB.

The balloons are deflated and the catheter is then inserted into the patient, the outer balloon is inflated and the inner balloon is inflated via insertion of the pin into the air lumen, and the pressure measuring/monitoring function commences as described above, which in preferred embodiments, is monitored continuously. If the pressure sensing of the patient is not complete, but there is a shift change requiring disconnection and reconnection of the cable from the catheter in accordance with the hospital or clinic policy/procedure, the cable 700 is disconnected from the catheter. The monitor would then display pressure in open atmosphere (which would have a negative value due to the prior zeroing function). The clinician would then zero out the electronic sensor by activation of the button on the monitor as discussed above to provide a zero sensor reading at room (atmospheric) pressure. The zero-tare value of the balloon has been stored in the cable so when reconnected the tare value from the previous calibration provides the measurement baseline. In this manner, the catheter can remain in the body with the balloons inflated during the shift change. These steps can be done for each of the multiple shift changes.

When the pressure sensing procedure is complete, the cable and catheter connectors are disconnected and the catheter is discarded. The cable can be reused.

Figure 74:
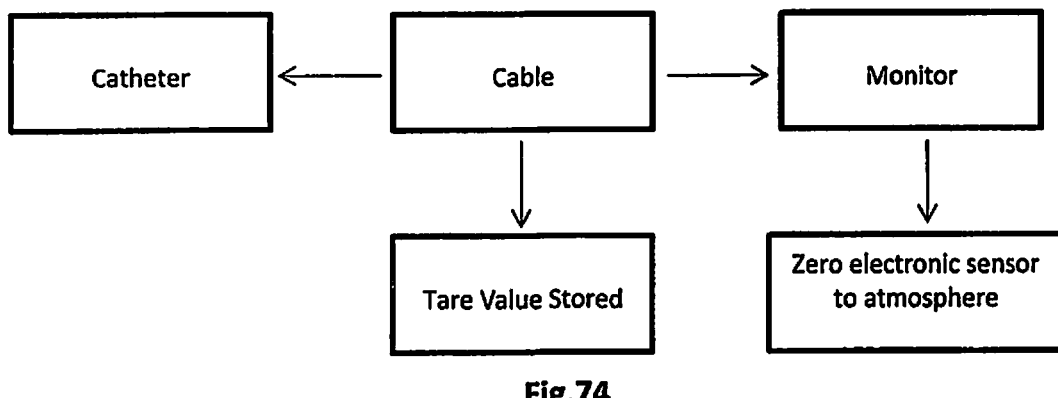
FIG. 74 is a diagram showing the system of connection of the cable of FIG. 70 to the monitor and the catheter.
Figure 75:
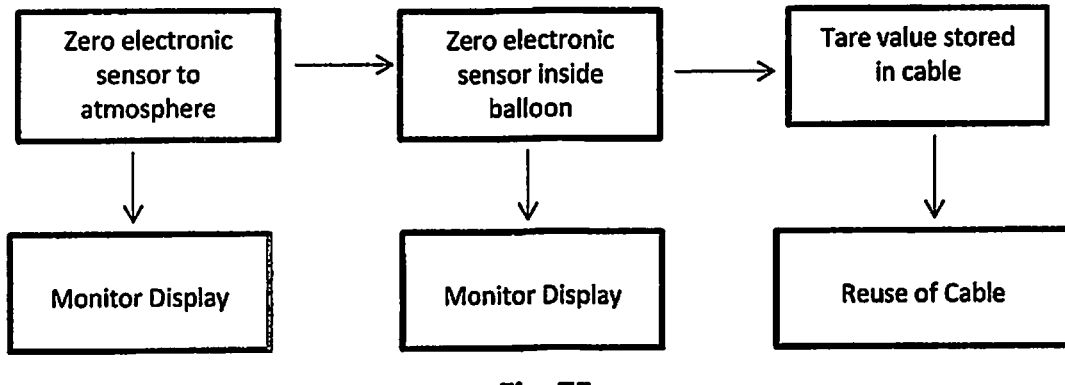
FIG. 75 is a diagram showing the zeroing functions of the system using the cable of FIG. 70.
Figure 76:
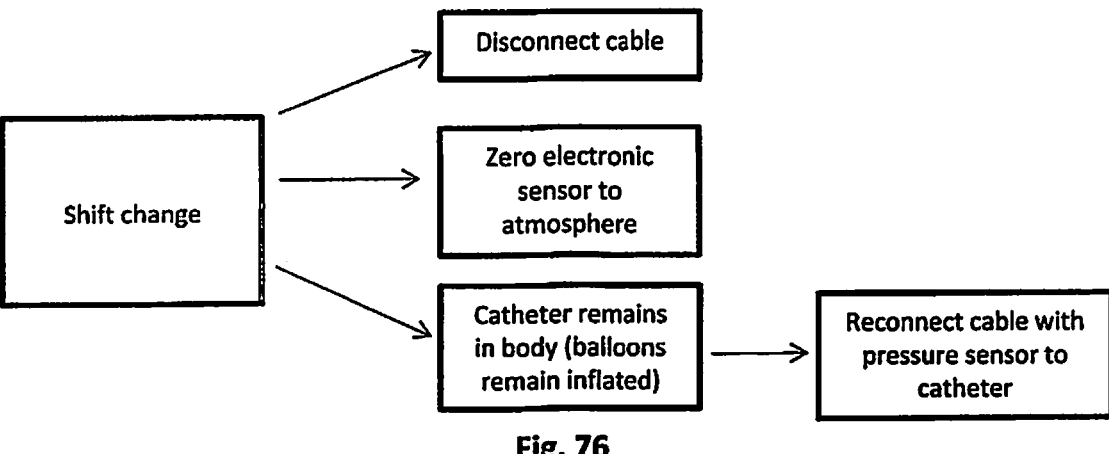
FIG. 76 is a diagram showing the system function on a shift change.

The block diagrams of FIGS. 74-76 illustrate segments of these functions. In FIG. 74, the overall function is depicted with the cable attached at opposite ends to the catheter and monitor. The tare value is stored in the cable. The zeroing of the electronic sensor to atmosphere is a monitor function. The diagram of FIG. 75 schematically shows the monitor displays resulting from the zeroing function and storage of the tare value in the cable. FIG. 76 illustrates the shift change procedure with the cable disconnected, the zeroing of the electronic sensor to atmosphere and the catheter remaining in the body with the balloons inflated due to the stored tare value in the cable when reconnected for continued use of the catheter for monitoring pressure within the patient.

The software and hardware functions of the system will now be described in conjunction with the system having a tared function for the pressure balloon and a delta function to accommodate movement of the patient from the supine position.

The system in its simpler form can include the cable, catheter and monitor, with the pressure readings available only on the monitor. In other embodiments, the system includes a Bluetooth component including an app to enable also reading pressure on a remote device such as a phone or tablet. The component could also be used to turn on features of the system. This system with the Bluetooth component is described below.

The hardware comprises the following components: 1) Mode Button; 2) Tare button; and 3) LED, e.g. RBG (red, blue, green) LED. The Mode Button is used to cycle through the 5 modes of operation. These modes are:

1) Raw Data
2) TARE unfiltered sensor Data
3) Filtered Data
4) Set point reference—supine position
5) Set seated position The Raw Data provides unfiltered sensor data, used for calibration of the sensor to the monitor. The TARE unfiltered sensor data is for use when zeroing out the inner sensing balloon to outer prior to insertion, The inflated outer balloon exerts a pressure on the inner balloon so zeroing out the inner balloon so pressure of outer balloon is at zero. The filtered sensor data is real time running with tared value. The set point reference creates a reference for the supine position. The set seated position output is sensor data, filtered with removal of data between the seated and supine set point.

The TARE button can be configured for actuation by pressing and holding for a preselected time. By way of example, in one embodiment, the TARE Button can be designed so that if it is pressed and held for less than 500 consecutive milliseconds (0.5 seconds), it will initiate a TARE Data Capture. The average value of the pressure input will be calculated and stored over a 2 second window. The Mode Button is configured to be disabled during a TARE data capture. After the TARE data capture is over, the Mode Button is enabled and TARE Data mode operation takes place, no matter the previous mode of operation. Pressing the TARE1 Button for 500 consecutive milliseconds (0.5 seconds) or less will interrupt any mode. It should be appreciated that other time periods are also contemplated. The buttons are preferably provided on hub 720.

A Filtered data button can be provided on the cable housing for actuation. Separate buttons can also be provided for the set point and set seated position to accommodate for the patient's change in position as discussed herein. These buttons can also be provided on the cable housing 720.

More specifically, the various modes can be provided as follows by way of example. Note the time periods are provided by way of example, it being understood that other time periods can be utilized.

1) Raw Data Mode—the unit outputs the sampled pressure every 50 milliseconds, scaled appropriately between −10 mV and +10 mV.
2) TARE Data Mode—identical to Raw Data mode except that the pressure value captured during TARE Data Capture is subtracted from every raw pressure value. The default TARE1 value is 0 mmHg. The TARE1 value is "remembered" through power cycles.
3) Filtered Data Mode—the filtered smallest pressure value sampled during a 6 second window minus the TARE1 Value will be output. The most recent "four least samples" are averaged.

4) Set point—the pressure value at a point in the supine position right before movement to the seated position. This provides a base for comparison to the pressure value when seated.
5) Set seated position—the pressure value at a point in the seated position right after movement to the seated position. This provides a value for comparison to the pressure value when in the supine position to determine the difference for subsequent subtraction of the difference to maintain proper comparable value.

Figure 78:
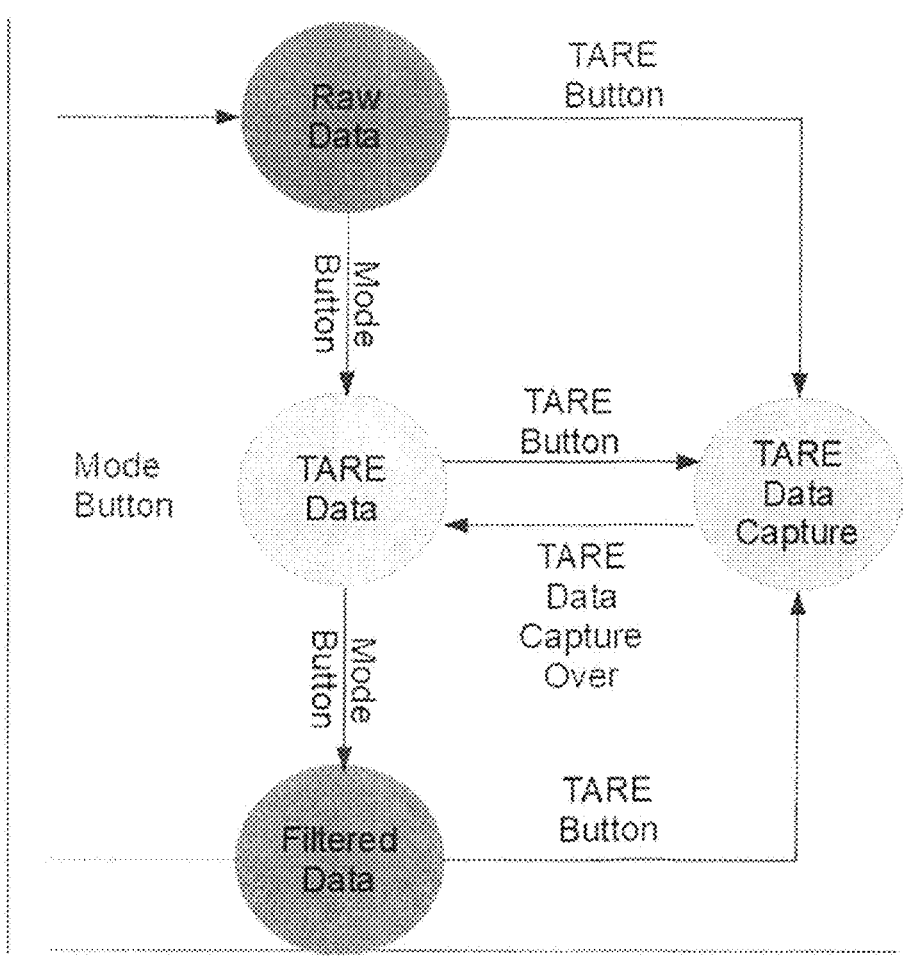
FIG. 78 is a diagram showing the function of the mode and tare buttons of the cable of FIG. 70.

When the unit is powered on, it will enter Raw Data mode. Every subsequent press of the Mode Button will cycle through all the modes. The diagram of FIG. 78 depicts the mode changes initiated by the Mode Button and the TARE Button.

Various color modes can be utilized. For example, in one embodiment, green is for raw data, yellow is for tared unfiltered data and blue is for filtered data. The user will be able to determine the current mode based on the state of the RGB LED. If in Raw Data mode, the RGB LED will stay on, or alternatively, flash green; in TARE Data Mode, the RGB LED will stay on, or alternatively, flash yellow; and in the Filtered Data Mode, the RGB LED will stay on, or alternatively flash blue. Other color codes to indicate various states/modes are also contemplated.

Color codes can also be used to enable the user to determine if the unit is connected to the Android Application via BLE.

The system as noted above is designed to run with or without Bluetooth. Below is a description of an android application for the Bluetooth component. The component can be programmed to provide pressure displays remote from the patient. The component can also in some embodiments provide readings from catheters of different patients. Alarms in the hand held component can be provided to provide an alert if the pressure reading exceeds a predetermined value. The component can also provide displays of other features and parameters after the user has initiated a connection with the cable such as being able to view the current mode of operation or the current TARE values. In some embodiments, the user can initiate mode changes via a virtual Mode button and virtual TARE1 button on the component (in lieu of pressing and holding the existing TARE button) and be able to change the maximum mmHg.

In use, when the application starts, the user is presented with a splash screen with a project logo centered on the screen, the android application software revision ND "Connect" button. When the user presses the Connect button, a list of available SSI units (available cables) is presented. If no SSI units (cables) are discovered, the app will inform the user and return to the main splash screen.

After selection of the SSI unit, the following information is presented:

a) current maximum mmHg setting for the unit and accompanying update button
b) current Rate value in mmHG and an accompanying button to trigger a new tare value (the Tare value is non-editable)
c) hardwRD nd software revision of the unit
d) Disconnect from SSI unit button Note if the handheld device is not paired with the SSI unit (the cable 700), the user will be required to pair the handheld device with the unit.

When the user clicks the "Update Max mmHg" button, the application verifies the value entered in the textbox by the user is between 1 and 400 MMHg. If the value entered is outside this range, the user will be informed of the error via a MESSAGE BOX. When the user clicks the "new Tare" button, N "Are you Sure" message box will be displayed; if the user clicks "Yes", a TARE will be triggered on the connected SSI unit ND THE NEW tare value will be updated when the SSI unit completes the TARE function. The Android application indicates that the TARE function is in progress. When the TARE function is in progress, the TARE button is disabled. When the user clicks the Disconnect button, the main splash screen is displayed.

The BLE Controller Board is designed to operate from a nominal 5V power supply, with a range of 4.5V-5.2V. An on-board microcontroller is provided for intelligent monitoring and filtering of the pressure sensor signal. The microcontroller incorporates a Bluetooth interface for wireless communication to the external Android device. The controller board provides an interface to the external sensor such as a SM5G-GGG-S-0155-000 pressure sensor. A single on-board pushbutton switch is provided for taring and resetting tared values and a single on-board RGB LED is be provided for status indication. This LED is visible through the housing 700.

The cable software provides for the following: 1) reading the pressure sensor every 50 milliseconds and converts the value to mmHg; 2) recognizing the push button as being pressed if it is pressed for 100 milliseconds consecutively; 3) recognizing the push button as being released if it is released for 100 milliseconds consecutively; 4) making the LED a solid GREEN when the software is running and the Android device is not connected; 5) make the LED a solid BLUE when the software is running and the unit is connected to an Android device via BLE; 6) making the LED a solid BLUE when the Android device is bonding (pairing) with the unit; 7) making the LED a solid YELLOW when the software is running and the unit is performing the TARE function. Note different colors can be provided. Additionally, if a flashing rather than a solid (continuous) light is desired, than the software will toggle the LED every predetermined number of seconds, e.g., every 500 milliseconds. The software can also input the air pressure every 50 milliseconds.

When the Push Button is pressed for 3 consecutive seconds or when commanded via BLE, the software executes the TARE function & input air pressure every 50 milliseconds. As noted above, the TARE function consists of taking 5 seconds of pressure input data and averaging the result. The result is saved as persistent memory (maintained through power cycles) and presented to the Android application upon request. The software indicates to the Android application that the TARE function is in progress. The software shall ignore any start TARE command while TARE is in progress. The default value of the TARE is 0 mmHg. The current TARE value is maintained if a SSI unit software upgrade is performed. The software is capable of receiving a maximum mmHg value (MAX MMHG) via BLE and presenting the current value to the Android application. The software stores the maximum mmHg as persistent data (maintained through power cycles). The current mmHg value is maintained after a SSI unit software upgrade is performed. The default value of the maximum mmHg is 300.

The software maintains the Lowest Input Air Pressure (LIAP) level recorded over 6 seconds worth of samples (120 samples). After 6 seconds expire, the software subtracts (TARE) from (LIAP) and store this value in a 4 sample FIFO (First In First Out) buffer. Every 6 seconds, the software shall calculate the average value (AVG_LIAP) of the 4 samples in the FIFO. Every 6 seconds, the software updates the digital to analog converter (DAC).

FIG. 87 provides a flow chart of an alternate method of use of the catheter/cable of the present invention. The method can be used with the cable 700 or cable 800 of FIG. 79A and the catheters of the various embodiments disclosed herein, as well as with other catheters with air charged pressure balloons. The method of use is as follows:

1) with the patient in the supine position, connect a syringe to the valve/port for the outer balloon, pull a vacuum to evacuate excess air and inflate the outer distal balloon via the syringe, e.g., injecting 2.5 cc of sterile water;

2) disconnect the syringe;

3) insert the hub connector of the cable into the catheter port by aligning the two pins on the cable with the openings in the catheter port (the patient remains in the supine position); and 4) twist the locking mechanism, e.g., clockwise, to secure the connection of the cable and catheter.

Note at this stage, the LED on the cable is a first color such as white (or another predetermined color). It should be appreciated that the LED colors for the various stages provide one set of different colors which can be utilized, it being understood that different colors can alternately be used to differentiate the status/stages of the system. After the connection of the cable and catheter, and waiting about 60 seconds for the pressure to stabilize, the monitor displays real time unfiltered intra-abdominal pressure (IAP) with the patient in the supine position (see box/condition 902 of FIG. 87). To enter the Supine Filtered Mode which provides end-expiratory pressure, the Capture button on the cable is pressed and held for 3 seconds. This changes the LED color to green (or another predetermined color) (see box 904). The monitor now display filtered data in the supine position. It should be appreciated that the time segments discussed herein such as 3 seconds are one example which can be utilized, it being understood that different time periods can alternately be used to provide the status changes disclosed herein and depicted in FIG. 87.

Pressure, e.g., IAP, can also be monitored in the position with the patient's torso elevated (e.g., seated position). From the Supine Filter Mode (box 904), the capture button is pressed and held for 3 seconds. This locks the Supine Filtered pressure reading. The LED cable changes to the color Magenta (box 906). The patient is elevated to the desired angle. The Capture button on the cable is pressed and held for 3 seconds to capture filtered pressure at the elevated angle (The Elevated Filtered Mode). The LED changes to Cyan (box 908).

To change the patient position while using the Elevated Filtered Mode, the patient is placed in supine position, and the Mode button on the cable is pressed. The LED on the cable now returns to green as in box 902. Then follow the steps 904-908 followed to obtain filtered data. As can be appreciated, in this manner, pressure readings can be accurately taken in supine and elevated positions of the patient, and unfiltered (raw) data or filtered data can be obtained and displayed.

To reset, hold the Capture and Mode buttons are held together for 10 seconds. The LED returns to white (box 902)

Note if the cable is not properly communicating with the bedside monitor, then the LED can be red or another predetermined color to indicate this. In this case, the cable is disconnected from the catheter (by turning the locking ring) and unplugged from the monitor, then reconnected and the monitor zeroed to atmospheric pressure. The cable can then be reconnected as above. When properly connected, the LED should return to white (box 902)

FIGS. 79A-82H illustrate an alternate embodiment of the cable of the present invention. Cable 800 has a catheter connecting end 802 and a monitor connecting end 804 separated by loop 803. The catheter connecting region 808 has a locking member rotatable to secure the cable to the catheter. In this embodiment, the elongated rod for displacing air is on the catheter side rather than on the cable side as in FIG. 84F. The elongated rod on the catheter side is shown in FIG. 84F. Housing 807 for the PCB and sensor are provided proximal of the monitor connect end.

In summary, the monitor connector includes a temperature connector cable 840 with a temperature connection end 812 and a pressure connector cable 842 with a pressure connection end 810. These each connect to a cable which connects to a monitor to provide temperature and pressure readouts viewable on the monitor or alternatively can be configured to plug in directly to the monitor. These cables 840, 842 connect to PCB hub 806 so that the wires connect to the PCB as described above with respect to the PCB 721 of housing 720. The wires extend from the opposite sides of the PCB as in FIG. 72 within the cable which loops as shown in FIG. 79A and then extends in catheter connecting end 802. The wires connect to the sensor 820 (see FIG. 82F) and the thermistor wires 832 extend beyond the sensor 820 into the sensor housing 814. The sensor 820 communicates with a channel in the sensor housing.

The monitor connecting end can have a universal connector for the temperature and pressure as shown in FIG. 80. Alternatively, it could have a temperature connector 880 and pressure connector 882 (FIG. 85) for connection to a Phillips monitor such as the Intellivue or a temperature connector 890 and pressure connector 892 for connection to a CE monitor, such as the Dash Marquette.

Turning to the catheter connecting end 804, the catheter connecting end 804 has a connector region 808 which includes a locking member or locking ring 824 which locks onto the catheter hub or connector 874 (FIGS. 84F, 84G). The locking ring 824 has internal threads to engage the external threads 870 on the threaded outer cap 870 of catheter hub 874 to thereby lock the cable 800 to the catheter. The region 808 also includes a sensor 820 wired to the PCB via wires 833. Housings halves/covers 814 are placed over channels 836 of sensor housing 826 to shield the wires 828, 832. Clamshell covers 818a, 818b cover the sensor 820 and a portion of the wires.

FIGS. 81A-81D illustrated details of the sensor housing 826. Sensor housing 826, as noted above, includes channels 836 to receive the thermistor wires 828, 832. Wires 828, 832 extend through the channels 826 and their respective thermistor pins 830, 834 extend into through the cylindrical retainers 829 on opposing sides of the housing 826. The pins 830, 834 extend into openings 874, 876 of the catheter threaded outer cap 870 (FIG. 84A). A pair of spacers 850, 852 are positioned on respective proximal and distal sides of O-ring 854. The O-ring 854 provides a back seal to prevent escape of gas, e.g., air, when the elongated rod 860 of the catheter 880 is positioned within the housing 826 to displace air in the catheter lumen when the sensor housing 826 is connected to the catheter. A further seal, i.e., a lower pressure seal, is provided by the female stacker 856 which has an internal tapered region to engage the region 864 (FIG. 83A) of elongated rod 860.

Figures 81A, 81B, 81C, 81D:
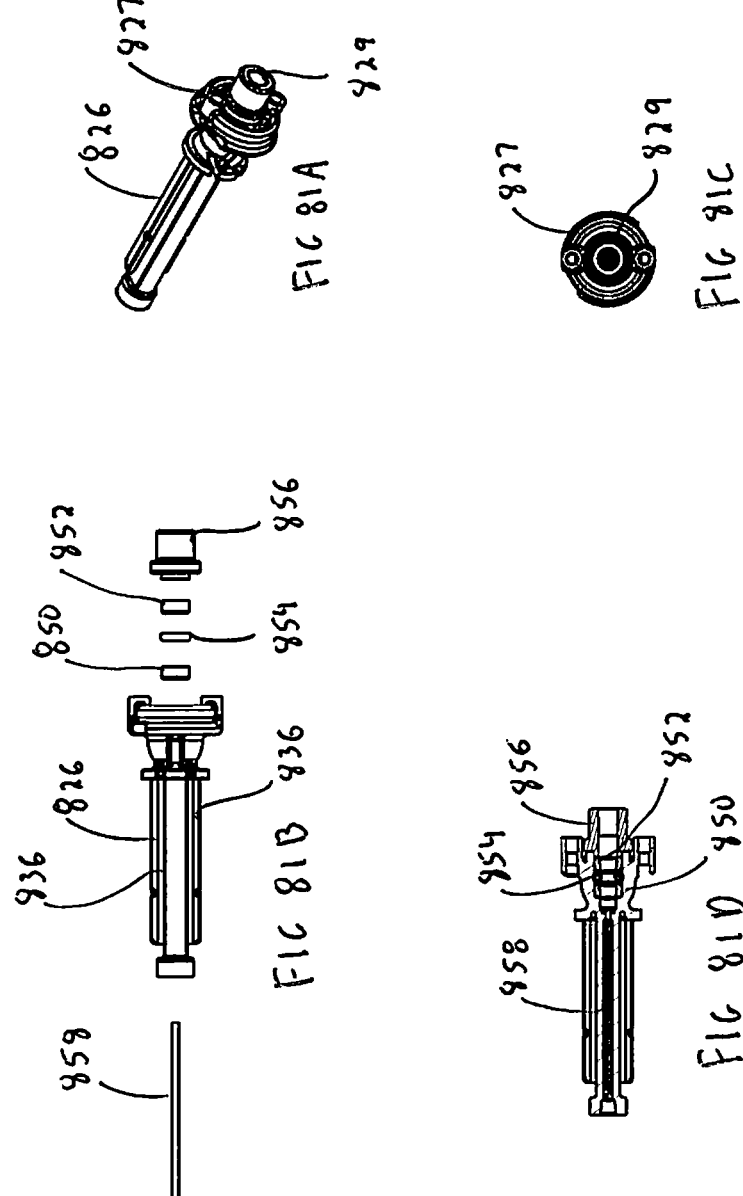
FIG. 81A is a perspective view of the sensor housing of the connector of FIG. 80.
FIG. 81B is an exploded view of the sensor housing of FIG. 81A.
FIG. 81C is a rear view of the of sensor housing of FIG. 81A.
FIG. 81D is a cross-sectional view of the sensor housing of FIG. 81A.

The two spacers 850, 852 are on each side of the O-ring 854, and can be adjusted during manufacture to adjust the amount of displaced air for charging the inner balloon of the catheter 880. That, is by providing more space, additional gas can fill the balloon. For example, the further the O-ring is positioned to the distal (catheter) side (right side as shown in FIG. 81B), the more air will be pushed by the elongated rod 860 because of tis more proximal contact with the O-ring. Tapered female stacker 856 is compressed by the lock ring 824 of the cable 800 (described below) to lock the elongated rod 860 in place. The seal is created when the elongated rod 856 contacts the O-ring 854. Tubing 858 can be a separate tubing attached or integral with the sensor housing. The tubing 858 (FIGS. 81B and 81D) narrows the channel of communication from the channel of elongated rod 860 (and air charged chamber) to the sensor 820.

The elongated rod 860, which is attached to the catheter, has a larger diameter portion 864 and a proximal tapered portion 862. Lumen 870 communicates with opening 866 for passage of pressure waves to the sensor 830. Region 862 passes through the opening in O-ring 854 and region 862 is engaged by the female stacker 856 of sensor housing 826. Flange 868 is provided for assembly to the catheter hub.

Figures 82E, 82F:
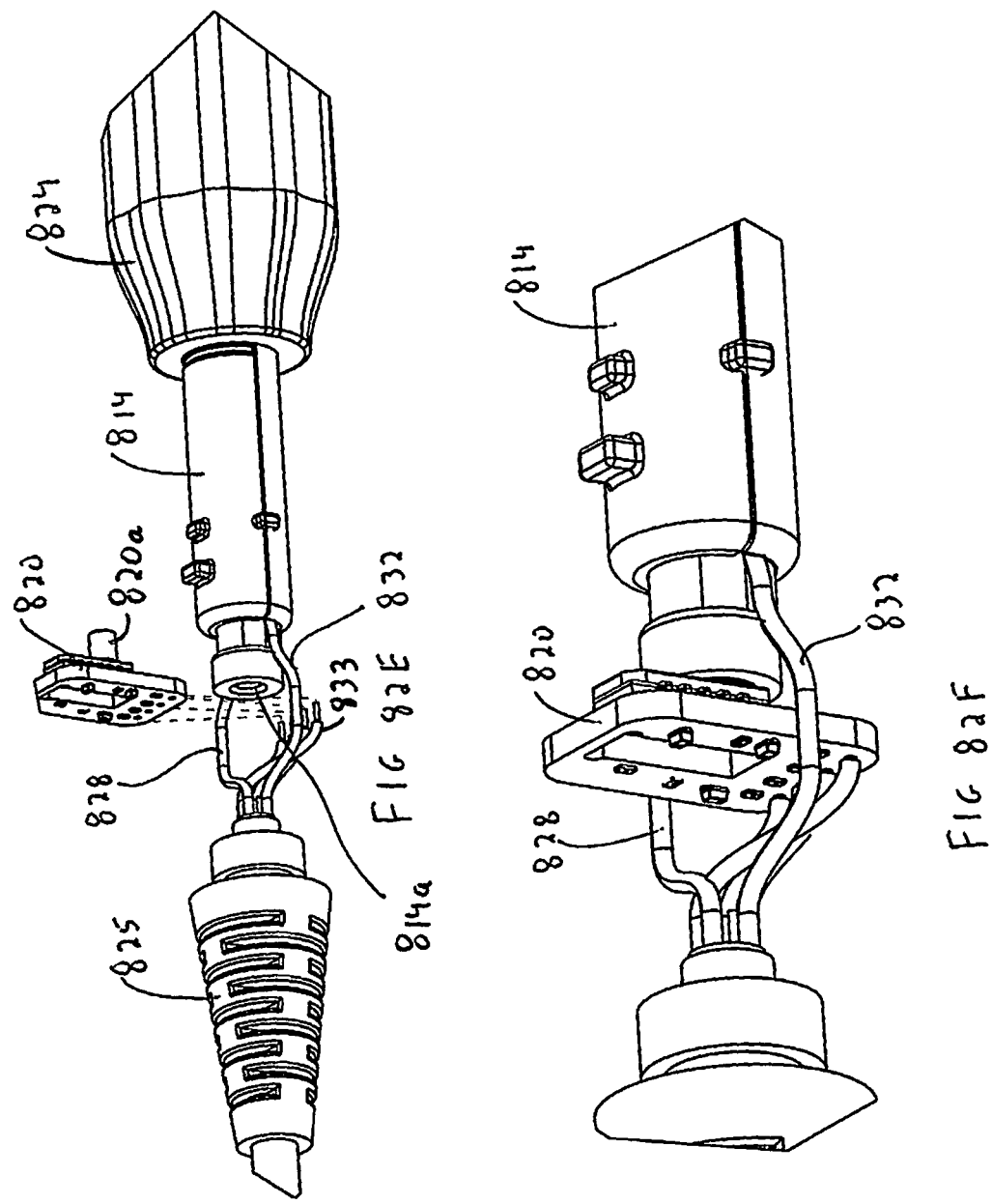
Figures 82G, 82H:
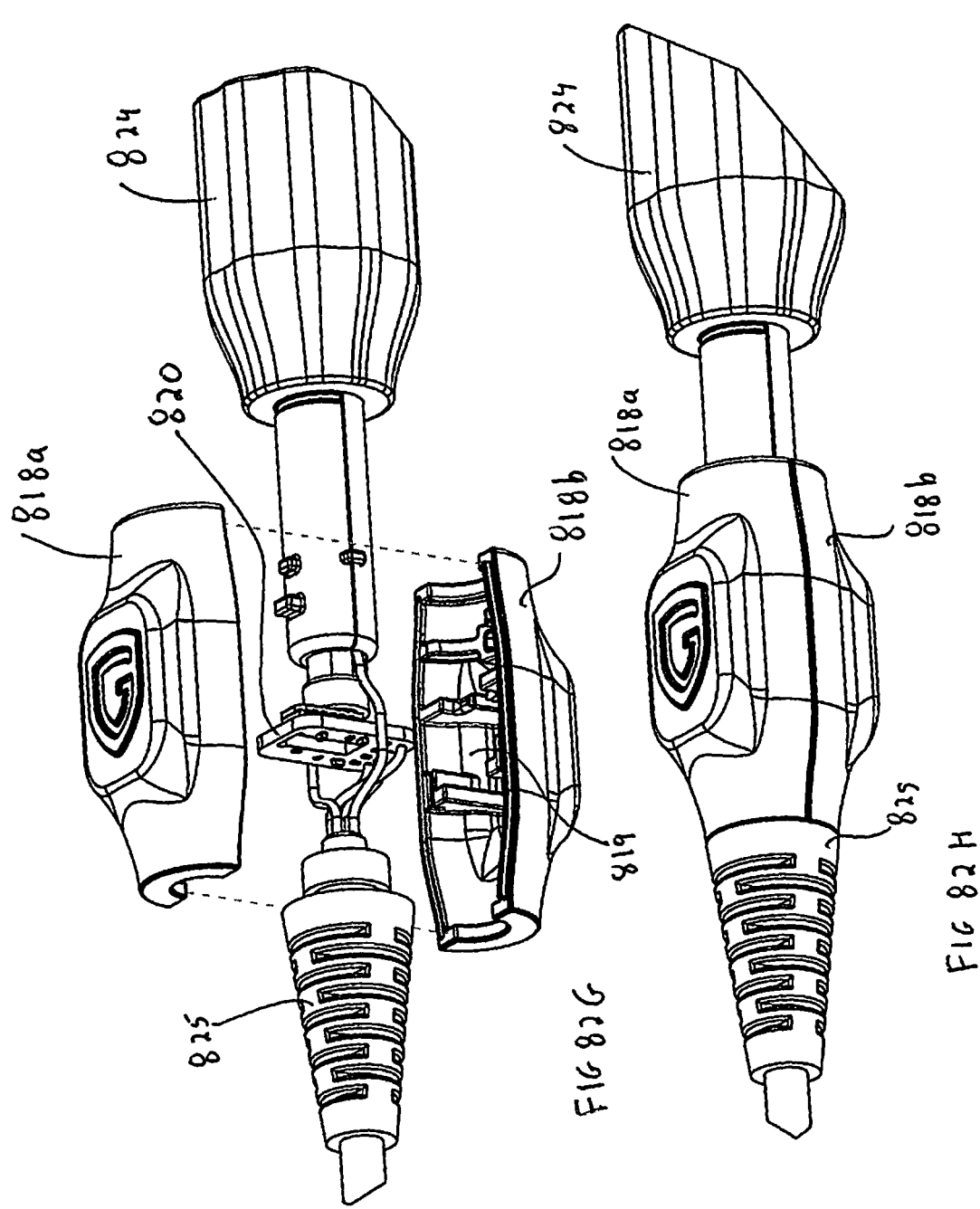
Figure 94F:
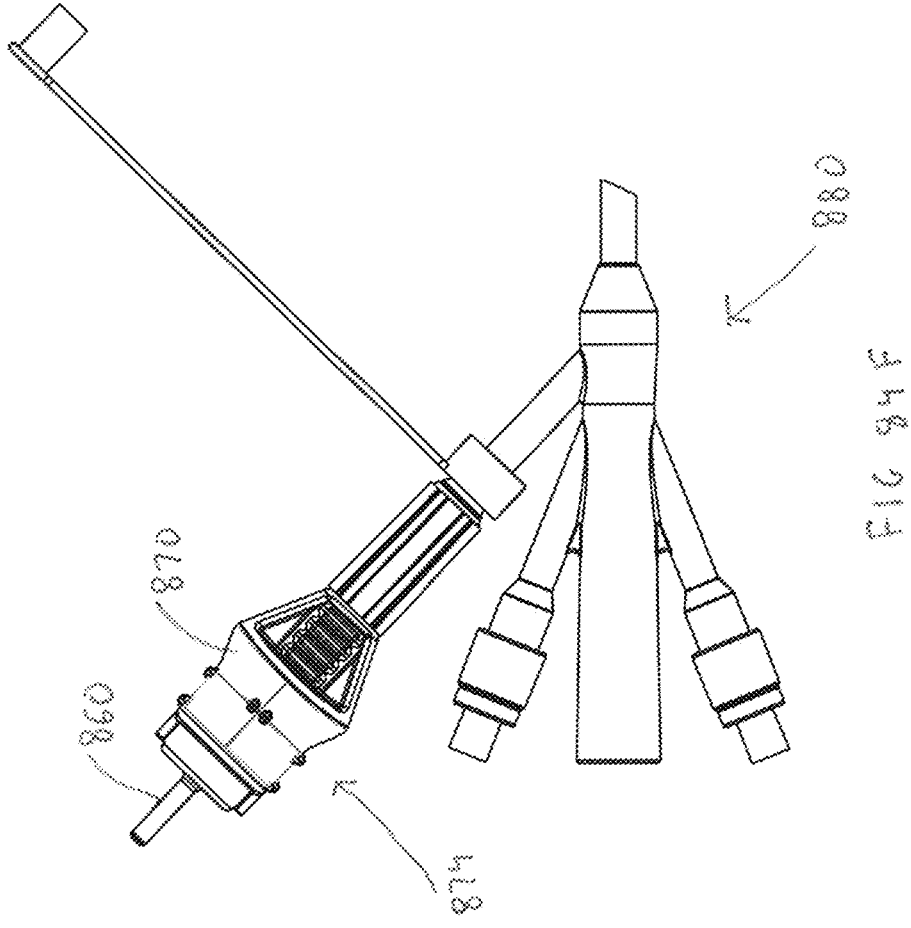

The steps for assembly of components of cable 800 will now be discussed and are shown in FIGS. 82A-82H. First, wires 828, 832, with thermistor pins 830, 834, are inserted through the outer lock ring 824 and into channels 828, on opposing sides of sensor housing 826. The pins extend through holders 833 of opposing sides of the housing 826, aligned with the channels 828 (for later connection to the outer threaded cap 870 of the catheter). Next, the outer lock ring 824 is moved forward (toward the catheter side) from tapered strain relief 825 to overlie/cover the pins 830, 834 as shown in FIG. 82C and is attached to the housing, e.g., by glue. Housing covers 814 are placed over the channels 828 to cover the channels and wires 828, 832 as shown in FIG. 82D. The sensor assembly 820 is then positioned in the space between the wires 828, 832, with post 820a extending into opening 814a of sensor housing 814 and the four wires are connected to the board of the sensor assembly 820 as shown in FIGS. 82E and 82F. After attachment of the sensor, clamshell halves (covers) 818a and 818b (FIG. 82G) are placed over the sensor 820 and the exposed wires 828, 832 to fully cover these components as shown in FIG. 82H. The clamshell halves 818a, 818b are attached, e.g., glued, to a distal end of the strain relief 825.

The smart cables of the present invention can be utilized with monitors reading a multitude of parameters. By adding sensors to the catheter, the smart cables of the present invention can process and output data to reflect these various parameters. The parameters read, processed/manipulated and outputted by the cables are not limited to parameters relating to a condition of the patient, e.g., temperature, but can also include external parameters such as outside temperature, patient position, etc. In some embodiments, in lieu of or in addition to the monitor reading and displaying the data outputted by the cable, the data can be displayed on a screen on the cable, e.g., on the hub of the cable, or outputted via/to Bluetooth connections/applications. The data can be interpreted and outputted via external devices, such as laptops, tablets or smart phones. In some embodiments, the software can allow multiple patients to be viewed at the same time by a remote device, e.g., laptop, phone or tablet, carried by the clinician.

Although the apparatus and methods of the subject invention have been described with respect to preferred embodiments, those skilled in the art will readily appreciate that changes and modifications may be made thereto without departing from the spirit and scope of the present invention as defined by the appended claims.

Additionally, persons skilled in the art will understand that the elements and features shown or described in connection with one embodiment may be combined with those of another embodiment without departing from the scope of the present disclosure.

Throughout the present disclosure, terms such as "approximately," "generally," "substantially," and the like should be understood to allow for variations in any numerical range or concept with which they are associated. For example, it is intended that the use of terms such as "approximately" and "generally" should be understood to encompass variations on the order of ±25%, or to allow for manufacturing tolerances and/or deviations in design.

Although terms such as "first," "second," "third," etc., may be used herein to describe various operations, elements, components, regions, and/or sections, these operations, elements, components, regions, and/or sections should not be limited by the use of these terms in that these terms are used to distinguish one operation, element, component, region, or section from another. Thus, unless expressly stated otherwise, a first operation, element, component, region, or section could be termed a second operation, element, component, region, or section without departing from the scope of the present disclosure.

Each and every claim is incorporated as further disclosure into the specification and represents embodiments of the present disclosure. Also, the phrases "at least one of A, B, and C" and "A and/or B and/or C" should each be interpreted to include only A, only B, only C, or any combination of A, B, and C.

What is claimed is:

1. A cable for use with a pressure monitoring catheter, the cable having a first end configured to operably connect to the pressure monitoring catheter, a second end configured to operably connect to a monitor which is configured to display pressure values, and a printed circuit, the cable configured to obtain a plurality of pressure readings and configured to store in memory the pressure readings, the cable including a movement adjustment feature configured to adjust pressure values by calculating and comparing pressure differences in response to a patient moving from a supine position to an elevated position to account for changes in the pressure due to the patient moving, the movement adjustment feature configured to compare pressure readings in the elevated position to pressure readings in the supine position and calculate a difference for adjustment of the pressure readings in the elevated position.

2. The cable of claim 1, wherein the cable includes a temperature adjustment feature configured to adjust pressure values in response to temperature changes.

3. The cable of claim 1, wherein the cable includes a barometric pressure adjustment feature configured to adjust pressure values in response to barometric pressure changes.

4. The cable of claim 1, wherein the cable includes a filtering system configured to collect and analyze a data input, the filtering system configured to filter out upper values of pressure values and take lower values of the pressure values over specific periods of time.

5. The cable of claim 4, wherein the filtering system is configured to take a predetermined number of samples representative of a lowest value of the pressure values and calculate an average value from the predetermined number of samples for display of the average value based solely on the lower values.

6. The cable of claim 5, wherein the cable is configured to calculate the average value multiple times and wherein the cable is configured to communicate with a monitor which is configured to display the average value in a line readout.

7. The cable of claim 1, wherein the cable further comprises a housing with a channel, the channel configured to receive an elongated rod of the catheter, the channel including an O-ring seal through which the elongated rod passes, wherein the channel includes a first spacer and a second spacer, the first spacer on a first side of the O-ring and the second spacer on a second side of the O-ring, and wherein the O-ring is configured so the position of the O-ring effects an amount of air displaced by the elongated rod when inserted into the channel to charge the second balloon.

8. The cable of claim 1, wherein a data output of the cable is filtered data.

9. The cable of claim 1, further comprising an indicator on the cable, the indicator configured to indicate if a data output of the cable is for the supine position or the elevated position.

10. The cable of claim 1, further including a pressure sensor and locking mechanism for locking to a connector of the pressure monitoring catheter, wherein attachment of the cable displaces air within the catheter to inflate a pressure measuring balloon of the catheter.

11. The cable of claim 8, wherein the cable is configured to selectively activate a display of the monitor in communication with the cable, the selective activation alternating from unfiltered pressure data to the filtered data.

12. The cable of claim 8, wherein the cable includes a capture button, the capture button configured to be activated, the activation causing the cable to capture and store into the memory the filtered data in the supine position and the elevated position of the patient.

13. The cable of claim 1, wherein the cable is configured to store into memory a supine pressure measurement when the patient is in the supine position and store into memory an elevated pressure measurement when the patient is in an elevated position.

14. The cable of claim 13, wherein the cable is configured to subtract the difference from the elevated pressure measurement.

* * * * *